(12) United States Patent
Chen et al.

(10) Patent No.: US 7,868,158 B2
(45) Date of Patent: Jan. 11, 2011

(54) MODULATION OF CYTOKINE SIGNALING REGULATORS AND APPLICATIONS FOR IMMUNOTHERAPY

(75) Inventors: Si-Yi Chen, Pearland, TX (US); Lei Shen, Houston, TX (US); Kevin C. Evel-Kabler, Rosharon, TX (US); Xue F. Huang, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 564 days.

(21) Appl. No.: 11/165,091

(22) Filed: Jun. 23, 2005

(65) Prior Publication Data

US 2006/0269519 A1  Nov. 30, 2006

Related U.S. Application Data

(60) Provisional application No. 60/589,052, filed on Jul. 19, 2004.

(51) Int. Cl.
C07H 21/04 (2006.01)
(52) U.S. Cl. .................. 536/24.5; 536/24.31; 536/24.1; 514/44
(58) Field of Classification Search .................. None
See application file for complete search history.

(56) References Cited

U.S. PATENT DOCUMENTS

| | | | |
|---|---|---|---|
| 4,082,735 A | 4/1978 | Jones et al. | |
| 4,082,736 A | 4/1978 | Jones et al. | |
| 4,101,536 A | 7/1978 | Yamamura et al. | |
| 4,185,089 A | 1/1980 | Derrien et al. | |
| 4,235,771 A | 11/1980 | Adam et al. | |
| 4,406,890 A | 9/1983 | Tarcsay et al. | |
| 4,606,918 A | 8/1986 | Allison et al. | |
| 4,683,202 A | 7/1987 | Mullis et al. | |
| 4,962,091 A | 10/1990 | Eppstein et al. | |
| 5,023,243 A | 6/1991 | Tullis et al. | |
| 5,168,053 A | 12/1992 | Altman et al. | |
| 5,190,931 A | 3/1993 | Inouye | |
| 5,199,942 A | 4/1993 | Gillis et al. | |
| 5,350,674 A | 9/1994 | Boenisch et al. | |
| 5,580,859 A | 12/1996 | Felgner et al. | |
| 5,585,362 A | 12/1996 | Wilson et al. | |
| 5,710,123 A * | 1/1998 | Heavner et al. | 514/2 |
| 5,710,129 A | 1/1998 | Lynch et al. | |
| 5,928,906 A | 7/1999 | Koster et al. | |
| 6,326,193 B1 | 12/2001 | Liu et al. | |
| 6,716,422 B1* | 4/2004 | Gajewski et al. | 424/85.2 |
| 2003/0138413 A1* | 7/2003 | Vicari et al. | 424/93.21 |
| 2003/0166140 A1 | 9/2003 | Chen et al. | |
| 2003/0171253 A1 | 9/2003 | Ma et al. | |
| 2003/0175971 A1* | 9/2003 | Lindeman et al. | 435/455 |
| 2004/0259247 A1 | 12/2004 | Tuschl et al. | |
| 2005/0147608 A1* | 7/2005 | Ryo et al. | 424/145.1 |
| 2006/0239971 A1 | 10/2006 | Mohapatra | |
| 2006/0292119 A1 | 12/2006 | Chen et al. | |

FOREIGN PATENT DOCUMENTS

| | | |
|---|---|---|
| WO | WO 92/07065 | 4/1992 |
| WO | WO 94/07529 | 4/1994 |
| WO | WO 01/29058 | 4/2001 |
| WO | WO 01/75164 | 10/2001 |
| WO | WO 01/96584 | 12/2001 |

OTHER PUBLICATIONS

Akira et al. Toll-Like Receptor Signaling. Journal of Biological Chemistry 2003, vol. 278, No. 40: 38105-38108.*
Brummelkamp et al. Stable Suprresion of tumorigenicity by virus-mediated RNA interference. Cancer Cell 2002, pp. 243-247.*
Matsuda et al. SOCS-1 can suppress CD3 and Syk-mediated NF-AT activation in a non-lymphoid cell line. FEBS Letters 2000, vol. 472: 235-240.*
Rao et al. IL-12 Is an Effective Adjuvant to Recombinant Vaccinia Virus-Based Tumor Vaccines. Journal of Immunology 1996, vol. 156: 3357-3365.*
Yamamoto et al. SOCS-3 inhibits IL-12 induced STAT4 activation by binding through tis SH2 domain to the STAT4 docking site in the IL-12 receptor B2 subunit. Bichem and Biophys Research Comm 2003, Vool. 310: 1188-1193.*
Schnidt et al. Survivin is a shared tumor-associated antigen expressed in a broad variety of malignancies and recognized by specific cytotoxic T cells. Blood 2003, vol. 102, No. 2: 571-576.*
Song et al. Suppressor of Cytokine Signaling SOCS1 and SOCS3 but not SOCS2 proteins inhibit interferon-mediated antiviral and anti-proliferative activities. JBC, vol. 273, No. 52: pp. 35056-35062.*
Akira et al., "Toll-like Receptor Signaling", Nat. Rev. Immunol. 4:499-511 (2004).
Alexander et al., "SOCS1 Is a Critical Inhibitor of Interferon γ Signaling and Prevents the Potentially Fatal Neonatal Actions of the Cytokine", Cell 98:597-608 (1999).
Alexander et al., "The Role of Suppressors of Cytokine Signaling (SOCS) Proteins in Regulation of the Immune Response", Annu. Rev. Immunol. 22:503-29 (2004).
Baetz et al., "Suppressor of Cytokine Signaling (SOCS) Proteins Indirectly Regulate Toll-like Receptor Signaling in Innate Immune Cells", J. Biol. Chem. 279:54708-54715 (2004).

(Continued)

*Primary Examiner*—Kimberly Chong
(74) *Attorney, Agent, or Firm*—Foley & Lardner LLP; James F. Ewing

(57) ABSTRACT

The present invention relates to regulation of antigen presentation by cytokine signaling regulators in antigen presenting cells, such as dendritic cells. The invention provides methods of modulating antigen presentation through modulation of cytokine signaling regulators, such as SOCS (SOCS1-7, CIS), SHP (SHP-1 and SHP-2) or PIAS (PIAS1, PIAS3, PIASx and PIASy). The present invention provides vaccines and therapies in which antigen presentation is enhanced through modulation of cytokine signaling regulators. The present invention also provides a mechanism to break self tolerance in tumor vaccination methods that rely on presentation of self tumor antigens.

39 Claims, 87 Drawing Sheets

OTHER PUBLICATIONS

Crespo et al., "Indirect induction of suppressor of cytokine signaling-1 in macrophages stimulated with bacterial lipopolysaccharide: partial role of autocrine/paracrine interferon-α/β", Biochem. J. 349:99-104 (2000).

Curtisinger et al., "Signal 3 Determines Tolerance versus Full Activation of Naïve CD8 T Cells: Dissociating Proliferation and Development of Effector Function", J. Exp. Med. 197:1141-1151 (2003).

Dalpke et al., "Suppressors of Cytokine Signaling (SOCS)-1 and SOCS-3 Are Induced by CpG-DNA and Modulate Cytokine Responses in APCs", J. Immunol. 166:7082-7089 (2001).

Eyles et al., "Negative Regulation of Inerleukin-12 Signaling by Suppressor of Cytokine Signaling-1", J. Biol. Chem. 277:43735-43740 (2002).

Hanada et al., "Suppressor of Cytokine Signaling-1 Is Essential for Suppressing Dendritic Cell Activation and Systemic Autoimmunity", Immunity 19:437-450 (2003).

Kinjyo et al., "SOCS1/JAB Is a Negative Regulator of LPS-Induced Macrophage Activation", Immunity 17:583-591 (2002).

Kubo et al., "Suppressors of cytokine signaling and immunity", Nature Immunity 4:1169-1176 (2003).

Marine et al., "SOCS1 Deficiency Causes a Lymphocyte-Dependent Perinatal Lethality", Cell 98:609-616 (1999).

Naka et al., "SOCS-1/SSSI-1-Deficient NKT Cells Participate in Severe Hepatitis through Dysregulated Cross-Talk Inhibition of IFN-γ and IL-4 Signaling In Vivo", Immunity 14:535-545 (2001).

Nakagawa et al., "SOSC-1 Participates in Negative Regulation of LPS Responses", Immunity 17:677-687 (2002).

Ryo et al., "Regulation of NF-κB Signaling by Pin 1-Dependent Prolyl Isomerization and Ubiquitin-Mediated Proteolysis of p65/ReIA", Molecular Cell 12:1413-1426 (2003).

Valenzuela et al., "The Roles of IL-12 in Providing a Third Signal for Clonal Expansion of Naïve CD8 T Cells", J. Immunol. 169:6842-6849 (2002).

Wormald et al., "Inhibitors of Cytokine Signal Transduction", J. Biol. Chem. 279:821-824 (2004).

Heyninck, et al., "A20 Inhibits NF-κB Activation by Dual Ubiquitin-Editing Functions", Trends Biochem Sci., Jan. 2005, vol. 1, pp. 1-4.

PCT International Search Report—(PCT/US2006/001751) Date of Mailing Aug. 14, 2008.

PCT International Search Report—(PCT/US2005/022396) Date of Mailing Jul. 15, 2008.

Agrwal et al., Oligodeoxynucleoside methylphosphonates: Synthesis and enzymic degradation, Tetrahedron Letters, 28:3539-3542, 1987.

Allen et al., Th1-Th2: reliable 392, 1997. paradigm or matrices dangerous dogma?, Immunol. Today, 18:387-392, 1997.

Altschul, Amino acid substitution matrices from an information theoretic perspective, J. Mol. Biol., 219:555-565, 1991.

Balazs et al., Blood dendritic cells interact with splenic marginal zone B Cells to initiate T-independent immune responses, Immunity, 17:341-352, 2002.

Banchereau et al., Autoimmunity through cytokine-induced dendritic cell activation, Immunity, 20:539-550, 2004.

Banchereau et al., Dendritic cells and the control of Immunity, Nature, 392:245-252, 1998.

Barron et al., Influence of plasma viremia on defects in number and immunophenotype of blood dendritic cel subsets in human immunodeficiency virus 1-infected individuals, J. Infect. Dir., 187:26-37, 2003.

Beutler et al., Innate immune sensing and its roots: the story of endotoxin, Nat. Rev. Immunol., 3:169-176, 2003.

Brummelkamp, et al., A system for stable expression of short interfering RNAs in mammalian cells, Science, 296:550-553, 2002.

Burton et al., HIV vaccine design and the neutralizing antibody problem, Nat. Immunol., 5:233-236, 2004.

Carbonneil et al., Defective dendritic cell function in HIV-infected patients receiving effective highly active antiretroviral therapy: neutralization of IL-10 production and depletion of $CD4^+CD25^+$ cells restore high levels of HIV-specific $CD4^+$ T cell responses induced by dendritic cells generated in the presence of IFN-$α^1$, J. Immunol., 172:7832-7840, 2004.

Cech et al., RNA catalysis by a group 1 ribozyme, J. Biol. Chem., 267:17479-17482, 1992.

Cech, Ribozymes and their medical implications, J. Amer. Med. Assn., 260:3030-3034, 1988.

Chong et al., Suppressor of cytokine signaling-1 is a critical regulator of interleukin-7-dependent $CD8^+$ T cell differentiation, Immunity, 18:475-487, 2003.

Colonna, Can we apply the $T_H1$-$T_H2$ paradigm to all lymphocytes?, Nat. Immunol., 2:899-900, 2001.

Darnell et al., Jak-STAT pathways and transcriptional activation in response to IFNs and other extracellular signaling proteins, Science, 264:1415-1421, 1994.

Dubois et al., Critical role of IL-12 in dendritic cell-induced differentiation of naive B lymphocytes, J. Immunol., 161:2223-2231, 1998.

Dubois et al., Dendritic cells enhance growth and differentiation of CD40-activated B lymphocytes, J. Exp. Med., 185:941-951, 1997.

Dustin et al., The immunological synapse and the actin cytoskeleton: molecular hardware for T cell signaling, Nat. Immunol,. 1:23-29, 2000.

Eckstein, Phosphorothioates in molecular biology, Trends Biol. Sci., 14:97-100, 1989.

Elbashir et al., Duplexes of 21-nucleotide RNAs mediate RNA interference in cultured mammalian Cells, Nature, 411:494-498, 2001.

Elbashir et al., RNA interference is mediated by 21-and 22-nucleotide RNAs, Genes & Development, 15:188-200, 2000.

Fantuzzi et al, Human immunodeficiency virus Type 1 gp120 induces abnormal maturation and functional alterations of dendritic cells: a novel mechanism for AIDS pathogenesis, J. Virol., 78:9763-9772, 2004.

Flamand et al., Murine dendritic cells pulsed In Vitro with tumor antigen induce tumor resistance In Vivo, Eur. J. Immunol., 24:605-610, 1994.

Garg et al., Genetic tagging shows increased frequency and longevity of antigen-presenting, skin-derived dendritic cells In Vivo, Nat. Immunol., 4:907-912, 2003.

Gett et al., T cell fitness determined by signal strength, Nat. Immunol., 4:355-360, 2003.

Gilboa, The promise of cancer vaccines, Nat. Rev. Cancer, vol. 4, :401-411, 2004.

Gingras et al., Re-examination of the role of suppressor of cytokine signaling 1 (SOCS 1) in the regulation of toll-like receptor signaling, J. Biol. Chem., 279:54702-54707, 2004.

Gor et al., $T_H1$-$T_H2$: a procrustean paradigm, Nat. Immunol., 4:503-505, 2003.

Grabarek et al., RNA interference by production of short hairpin dsRNA in ES cells, their differentiated derivatives, and in somatic cell lines, BioTechniques, 34:734-744, 2003.

Granelli-Piperno et al., HIV-1-infected monocyte-derived dendritic cells do not undergo maturation but can elicit IL-10 production and T cell regulation, Proc. Natl. Acad. Sci. USA. , 101:7669-7674, 2004.

Grohmann et al., IL-12 acts directly on DC to promote nuclear localization of NF-κB and primes DC for IL-12 production, Immunity, 9:315-323, 1998.

Hampel et al., RNA catalytic properties of the minimum (-)sTRSV sequence, Biochemistry, 28:4929-4933, 1989.

Hasselhoff et al., Simple RNA enzymes with new and highly specific endoribonuclease activities, Nature, 334:585-591, 1988.

Hauser et al., Secretory heat-shock protein as a dendritic cell-targeting molecule: a new strategy to enhance the potency of genetic vaccines, Gene Ther., 11:924-932, 2004.

Henikoff et al., Amino acid substitution matrices from protein blocks, Proc. Natl. Acad. Sci. USA, 89:10915-10919, 1992.

Hodi et al., Biologic activity of cytotoxic T lymphocyte-associated antigen 4 antibody blockage in previously vaccinated metastatic melanoma and ovarian carcinoma patients, Proc. Natl. Acad. Sci. USA, 100:4712-4717, 2003.

Huang et al., A broadly applicable, personalized heat shock protein-mediated oncolytic tumor vaccine, Cancer Res., 63:7321-7329, 2003.

Imami et al., A balanced type 1/type 2 response is associated with long-term nonprogressive human immunodeficiency virus type 1 infection, J. Virol., 76:9011-9023, 2002.

Inaba et al., Dendritic cells are critical accessory cells for thymus dependent antibody responses in mouse and in man, *Proc. Natl. Acad. Sci.* USA, 80:6041-6045, 1983.

Ingulli et al., In vivo detection of dendritic cell antigen presentation to CD4+ T cells, *J. Exp. Med.*, 185:2133-2141, 1997.

Janeway et al., Innate immune recognition, *Annu. Rev. Immunol.*, 20:197-216, 2002.

Kaech et al., Memory CD8+ T cell differentiation: initial antigen encounter triggers a developmental program in naive cells, *Nat. Immunol.*, 2:415-422, 2001.

Kundu et at, Enhancement of human immunodeficiency virus specific CD4+ and CD8+, cytotoxic, T-lymphocyte activities in HIV-infected asymptomatic patients given gp 160 vaccine, *PNAS*, 89:11204-11208, Dec. 1992.

Langenkamp et al., Kinetics of dendritic cell activation: impact on priming of TH 1, TH2 and nonpolarized T cells, *Nat. Immunol.*, 1:311-316, 2000.

Lanzavecchia et al., Antigen decoding by T lymphocytes: from synapses to fate determination, *Nat. Immunol.*, 2:487-492, 2001.

Lawrence et al., IKKα limits macrophage NF-κB activation and contributes to the resolution of inflammation, *Nature*, 434:1138-1143, 2005.

Le Bon et al., Type 1 interferons potently enhance humoral immunity and can promote isotype switching by stimulating dendritic cells in vivo, *Immunity*, 14:461-470, 2001.

Letvin et al., Immunopathogenesis and immunotherapy in AIDS virus infections, *Nat. Med.*, 9:861-866, 2003.

Letvin at al., Prospects for vaccine protection against HIV-1 infection and AIDS, *Annu. Rev. Immunol.*, 20:73-99, 2002.

Litinskiy et al., DCs induce CD40-independent immunoglobulin class switching through BIyS and APRIL, *Nat. Immunol.*, 3:822-829, 2002.

Livak et al., Analysis of relative gene expression data using real-time quantitative PCR and the $2^{-\Delta\Delta C}T$ method, *Methods*, 25:402-408, 2001.

Lu et al., Therapeutic dendritic-cell vaccine for chronic HIV-1 infection, *Nat. Med.* 10:1359-1365, 2004.

MacDonald et al., Cutting edge: polarized Th cell response induction by transferred antigen-pulsed dendritic cells is dependent on II-4 or IL-12 production by recipient cells, *J. Immunol.*, 168:3127-3130, 2002.

MacLennan at al., Dendritic cells, BAFF, and APRIL: innate players in adaptive antibody responses, 3:17:235-238, 2002.

Martinez et al., Single-stranded antisense siRNAs guide target RNA cleavage in RNAi, *Cell*, 110:563-574, 2002.

McMichael et al., HIV vaccines 1983-2003, *Nat. Med.*, 9:874-880, 2003.

Metcalf et at., The lethal effects of transplantation of Socs1$^{-/-}$ bone marrow cells into irradiated adult syngeneic recipients, *Proc. Natl. Acad. Sci.* USA, 100:8436-8441, 2003.

Moody et al., Regiospecific inhibition of DNA duplication by antisense phosphate-methylated oligodeoxynucleotides, *Nucleic Acids Res.*, 17:4769-4782, 1989.

Nabel, Challenges and opportunities for development of an AIDS vaccine, *Nature*, 410:1002-1007, 2001.

Pacanowski et al., Reduced blood CD123+(lymphoid) and CD11c+ (myeloid) dendritic cell numbers in primary HIV-1 infection, *Blood*, 98:3016-3020, 2001.

Paddison et al., Short hairpin RNAs (shRNAs) induce sequence-specific silencing in mammalian cells, *Genes Develop.*, 16:948-958, 2002.

Pan et al., Interferon-y is an autocrine mediator for dendritic cell maturation, *Immunol. Lett.*, 94:141-151, 2004.

Pardoll, Spinning molecular immunology into successful immunotherapy, *Nat. Rev. Immunol.*, 2:227-238, 2002.

Paul et al., Effective expression of small interfering RNA in human cells, *Nat. Biotechnol.*, 20:505-508, 2002.

Phan et al., Cancer regression and autoimmunity induced by cytotoxic T lymphocyte-associated antigen 4 blockage in patients with metastatic melanoma, *Proc. Natl. Acad: Sci.* U S A, 100:8372-8377, 2003.

Porgador et al., Predominant role for directly transfected dendritic cells in antigen presentation to CD8+ T cells after gene gun immunization, *Journal of Experimental Medicine*, 188:1075-1082, 1998.

Rosenberg et al., Cancer immunotherapy: moving beyond current vaccines, *Nat. Med.*, 10:909-915, 2004.

Rubinson et al., A lentivirus-based system to functionally silence genes in primary mammalian cells, stem cells and transgenic mice by RNA interference, *Nat. Genet.*, 33:401-406, 2003.

Ruedl et al., Anatomical origin of dendritic cells determines their life span in peripheral lymph nodes, *Journal of Immunology*, 165:4910-4916, 2000.

Schroers et al., Human telomerase reverse transcriptase-specific T-helper responses induced by promiscuous major histocompatibility complex class II-restricted epitopes, *Clinical Can. Res.*, 9:4743-4755, 2003.

Schroers et al., Lentiviral transduction of human dendritic cells, *Methods Mol. Biol.*, 246: 451-459, 2004.

Schulz et al., CD40 triggering of heterodimeric IL-12 p70 production by dendritic cells in vivo requires a microbial priming signal, *Immunity*, 13:453-462, 2000.

Shinohara et at., Dok-1 and Dok-2 are negative regulators of lipopolysaccharide-induced signaling, *J Exp Med.*, 3:333-339, 2005.

Siegel et al., Induction of antitumor immunity using survivin peptide-pulsed dendritic cells in a murine lymphoma model, *British Journal of Haematology*, 122:911-914, 2003.

Skok et al., Dendritic cell-derived IL-12 promotes B cell induction of Th2 differentiation: a feedback regulation of Th1 development, *J. Immunol.*, 163:4284-4291, 1999.

Soiffer et al., Vaccination with irradiated, autologous melanoma cells engineered to secrete granulocyte-macrophage colony-stimulating factor by adenoviral-mediated gene transfer augments antitumor immunity in patients with metastatic melanoma, *J. Clin. Oncol.*, 21:3343-3350, 2003.

Stec et al., Synthesis and absolute configuration of P-Chiral 0-Isopropyl oligonucleotide triesters, *Tetrahedron Letters*, 26:2191-2194, 1985.

Steinman et al., Tolerogenic dendritic cells, *Annu. Rev. Immunol.*, 21:685-711, 2003.

Trinchieri et al., Interleukin-12 and the regulation of innate resistance and adaptive immunity, *Nat. Rev. Immunol.*, 3:133-146, 2003.

Ui-Tei et al., Sensitive assay of RNA interference in drosophila and chinese hamster cultured cells using firy luciferase gene as target, *FEBS Letters*, 479:79-82, 2000.

Van Den Eynde et al., T cell defined tumor antigens, *Current Opinion in Immunology*, 9:684-693, 1997.

Van Elsas et al., Elucidating the autoimmune and antitumor effector mechanisms of a treatment based on cytotoxic T lymphocyte antigen-4 blockage in combination with a B16 melanoma vaccine: comparison of prophylaxis and therapy, *J. Exp. Med.*, 194:481-489, 2001.

Van Stipdonk et al., Naive CTLs require a single brief period of antigenic stimulation for clonal expansion and differentiation, *Nat. Immunol.*, 2:423-429, 2001.

Wu et al., SAP Controls T cell responses to virus and terminal differentiation of TH2 cells, *Nature Immunology*, 2:410-414, 2001.

Yang et al., Highly stable trimers formed by human immunodeficiency virus type 1 envelope glycoproteins fused with the trimeric motif of T4 bacteriophage fibritin, *J. Virol.*, 76:4634-4642, 2002.

You et al., Induction of vigorous helper and cytotoxic T cell as well as B cell responses by dendritic cells expressing a modified antigen targeting receptor-mediated internalization pathway, *J. Immunol.*, 165:4581-4591, 2000.

You et al., Targeting dendritic cells to enhance DNA vaccine potency, *Cancer Research*, 61:3704-3711, 2001.

Yu et al., Cancer vaccines: progress reveals new complexities, *Journal of Clinical Investigation*, 110:289-294, 2002.

Zaks et al., Immunization with a peptide epitope (pp. 369-377) from HER-2Neu leads to peptide-specific cytotoxic T lymphocytes that fail to recognize HER-2Neu+Tumors, *Cancer Research*, 58:4902-4908, 1998.

Zolla-Pazner, Identifying epitopes of HIV-1 that induce protective antibodies, *Nat Rev. Immunol.*, 4:199-210, 2004.

* cited by examiner

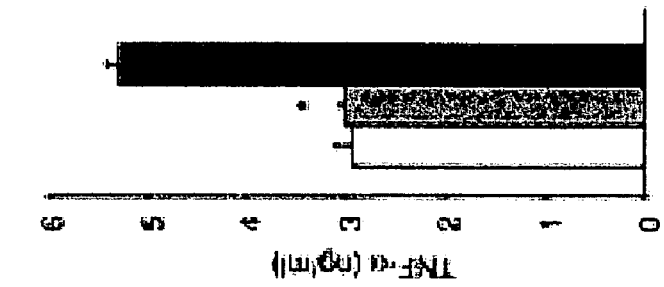
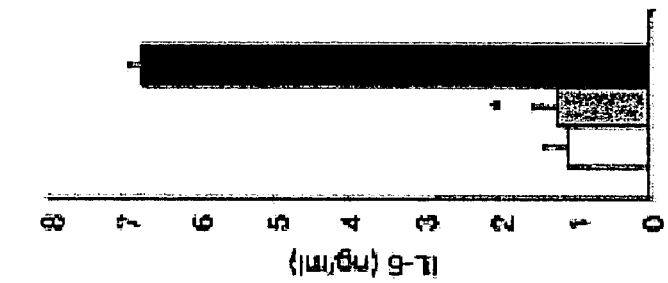
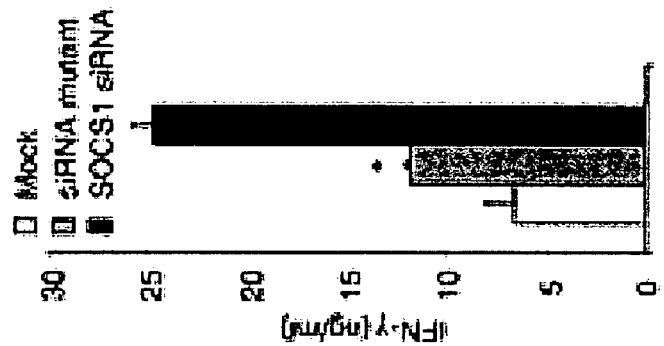
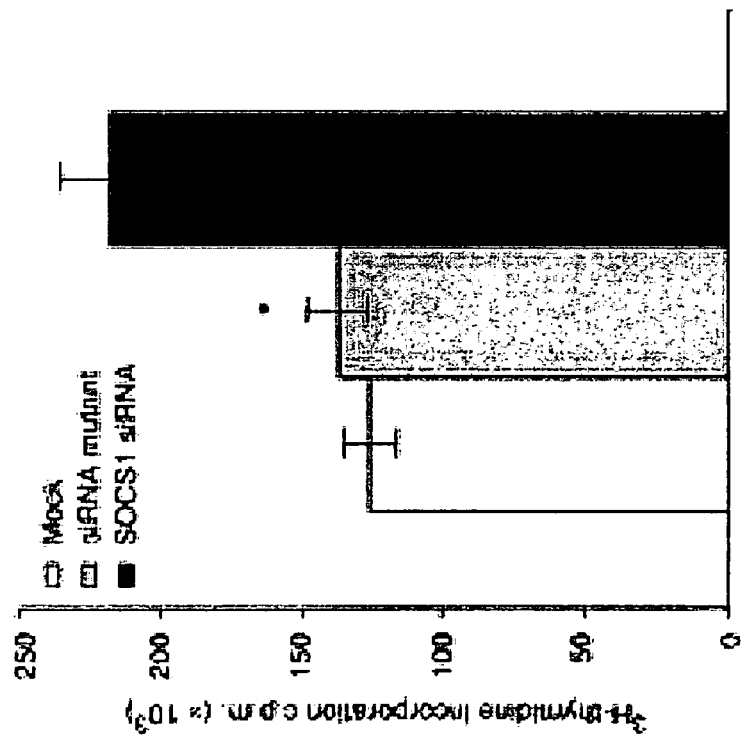
Fig. 4B
Fig. 4A

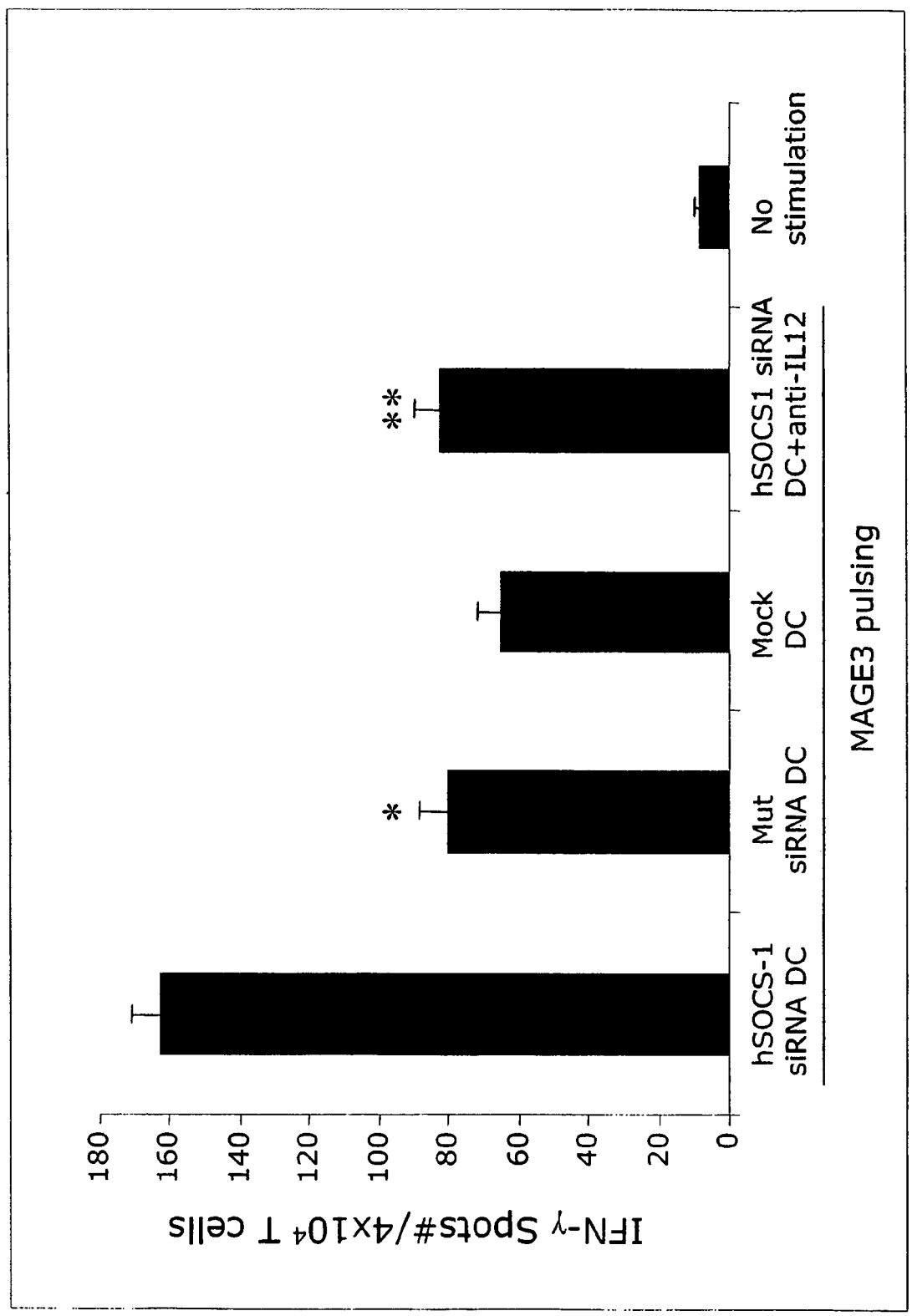

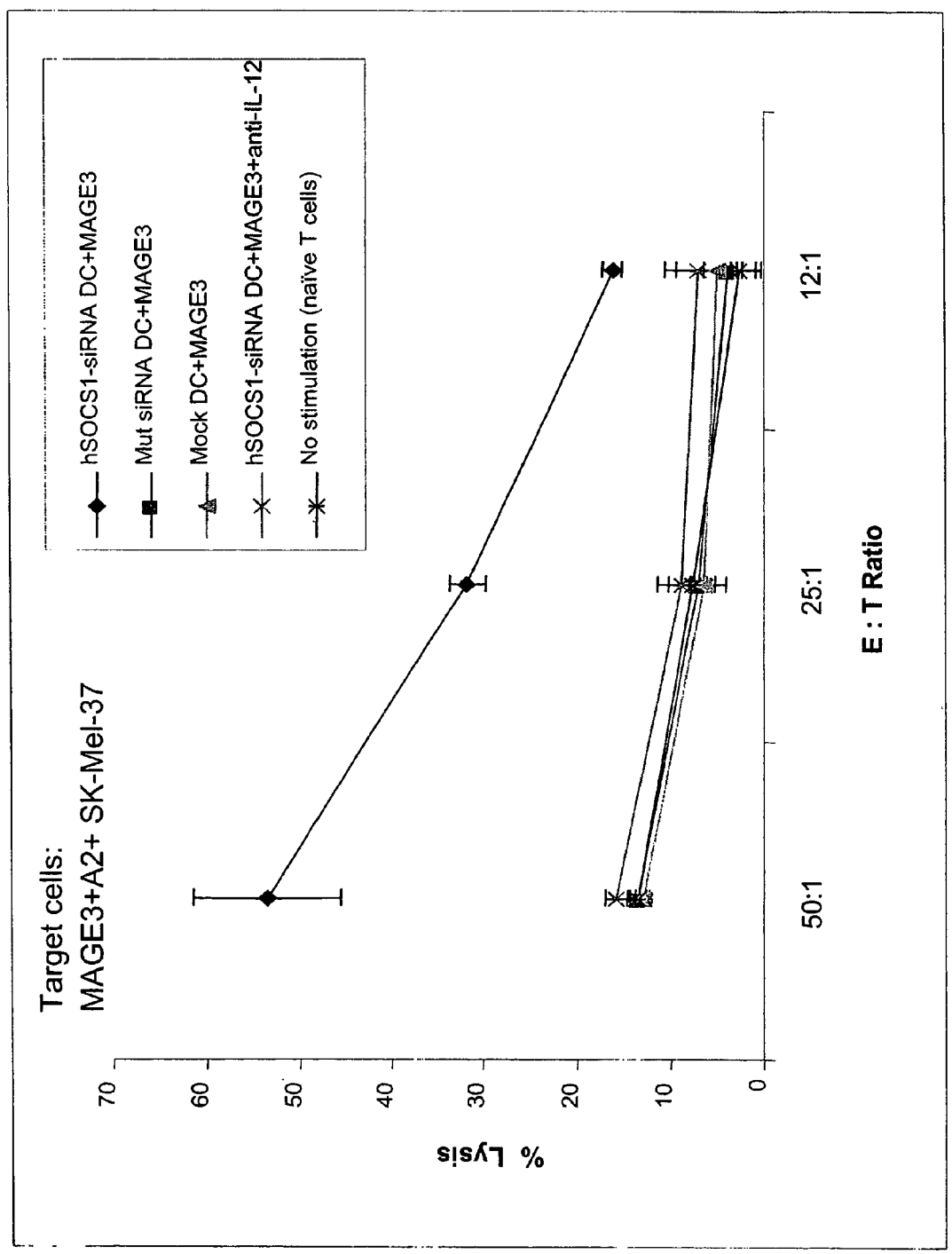

Figure 30

| Human PIAS1 | |
|---|---|
| SEQ ID NO:28 | CCACCAGTCCTCAAATAAA |
| SEQ ID NO:29 | TGATTGACCTAACCATAGA |
| SEQ ID NO:30 | GACACAAGCTACATTAATA |
| SEQ ID NO:31 | TGACGCAACTCTTTACATT |
| SEQ ID NO:32 | CCAGCCGACCAATTAATAT |
| SEQ ID NO:33 | TTACGACTTACAAGGATTA |
| Human PIAS3 | |
| SEQ ID NO:34 | AGAAGGTCGAAGTTATTGA |
| SEQ ID NO:35 | ATTACTCCTTGTCTGTGTA |
| SEQ ID NO:36 | AGATTGTGATGAGATCCAA |
| SEQ ID NO:37 | TTTGAGGAAGCGCACTTTA |
| SEQ ID NO:38 | AGCCGACATCCAAGGTTTA |
| SEQ ID NO:39 | CGACATCCAAGGTTTAGAT |
| Human PIASx-alpha | |
| SEQ ID NO:40 | CCAGAGCACTAATTAAAGA |
| SEQ ID NO:41 | CCATGTTATTACAGAGATT |
| SEQ ID NO:42 | GCTATTCCGCCTTCATTAA |
| SEQ ID NO:43 | TATTCCGCCTTCATTAACA |
| SEQ ID NO:44 | CCACCATACGCCAATATCA |
| SEQ ID NO:45 | GCGCTGCATTTATTGAAGA |
| Human PIASy | |
| SEQ ID NO:46 | AGAATCTGTTACTCAGACA |
| SEQ ID NO:47 | TCACTCACCTCATGTACCT |
| SEQ ID NO:48 | TCTGTCCGCTGGTGAAGAT |
| SEQ ID NO:49 | TCGCATTGACGCCAAGACA |
| SEQ ID NO:50 | GCTCTACGGAAAGTACTTA |
| SEQ ID NO:51 | CTACGGAAAGTACTTAAAC |
| Human SHP-1 | |
| SEQ ID NO:52 | CAAACAGCATCCAGATAGA |
| SEQ ID NO:53 | TGATGTTCCAGACAATAAT |
| SEQ ID NO:54 | TAAATGCGCCTGTGACTTA |
| SEQ ID NO:55 | TCACAACACCTCAAACATA |
| SEQ ID NO:56 | TCAGAAGTATTACGCAGAA |
| SEQ ID NO:57 | GACAACCGGTCGAAAGAAA |

SEQUENCE LISTING

<160> NUMBER OF SEQ ID NOS: 57

<210> SEQ ID NO 1
<211> LENGTH: 19
<212> TYPE: DNA
<213> ORGANISM: Artificial sequence
<220> FEATURE:
<223> OTHER INFORMATION: SOCS1-siRNA1

<400> SEQUENCE: 1
ccttccgctc ccactccga                                              19

<210> SEQ ID NO 2
<211> LENGTH: 19
<212> TYPE: DNA
<213> ORGANISM: Artificial sequence
<220> FEATURE:
<223> OTHER INFORMATION: SOCS1-siRNA2

<400> SEQUENCE: 2
cagtcgccaa cggaactgc                                              19

<210> SEQ ID NO 3
<211> LENGTH: 21
<212> TYPE: DNA
<213> ORGANISM: Artificial sequence
<220> FEATURE:
<223> OTHER INFORMATION: SOCS1-siRNA3

<400> SEQUENCE: 3
ctacctgagt tccttcccct t                                           21

<210> SEQ ID NO 4
<211> LENGTH: 19
<212> TYPE: DNA
<213> ORGANISM: Artificial sequence
<220> FEATURE:
<223> OTHER INFORMATION: cPPT/CTS primer

<400> SEQUENCE: 4
gatcgaattc acaaatggc                                              19

<210> SEQ ID NO 5
<211> LENGTH: 25
<212> TYPE: DNA
<213> ORGANISM: Artificial sequence
<220> FEATURE:
<223> OTHER INFORMATION: cPPT/CTS primer

<400> SEQUENCE: 5
ctagggatcc atcgccccaa agtgg                                       25

<210> SEQ ID NO 6
<211> LENGTH: 30
<212> TYPE: DNA
<213> ORGANISM: Artificial sequence
<220> FEATURE:
<223> OTHER INFORMATION: pBS-SK-WPRE primer

<400> SEQUENCE: 6
gatcctcgag gtcgacaatc aacctctgga                                  30

<210> SEQ ID NO 7
<211> LENGTH: 22
<212> TYPE: DNA
<213> ORGANISM: Artificial sequence
<220> FEATURE:
<223> OTHER INFORMATION: pBS-SK-WPRE primer

<400> SEQUENCE: 7
gatcggtacc caggcgggga gg                                          22

<210> SEQ ID NO 8
<211> LENGTH: 35
<212> TYPE: DNA
<213> ORGANISM: Artificial sequence

```
<220> FEATURE:
<223> OTHER INFORMATION: PYAP6 primer

<400> SEQUENCE: 8
cagtatcgat ttaattaatc aatattggcc attag                              35

<210> SEQ ID NO 9
<211> LENGTH: 34
<212> TYPE: DNA
<213> ORGANISM: Artificial sequence
<220> FEATURE:
<223> OTHER INFORMATION: PYAP6 primer

<400> SEQUENCE: 9
cagtgtcgac ttaattaagt ggccgcttta cttg                               34

<210> SEQ ID NO 10
<211> LENGTH: 22
<212> TYPE: DNA
<213> ORGANISM: Artificial sequence
<220> FEATURE:
<223> OTHER INFORMATION: siRNA mutant

<400> SEQUENCE: 10
actatctaag ttactacccc tt                                            22

<210> SEQ ID NO 11
<211> LENGTH: 8
<212> TYPE: PRT
<213> ORGANISM: Artificial sequence
<220> FEATURE:
<223> OTHER INFORMATION: ovalbumin-I peptide

<400> SEQUENCE: 11

Ser Ile Ile Asn Phe Glu Lys Leu
1               5

<210> SEQ ID NO 12
<211> LENGTH: 18
<212> TYPE: DNA
<213> ORGANISM: Artificial sequence
<220> FEATURE:
<223> OTHER INFORMATION: SOCS1 primer

<400> SEQUENCE: 12
accttcttgg tgcgcgac                                                 18

<210> SEQ ID NO 13
<211> LENGTH: 20
<212> TYPE: DNA
<213> ORGANISM: Artificial sequence
<220> FEATURE:
<223> OTHER INFORMATION: SOCS1 primer

<400> SEQUENCE: 13
aagccatctt cacgctgagc                                               20

<210> SEQ ID NO 14
<211> LENGTH: 23
<212> TYPE: DNA
<213> ORGANISM: Artificial sequence
<220> FEATURE:
<223> OTHER INFORMATION: hybridization probe

<400> SEQUENCE: 14
tcgccaacgg aactgcttct tcg                                           23
```

<210> SEQ ID NO 15
<211> LENGTH: 8
<212> TYPE: PRT
<213> ORGANISM: Artificial sequence
<220> FEATURE:
<223> OTHER INFORMATION: TRP2a

<400> SEQUENCE: 15

Val Tyr Asp Phe Phe Val Trp Leu
1               5

<210> SEQ ID NO 16
<211> LENGTH: 9
<212> TYPE: PRT
<213> ORGANISM: Artificial sequence
<220> FEATURE:
<223> OTHER INFORMATION: TRP2b

<400> SEQUENCE: 16

Ser Val Tyr Asp Phe Phe Val Trp Leu
1               5

<210> SEQ ID NO 17
<211> LENGTH: 21
<212> TYPE: DNA
<213> ORGANISM: Artificial sequence
<220> FEATURE:
<223> OTHER INFORMATION: BAFF sense primer

<400> SEQUENCE: 17
tgctatgggt catgtcatcc a                                        21

<210> SEQ ID NO 18
<211> LENGTH: 21
<212> TYPE: DNA
<213> ORGANISM: Artificial sequence
<220> FEATURE:
<223> OTHER INFORMATION: BAFF antisense primer

<400> SEQUENCE: 18
ggcagtgttt tgggcatatt c                                        21

<210> SEQ ID NO 19
<211> LENGTH: 22
<212> TYPE: DNA
<213> ORGANISM: Artificial sequence
<220> FEATURE:
<223> OTHER INFORMATION: APRIL sense primer

<400> SEQUENCE: 19
tcacaatggg tcaggtggta tc                                       22

<210> SEQ ID NO 20
<211> LENGTH: 25
<212> TYPE: DNA
<213> ORGANISM: Artificial sequence
<220> FEATURE:
<223> OTHER INFORMATION: APRIL antisense primer

<400> SEQUENCE: 20
tgtaaatgaa agacacctgc actgt                                    25

<210> SEQ ID NO 21
<211> LENGTH: 19
<212> TYPE: RNA

```
<213> ORGANISM: Artificial sequence
<220> FEATURE:
<223> OTHER INFORMATION: targeting human SOCS:hSOCS1-siRNA1

<400> SEQUENCE: 21
cacgcacuuc cgcacauuc                                                    19

<210> SEQ ID NO 22
<211> LENGTH: 19
<212> TYPE: RNA
<213> ORGANISM: Artificial sequence
<220> FEATURE:
<223> OTHER INFORMATION: targeting human SOCS:hSOCS1- siRNA2

<400> SEQUENCE: 22
uuccguucgc acgccgauu                                                    19

<210> SEQ ID NO 23
<211> LENGTH: 19
<212> TYPE: RNA
<213> ORGANISM: Artificial sequence
<220> FEATURE:
<223> OTHER INFORMATION: targeting human SOCS1:hSOCS1- siRNA3

<400> SEQUENCE: 23
gagcuucgac ugccucuuc                                                    19

<210> SEQ ID NO 24
<211> LENGTH: 20
<212> TYPE: DNA
<213> ORGANISM: Artificial sequence
<220> FEATURE:
<223> OTHER INFORMATION: human SOCS1 primer

<400> SEQUENCE: 24
tttttcgccc ttagcgggaa                                                   20

<210> SEQ ID NO 25
<211> LENGTH: 19
<212> TYPE: DNA
<213> ORGANISM: Artificial sequence
<220> FEATURE:
<223> OTHER INFORMATION: human SOCS1 primer

<400> SEQUENCE: 25
ctgccatcca ggtgaaagc                                                    19

<210> SEQ ID NO 26
<211> LENGTH: 20
<212> TYPE: DNA
<213> ORGANISM: Artificial sequence
<220> FEATURE:
<223> OTHER INFORMATION: probe

<400> SEQUENCE: 26
atggcctcgg gacccacgag                                                   20

<210> SEQ ID NO 27
<211> LENGTH: 9
<212> TYPE: PRT
<213> ORGANISM: Artificial sequence
<220> FEATURE:
<223> OTHER INFORMATION: MAGE3 CTL peptide

<400> SEQUENCE: 27

Phe Leu Trp Gly Pro Arg Ala Leu Val
```

```
<210> SEQ ID NO 28
<211> LENGTH: 19
<212> TYPE: DNA
<213> ORGANISM: Artificial sequence
<220> FEATURE:
<223> OTHER INFORMATION: Human PIAS1 siRNA candidate

<400> SEQUENCE: 28
ccaccagtcc tcaaataaa                                               19

<210> SEQ ID NO 29
<211> LENGTH: 19
<212> TYPE: DNA
<213> ORGANISM: Artificial sequence
<220> FEATURE:
<223> OTHER INFORMATION: Human PIAS1 siRNA candidate

<400> SEQUENCE: 29
tgattgacct aaccataga                                               19

<210> SEQ ID NO 30
<211> LENGTH: 19
<212> TYPE: DNA
<213> ORGANISM: Artificial sequence
<220> FEATURE:
<223> OTHER INFORMATION: Human PIAS1 siRNA candidate

<400> SEQUENCE: 30
gacacaagct acattaata                                               19

<210> SEQ ID NO 31
<211> LENGTH: 19
<212> TYPE: DNA
<213> ORGANISM: Artificial sequence
<220> FEATURE:
<223> OTHER INFORMATION: Human PIAS1 siRNA candidate

<400> SEQUENCE: 31
tgacgcaact ctttacatt                                               19

<210> SEQ ID NO 32
<211> LENGTH: 19
<212> TYPE: DNA
<213> ORGANISM: Artificial sequence
<220> FEATURE:
<223> OTHER INFORMATION: Human PIAS1 siRNA candidate

<400> SEQUENCE: 32
ccagccgacc aattaatat                                               19

<210> SEQ ID NO 33
<211> LENGTH: 19
<212> TYPE: DNA
<213> ORGANISM: Artificial sequence
<220> FEATURE:
<223> OTHER INFORMATION: Human PIAS1 siRNA candidate

<400> SEQUENCE: 33
ttacgactta caaggatta                                               19

<210> SEQ ID NO 34
<211> LENGTH: 19
<212> TYPE: DNA
<213> ORGANISM: Artificial sequence
```

```
-continued

<220> FEATURE:
<223> OTHER INFORMATION: Human PIAS3 siRNA candidate

<400> SEQUENCE: 34
agaaggtcga agttattga                                              19

<210> SEQ ID NO 35
<211> LENGTH: 19
<212> TYPE: DNA
<213> ORGANISM: Artificial sequence
<220> FEATURE:
<223> OTHER INFORMATION: Human PIAS3 siRNA candidate

<400> SEQUENCE: 35
attactcctt gtctgtgta                                              19

<210> SEQ ID NO 36
<211> LENGTH: 19
<212> TYPE: DNA
<213> ORGANISM: Artificial sequence
<220> FEATURE:
<223> OTHER INFORMATION: Human PIAS3 siRNA candidate

<400> SEQUENCE: 36
agattgtgat gagatccaa                                              19

<210> SEQ ID NO 37
<211> LENGTH: 19
<212> TYPE: DNA
<213> ORGANISM: Artificial sequence
<220> FEATURE:
<223> OTHER INFORMATION: Human PIAS3 siRNA candidate

<400> SEQUENCE: 37
tttgaggaag cgcacttta                                              19

<210> SEQ ID NO 38
<211> LENGTH: 19
<212> TYPE: DNA
<213> ORGANISM: Artificial sequence
<220> FEATURE:
<223> OTHER INFORMATION: Human PIAS3 siRNA candidate

<400> SEQUENCE: 38
agccgacatc caaggttta                                              19

<210> SEQ ID NO 39
<211> LENGTH: 19
<212> TYPE: DNA
<213> ORGANISM: Artificial sequence
<220> FEATURE:
<223> OTHER INFORMATION: Human PIAS3 siRNA candidate

<400> SEQUENCE: 39
cgacatccaa ggtttagat                                              19

<210> SEQ ID NO 40
<211> LENGTH: 19
<212> TYPE: DNA
<213> ORGANISM: Artificial sequence
<220> FEATURE:
<223> OTHER INFORMATION: Human PIASx-alpha siRNA candidate

<400> SEQUENCE: 40
ccagagcact aattaaga                                               19
```

```
<210> SEQ ID NO 41
<211> LENGTH: 19
<212> TYPE: DNA
<213> ORGANISM: Artificial sequence
<220> FEATURE:
<223> OTHER INFORMATION: Human PIASx-alpha siRNA candidate

<400> SEQUENCE: 41
ccatgttatt acagagatt                                                19

<210> SEQ ID NO 42
<211> LENGTH: 19
<212> TYPE: DNA
<213> ORGANISM: Artificial sequence
<220> FEATURE:
<223> OTHER INFORMATION: Human PIASx-alpha siRNA candidate

<400> SEQUENCE: 42
gctattccgc cttcattaa                                                19

<210> SEQ ID NO 43
<211> LENGTH: 19
<212> TYPE: DNA
<213> ORGANISM: Artificial sequence
<220> FEATURE:
<223> OTHER INFORMATION: Human PIASx-alpha siRNA candidate

<400> SEQUENCE: 43
tattccgcct tcattaaca                                                19

<210> SEQ ID NO 44
<211> LENGTH: 19
<212> TYPE: DNA
<213> ORGANISM: Artificial sequence
<220> FEATURE:
<223> OTHER INFORMATION: Human PIASx-alpha siRNA candidate

<400> SEQUENCE: 44
ccaccatacg ccaatatca                                                19

<210> SEQ ID NO 45
<211> LENGTH: 19
<212> TYPE: DNA
<213> ORGANISM: Artificial sequence
<220> FEATURE:
<223> OTHER INFORMATION: Human PIASx-alpha siRNA candidate

<400> SEQUENCE: 45
gcgctgcatt tattgaaga                                                19

<210> SEQ ID NO 46
<211> LENGTH: 19
<212> TYPE: DNA
<213> ORGANISM: Artificial sequence
<220> FEATURE:
<223> OTHER INFORMATION: Human PIASy siRNA candidate

<400> SEQUENCE: 46
agaatctgtt actcagaca                                                19

<210> SEQ ID NO 47
<211> LENGTH: 19
<212> TYPE: DNA
<213> ORGANISM: Artificial sequence
<220> FEATURE:
<223> OTHER INFORMATION: Human PIASy siRNA candidate
```

```
<400> SEQUENCE: 47
tcactcacct catgtacct                                                19

<210> SEQ ID NO 48
<211> LENGTH: 19
<212> TYPE: DNA
<213> ORGANISM: Artificial sequence
<220> FEATURE:
<223> OTHER INFORMATION: Human PIASy siRNA candidate

<400> SEQUENCE: 48
tctgtccgct ggtgaagat                                                19

<210> SEQ ID NO 49
<211> LENGTH: 19
<212> TYPE: DNA
<213> ORGANISM: Artificial sequence
<220> FEATURE:
<223> OTHER INFORMATION: Human PIASy siRNA candidate

<400> SEQUENCE: 49
tcgcattgac gccaagaca                                                19

<210> SEQ ID NO 50
<211> LENGTH: 19
<212> TYPE: DNA
<213> ORGANISM: Artificial sequence
<220> FEATURE:
<223> OTHER INFORMATION: Human PIASy siRNA candidate

<400> SEQUENCE: 50
gctctacgga aagtactta                                                19

<210> SEQ ID NO 51
<211> LENGTH: 19
<212> TYPE: DNA
<213> ORGANISM: Artificial sequence
<220> FEATURE:
<223> OTHER INFORMATION: Human PIASy siRNA candidate

<400> SEQUENCE: 51
ctacggaaag tacttaaac                                                19

<210> SEQ ID NO 52
<211> LENGTH: 19
<212> TYPE: DNA
<213> ORGANISM: Artificial sequence
<220> FEATURE:
<223> OTHER INFORMATION: Human SHP-1 siRNA candidate

<400> SEQUENCE: 52
caaacagcat ccagataga                                                19

<210> SEQ ID NO 53
<211> LENGTH: 19
<212> TYPE: DNA
<213> ORGANISM: Artificial sequence
<220> FEATURE:
<223> OTHER INFORMATION: Human SHP-1 siRNA candidate

<400> SEQUENCE: 53
tgatgttcca gacaataat                                                19

<210> SEQ ID NO 54
```

-continued

```
<211> LENGTH: 19
<212> TYPE: DNA
<213> ORGANISM: Artificial sequence
<220> FEATURE:
<223> OTHER INFORMATION: Human SHP-1 siRNA candidate

<400> SEQUENCE: 54
taaatgcgcc tgtgactta                                                  19

<210> SEQ ID NO 55
<211> LENGTH: 19
<212> TYPE: DNA
<213> ORGANISM: Artificial sequence
<220> FEATURE:
<223> OTHER INFORMATION: Human SHP-1 siRNA candidate

<400> SEQUENCE: 55
tcacaacacc tcaaacata                                                  19

<210> SEQ ID NO 56
<211> LENGTH: 19
<212> TYPE: DNA
<213> ORGANISM: Artificial sequence
<220> FEATURE:
<223> OTHER INFORMATION: Human SHP-1 siRNA candidate

<400> SEQUENCE: 56
tcagaagtat tacgcagaa                                                  19

<210> SEQ ID NO 57
<211> LENGTH: 19
<212> TYPE: DNA
<213> ORGANISM: Artificial sequence
<220> FEATURE:
<223> OTHER INFORMATION: Human SHP-1 siRNA candidate

<400> SEQUENCE: 57
gacaaccggt cgaaagaaa                                                  19
```

MODULATION OF CYTOKINE SIGNALING REGULATORS AND APPLICATIONS FOR IMMUNOTHERAPY

CROSS REFERENCE TO RELATED APPLICATIONS

This application claims priority under 35 U.S.C. §119(e) to U.S. Provisional Patent Application No. 60/589,052, filed Jul. 19, 2004, which is incorporated by reference herein in its entirety.

STATEMENT REGARDING FEDERALLY SPONSORED RESEARCH OR DEVELOPMENT

This invention was made, in part, using funds obtained from the U.S. Government (National Institutes of Health Grant Nos. R01CA90427, R0148480, and R01AI48711), and the U.S. Government may therefore have certain rights in this invention.

BACKGROUND OF THE INVENTION

Inadequate antigen presentation and activation of innate and adaptive immunity in humans result in the failure of the human immune system to control and clear many pathogenic infections and malignant cell growth. Successful therapeutic vaccines and immunotherapies for chronic infection and cancer rely on the development of new approaches for efficient means to induce a vigorous immune response which is capable of controlling and clearing offensive antigens associated with their pathologies.

The ability of T cells to recognize an antigen is dependent on the association of the antigen with either major histocompatibility complex (MHC) I or MHC II proteins. For example, cytotoxic T cells respond to an antigen that is presented in association with MHC-I proteins. Thus, a cytotoxic T cell that should kill virus-infected cell will not kill that cell if the cell does not also express the appropriate MHC-I protein. Helper T cells recognize MHC-II proteins. Helper T cell activity depends, in general, on both the recognition of the antigen on antigen presenting cells and the presence on these cells of "self" MHC-II proteins. The requirement for recognition of an antigen in association with a self-MHC protein is called MHC restriction. MHC-I proteins are found on the surface of virtually all nucleated cells. MHC-II proteins are found on the surface of certain cells including macrophages, B cells, and dendritic cells of the spleen and Langerhans cells of the skin.

A crucial step in mounting an immune response in mammals is the activation of CD4+ helper T-cells that recognize MHC-II restricted exogenous antigens. These antigens are captured and processed in the cellular endosomal pathway in antigen presenting cells, such as dendritic cells (DCs). In the endosome and lysosome, the antigen is processed into small antigenic peptides that are complexed onto the MHC-II in the Golgi compartment to form an antigen-MHC-II complex. This complex is expressed on the cell surface, which expression induces the activation of CD4+ T cells.

Other crucial events in the induction of an effective immune response in a mammal involve the activation of CD8+ T-cells and B cells. CD8+ cells are activated when the desired protein is routed through the cell in such a manner so as to be presented on the cell surface as a processed protein, which is complexed with MHC-I antigens. B cells can interact with the antigen via their surface immunoglobulins (IgM and IgD) without the need for MHC proteins. However, the activation of the CD4+ T-cells stimulates all arms of the immune system. Upon activation, CD4+ T-cells (helper T cells) produce interleukins. These interleukins help activate the other arms of the immune system. For example, helper T cells produce interleukin-4 (IL-4) and interleukin-5 (IL-5), which help B cells produce antibodies; interleukin-2 (IL-2), which activates CD4+ and CD8+ T-cells; and gamma interferon, which activates macrophages. Since helper T-cells that recognize MHC-II restricted antigens play a central role in the activation and clonal expansion of cytotoxic T-cells, macrophages, natural killer cells and B cells, the initial event of activating the helper T cells in response to an antigen is crucial for the induction of an effective immune response directed against that antigen. Attempts to stimulate helper T-cell activation using a sequence derived from the lysosomal transmembrane proteins have been reported. However, these attempts did not result in the induction of effective immune responses with respect to CD8+ T-cells and B cells in the mammals being tested.

In addition to the critical roles that T cells play in the immune response, DCs are equally important. DCs are professional antigen-presenting cells having a key regulatory role in the maintenance of tolerance to self-antigens and in the activation of innate and adaptive immunity (Banchereau et al., 1998, Nature 392:245-52; Steinman et al., 2003, Annu. Rev. Immunol. 21:685-711). When DCs encounter pro-inflammatory stimuli such as microbial products, the maturation process of the cell is initiated by up-regulating cell surface expressed antigenic peptide-loaded MHC molecules and co-stimulatory molecules. Following maturation and homing to local lymph nodes, DCs establish contact with T cells by forming an immunological synapse, where the T cell receptor (TCR) and co-stimulatory molecules congregate in a central area surrounded by adhesion molecules (Dustin et al., 2000, Nat. Immunol. 1:23-9). Once activated, CD8+ T cells can autonomously proliferate for several generations and acquire cytotoxic function without further antigenic stimulation (Kaech et al., 2001, Nat. Immunol. 2:415-22; van Stipdonk et al., 2001, Nat. Immunol. 2:423-9). It has therefore been proposed that the level and duration of peptide-MHC complexes (signal 1) and co-stimulatory molecules (signal 2) provided by DCs are essential for determining the magnitude and fate of an antigen-specific T cell response (Lanzavecchia et al., 2001, Nat. Immunol. 2:487-92; Gett et al., 2003, Nat. Immunol. 4:355-60).

Major efforts to develop tumor vaccines have attempted to promote DC maturation and costimulation as a means of enhancing antitumor immunity. However, the induction of immunity against self tumor-associated antigens (TAAs) is restricted by intrinsic inhibitory mechanisms, many of which remain to be defined. A known inhibitory mechanism is employed by cytotoxic T-lymphocyte antigen 4 (CTLA4) and related molecules on T-cells to control the magnitude of effector T-cell activation via cell-cell contact with B7 family molecules on DCs or other cells. DC maturation serves as the critical switch from the maintenance of self-tolerance to the induction of immunity. However, it remains unclear whether mature antigen-presenting DCs possess a negative regulatory mechanism that would allow them to control the magnitude and duration of adaptive immunity beyond the point of maturation.

Cytokines are critically involved in the regulation of multiple immune cell functions (Curtsinger et al., 2003, J. Exp. Med. 197:1141-51; Valenzuela et al., 2002, J. Immunol. 169:6842-9). DCs use toll-like receptors (TLRs), which recognize conserved microbial structures such as lipopolysaccharide (LPS), to promote DC maturation by activating the nuclear factor-κB (NF-κB) signalling pathway (Akira et al., 2004, Nat. Rev. Immunol. 4:499-511). NF-κB family members then mediate the expression of pro-inflammatory cytokines, such as IL-12, resulting in the induction of innate and adaptive immunity (Akira et al., 2004, Nat. Rev. Immunol. 4:499-511; Beutler et al., 2003, Nat. Rev. Immunol. 3:169-76; Janeway et al., 2002, Annu. Rev. Immunol. 20:197-216). Following DC maturation, cytokine production and intracellular signalling pathways are thought to be tightly regulated to promote beneficial immune responses against foreign antigens while limiting excessive autoimmune activation. However, the importance of specific feedback inhibition mechanisms for these pathways and the resulting control of self-antigen specific immune responses remain poorly defined.

SOCS1 is an inducible negative feedback regulator of signalling by various cytokines including interferon (IFN)-γ, interleukin (IL)-2, IL-6, IL-7, IL-12 and IL-15 (Kubo et al., 2003, Nat. Immunol. 4:1169-76; Alexander et al., 2004, Annu. Rev. Immunol. 22:503-29). SOCS1 suppresses multiple signal transducer and activator of transcription (STAT) signalling pathways by binding to the activation loop of the upstream Janus kinases (JAKs) as a pseudosubstrate inhibitor and/or targeting JAK for proteasomal degradation (Kubo et al., 2003, Nat. Immunol. 4:1169-76; Alexander et al., 2004, Annu. Rev. Immunol. 22:503-29). SOCS1 also blocks NF-κB signalling by targeting p65 protein for ubiquitin-mediated proteolysis through its SOCS Box region (Ryo et al., 2003, Mol. Cell. 12:1413-26). SOCS1-deficient (−/−) mice die as neonates with severe systemic inflammation and aberrant activation of T and NKT cells, mainly as a result of unbridled cytokine signalling (Marine et al., 1999, Cell 98:609-16; Alexander et al., 1999, Cell 98:597-608; Naka et al., 2001, Immunity 14:535-45). Although little is known about SOCS1 functions in DCs, recent studies suggest a role for SOCS1 in controlling signalling in antigen presenting cells (APCs) (Kubo et al., 2003, Nat. Immunol. 4:1169-76; Hanada et al., 2003, Immunity 19:437-50). SOCS1 expression in macrophages is induced by LPS or CpG-DNA stimulation and SOCS1−/− mice are more sensitive to LPS-induced shock than are their wild-type littermates (Crespo et al., 2000, Biochem. J. 349:99-104; Dalpke et al., 2001, J. Immunol. 166: 7082-9; Nakagawa et al., 2002, Immunity 17:677-87; Kinjyo et al., 2002, Immunity 17:583-91). Moreover, SOCS1−/− DCs from mice in which SOCS1 expression has been restored in T and B cells on a SOCS1−/− background are hyperresponsive to IFNγ and LPS, trigger allogeneic T cell expansion and induce aberrant expansion of B cells and autoreactive antibody production (Hanada et al., 2003, Immunity 19:437-50).

Although little is known about SOCS1 functions in DCs, a recent study has demonstrated a role of SOCS1 in regulating cytokine signaling transduction pathways. For example, it has been demonstrated that SOCS1−/− DCs exhibited a more mature phenotype and were observed to be hyperresponsive to lipopolysaccharide (LPS), which interacts with Toll-like receptor (TLR) 4 for signalling. Also observed was that SOCS1−/− DCs induced autoreactive antibody production. These observations hinted at a possible role for SOCS1 in the negative regulation of DCs possibly by controlling the JAK/STAT pathway and the TLR/NF-κB pathway.

There have been many attempts made to use DCs in immunotherapy to stimulate the immune response in a mammal. In these efforts, DCs were manipulated by loading them with antigen and causing them to mature in an ex vivo context so that they stimulate anti-tumor immunity in a cancer patient. With respect to the use of immunotherapy to combat human immunodeficiency virus (HIV), no effective human immunodeficiency virus (HIV) vaccine has yet emerged. Thus, there is a long felt need in the art for efficient and directed means of eliciting an immune response for the treatment of diseases in mammals. The present invention satisfies this need.

BRIEF SUMMARY OF THE INVENTION

The present invention encompasses is composition for enhancing the immunopotency of an immune cell. Preferably, the composition comprises an inhibitor of any one or more of a suppressor of cytokine signaling (SOCS), an SH2-containing phosphatase (SHP) or a protein inhibitor of activated STATs (PIAS). More preferably, the inhibitor interferes with a negative regulatory pathway in said cell.

In a specific embodiment, the inhibitor is selected from the group consisting of a small interfering RNA (siRNA), a microRNA, an antisense nucleic acid, a ribozyme, an expression vector encoding a transdominant negative mutant, an intracellular antibody, a peptide and a small molecule. Preferably, the inhibitor is an siRNA.

In a further aspect, the siRNA is selected from the group consisting of a double stranded oligonucleotide, a single stranded oligonucleotide, and a polynucleotide.

In yet another aspect, the siRNA is chemically synthesized.

Another embodiment of the invention includes a composition comprising an inhibitor of a cytokine signaling regulator, wherein the composition further comprises a physiologically acceptable carrier. Preferably, the physiologically acceptable carrier is a liposome.

In another embodiment, the inhibitor of a cytokine signaling regulator is encoded by an isolated polynucleotide cloned into an expression vector. The expression vector is selected from the group consisting of a plamsid DNA, a viral vector, a bacterial vector and a mammalian vector. In another aspect, the expression vector further comprises an integration signal sequence which facilitates integration of the isolated polynucleotide into the genome of a host cell.

The invention also includes an inhibitor of a suppressor of cytokine signaling (SOCS), wherein SOCS is selected from the group consisting of SOCS1, SOCS2, SOCS3, SOCS4, SOCS5, SOCS6, SOCS7 and a cytokine-inducible SH2-domain-containing protein (CIS).

In another aspect, the invention includes an inhibitor of an SH2-containing phosphatase (SHP), wherein SHP is selected from the group consisting of SHP-1 and SHP-2.

In a further aspect, the invention includes an inhibitor of a protein inhibitor of activated STATs (PIAS), wherein PIAS is selected from the group consisting of PIAS1, PIAS3, PIASx and PIASy.

The invention also includes a composition for enhancing the immunopotency of an immune cell, wherein the composition further comprises an antigen having at least one epitope. Preferably, the epitope is capable of eliciting an immune response in a mammal. In another aspect, the epitope induces a CD4+ T-cell response in a mammal. In yet another aspect, the epitope induces a CD8+ T-cell response in a mammal. In a further aspect, the epitope induces a B cell response in a mammal.

In another embodiment, the antigen is expressed by an expression vector. In a further aspect, the antigen is an isolated polypeptide.

In yet another embodiment, the antigen is associated with a disease. Preferably, the disease is selected from the group consisting of an infectious disease, a cancer and an autoimmune disease.

In one aspect the infectious disease is caused by a pathogenic microorganism selected from the group consisting of a virus, a bacterium, a fungus and a protozoan.

In another embodiment, the antigen is encoded by a viral gene. Preferably, the viral gene is derived from a virus selected from the group consisting of a hepatitis B virus, a hepatitis C virus, a human immunodeficiency virus, a papillomavirus, and a herpesvirus.

In one aspect, the antigen is encoded by a viral gene selected from the group consisting of a hepatitis B virus e antigen gene, a hepatitis B virus surface antigen gene, and a hepatitis B virus core antigen gene.

In another aspect, the antigen is encoded by a viral gene selected from the group consisting of a human immunodeficiency virus Env gp160 gene, Gag gene, Pol gene, Rev gene, Tat gene, Vif gene, and Nef gene.

In a further aspect, the antigen is encoded by a viral gene selected from the group consisting of a papillomavirus E7 gene and a papillomavirus E6.

In yet another aspect, the antigen is encoded by a viral gene derived from a herpesvirus selected from the group consisting of a herpes simplex virus type 1, a herpes simplex virus type 2, an Epstein-Barr virus, a cytomegalovirus, a human herpes virus 6, a human herpes virus 7 and a human herpes virus 8.

In one embodiment, the antigen is associated with a cancer, wherein the cancer is selected from the group consisting of a breast cancer, a cervical cancer, a melanoma, a renal cancer and a prostate cancer.

In a further aspect, the tumor-associated antigen is selected from the group consisting of an overexpressed tumor-associated antigen, a testis-tumor antigen, a mutated tumor-associated antigen, differentiation tumor-associated antigen tyrosinase, MART, trp, MAGE-1, MAGE-2, MAGE-3, gp100, HER-2, Ras and PSA.

In yet another aspect, the tumor-associated antigen is selected from the group consisting of BCR-ABL, CASP, CDK, Ras, p53, HER-2/neu, CEA, MUC, TW1, PAP, survivin, telomerase, EGFR, PSMA, PSA, PSCA, tyrosinase, MART, TRP, gp100, MART, MAGE, BAGE, GAGE, LAGE/NY-ESO, RAGE, SSX-2, CD19, and CD20.

In another embodiment, the antigen is associated with a disease selected from the group consisting of rheumatoid arthritis, systemic lupus erythematosus, multiple sclerosis, psoriasis and Crohn's disease.

The invention also includes a composition comprising an inhibitor of a cytokine signaling regulator and an antigen having at least one epitope capable of eliciting an immune response, and further comprising a cytokine or a Toll-like receptor (TLR) agonist.

In one aspect, the cytokine or TLR agonist is expressed by an expression vector. Preferably, the cytokine or TLR agonist is an isolated polypeptide.

In another aspect, the cytokine is selected from the group consisting of IL-12, TNFα, IFNα, IFNβ, IFNγ, IL-7, IL-2, IL-6, IL-15, IL-21, and IL-23.

The invention also includes a composition comprising an inhibitor of a cytokine signaling regulator, wherein the inhibitor suppresses the inhibition of Janus kinase (JAK) signaling.

In another embodiment, the composition comprises an inhibitor of a cytokine signaling regulator suppresses the inhibition of Toll-like receptor (TLR) signaling.

In yet another embodiment, the composition comprises an inhibitor of a cytokine signaling regulator suppresses the inhibition of NF-κB signaling.

The invention includes a composition for enhancing immunopotency of a cell, wherein the composition comprises a vector comprising a first polynucleotide encoding an inhibitor, wherein the inhibitor inhibits a regulator of cytokine signaling in said cell, and a second polynucleotide encoding an antigen having at least one epitope, wherein at least one epitope induces an immune response in a mammal.

The invention also includes a composition for enhancing immunopotency of a cell, wherein the composition comprises a vector comprising a first polynucleotide encoding an inhibitor, further wherein the inhibitor inhibits a regulator of cytokine signaling in said cell, and a second polynucleotide encoding a cytokine. Preferably, the second polynucleotide encoding a cytokine is selected from group consisting of IL-12, TNFα, IFNα, IFNβ, IFNγ, IL-7, IL-2, IL-6, IL-15, IL-21, and IL-23.

The invention also includes a cell comprising an inhibitor of a cytokine signaling regulator. Preferably, the cell is an immune cell selected from the group consisting of an APC, a dendritic cell, a monocyte/macrophage, a T cell and a B cell.

In another aspect, the cell further comprises an antigen having at least one epitope, wherein at least one epitope is capable of eliciting an immune response in a mammal.

In yet another aspect, the cell further comprises an expression vector comprising a polynucleotide encoding a cytokine.

The invention also includes a method of generating a silenced cell comprising contacting a cell with an inhibitor of a cytokine signaling regulator.

In another embodiment, the invention includes a method of generating a silenced and pulsed cell comprising contacting a cell with an inhibitor of a cytokine signaling regulator and further contacting the cell with an antigen having at least one epitope, wherein at least one epitope is capable of eliciting an immune response in a mammal.

The invention also includes a method of eliciting an immune response in a mammal comprising administering a composition comprising an inhibitor of a cytokine signaling regulator into the mammal in need thereof.

Another embodiment of the invention includes a method of eliciting an immune response in a mammal comprising administering a composition comprising a silenced cell into the mammal in need thereof, wherein the silenced cell comprises an inhibitor of a cytokine signaling regulator. Preferably, the silenced cell is contacted with an antigen in vitro prior to administering the silenced cell into a mammal in need thereof. In another aspect, the silenced cell can also be contacted with an antigen in vivo following the administration of the silenced cell into a mammal in need thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A depicts a western blot assay of 293T cells cotransfected with mouse SOCS1 siRNA. FIG. 1B depicts a quantitative RT-PCR assay of oligo-transfected DCs with SOCS1 siRNA.

FIG. 4, comprising FIGS. 4A and 4B, is a series of charts demonstrating that SOCS1 negatively regulates the ability of DCs to stimulate antigen-specific CTL in vitro. FIG. 4A depicts the fact that ovalbumin-specific TCR T cells (OT-I) proliferated more in a SOCS1-siRNA-DC coculture than in an siRNA-DC mutant coculture. Consistent with these data, higher levels of proinflammatory cytokines were secreted in the SOCS1-siRNA-DC coculture (FIG. 4B).

FIG. 5, comprising FIG. 5A indicates the percentages of H2-K$^b$/ovalbumin-PE tetramer$^+$ T cells in the total gated CD8$^+$ T-cell population. FIG. 5B depicts an interferon-γ (IFNγ) ELISPOT assay. FIG. 5C depicts a CTL assay demonstrating a more potent cytotoxicity against ovalbumin$^+$ target cells of the splenocytes from mice given immature LV-SOCS1-siRNA-DCs.

FIG. 6, comprising FIG. 6A depicts the percentages of ovalbumin-PE tetramer-positive T cells in the gated CD8$^+$ T cells. FIG. 6B depicts IFN-γ ELISPOT numbers of CD8$^+$ T cells in mice immunized with ovalbumin-pulsed, transduced or mock DCs without LPS-induced maturation ex vivo, followed by in vivo LPS stimulation. FIG. 6C and FIG. 6D depict ovalbumin-PE tetramer$^+$ percentages and IFN-γ ELISPOT numbers, respectively, of CD8$^+$ T cells in mice immunized with matured DCs, followed by in vivo LPS stimulation. FIG. 6E demonstrates that in vivo stimulation with various cytokines and TLR agonists enhances CTL responses (ELISPOT) by SOCS1-silenced DCs.

FIG. 7, comprising FIG. 7A depicts the fact that immunization with ovalbumin-pulsed LV-SOCS1-siRNA-DCs blocked the growth of pre-established ovalbumin$^+$ EG7 tumors. FIG. 7B depicts the fact that anti-CD8 antibody, but not anti-CD4 antibody, abolished the anti-tumor activity induced by ovalbumin-pulsed LV-SOCS1-siRNA-DCs. FIGS. 7C through 7E depict enhanced antitumor activities by SOCS1 siRNA oligo duplex-transfected DCs in mice.

FIG. 8, comprising FIG. 8 depicts the fact that mature LV-SOCS1-siRNA-DCs effectively blocked the growth of pre-established B16 tumors, whereas mature LV-GFP-siRNA-DCs did not have any observable inhibitory effect. FIG. 8B and FIG. 8C depict IFN-γ ELISPOT and CTL assays, respectively, of potent TRP2-specific CTL responses in LV-SOCS1-siRNA-DCs mice.

FIG. 9, comprising FIG. 9A depicts percentages of H2-K$^b$-TRP2-PE tetramer-positive T-cells in the CD8+ T-cells of splenocytes in mice two weeks after immunization. FIG. 9B depicts representative vitiligo in TRP2a-pulsed SOCS1-siRNA DC-immunized mice receiving in vivo LPS stimulation once or three times at three months after immunization. FIG. 9C depicts cytotoxicities against TRP2$^+$ B 16 (upper panel) of splenocytes pooled from groups of immunized mice and against TRP2$^-$ EG.7 target cells (lower panel) of splenocytes of wild type mice immunized with SOCS1 siRNA DC after in vitro restimulation with TRP2a peptide.

FIG. 10, comprising FIGS. 10A and 10B depict tumor growth curves in wild type mice without and with LPS in vivo stimulation, respectively. FIG. 10C depicts the percent survival of the mice monitored for sixty days. FIG. 10D depicts an IFN-γ ELISPOT assays of CD8+ T-cells isolated from the pooled splenocytes of immunized mice co-injected with LPS and subjected to stimulated with TRP2a peptide.

FIG. 11, comprising FIG. 11A depicts a flow cytometric analysis of co-stimulatory/inhibitory molecules on transduced DCs without (FIG. 11A-1) or with LPS (FIG. 11A-2) stimulation. FIG. 11B depicts eradication of pre-established B16 tumor by SOCS1-siRNA DCs pulsed with low or high affinity peptide. FIG. 11C depicts a comparison of antigen-specific CTL responses as measured by IFNγ ELISPOT assays stimulated with TRP2a or TRP2b peptide.

FIG. 12, comprising FIG. 12A and FIG. 12B depict tumor volumes and survival, respectively. FIG. 12C depict IFNγ ELISPOT assays after in vitro stimulation with TRP2a peptide. FIG. 12D depict CTL assays after in vitro stimulation with TRP2a peptide using TRP2+ B 16 target cells.

FIG. 13, comprising FIG. 13A depicts the levels of IL-12 secreted by SOCS1 siRNA DC in response to continuous stimulation with LPS and plate-coated anti-CD40 mAb. FIG. 13B depicts the IL-12 levels followed by the removal of these stimuli after the first 24 hour stimulation. FIG. 13C depicts that levels of TNFα and IL-6 secreted by SOCS1 siRNA DC in response to stimulation with LPS and plate-coated anti-CD40 mAb for 24 hours, followed by the removal of the stimuli. FIG. 13D depicts the levels of TNFα and IL-6 secreted by p35−/− or wt SOCS1-siRNA DC in response to continuous stimulation with LPS and plate-coated anti-CD40 mAb.

FIG. 14, comprising FIG. 14A depicts antitumor activities enhanced by in vivo IL-12 administration. FIG. 14B depicts enhanced TRP2-specific CTL responses by IL-12.

FIG. 15, comprising FIG. 15A illustrates that LV-SOCS1-siRNA-DCs elicited significantly more robust gp120-specific IgM and IgG responses than did the control LV-GFP-siRNA-DCs. FIG. 15B shows drastic increases in HIV Env-specific antibody titers in all IgG subclasses in mice immunized with LV-SOCS1-siRNA-DCs, compared with the corresponding subclasses in LV-GFP siRNA-DC mice. FIG. 15C shows that CTL activities against gp120-pulsed target cells in the LV-SOCS1-siRNA-DC mice were significantly more potent than those in the LV-GFP-siRNA-DC mice. FIG. 15D shows a higher percentages of IFN-γ+ T cells in LV-SOCS-siRNA-DC mice.

FIG. 16, comprising FIG. 16A depicts the levels of IL-12, IFN-γ, and TNFα produced by LV-SOCS1-siRNA-DCs, compared with GFP-siRNA-DCs after stimulation with LPS. FIG. 16B depicts the frequencies of gp120-specific CD4+ T cells. FIG. 16C illustrates that CD4+ T cells from LV-SOCS1-siRNA-DC mice proliferated more actively than those from LV-GFP-siRNA-DC mice in response to stimulation with gp120-pulsed DCs. FIG. 16D shows increased levels of both Th1-polarizing (IFN-γ, IL-2, and TNFα) and Th2-polarizing (IL-4 and IL-10) cytokines in SOCS1-silenced DCs.

FIG. 17, comprising FIG. 17A depicts expression levels of APRIL and BAFF mRNA upon LPS stimulation. FIG. 17B depicts the frequencies of anti-gp120 IgG-producing B cells in LV-SOCS1-siRNA-DC and LV-GFP-siRNA-DC mice. FIG. 17C depicts that B cells from LV-SOCS1-siRNA-DC mice proliferated more vigorously when co-stimulated with anti-CD40 and IL-4 than did B cells from LV-GFP-siRNA-DC mice. FIG. 17D depicts that B cells from LV-SOCS1-siRNA-DCs mice produced higher levels of various cytokines, including IL-6, IL-2, and TNF-α, in response to various stimuli.

FIG. 18, comprising FIG. 18A depicts gp120-specific antibodies in mice immunized with LV-GFP-siRNA-DCs compared with mice immunized with LV-SOCS1-siRNA-DC. FIG. 18B illustrates gp120-specific CTL responses in LV-SOCS1-siRNA-DC mice compared with LV-GFP-siRNA-DC mice.

FIG. 19, comprising FIG. 19A illustrates that LV-SOCS1 siRNA-DCs in the presence of gp120 proteins retained the ability to respond to LPS. Pre-exposure to gp120 proteins did not have apparent effects on the ability of LV-SOCS1-siRNA-DCs to induce OVA-specific antibody responses (FIGS. 19B and 19C), nor did it compromise OVA-specific CD8+ CTL and CD4+ Th responses induced by LV-SOCS1-siRNA-DCs (FIGS. 19D and 19E).

FIG. 20, comprising FIG. 20A depicts enhancement of HIV Env-specific antibody titers in mice co-immunized with pSuper-SOCS1-siRNA DNA. FIGS. 20B and 20C illustrate that HIV Env-specific CTL responses were significantly enhanced by co-injection of pSuper-SOCS1-siRNA DNA, as demonstrated by CTL and ELISPOT assays, respectively. FIG. 20D depicts the fact that HIV Env-specific CD4+ Th responses were enhanced by co-injection of SOCS1-siRNA DNA.

FIG. 21, comprising FIG. 21A illustrates that human SOCS1 siRNA efficiently downregulated human SOCS1 expression. FIG. 21B illustrates the transfection efficiency of synthetic siRNA duplexes into DCs derived from human monocytes. FIG. 21C depicts the level of hSOCS1 mRNA in the total DC population transfected with the hSOCS1 siRNA duplexes.

FIG. 22, comprising FIG. 22A depicts a flow cytometic analysis for human SOCS1 indicated. FIGS. 22B and 22C illustrate the level of secretion of proinflammatory cytokines, such as IL-12, IL-6 and TNF-α in hSOCS1 siRNA transfected DCs compared with human DCs transfected with siRNA mutant.

FIG. 23, comprising FIGS. 23A through 23C, is a series of charts demonstrating enhanced immunostimulatory potency of human SOCS1-silenced DCs to prime antigen-specific CTL responses. MAGE3-PE tetramer+ T cell percentages (FIG. 23A), intracellular IFNγ+ T cell percentages (FIG. 23B) in the gated CD3+ and CD8+ T cell populations, and IFN-γ+ ELISPOT numbers (FIG. 23C) are shown from one of four independent experiments using different HLA-A2+ donors.

FIG. 25, comprising FIGS. 25A and 25B, is a series of charts demonstrating tumor lytic activities of human CTLs activated by human SOCS1-siRNA-DCs. Cytolytic activities against human MAGE3+, HLA-A2+ melanoma cells (SK-Mel-37) (FIG. 25A) and control human MAGE3$^+$, HLA-A2$^-$ melanoma cells (NA-6-Mel) (FIG. 25B) after a two-week coculture of MAGE3-pulsed hSOCS1-siRNA DCs or control DCs and autologous T-cells in the absence or presence of anti-human IL-12 antibodies are shown from one of four independent experiments.

FIG. 26, comprising

FIG. 27, comprising

FIG. 28 also demonstrates the transfection of human DCs by Ad-human SOCS1 siRNA.

FIG. 30 is a chart depiciting the nucleic acid sequence of the siRNA candidates.

DETAILED DESCRIPTION

Figure 1A:
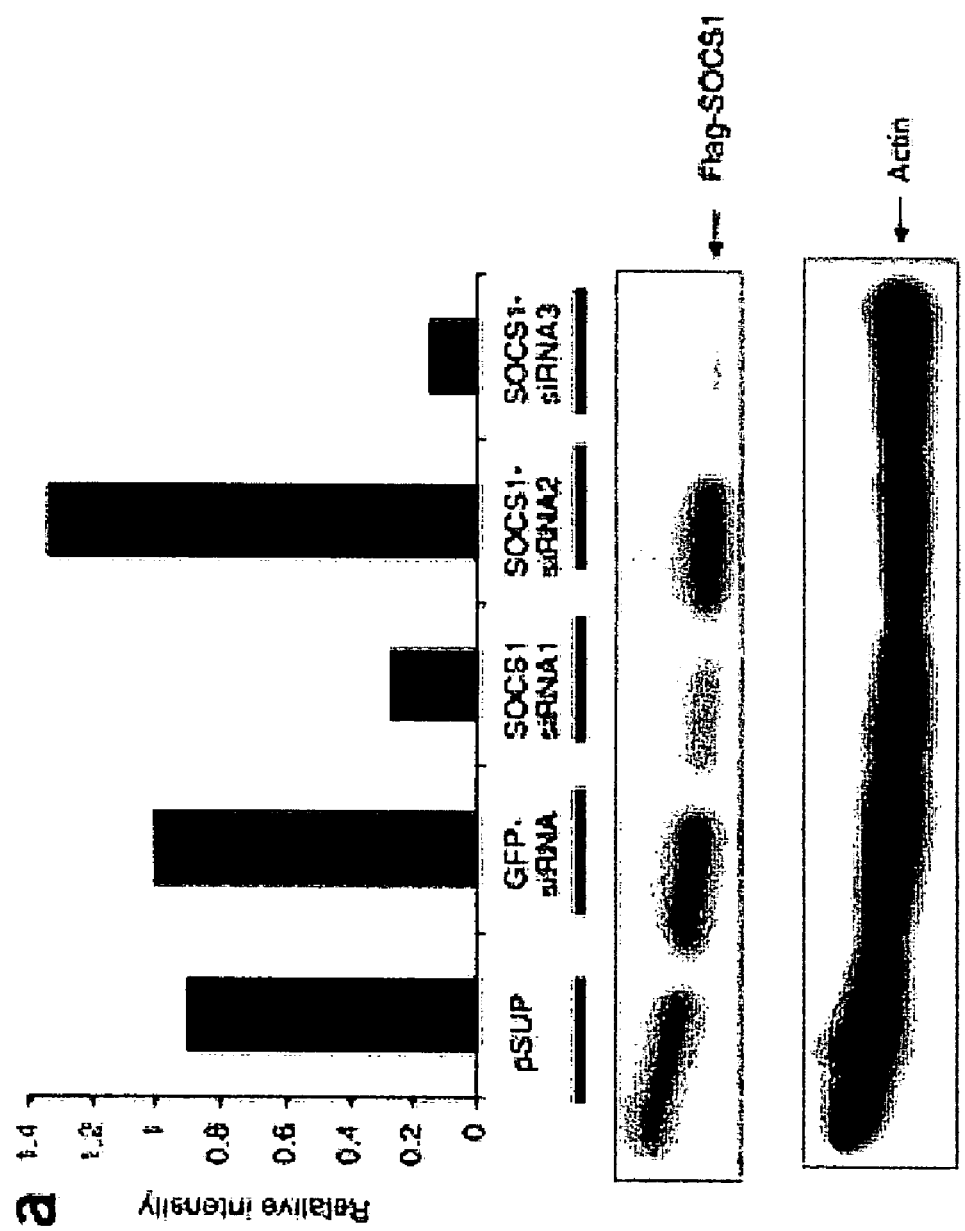
FIGS. 1A and 1B, is a series of charts demonstrating that expression of SOCS1 is downregulated by SOCS1-siRNA.

The present invention relates to enhancing the immunopotency of an immune cell by modulating a cytokine signaling regulator in the immune cell. The invention provides compositions and methods for modulating antigen presentation in an immune cell by modulation of cytokine signaling regulators such as suppressor of cytokine signaling (SOCS), SH2-containing phosphate (SHP) or protein inhibitor of activated STASs (PIAS). The present invention provides vaccines and therapies in which the immunopotency of an immune cell is enhanced by modulation of cytokine signaling regulators. In addition, the present invention also provides a mechanism for breaking self tolerance in tumor vaccination. Therefore the present invention provides a therapeutic benefit of interfering with a negative regulatory signal transduction pathway in an immune cell by enhancing the immunostimulatory capacity of the cell.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Allogeneic" refers to a graft derived from a different animal of the same species.

"Alloantigen" is an antigen that differs from an antigen expressed by the recipient.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded soley by a full length nucleotide sequence of a gene. It is readily apparent that the present invention includes, but is not limited to, the use of partial nucelotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"An antigen presenting cell" (APC) is a cell that are capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

As used herein, an "activated DC" is a DC that has been pulsed with an antigen and capable of activating an immune cell.

The term "mature DC" as used herein, is defined as a dendritic cell that expresses high levels of MHC class II, CD80 (B7.1) and CD86 (B7.2) molecules. In contrast, immature dendritic cells express low levels of MHC class II, CD80 (B7.1) and CD86 (B7.2) molecules but have a great capacity to take up an antigen.

"Antigen-loaded APC" or an "antigen-pulsed APC" includes an APC, which has been exposed to an antigen and activated by the antigen. For example, an APC may become Ag-loaded in vitro, e.g., during culture in the presence of an antigen. The APC may also be loaded in vivo by exposure to an antigen.

An "antigen-loaded APC" is traditionally prepared in one of two ways: (1) small peptide fragments, known as antigenic peptides, are "pulsed" directly onto the outside of the APCs; or (2) the APC is incubated with whole proteins or protein particles which are then ingested by the APC. These proteins are digested into small peptide fragments by the APC and are eventually transported to and presented on the APC surface. In addition, the antigen-loaded APC can also be generated by introducing a polynucleotide encoding an antigen into the cell.

As used herein, the term a "silenced APC" or a "silenced DC" refers to an APC or a DC, respectively, which has been exposed to an inhibitor of a cytokine signaling regulator of the present invention. The inhibitor is preferably in the form of an siRNA. The inhibitor is capable of inhibiting a cytokine signaling regulator including, but not limited to SOCS, SHP, PIAS and the like. The silenced APC has enhanced immunopotency when compared to an otherwise identical APC that has not been treated with an inhibitor of cytokine signaling regulator.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "cytokine signaling regulator" or "regulator of cytokine signaling" or "regulator of cytokine signal transduction" refers to a protein that is capable of negatively regulating a cytokine signaling transduction pathway in a cell. Regulators of cytokine signal transduction including but are not limited to, suppressors of cytokine signal transduction (SOCS1-SOCS7, cytokine-inducible SH2-domain-containing protein (CIS)), SH2-containing phosphataes (SHP), and protein inhibitors of activated STATs (PIAS).

The term "DNA" as used herein is defined as deoxyribonucleic acid.

"Donor antigen" refers to an antigen expressed by the donor tissue to be transplanted into the recipient.

"Recipient antigen" referes to a target for the immune response to the donor antigen.

As used herein, an "effector cell" refers to a cell which mediates an immune response against an antigen. An example of an effector cell includes, but is not limited to a T cell and a B cell.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "helper Tcell" as used herein is defined as an effector Tcell whose primary function is to promote the activation and functions of other B and T lymphocytes and or macrophages. Most helper T cells are CD4 T-cells.

The term "heterologous" as used herein is defined as DNA or RNA sequences or proteins that are derived from the different species.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

As used herein, "immunogen" refers to a substance that is able to stimulate or induce a humoral antibody and/or cell-mediated immune response in a mammal.

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "major histocompatibility complex", or "MHC", as used herein is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes.

As used herein, the term "modulate" is meant to refer to any change in biological state, i.e. increasing, decreasing, and the like. For example, the term "modulate" refers to the ability to regulate positively or negatively the expression or activity of SOCS1, including but not limited to transcription of SOCS1 mRNA, stability of SOCS1 mRNA, translation of SOCS1 mRNA, stability of SOCS1 polypeptide, SOCS1 post-translational modifications, or any combination thereof. Further, the term modulate can be used to refer to an increase, decrease, masking, altering, overriding or restoring of activity, including but not limited to, SOCS1 activity associated with immunopotency of dendritic cells. The term "modulate" also may apply to SOCS2, SOCS3, SOCS4, SOCS5, SOCS6, SOCS7, CIS, PIAS (PIAS1, PIAS3, PIASx and PIASy), SHP (SHP-1 and SHP-2), or any other activity that is relavent.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

As used herein, a "substantially purified" cell is a cell that is essentially free of other cell types. A substantially purified cell also refers to a cell which has been separated from other cell types with which it is normally associated in its naturally occurring state. In some istances, a population of substantially purified cells refers to a homogenous population of cells. In other instances, this term refers simply to cell that have been separated from the cells with which they are naturally associated in their natural state. In some embodiments, the cells are culture in vitro. In other embodiments, the cells are not cultured in vitro.

The term "T-cell" as used herein is defined as a thymus-derived cell that participates in a variety of cell-mediated immune reactions.

The term "B-cell" as used herein is defined as a cell derived from the bone marrow and/or spleen. B cells can develop into plasma cells which produce antibodies.

As used herein, a "therapeutically effective amount" is the amount of a therapeutic composition sufficient to provide a beneficial effect to a mammal to which the composition is administered.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

The term "vaccine" as used herein is defined as a material used to provoke an immune response after administration of the material to a mammal.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "virus" as used herein is defined as a particle consisting of nucleic acid (RNA or DNA) enclosed in a protein coat, with or without an outer lipid envelope, which is capable of replicating within a whole cell.

"Xenogeneic" refers to a graft derived from an animal of a different species.

Description

Uncontrolled signal transduction based on cytokine signaling in a mammal can have disastrous biological consequences. Therefore, signaling pathways are tightly controlled at different levels. There exists various types of regulators of cytokine signaling including, but are not limited to, suppressors of cytokine signal transduction (SOCS), SH2-containing phosphataes (SHP), and protein inhibitors of activated STATs (PIAS).

Inducible inhibitors of cytokine signaling are the suppressor of cytokine signaling (SOCS) proteins, of which there are eight family members: SOCS1-SOCS7 and the cytokine-inducible SH2-domain-containing protein (CIS). SOCS proteins recognize cytokine receptors or the associated JAKs and attenuate signal transduction both by direct interference with signaling and by targeting the receptor complex for ubiquitin-mediated proteasomal degradation.

SHP proteins, including but not limited to (SHP-1 and SHP-2), are constitutively expressed and can attenuate cytokine signal transduction by dephosphorylating signaling intermediates such as Janus kinase (JAK) and its receptor. Members of the protein inhibitors of activated STATs (PIAS) family, including but not limited to PIAS1, PIAS3, PIASx and PIASy, are also constitutively expressed and attenuate signal transduction by repressing STAT activity. The process of sumoylation has been implicated in PIAS-mediated repression of STAT activity.

The present invention relates to the discovery that inhibition of any one or more of these types of cytokine signal regulators provide a therapeutic benefit. Thus, the invention comprises compositions and methods for modulating cytokine signaling regulators in an immune cell thereby enhancing immunopotency of the immune cell. The composition includes any combination of at least one or more of the following: an inhibitor of a cytokine signaling regulator, an antigen, a silenced immune cell, a pulsed cell, a silenced immune cell pulsed with an antigen, a cytokine, and the like. The composition may be a vaccine for in vivo immunization and/or ex vivo therapy.

The present invention provides a silenced APC as a generic means to enhance vaccine potency by disabling a critical control point in an APC. Vaccination with an inhibitor of a cytokine signaling regulator or a silenced APC of the invention enhances antigen-specific immunity, because silencing of a cytokine signaling regulator, permits antigen-presenting immunogenic APCs to persistently stimulate antigen-specific T cells in vivo. In an embodiment of the invention, silenced APCs are capable of turning off regulatory T cells by enhancing APC maturation and the production of proinflammatory cytokines that inhibit regulatory T-cell suppression.

In addition to generating a silenced APC, the present invention also includes a silenced cytotoxic T lymphocyte (CTL). The present disclosure demonstrates that a CTL that has been silenced using the methods of the present invention exhibits an enhanced cytolytic activity. A CTL having an enhanced cytolytic activity offers a therapeutic benefit in cell therapy and/or vaccination.

Inhibitor of the Regulator

Based on the disclosure herein, the present invention includes a generic concept for inhibiting a cytokine signaling regulator, whereby the regulator is associated with regulating a signal transduction pathway relating to an immune response.

In one embodiment, the invention comprises a composition for enhancing the immunopotency of an immune cell. The compostion comprises an inhibitor of any one or more of the following regulators: SOCS, SHP or PIAS. In another aspect of the invention, the composition interferes with a negative regulatory pathway in a cell.

The composition comprising the inhibitor of the cytokine signaling regulator is selected from the group consisting of a small interfering RNA (siRNA), a microRNA, an antisense nucleic acid, a ribozyme, an expression vector encoding a transdominant negative mutant, an intracellular antibody, a peptide and a small molecule.

One skilled in the art will appreciate, based on the disclosure provided herein, that one way to decrease the mRNA and/or protein levels of a cytokine signaling regulator in a cell is by reducing or inhibiting expression of the nucleic acid encoding the regulator. Thus, the protein level of the cytokine signaling regulator in a cell can also be decreased using a molecule or compound that inhibits or reduces gene expression such as, for example, an antisense molecule or a ribozyme.

In a preferred embodiment, the modulating sequence is an antisense nucleic acid sequence which is expressed by a plasmid vector. The antisense expressing vector is used to transfect a mammalian cell or the mammal itself, thereby causing reduced endogenous expression of a desired inhibitor of cytokine signaling regulator in the cell. However, the invention should not be construed to be limited to inhibiting expression of a cytokine signaling regulator by transfection of cells with antisense molecules. Rather, the invention encompasses other methods known in the art for inhibiting expression or activity of a protein in the cell including, but not limited to, the use of a ribozyme, the expression of a non-functional cytokine signaling regulator (i.e. transdominant negative mutant) and use of an intracellular antibody.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of a cytokine signaling regulator may be designed by incorporating target sequences into the basic ribozyme structure which are complementary to the mRNA sequence of the desired cytokine signaling regulator of the present invention, including but are not limited to, SOCS (SOCS1-7, CIS), SHP (SHP-1 and SHP-2) and PIAS (PIAS1, PIAS3, PIASx and PIASy). Ribozymes targeting the desired cytokine regulator may be synthesized using commercially available reagents (Applied Biosystems, Inc., Foster City, Calif.) or they may be genetically expressed from DNA encoding them.

In another aspect of the invention, the cytokine signaling regulator can be inhibited by way of inactivating and/or sequestering the cytokine signaling regulator. As such, inhibiting the effects of a cytokine signaling regulator can be accomplished by using a transdominant negative mutant. Alternatively an intracellular antibody specific for the desired cytokine signaling regulator, otherwise known as an antagonist to the cytokine signaling regulator may be used. In one embodiment, the antagonist is a protein and/or compound having the desirable property of interacting with a binding partner of the cytokine signaling regulator and thereby competing with the corresponding wild-type cytokine signaling regulator. In another embodiment, the antagonist is a protein and/or compound having the desirable property of interacting with the cytokine signaling regulator and thereby sequestering the cytokine signaling regulator.

Small Interfering RNA (siRNA)

A small interfering RNA (siRNA) is an RNA molecule comprising a set of nucleotides that is targeted to a gene or polynucleotide of interest. As used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein.

An siRNA in the form of a double stranded polynucleotide comprises about 18 base pairs, about 19 base pairs, about 20 base pairs, about 21 base pairs, about 22 base pairs, about 23 base pairs, about 24 base pairs, about 25 base pairs, about 26 base pairs, about 27 base pairs, about 28 base pairs, about 29 base pairs or about 30 base pairs in length. The double stranded siRNA capable of interfering with the expression and/or the activity of a cytokine signaling regulator.

A single stranded siRNA comprises a portion of an RNA polynucleotide sequence that is targeted to a gene or polynucleotide of interest. A single stranded siRNA comprises a polynucleotide of about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides or about 30 nucleotides in length. The single stranded siRNA is capable of interfering with expression and/or activity of a target polynucleotide such as SOCS(SOCS1-SOCS7, CIS), SHP, PIAS, or a variant thereof. The single strand siRNA is also capable of annealing to a complementary sequence to result in a dsRNA that is capable of interfering with the expression and/or the activity of a cytokine signaling regulator.

In yet another aspect, the siRNA comprises a polynucleotide comprising either a double stranded or a single stranded polynucleotide, wherein the siRNA has one, two, three, four or more nucleotide alterations or substitutions therein.

An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002 Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well established principles of complementary nucleotide base-pairing.

An siRNA may be transcribed using as a template a DNA (genomic, cDNA, or synthetic) that contains a promoter for an RNA polymerase promoter. For example, the promoter can be the U6 promoter or the H1 RNA polymerase III promoter.

Alternatively, the siRNA may be a synthetically derived RNA molecule. In certain embodiments, the siRNA polynucleotide may have blunt ends. In certain other embodiments, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs, whereby the use of "about" indicates that in certain embodiments and under certain conditions the processive cleavage steps that may give rise to functional siRNA polynucleotides that are capable of interfering with expression of a selected polypeptide may not be absolutely efficient. Hence, siRNA polynucleotides, may include one or more siRNA polynucleotide molecules that may differ (e.g., by nucleotide insertion or deletion) in length by one, two, three, four or more base pairs as a consequence of the variability in processing, in biosynthesis, or in artificial synthesis of the siRNA. The siRNA polynucleotide of the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Polynucleotides that comprise the siRNA polynucleotides of the present invention may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide. Preferably, the spacer sequence comprises at least 4 nucleotides. In certain embodiments, the spacer may comprise 5, 6, 7, 8, 9, 10, 11, 12, 13, 14, 15, 16, 17, 18, 19, 20, 21-25, 26-30, 31-40, 41-50, 51-70, 71-90, 91-110, 111-150, 151-200 or more nucleotides. Examples of siRNA polynucleotides derived from a single nucleotide strand comprising two complementary nucleotide sequences separated by a spacer have been described (e.g., Brummelkamp et al., 2002 Science 296:550; Paddison et al., 2002 Genes Develop. 16:948; Paul et al., 2002 Nat. Biotechnol. 20:505-508; Grabarek et al., 2003 BioTechniques 34:734-44).

Polynucleotide variants may contain one or more substitutions, additions, deletions, and/or insertions such that the activity of the siRNA polynucleotide is not substantially diminished. The effect of any such alterations in nucleotide content on the activity of the siRNA polynucleotide may generally be assessed as described elsewhere herein. Variants preferably exhibit at least about 75%, 78%, 80%, 85%, 87%, 88% or 89% identity and more preferably at least about 90%, 92%, 95%, 96%, or 97% identity to a portion of a polynucleotide sequence that encodes a native SOCS(SOCS1-SOCS7, CIS), a SHP (SHP-1 and SHP-2) or a PIAS (PIAS1, PIAS3, PIASx and PIASy). The percent identity may be readily determined by comparing sequences of the polynucleotides to the corresponding portion of the target polynucleotide, using any method including using computer algorithms well known to those having ordinary skill in the art. These include the Align or the BLAST algorithm (Altschul, 1991 J. Mol. Biol. 219: 555-565; Henikoff and Henikoff, 1992, Proc. Natl. Acad. Sci. USA 89:10915-10919).

Certain siRNA polynucleotide variants can be substantially homologous to a portion of a polynucleotide encoding a target polypeptide. Single-stranded polynucleotides derived from these polynucleotide variants are capable of hybridizing under moderately stringent conditions to a naturally occurring DNA or RNA sequence encoding the target polypeptide. An siRNA polynucleotide that detectably hybridizes to the polynucleotide sequence encoding the target polypeptide under moderately stringent conditions may have a nucleotide sequence that includes at least 10 consecutive nucleotides, more preferably 11, 12, 13, 14, 15, 16, 17, 18, 19, 20, 21, 22, 23, 24, 25, 26, 27, 28, 29 or 30 consecutive nucleotides that are complementary to a particular target polynucleotide. In certain preferred embodiments, such an siRNA sequence (or its complement) will be unique to a single particular polynucleotide encoding the target polypeptide for which interference with expression is desired. In certain other embodiments, the sequence (or its complement) may be shared by two or more related polynucleotides encoding the target polypeptide for which interference with polypeptide expression is desired.

Suitable moderate stringent conditions include, for example, pre-washing the polynucleotide in a solution of 5×SSC, 0.5% SDS, 1.0 mM EDTA (pH 8.0); hybridizing the polynucleotide at 50° C.-70° C., 5×SSC for 1-16 hours (e.g., overnight); followed by washing the polynucleotide once or twice at 22-65° C. for 20-40 minutes with one or more each of 2×, 0.5× and 0.2×SSC containing 0.05-0.1% SDS. For additional stringency, hybridization conditions may include an additional wash in 0.1×SSC and 0.1% SDS at 50-60° C. for 15-40 minutes. Those of ordinary skill in the art will understand that, variations in stringency of hybridization conditions may be achieved by altering the time, temperature, and/or concentration of the solutions used for the pre-hybridization, hybridization, and wash steps. Suitable conditions may also depend in part on the particular nucleotide sequences of the probe used, and of the blotted, proband nucleic acid sample. Accordingly, it will be appreciated that suitably stringent conditions can be readily selected, without undue experimentation, when a desired selectivity of the polynucleotide is identified, based on its ability to hybridize to one or more certain proband sequences while not hybridizing to certain other proband sequences.

Sequence specific siRNA polynucleotides of the present invention may be designed using one or more of several criteria. For example, to design an siRNA polynucleotide that has about 21 consecutive nucleotides identical to a sequence encoding a polypeptide of interest, the open reading frame of the polynucleotide sequence may be scanned for about 21-base sequences length that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence. Alternatively, an siRNA polynucleotide sequence may be designed and chosen using a computer software available commercially from various vendors, e.g., OligoEngine™ (Seattle, Wash.); Dharmacon, Inc. (Lafayette, Colo.); Ambion Inc. (Austin, Tex.); and QIAGEN, Inc. (Valencia, Calif.)). See also Elbashir et al., 2000 Genes & Development 15:188-200; Elbashir et al., 2001 Nature 411:494-98. The siRNA polynucleotide may then be tested for the ability to interfere with the expression of the target polypeptide according to methods known in the art and described elsewhere herein. The determination of the effectiveness of an siRNA polynucleotide includes not only consideration of its ability to interfere with the expression of the target polypeptide, but also whether the siRNA polynucleotide is toxic to the host cell. For example, a desireable siRNA would exhibit an RNA interference activity and would also not exhibit an unwanted biological consequence. An example of an unwanted biological consequence is apoptosis of a cell for which cell death is not a desired as a result of the introduction of the siRNA into the host cell.

Based on the present disclosure, it should be appreciated that the siRNAs of the present invention may effect silencing of the target polypeptide expression to different degrees. The siRNAs thus must first be tested for their effectiveness. Selection of siRNAs are made therefrom based on the ability of a given siRNA to interfere with or modulate the expression of the target polypeptide. Accordingly, identification of specific siRNA polynucleotide sequences that are capable of interfering with expression of a desired target polypeptide requires production and testing of each siRNA. The methods for testing each siRNA and selection of suitable siRNAs for use in the present invention are fully set forth herein the Examples. Since not all siRNAs that interfere with protein expression will have a physiologically important effect, the present disclosure also sets forth various physiologically relevant assays for determining whether the levels of interference with target protein expression using the siRNAs of the invention have clinically relevant significance.

One skilled in the art will readily appreciate that as a result of the degeneracy of the genetic code, many different nucleotide sequences may encode the same polypeptide. That is, an amino acid may be encoded by one of several different codons, and a person skilled in the art can readily determine that while one particular nucleotide sequence may differ from another, the polynucleotides may in fact encode polypeptides with identical amino acid sequences. As such, polynucleotides that vary due to differences in codon usage are specifically contemplated by the present invention.

Polynucleotides of the siRNA may be prepared using any of a variety of techniques, which are useful for the preparation of specifically desired siRNA polynucleotides. For example, a polynucleotide may be amplified from a cDNA prepared from a suitable cell or tissue type. Such a polynucleotide may be amplified via polymerase chain reaction (PCR). Using this approach, sequence-specific primers are designed based on the sequences provided herein, and may be purchased or synthesized directly. An amplified portion of the primer may be used to isolate a full-length gene, or a desired portion thereof, from a suitable DNA library using well known techniques. A library (cDNA or genomic) is screened using one or more polynucleotide probes or primers suitable for amplification. Preferably, the library is size-selected to include larger polynucleotide squences. Random primed libraries may also be preferred in order to identify 5' and other upstream regions of the genes. Genomic libraries are preferred for obtaining introns and extending 5' sequences. The siRNA polynucleotide contemplated by the present invention may also be selected from a library of siRNA polynucleotide sequences.

For hybridization techniques, a partial polynucleotide sequence may be labeled (e.g., by nick-translation or end-labeling with $^{32}$P) using well known techniques. A bacterial or bacteriophage library may then be screened by hybridization to filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis.

Alternatively, numerous amplification techniques are known in the art for obtaining a full-length coding sequence from a partial cDNA sequence. Within such techniques, amplification is generally performed via PCR. One such technique is known as "rapid amplification of cDNA ends" or RACE (see, e.g., Sambrook et al., Molecular Cloning: A Laboratory Manual, Cold Spring Harbor Laboratories, Cold Spring Harbor, N.Y., 2001).

A number of specific siRNA polynucleotide sequences useful for interfering with target polypeptide expression are presented in the Examples, the Drawings, and in the Sequence Listing included herein. siRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated with other molecules to improve their stability and/or delivery properties. Included as one aspect of the invention are siRNAs as described herein, wherein one or more ribose sugars has been removed therefrom.

Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful). In addition, an siRNA polynucleotide may be administered to a mammal, as may be a DNA sequence (e.g., a recombinant nucleic acid construct as provided herein) that supports transcription (and optionally appropriate processing steps) such that a desired siRNA is generated in vivo.

In one embodiment, an siRNA polynucleotide, wherein the siRNA polynucleotide is capable of interfering with expression of a target polypeptide can be used to generate a silenced cell. Any siRNA polynucleotide that, when contacted with a biological source for a period of time, results in a significant decrease in the expression of the target polypeptide is included in the invention. Preferably the decrease is greater than about 10%, more preferably greater than about 20%, more preferably greater than about 30%, more preferably greater than about 40%, about 50%, about 60%, about 70%, about 75%, about 80%, about 85%, about 90%, about 95% or about 98% relative to the expression level of the target polypeptide detected in the absence of the siRNA. Preferably, the presence of the siRNA polynucleotide in a cell does not result in or cause any undesired toxic effects, for example, apoptosis or death of a cell in which apoptosis is not a desired effect of RNA interference.

In another embodiment, the siRNA polynucleotide that, when contacted with a biological source for a period of time, results in a significant decrease in the expression of the target polypeptide. Preferably the decrease is about 10%-20%, more preferably about 20%-30%, more preferably about 30%-40%, more preferably about 40%-50%, more preferably about 50%-60%, more prefereably about 60%-70%, more preferably about 70%-80%, more preferably about 80%-90%, more preferably about 90%-95%, more preferably about 95%-98% relative to the expression level of the target polypeptide detected in the absence of the siRNA. Preferably, the presence of the siRNA polynucleotide in a cell does not result in or cause any undesired toxic effects.

In yet another embodiment, the siRNA polynucleotide that, when contacted with a biological source for a period of time, results in a significant decrease in the expression of the target polypeptide. Preferably the decrease is about 10% or more, more preferably about 20% or more, more preferably about 30% or more, more preferably about 40% or more, more preferably about 50% or more, more preferably about 60% or more, more preferably about 70% or more, more preferably about 80% or more, more preferably about 90% or more, more preferably about 95% or more, more preferably about 98% or more relative to the expression level of the target polypeptide detected in the absence of the siRNA. Preferably, the presence of the siRNA polynucleotide in a cell does not result in or cause any undesired toxic effects.

As such, the invention comprises an siRNA polynucleotide, such as siRNAs as exemplified in SEQ ID NOs:1-3, 21-23 and 27-56. SEQ ID NOs:1-3 and 21-23 are sequences of murine and human siRNA candidate sequences for SOCS1, respectively. SEQ ID NOs:27-32, 33-38, 39-44, 45-50 and 51-56 are sequences of human siRNA candidate sequences for PIAS1, PIAS3, PIASx, PIASy and SHP-1, respectively. The sequences of the siRNAs are depicted in FIG. 30. The polynucleotide and polypeptide sequences for various regulators of cytokine signaling may be found at computerized databases known to those of ordinary skill in the art. One such database is the National Center for Biotechnology Information's Genbank and GenPept databases. The nucleic acid sequences for these known genes may be amplified, combined with the sequences disclosed herein (e.g., ligated) and/or expressed using the techniques disclosed herein or by any technique that would be know to those of ordinary skill in the art (e.g., Sambrook et al., 2001). Though a nucleic acid may be expressed in an in vitro expression system, in preferred embodiments the nucleic acid comprises a vector for in vivo replication and/or expression.

Modification of siRNA

Following the generation of the siRNA polynucleotide of the present invention, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide of the invention may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Vectors

In other related aspects, the invention includes an isolated nucleic acid encoding an inhibitor, wherein the inhibitor preferably an siRNA, inhibits a cytokine signaling regulator, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

In another aspect, the invention includes a vector comprising an siRNA polynucleotide. Preferably, the siRNA polynucleotide is capable of inhibiting the expression of a target polypeptide, wherein the target polypeptide is selected from the group consisting of SOCS(SOCS1-7, CIS), SHP or PIAS. The incorporation of a desired polynucleotide into a vector and the choice of vectors is well-known in the art as described in, for example, Sambrook et al., supra, and Ausubel et al., supra.

The siRNA polynucleotide can be cloned into a number of types of vectors. However, the present invention should not be construed to be limited to any particular vector. Instead, the present invention should be construed to encompass a wide plethora of vectors which are readily available and/or well-known in the art. For example, an siRNA polynucleotide of the invention can be cloned into a vector including, but not limited to a plasmid, a phagemid, a phage derivative, an animal viruse, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the siRNA, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of the siRNA, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Generation of a Silenced Immune Cell

In one embodiment, the instant invention provides a cell-based system for expressing an inhibitor of a cytokine signaling regulator into a cell. The cell-based system, refers to a "silenced cell", comprises a cell and an expression vector for expressing the inhibitor. However, the present invention should not be limited to a cell comprising an expression vector, but rather, the silenced cell of the present invention should be construed to included a cell that has been modified with any type of inhibitor of the present invention, i.e. a chemical synthesized siRNA. In any event, the silenced cell comprising the inhibitor possesses a heightened immunopotency as compared to an otherwise identical cell not so silenced with the inhibitor. The silenced cell is suitable for administration to a mammalian recipient alone or in combination with other therapies.

This invention includes a cell comprising an inhibitor of a cytokine signaling regulator. The inhibitor is capable of inhibiting a cytokine signaling regulator including, but not limited to SOCS, SHP or PIAS. In one aspect, the cell can be transfected with a vector comprising a polynucleotide encoding an inhibitor. The polynucleotide need not be integrated into the cell. In another aspect, the cell need not be transfected with a vector at all, but rather, the cell is exposed to an inhibitor that is not expressed from a vector. An example of such an inhibitor is a chemically synthesized siRNA.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a cytokine signaling regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To generate a silenced cell, any DNA vector or delivery vehicle can be utilized to transfer the desired siRNA polynucleotide to an immune cell in vitro or in vivo. In the case where a non-viral delivery system is utilized, a preferred delivery vehicle is a liposome. The above-mentioned delivery systems and protocols therefore can be found in Gene Targeting Protocols, 2ed., pp 1-35 (2002) and Gene Transfer and Expression Protocols, Vol. 7, Murray ed., pp 81-89 (1991).

The use of lipid formulations is contemplated for the introduction of the inhibitor of cytokine signaling regulator of the present invention, into host cells (in vitro, ex vivo or in vivo). In a specific embodiment of the invention, the inhibitor may be associated with a lipid. The inhibitor associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/siRNA or lipid/expression vector associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma, St. Louis, Mo. Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and/or the presence of divalent cations. Liposomes can show low permeability to ionic and/or polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and/or results in an increase in permeability to ions, sugars and/or drugs.

Liposomes interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer and expression of an oligonucleotide in vitro and in vivo, then they are applicable for the present invention. Where a bacterial promoter is employed in the DNA construct, it also will be desirable to include within the liposome an appropriate bacterial polymerase.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in Drug Carriers in Biology and Medicine, G. Gregoriadis ed. (1979) pp. 287-341, the contents of which are incorporated herein by reference; the method of Deamer and Uster, 1983, the contents of which are incorporated by reference; and the reverse-phase evaporation method as described by Szoka and Papahadjopoulos, 1978. The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50-200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

Generation of an Activated (Pulsed) Immune Cell

The invention includes a cell that has been exposed or otherwised "pulsed" with an antigen and activated by the antigen. For example, an APC may become Ag-loaded in vitro, e.g., by culture ex vivo in the presence of an antigen, or in vivo by exposure to an antigen.

A skilled artisan would also readily understand that an APC can be "pulsed" in a manner that exposes the APC to an antigen for a time sufficient to promote presentation of that antigen on the surface of the APC. For example, an APC can be exposed to an antigen in in a form small peptide fragments, known as antigenic peptides, are "pulsed" directly onto the outside of the APCs (Mehta-Damani et al., 1994); or APCs can be incubated with whole proteins or protein particles which are then ingested by the APCs. These whole proteins are digested into small peptide fragments by the APC and eventually carried to and presented on the APC surface (Cohen et al., 1994). Antigen in peptide form may be exposed to the cell by standard "pulsing" techniques described herein.

Without wishing to be bound by any particular theory, the antigen in the form of a foreign or an autoantigen is processed by the APC of the invention in order to retain the immunogenic form of the antigen. The immunogenic form of the antigen implies processing of the antigen through fragmentation to produce a form of the antigen that can be recognized by and stimulate immune cells, for example T cells. Preferably, such a foreign or an autoantigen is a protein which is processed into a peptide by the APC. The relevant peptide which is produced by the APC may be extracted and purified for use as an immunogenic composition. Peptides processed by the APC may also be used to induce tolerance to the proteins processed by the APC.

It is believed that autoimmune diseases result from an immune response being directed against "self-proteins," otherwise known as autoantigens, i.e., autoantigens that are present or endogenous in an individual. In an autoimmune response, these "self-proteins" are presented to T cells which cause the T cells to become "self-reactive." According to the method of the invention, APCs are pulsed with an antigen to produce the relevant "self-peptide." The relevant self-peptide is different for each individual because MHC products are highly polymorphic and each individual MHC molecule might bind different peptide fragments. The "self-peptide" and an agonist of inhibitors of cytokine signaling can then be used to design competing peptides or to induce tolerance to the self protein in the individual in need of treatment.

The antigen-activated APC, otherwise known as a "pulsed APC" of the invention, is produced by exposure of the APC to an antigen either in vitro or in vivo. In the case where the APC is pulsed in vitro, the APC is plated on a culture dish and exposed to an antigen in a sufficient amount and for a sufficient period of time to allow the antigen to bind to the APC. The amount and time necessary to achieve binding of the antigen to the APC may be determined by using methods known in the art or otherwise disclosed herein. Other methods known to those of skill in the art, for example immunoassays or binding assays, may be used to detect the presence of antigen on the APC following exposure to the antigen.

In a further embodiment of the invention, the APC may be transfected with a vector which allows for the expression of a specific protein by the APC. The protein which is expressed by the APC may then be processed and presented on the cell surface on an MHC receptor. The transfected APC may then be used as an immunogenic composition to produce an immune response to the protein encoded by the vector.

As discussed elsewhere herein, vectors may be prepared to include a specific polynucleotide which encodes and expresses a protein to which an immunogenic response is desired. Preferably, retroviral vectors are used to infect the cells. More preferably, adenoviral vectors are used to infect the cells.

In another embodiment of this invention, a vector may be targeted to an APC by modifying the viral vector to encode a protein or portions thereof that is recognized by a receptor on the APC, whereby occupation of the APC receptor by the vector will initiate endocytosis of the vector allowing for processing and presentation of the antigen encoded by the nucleic acid of the viral vector. The nucleic acid which is delivered by the virus may be native to the virus which when expressed on the APC encodes viral proteins which are then processed and presented on the MHC receptor of the APC.

As discussed elsewhere herein, various methods can be used for transfecting a polynucleotide into a host cell. The methods include, but are not limited to, calcium phosphate precipitation, lipofection, particle bombardment, microinjection, electroporation, colloidal dispersion systems (i.e. macromolecule complexes, nanocapsules, microspheres, beads, and lipid-based systems including oil-in-water emulsions, micelles, mixed micelles, and liposomes).

In another aspect, a polynucleotide encoding an antigen can be cloned into an expression vector and the vector can be introduced into an APC to otherwise generate an activated APC. Various types of vectors and methods of introducing nucleic acids into a cell are dicussed elsewhere herein. For example, a vector encoding a antigen may be introduced into a host cell by any method in the art. For example, the expression vector can be transferred into a host cell by physical, chemical or biological means. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York). It is readily understood that the introduction of the expression vector comprising a polynucleotide encoding an antigen yields a pulsed cell.

The present invention includes various methods for pulsing APCs including, but not limited to, loading APCs with whole antigen in the form of a protein, cDNA or mRNA. However, the invention should not be construed to be limited to the specific form of the antigen used for pulsing the APC. Rather, the invention encompasses other methods known in the art for generating an antigen loaded APC. Preferably, the APC is tranfected with mRNA encoding a defined antigen. mRNA corresponding to a gene product whose sequence is known can be rapidly generated in vitro using appropriate primers and reverse transcriptase-polymerase chain reaction (RT-PCR) coupled with transcription reactions. Transfection of an APC with an mRNA provides an advantage over other antigen-loading techniques for generating a pulsed APC. For example, the ability to amplify RNA from a microscopic amount of tissue, i.e. tumor tissue, extends the use of the APC for vaccination to a large number of patients.

The antigen may be derived from a virus, a fungus, or a bacterium. The antigen may be a self-antigen or an antigen associated with a disease selected from the group consisting of an infectious disease, a cancer, an autoimmune disease.

For an antigenic composition to be useful as a vaccine, the antigenic composition must induce an immune response to the antigen in a cell, tissue or mammal (e.g., a human). As used herein, an "immunological composition" may comprise an antigen (e.g., a peptide or polypeptide), a nucleic acid encoding an antigen (e.g., an antigen expression vector), a cell expressing or presenting an antigen or cellular component. In particular embodiments the antigenic composition comprises or encodes all or part of any antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

A vaccine of the present invention may vary in its composition of nucleic acid and/or cellular components. In a non-limiting example, a nucleic encoding an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an antigen of the present invention in an in vitro translation system or in a living cell. In addition, an antigenic composition can comprise a cellular component isolated from a biological sample. Preferably the antigenic composition isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will preferably not substantially interfere with the antibody recognition of the epitopic sequence.

A peptide or polypeptide corresponding to one or more antigenic determinants of the present invention should generally be at least five or six amino acid residues in length, and may contain up to about 10, about 15, about 20, about 25, about 30, about 35, about 40, about 45 or about 50 residues or so. A peptide sequence may be synthesized by methods known to those of ordinary skill in the art, such as, for example, peptide synthesis using automated peptide synthesis machines, such as those available from Applied Biosystems, Inc., Foster City, Calif. (Foster City, Calif.).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

In certain embodiments, an immune response may be promoted by transfecting or inoculating a mammal with a nucleic acid encoding an antigen. One or more cells comprised within a target mammal then expresses the sequences encoded by the nucleic acid after administration of the nucleic acid to the mammal. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In preferred aspects, the nucleic acid comprises a coding region that encodes all or part of the sequences encoding an appropriate antigen, or an immunologically functional equivalent thereof. Of course, the nucleic acid may comprise and/or encode additional sequences, including but not limited to those comprising one or more immunomodulators or adjuvants.

Tumor-Associated Antigens

In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal.

Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965). Furthermore, as described in Renkvist et al. (2001), there are numerous antigens known in the art. The following tables describe T cell-defined epitopes encoded by tumor antigens, and only those tumor antigens recognized by T cells (either cytotoxic CD8+ or helper CD4+) are listed. Although analogs or artificially modified epitopes are not listed, a skilled artisan recognizes how to obtain or generate them by standard means in the art. Other antigens, identified by antibodies and as detected by the Serex technology (see Sahin et al. (1997) and Chen et al. (2000)), are identified in the database of the Ludwig Institute for Cancer Research.

Microbial Antigens

Microbial antigens may be viral, bacterial, or fungal in origin. Examples of infectious virus include: Retroviridae (e.g. human immunodeficiency viruses, such as HIV-I (also referred to as HTLV-III, LAV or HTLV-III/LAV, or HIV-III; and other isolates, such as HIV-LP; Picornaviridae (e.g. polio viruses, hepatitis A virus; enteroviruses, human coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviruses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include: *Helicobacter pyloris, Borelia burgdorferi, Legionella pneumophilia, Mycobacteria* sps (e.g. *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema Treponema pertenue, Leptospira*, and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) including: *Plasmodium falciparum* and *Toxoplasma gondii*.

A Silenced and Pulsed Immune Cell

In another embodiment, a cell may be isolated from a culture, tissue, organ or organism and administered to a mammal as a cellular vaccine. Thus, the present invention contemplates a "cellular vaccine." Of course, the cell may also express one or more additional vaccine components, such as immunomodulators or adjuvants. The vaccine may comprise all or part of the cell. In a preferred embodiment, the cellular vaccine of the present invention comprises a human APC and in a more preferred embodiment, the APC is a DC.

The cellular vaccine can comprise of an APC that has been silenced according to the present invention to enhance its immunopotency. The silenced APC can then be transfected with a nucleic acid encoding an antigen to generate an antigen-loaded cell. In another aspect, the silenced APC can be pulsed with an immunostimulatory protein comprising an antigen to generate an antigen-loaded cell. Based on the present disclosure, the silenced APC can be pulsed by any method using any type of antigen to load the antigen. In addition, an APC can be pulsed by any method prior to, concurrently with or following silencing of the APC with an inhibitor of the present invention.

As disclosed elsewhere herein, a cell can be pulsed with an antigen using various methods. An antigen of the present invention contains at least one epitope, wherein said epitope is capable of eliciting an immune response in a mammal. In one embodiment, the antigen is expressed by an expression vector. In another embodiment, the antigen is an isolated polypeptide. Preferably, the antigen is associated with a disease selected from the group consisting of an infectious disease, a cancer and an autoimmune disease. A number of preferred antigens useful for pulsing the cells of the invention are disclosed elsewhere herein. The antigen can be in the form of at least one or more of the following: a tumor lysate, a protein, a peptide, an mRNA, a DNA, expressed from a vector, a liposome and the like.

The APC that has been silenced with an inhibitor of a cytokine signaling regulator possesses a heightened immunopotency and therefore elicits an enhanced immune response, i.e. an enhanced ability to present antigen and activate an immune response thereto. An APC that has been silenced and pulsed according to the present invention is able to stimulate effector T cells and elicit an improved immune response to the antigen thereto compared to an otherwise identical APC that has not been silenced.

Therapeutic Application

The present invention includes a composition useful for enhancing immunopotency of an immune cell such as an APC. The response to an antigen presented by an APC maybe measured by monitoring the induction of a cytolytic T-cell response, a helper T-cell response, and/or antibody response to the antigen using methods well known in the art.

The present invention includes a method of enhancing the immune response in a mammal comprising the steps of contacting one or more lymphocytes with an antigenic composition, wherein the antigen is presented by an immune cell, such as an APC. Based on the present disclosure, an APC can be silenced by exposure to an inhibitor of a cytokine signaling regulator, whereby the exposure to the inhibitor enhances the immunopotency of the APC. The APC can be silenced using methods disclosed herein prior to, concurrently with or following exposure of the APC with an antigenic composition to otherwise pulse the APC.

The enhanced immune response may be an active or a passive immune response. The response may be part of an adoptive immunotherapy approach in which APCs, such as dendritic cells, B cells or moncytes/macrophages, are obtained from a mammal (e.g., a patient), then pulsed with a composition comprising an antigenic composition (prior to, concurrently with or following the exposure of the cell to an inhibitor of a cytokine signaling regulator to otherwise silence the immune cell), and then administering the APC to a mammal in need thereof.

The composition includes any combination of at least one or more of the following: an inhibitor of a cytokine signaling regulator, an antigen, a silenced immune cell, a pulsed cell, and a silenced immune cell that is also pulsed with an antigen. The composition may be a vaccine for ex vivo immunization and/or in vivo therapy in a mammal. Preferably, the mammal is a human.

With respect to ex vivo immunization, at least one of the following occurs in vitro prior to administering the cell into a mammal: i) silencing of the cell, ii) pulsing of the cell or iii) silencing and pulsing of the cell. It should be appreciated that an immune cell (i.e. APC) of the present invention can be silenced using the methods disclosed elsewhere herein prior to, concurrently with or following treatment of the APC with an antigen to pulse the immune cell.

In another embodiment, the silenced APC can be administered to the patient in need thereof without prior in vitro exposure to the antigen. That is, the present invention encompasses administration of a silenced APC to a patient, wherein pulsing of the cell occurs in vivo in the patient.

In yet another embodiment, the pulsed APC can be administered to the patient in need thereof without prior in vitro exposure of the cell to an inhibitor of a cytokine signaling regulator. That is, the present invention encompasses administration of a pulsed APC to a patient, wherein silencing of the cell occurs in vivo in the patient.

Ex vivo procedures are well known in the art and are discussed more fully below. Briefly, cells are isolated from a mammal (preferably a human) and silenced (i.e., transduced or transfected in vitro) with a vector expressing an inhibitor of a cytokine signaling regulator or with any other form of the inhibitor of cytokine signaling regulator disclosed herein (i.e. chemically synthesized siRNA). The silenced cell can be administered to a mammalian recipient to provide a therapeutic benefit. The mammalian recipient may be a human and the cell so silenced can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of DCs comprises: (I) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

A variety of cell selection techniques are known for identifying and separating CD34+ hematopoietic stem or progenitor cells from a population of cells. For example, monoclonal antibodies (or other specific cell binding proteins) can be used to bind to a marker protein or surface antigen protein found on stem or progenitor cells. Several such markers or cell surface antigens for hematopoietic stem cells (i.e., flt-3, CD34, My-10, and Thy-1) are known in the art.

The collected CD34+ cells are cultured with suitable cytokines. CD34+ cells then are allowed to differentiate and commit to cells of the dendritic lineage. These cells are then further purified by flow cytometry or similar means, using markers characteristic of dendritic cells, such as CD1a, HLA DR, CD80 and/or CD86. Following isolation of culturing of DCs, the cells can be modified according to the methods of the present invention. Alternatively, the progenitor cells can be modified prior to being differentiated to DC-like cells.

In addition to using a cell-based vaccine in terms of ex vivo immunization, the present invention also provides compositions and methods for in vivo immunization to elicit an immune response directed against an antigen in a patient.

With respect to in vivo immunization, the present invention provides a use of an inhibitor of a cytokine signaling regulator as a generic means to enhance vaccine potency by disabling a critical control point in an APC. As such, a vaccine useful for in vivo immunization comprises at least an inhibitor component, wherein the inhibitor component is able to inhibit a cytokine signaling regulator. In another aspect, the vaccine comprises both an inhibitor component and an antigen component, wherein the antigen component is capable of eliciting an immune response in a mammal.

Regarding vivo immunization, a cell obtained from a patient is transfected or transduced in vivo to otherwise generate a silenced cell. The cell is silenced in vivo with a vector expressing an inhibitor of cytokine regulator. Alternatively, the cell is silenced using any other form of an inhibitor of cytokine signaling regulator disclosed herein that is not expressed by a vector (i.e. chemically synthesized siRNA). Methods of generating a silenced cell in vivo are discussed elsewhere herein.

Another aspect of the vaccine includes an antigen component useful for pulsing a cell in vivo. Any antigen can be administered in combination with the inhibitor of a cytokine signaling regulator of the invention. A cell can be pulsed using any method as discussed elsewhere herein prior to, concurrently with or following silencing of the cell with a vaccine comprising an inhibitor. It is readily appreciated that in the event that a cell is to be pulsed and silenced concurrently, the mammal can be immunized with a single vaccine comprising both an inhibitor and a antigen. Alternatively, the mammal can be immunized with two separate vaccines, one comprising an inhibitor and a second vaccine comprising an antigen.

The invention encompasses in vivo immunization for cancer and infectious diseases. In one embodiment, the disorder or disease can be treated by in vivo administration of an siRNA alone or in combination with an antigen to generate an immune response against the antigen in the patient. Based on the present disclosure, administration of an inhibitor of a cytokine signaling regulator (i.e. SOCS1 siRNA) in combination with a antigenic formulation enhances the potency of an otherwise identical vaccination protocol without the use of an inhibitor of a cytokine signaling regulator. Without wishing to be bound by any particular theory, it is believed that immune response to the antigen in the patient depends upon (1) the siRNA composition administered, (2) the duration, dose and frequency of administration, (3) the general condition of the patient, and if appropriate (4) the antigenic composition administered.

In one embodiment, the mammal has a type of cancer which expresses a tumor-specific antigen. In accordance with the present invention, an immunostimulatory protein can be made which comprises a tumor-specific antigen sequence component. In such cases, the inhibitor of cytokine signaling regulator is administered in combination with an immunostimulatory protein to a patient in need thereof, resulting in an improved therapeutic outcome for the patient, evidenced by, e.g., a slowing or diminution of the growth of cancer cells or a solid tumor which expresses the tumor-specific antigen, or a reduction in the total number of cancer cells or total tumor burden.

In a related embodiment, the patient has been diagnosed as having a viral, bacterial, fungal or other type of infection, which is associated with the expression of a particular antigen, e.g., a viral antigen. In accordance with the present invention, an immunostimulatory protein may be made which comprises a sequence component consisting of the antigen, e.g., an HIV-specific antigen. In such cases, an inhibitor of a cytokine signaling regulator is administered in combination with the immunostimulatory protein to the patient in need thereof, resulting in an improved therapeutic outcome for the patient as evidenced by a slowing in the growth of the causative infectious agent within the patient and/or a decrease in, or elimination of, detectable symptoms typically associated with the particular infectious disease.

In either situation, the disorder or disease can be treated by administration of an inhibitor of a cytokine signaling regulator in combination with an antigen to a patient in need thereof. The present invention provides a means to generate a protective DC-induced immune response to the antigen in the patient. Based on the present disclosure, a skilled artisan would appreciate that a proinflammatory cytokine (i.e. IL-12, TNFα, IFNα, IFNβ, IFNγ and the like) can be added to the treatment regiment disclosed herein to enhance the potency of the inhibitor of a cytokine signaling regulator vaccine.

Dosage and Formulation (Pharmaceutical Compositions)

The present invention envisions treating a disease, for example, HIV infection, cancer and the like, in a mammal by the administration of therapeutic agent, e.g. an siRNA. Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art Administration of siRNA may be accomplished through the administration of the nucleic acid molecule encoding the siRNA (see, for example, Felgner et al., U.S. Pat. No. 5,580, 859, Pardoll et al. 1995; Stevenson et al. 1995; Molling 1997; Donnelly et al. 1995; Yang et al. II; Abdallah et al. 1995). Pharmaceutical formulations, dosages and routes of administration for nucleic acids are generally disclosed, for example, in Felgner et al., supra.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly(lactic acid) or ethylenevinylacetate copolymers. In addition to being incorporated, these agents can also be used to trap the compound in microcapsules.

Accordingly, the pharmaceutical composition of the present invention may be delivered via various routes and to various sites in an mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Gene Therapy Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidylate kinase (Tdk::Tmk) and AZT; and deoxycytidine kinase and cytosine arabinoside.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXAMPLES

The invention is now described with reference to the following Examples. These Examples are provided for the purpose of illustration only, and the invention is not limited to these Examples, but rather encompasses all variations which are evident as a result of the teachings provided herein.

The experiments disclosed herein were conducted to explore the regulation of antigen presentation by DCs in order to exploit DCs for development of effective vaccines against a variety of cancers and infectious agents. The results disclosed herein demonstrate that interfering with a negative regulatory pathway, otherwise known as inhibiting an inhibitor, in an immune cell enhances its immunostimulatory capacity. The concept of inhibiting an inhibitor to potentiate the immunopotency of a cell serves as a novel method of developing more effective vaccines.

The materials and methods employed in the experiments disclosed herein are now described.

DC Transfection by siRNA Oligo

Bone-marrow DCs were also transfected with 21 base-pair siRNA oligonucleotides (5'-CTACCTGAGTTCCTTC-CCCTT-3'; SEQ ID NO:3) using GenePorter, following the manufacturer's protocol (Genlantis, San Diego, Calif.). Briefly, 3 µl of a solution of 20 µM oligonucleotides was added to 3 µl of GenePorter reagent and 94 µl of serum-free RPMI1640. The mixture was incubated at 25° C. for 30 min, after which 100 µl of the GenePorter/oligonucleotide mixture was added to each well of bone marrow-DCs and incubated for 4 h at 37° C. After incubation, 500 µl/well of RPMI1640 supplemented with 20% FBS was added to the bone-marrow DCs.

Transduction of Bone Marrow-Derived DCs with Lentiviral Vectors

Mouse bone marrow derived DCs were prepared using methods known in the art. Briefly, mouse bone marrow was flushed from limbs, passed through a nylon mesh, and depleted of red cells with ammonium chloride. After extensive washing with RPMI-1640, cells were cultured with 2.5 ml of RPMI-1640 supplemented with 10% FBS, mGM-CSF/ml (20 ng/ml) and recombinant mouse IL-4 (20 ng/ml; PeproTech, Inc., Rocky Hill, N.J.). On days 2 and 4 of culture, the supernatant was removed and replaced with fresh media containing 20 ng/ml of rmGM-CSF and 20 ng/ml of rmIL-4. All cultures were incubated at 37° C. in 5% humidified $CO_2$. Nonadherent granulocytes were removed after 48 hours of culture and fresh medium was added. After 7 days of culture, >80% of the cells expressed characteristic DC-specific markers as determined by FACS. Transductions of mouse bone marrow-derived DCs (day 5 to 7 of culture) were performed on 24-well plates with addition of 5 µg/ml Polybrene (Sigma, St. Louis, Mo.). DCs were washed and plated in 24-well plates at a concentration of $2 \times 10^5$ cells/well in 400 µl of serum-free RPMI 1640. The cells were exposed to lentiviral vectors with different multiplicities of infection (MOIs) at a cell density of $5 \times 10^5$ cells/ml. After 8 hours of transduction, the cells were washed with PBS and further incubated in fresh tissue culture medium.

Cytokine and Western Blotting

Levels of various cytokines were quantified using the supernatant of cell cultures using ELISA analysis (BD Biosciences, Lincoln Park, N.J.) according to the manufacturer's instructions. For western blot analysis, 293T cells were cotransfected with pSUPER vectors expressing mouse SOCS1-siRNA or irrelevant GFP-siRNA, and a FLAG-tagged SOCS1 vector at a 10:1 ratio. The cells were harvested 48 hours later and subjected to SDS-PAGE. Following transfer to Hybond-P membrane (Amersham, Arlington Heights, Ill.), the samples were analyzed by western blotting with anti-Flag (Sigma, St. Louis, Mo.) or actin (Santa Cruz Biotechnology, Inc. Santa Cruz, Calif.) antibodies, followed by detection with ECL-Plus reagent (Amersham, Arlington Heights, Ill.). Films were scanned with a Densitometer SI and SOCS-1/actin bands were quantified with ImageQuant software (Molecular Dynamics, Piscataway, N.J.). The intensity of SOCS1 bands was normalized to the intensity of beta-actin bands.

Quantitative RT-PCR Analysis of SOCS1

The relative expression of SOCS1 in transfected mouse BM-DC was evaluated by quantitative real-time PCR. Total RNA was extracted from $3.5-5 \times 10^5$ BM-DC using Trizol reagent (Invitrogen, Carlsbad, Calif.). 1.0 µg of total RNA for each sample was reverse transcribed with random hexamer primers and SuperScript First-Strand Synthesis Kit (Invitrogen, Carlsbad, Calif.). Real-time 5'-nuclease fluorogenic PCR analysis was performed on an ABI 7900HT Sequence Detection System (Applied Biosystems, Inc., Foster City, Calif.) in 20 µl quadruplicate reactions with the equivalent of 5 ng starting RNA material per reaction as template. Pre-developed primer/probe sets for mouse SOCS1 (6FAM) and 18S ribosomal control (VIC) were purchased from Applied Biosystems, Inc., Foster City, Calif. (primers for SOCS1, 5'-ACCTTCTTGGTGCGCGAC-3'; SEQ ID NO:12 and 5'-AAGCCATCTTCACGCTGAGC-3'; SEQ ID NO:13 and the hybridization probes, 6FAM-TCGCCAACGGAACT-GCTTCTTCG-TAMRA; SEQ ID NO:14). PCR parameters were as recommended for the TaqMan Universal PCR Master Mix kit (Applied Biosystems, Inc., Foster City, Calif.), with SOCS1 and 18S reactions performed in separate tubes. SOCS1 levels were normalized to 18S rRNA. SOCS1 expression relative to the control value of mock-transfected and stimulated BM-DCs was calculated using the Comparative Ct method (Livak, et al, 2001, Methods 25:402-408).

In Vitro Assay of OT-I Cells

Spleens were harvested from OT-I mice, pooled, and disrupted to obtain a single cell suspension. $CD8^+$ OT-I T cells were collected by negative selection using the MACS $CD8^+$ T cell isolation kit (Miltenyi Biotec Inc., Auburn, Calif.). In brief, cells were coated with biotin-labeled antibodies specific for CD4 (L3T4), CD45R (B220), DX5, CD11b (Mac-1), and Ter-119. Anti-biotin magnetic MicroBeads (Miltenyi Biotec Inc., Auburn, Calif.) were added to the cells, which were passed over separation columns attached to the MACS magnet. The cells that did not bind to the column were collected and were >95% $CD8^+$ as determined by FACS. A total of $5 \times 10^4$ purified $CD8^+$ OT-1 T cells and $5 \times 10^3$ immature DCs were placed in each well of a round-bottom 96-well microtiter plate in 200 µl RPMI 1640 medium supplemented with 10% FCS, 4 mM L-glutamine, 1 mM sodium pyruvate, 100 U/ml penicillin and streptomycin, 10 mM HEPES, and 5

μM 2-ME. Proliferation was measured after 2 days by addition of 1 μCi [$^3$H] TdR per well for the last 8 hours of culture. Triplicate determinations were done and are representative of triplicate experiments. Cytokine secretion in the OT-I/DC coculture was determined using ELISA analysis for the indicated cytokines (BD Biosciences, San Jose, Calif.).

Flow Cytometric Analysis

Cells were stained with FITC, PE, allophycocyanin (APC), or PerCP-conjugated mAbs in PBS containing 0.1% NaN$_3$ and 2% FCS after preblocking FCγ receptors. Rat mAbs specific for mouse CD4 (RM4-5), CD8 (53-6.7), CD11c (HL3), CD40 (3/23), CD80 (16-10A1), CD86 (GL1) and matched isotype controls were purchased from BD Biosciences, San Jose, Calif. Stained cells were analyzed on a FACSCalibur (Becton Dickinson, Lincoln Park, N.J.) flow cytometer and CELLQuest software.

Tetramer Staining

H2-K$^b$/ovalbumin tetramer assays were used to detect ovalbumin-specific CD8$^+$ T cells. Splenocytes or T cells from immunized mice were double stained with anti-CD8α-FITC and H2-K$^b$/ovalbumin (SIINFEKL)-PE tetramers; SEQ ID NO:11 (Beckman Coulter Immunomics, San Diego, Calif.) on different days after DC immunization. Tetramer staining was done at 4° C., for 1 hour with 1 μg of anti-CD8α and 10 μl of ovalbumin tetramers per $10^6$ cells, according to the manufacturer's instruction.

Enzyme-Linked Immunospot (ELISPOT)

CTL peptides were used for CD8$^+$ T-cell stimulation. Irrelevant peptide from human CD20 molecule was also used as a negative control. CD8$^+$ T cells were isolated from splenocytes by using MACS CD4 (L3T4) or MACS CD8 (Ly-2) MicroBeads (Miltenyi Biotec Inc., Auburn, Calif.).

The CTL and NK Assays

CD8$^+$ CTL responses were assessed with a standard chromium release assay, which measures the ability of in vitro-restimulated splenocytes to lyse target cells. Splenocytes pooled from immunized mice were restimulated in vitro in RPMI-1640 containing peptide for 4-6 days. Target cells and control cells were labeled with sodium $^{51}$Cr chromate solution for 90 minutes. Different numbers of effector cells were incubated with a constant number of target cells ($1 \times 10^4$/well) in 96-well V-bottomed plates (200 μl/well) for 3 hours at 37° C. The supernatants (100 μl) from triplicate cultures were collected. Percent lysis was calculated as (experimental release−spontaneous release)/(maximum release−spontaneous release)×100. NK cells were generated from the splenocytes of mice by culturing $1 \times 10^6$ cells/ml with 500 U/ml of recombinant murine IL-2. YAC-1 cells that are highly susceptible to lysis by NK cells were incubated with $^{51}$Cr for 1 hour at 37° C., washed, and resuspended at $10^5$ cells/ml. NK cells were added in triplicate to the target cells to obtain different E:T cell ratios. After incubation, the plates were centrifuged and the radioactivity in supernatant fluids were counted with a gamma counter (Beckman Coulter, Inc., Fullerton, Calif.).

DC Immunization and Tumor Models

Bone marrow-derived DCs (day 5 of bone marrow culture) were transduced with LV-SOCS1-siRNA or LV-GFP-siRNA at an MOI of 5. DCs were then pulsed with ovalbumin proteins or TRP2 peptide for 8 hours, washed with PBS three times, and used for immunization after an additional 36 hours in culture. For some experiments, antigen-pulsed DCs were stimulated with LPS (100 ng/ml, Sigma, St. Louis, Mo.) for 24 hours, washed with PBS, and then injected into C57BL/6 mice (Jackson Laboratory) via footpads. In the therapeutic model, EG7 or B16 tumor cells (2.5 to $5 \times 10^5$) were injected subcutaneously (s.c.) into the right flank of syngeneic C57BL/6 mice. On different days after tumor inoculation, the mice were randomly divided into groups and injected with 50 μl of antigen-pulsed, transduced DCs, or PBS control. In some mice, LPS was administered intraperitoneally (i.p.) at indicated days after vaccination. Tumor volumes were measured 2 or 3 times a week with a caliper.

Statistical Anaylsis

For statistical analysis, Student's t test was used, and a 95% confidence limit was taken to be significant, defined as P<0.05. Results are typically presented as means±standard errors.

The results of the experiments presented in this Example are now described.

Example 1

Identification and Analysis of Murine SOC-1 siRNA

A computer program was used to select siRNA sequences targeting mouse SOCS1: SOCS1-siRNA1 (CCTTCCGCTC-CCACTCCGA; SEQ ID NO:1), SOCS1-siRNA2 (CAGTCGCCAACGGAACTGC; SEQ ID NO:2) and SOCS1-siRNA3 (CTACCTGAGTTCCTTCCCCTT; SEQ ID NO:3). All target sequences were subjected to NCBI Blast query to confirm the lack of homology to other known genes. Forward and reverse oligos were designed to encode the sense and antisense 19 nt target sequences separated by a 9 nt spacer. This core siRNA sequence was flanked by the H1 RNA transcription initiation and ST terminator sequences, and incorporated 5' BglII and 3'HindIII compatible overhangs upon annealing. The DNA-based siRNA expression vector pSUPER (Brummelkamp, et al., 2002, Science 296:550-553) uses the H1-RNA promoter to direct de novo synthesis of siRNAs. Oligonucleotide pairs synthesized and annealed were cloned into a BglII/HindIII digested pSUPER vector. Positive clones were identified by restriction digest and confirmed by DNA sequencing.

Generation and Production of Lentiviral Vectors for Mouse SOCS1-siRNA

The HIV transfer vector used in this study was pTRIP ΔU3 CMV eGFP, which comprises an internal cytomegalovirus (CMV) promoter and is self-inactivating (SIN vectors) with a 400 bp deletion in the U3 region of the 3' long terminal repeat (LTR), which removes the transcriptionally active sequence. The lentiviral transfer vector, pTRIPΔU3 CMV GFP, contains a 178-bp fragment encompassing the central polypurine tract (cPPT) and the central termination sequence (CTS) in the unique ClaI site of the original pHR' backbone. pTRIPΔU3CMV GFP was modified for expression of siRNA from the H1 RNA promoter and co-expression of a bicistronic blasticidin resistance/eYFP selection marker. To accommodate cloning and remove the native CMV promoter, the central polypurine tract/central termination sequence (cPPT/CTS) of the pTRIP vector was PCR amplified using the primers (5'-GATCGAATTCACAAATGGC-3'; SEQ ID NO:4 and 5'-CTAGGGATCCATCGCCCCAAAGTGG-3'; SEQ ID NO:5) to insert 5'-EcoRI and 3'-BamHI sites for cloning. cPPT-CTS PCR product was then digested with EcoRI/BamHI and re-inserted into EcoRI/BamHI digested pTRIPΔU3CMV GFP vector. The woodchuck posttranscriptional regulatory element (wPRE) sequence was PCR amplified from pBS-SK-WPRE using the primers (5'-GATCCTC-GAGGTCGACAATCAACCTCTGGA-3'; SEQ ID NO:6 and 5'-GATCGGTACCCAGGCGGGGAGG-3'; SEQ ID NO:7) to add 5'-XhoI/SalI and 3'KpnI sites. The WPRE fragment was then digested with XhoI/KpnI, and inserted into the modified pTRIPΔU3CMV GFP backbone to generate pTRIP-W. The siRNA and bicistronic selection marker cassettes were first assembled in the pSUPER backbone for transfer into pTRIP-W. The bicistronic selection marker CMV-Blasti$^R$-IRES-eYFP (BY) was PCR amplified from the plasmid PYAP6 using the primers (5'-CAGTATCGATT-TAATTAATCAATATTGGCCATTAG-3'; SEQ ID NO:8 and 5'-CAGTGTCGACTTAATTAAGTGGCCGCTTTACTTG-3'; SEQ ID NO:9) to incorporate 5'-ClaI and 3'-SalI sites. PCR product was digested with ClaI and SalI, then ligated into ClaI/SalI digested pSUPER vector to add the BY marker at the 3'-end of the H1-RNA promoter and pSUPER MCS, generating pSUPER-BY. pSUPER-BY was then BamHI/SalI digested and ligated into pTRIP-W backbone to generate pTRIP-H1-BY-W.

Subsequent pSUPER vectors containing hrGFP or the SOCS1(3) siRNA hairpin sequence were digested with BstBI and ClaI for insertion into pTRIP-H1-BY-W to generate pTRIP-hrGFP-siRNA-BY-W (GFP-siRNA), and pTRIP-SOCS1-siRNA-BY-W (SOCS1-siRNA). A final 390 bp spacer fragment was inserted at the ClaI site of the final vector to space the termination sequence of the siRNA from the beginning of the CMV promoter. All vectors were verified by DNA sequencing (Lone Star Labs, Houston, Tex., USA).

Recombinant pseudotyped lentiviral vectors were generated by co-transfection of three plasmids into 293T cells. The HIV-derived packaging construct pCMVΔR8.9 encodes the HIV-1 gag, and pol precursors, as well as the regulatory proteins tat and rev. Glycoprotein G of the vesicular stomatitis virus (VSV-G) was expressed from the plasmid pMD.G. Pseudotyped lentivirus was produced by transient calcium-phosphate co-transfection of 293T cells with pCMVAR8.9, pMD.G, and the lentiviral pTRIP siRNA transfer vectors. 60 to 72 hours after transfection, the supernatants were concentrated by ultracentrifugation at 50,000×g for 2 hours at 4° C. Virus pellets were resuspended in RPMI and frozen at −80° C. for future study. Viral titers were determined by incubating 293T cells with serial dilutions of concentrated virus and 8 µg/ml Polybrene for 6 hours, followed by fluorescence-activated cell sorting (FACS) analysis to determine eYFP-positive cells 72 to 96 hours later. Vector titers were calculated as follows: titer=F×2×C$_0$/V×D (where D is the virus dilution factor, V is the volume of inoculum, F is the frequency of eYFP-positive 293T cells, and C$_0$ is the number of target cells at the time of seeding).

Example 2

Transfection and SOCS1 mRNA Downregulation of Murine BM-DCs with SOCS1 siRNA with GenePorter To investigate SOCS1 regulation of antigen presentation by DCs, a small interfering RNA (siRNA) that specifically downregulates SOCS1 was first identified as described below.

Synthetic siRNA oligo duplexes were efficiently transfected into DCs derived from mouse bone marrow cells ex vivo in the presence of granulocyte-macrophage colony-stimulating factor (GM-CSF) and IL-4 by GenePorter with a transfection efficiency of 83%. Briefly, bone-marrow DCs were transfected with 21 base-pair siRNA oligonucleotides (5'-CTACCTGAGTTCCTTCCCCTT-3'; SEQ ID NO:3) using GenePorter, following the manufacturer's protocol. 3 µl of 20 µM oligonucleotides was added to 3 µl of GenePorter reagent and 94 µl of serum-free RPMI1640 and incubated at 25° C. for 30 minutes, after which 100 µl of the GenePorter/oligonucleotide mixture was added to each well of bone marrow-DCs and incubated for 4 hours at 37° C. After incubation, 500 µl/well of RPMI1640 supplemented with 20% FBS was added to the bone-marrow DCs. Based on the present disclosure, a synthetic siRNA ligo can be delivered to a cell in the context of a physiologically acceptable carrier. An example of an acceptable carrier is a liposome.

FIG. 1A demonstrates that SOCS1 is downregulated in a cell transduced with a vector expressing SOCS1-siRNA. Briefly, 293T cells were cotransfected with pSUPER (pSUP) vectors expressing mouse SOCS1-siRNA or irrelevant GFP-siRNA, and a FLAG-tagged mSOCS1 expression vector at a 10:1 ratio using GenePorter, and 48 hours later, were subjected to western blotting. The intensity of SOCS1 bands was normalized to that of beta-actin bands, and the relative intensities (ratios) are shown. SOCS1-siRNA3 (5'-CTACCT-GAGTTCCTTCCCCTT-3'; SEQ ID NO:3), designated as SOCS1-siRNA, was used in subsequent studies.

Figure 1B:
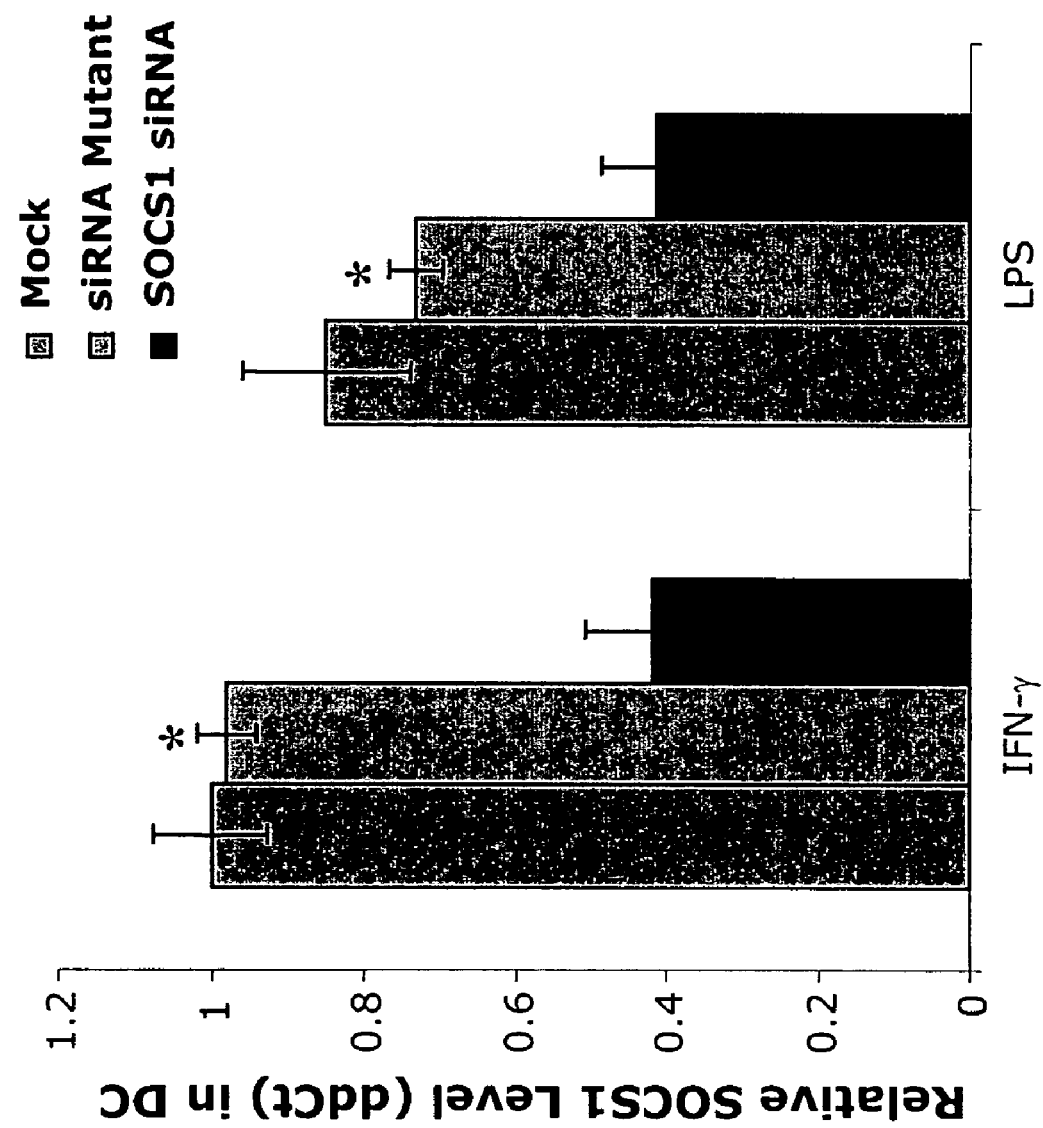

As verified by quantitative RT-PCR assays, the level of SOCS1 mRNA in the total DC population transfected with SOCS1 siRNA was specifically decreased by approximately 60%, compared with levels in DCs transfected with a SOCS1 siRNA mutant that cannot downregulate SOCS1 (FIG. 1B). In addition, it was observed that SOCS1 expression was higher during bone marrow DC culture in vitro and after maturation.

Figure 2:
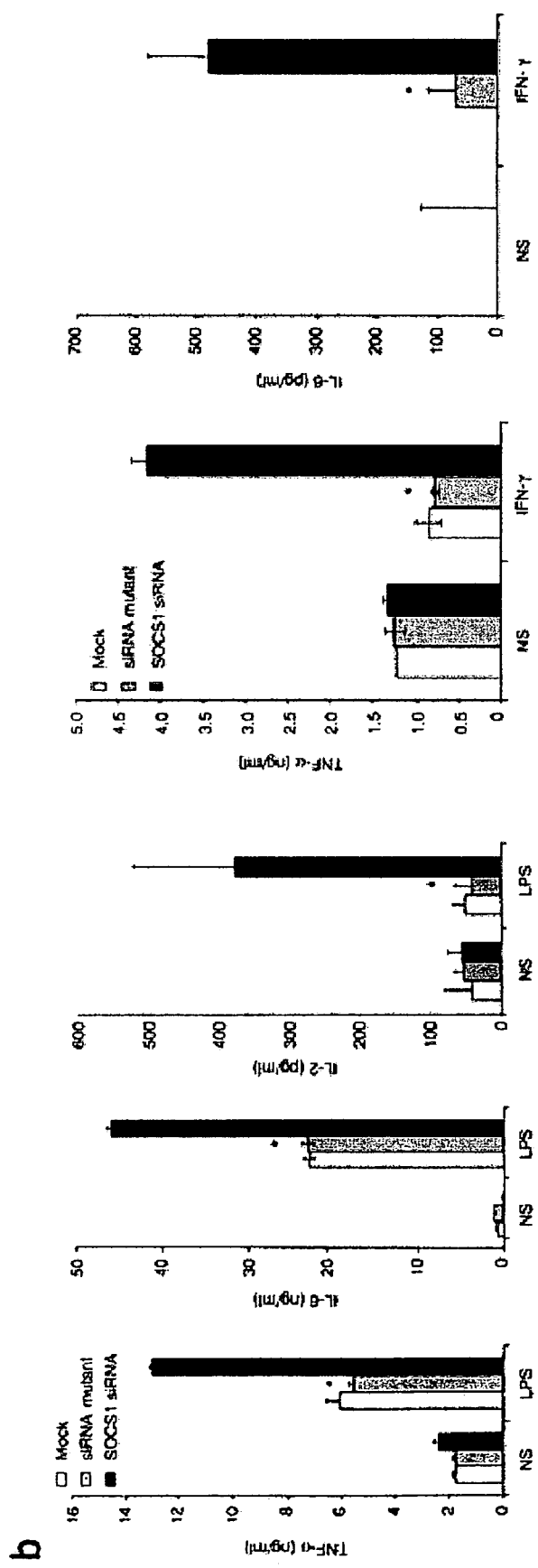
FIG. 2 is a chart demonstrating that DCs transfected with SOCS1 siRNA were more responsive to LPS or IFN-γ than were DCs transfected with siRNA mutant as indicated by enhanced secretion of proinflammatory cytokines, such as IL-6 and TNF-α.

It was also observed that DCs transfected with SOCS1 siRNA were more responsive to LPS or IFN-γ than were DCs with siRNA mutant as indicated by enhanced secretion of proinflammatory cytokines, such as IL-6 and TNF-α (FIG. 2), and by enhanced phosphorylation of STAT1, 1-κB, and JNK, upon stimulation. FIG. 1B depicts levels of cytokines secreted by siRNA oligo- or mock-transfected DCs in response to LPS (100 ng/ml) or IFN-γ (10 ng/ml) for 24 hours from one of three independent experiments. The siRNA mutant (5'-ACTATCTAAGTTACTACCCCTT-3'; SEQ ID NO:10) contains four mutations in the SOCS1 siRNA3 sequence.

These data are in agreement with the reported involvement of SOCS1 in regulation of the JAK/STAT pathway and the TLR/NF-κB pathway (Hanada et al. 2003, Immunity 19:437-450; Chong et al., 2003, Immunity 18:475-487). DCs transfected with SOCS1 siRNA indicated a slightly more mature phenotype than did siRNA-DC mutants either before or after IFN-γ and LPS stimulation. Both transfected DCs were more mature than mock-transfected DCs, which may reflect the effect of nonspecific activation of IFN genes by siRNA.

Example 3

Transfection of Murine BM-DCs with Viral Vectors

Figure 3:
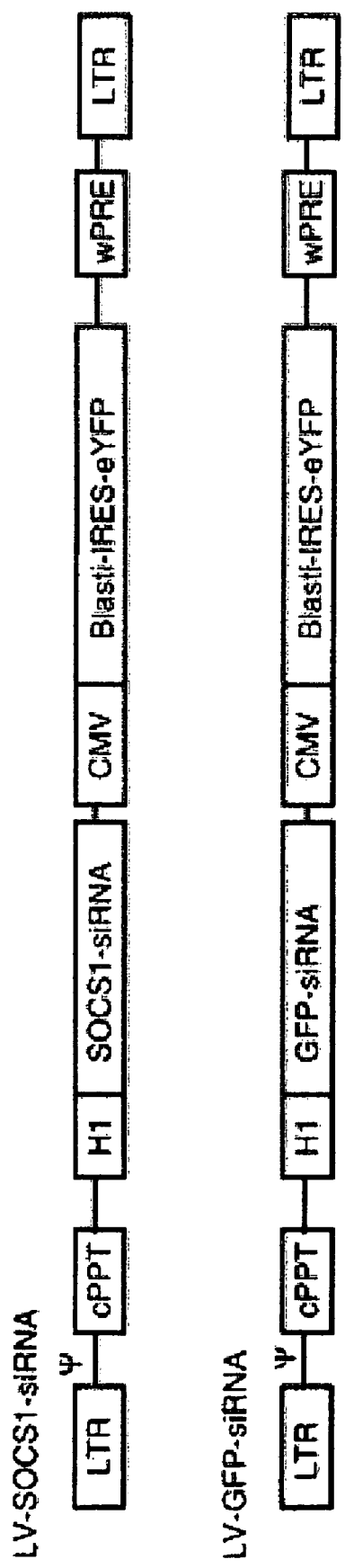
FIG. 3 is a schematic representation of recombinant lentiviral vectors; LV-SOCS1-siRNA and LV-GFP-siRNA.

To assess whether SOCS1 negatively regulates DC antigen presentation in vivo, SOCS1 siRNA or a control green fluorescent protein (GFP) siRNA was cloned into a lentiviral vector (LV), which is capable of stably transducing DCs (Rubinson et al., 2003, Nat. Genet. 33:401-406; Schroers et al., 2004, Methods Mol. Biol. 246:451-459), so that the effect of SOCS1 silencing could be assessed more reliably. Two constructs were generated, LV-SOCS1-siRNA and LV-GFP-siRNA, both containing the yellow fluorescent protein (YFP) marker (FIG. 3) according to the methods described elsewhere herein. Transduction of bone marrow-derived DCs (>80% CD11c$^+$) with either the LV-SOCS1-siRNA or the LV-GFP-siRNA vector routinely yielded 58-63% of culture cells positive for YFP. Consistent with the previous observation on siRNA oligo-transfected DCs, a lower level of SOCS1 mRNA in the total transduced DC population and enhanced secretion of proinflammatory cytokines upon stimulation of LV-SOCS1-siRNA-DCs in comparison with LV-GFP-siRNA-DCs was observed. To determine the level of SOCS1 mRNA in the transduced DCs, the YFP$^+$-transduced DCs were isolated using fluorescence-activated cell sorting (FACS) and the relative expression of SOCS1 mRNA was then determined by real-time quantitative PCR. It was observed that the level of SOCS1 mRNA in the YFP$^+$ LV-SOCS1-siRNA-DC population was about 90% lower, compared with levels in mock-transduced DCs. DCs transduced with LV-SOCS1-siRNA and LV-GFP-siRNA either with or without LPS stimulation indicated comparable levels of CD86 and CD40 expression. Without wishing to be bound by any particular theory, it is believed that the observation that LV-GFP-siRNA-DCs resulted in higher levels of CD86 and CD40 than mock DCs is likely due to the effects of nonspecific activation by siRNA and lentiviral transduction.

Example 4

OVA-Specific CTL and Antitumor Activity Induced by Mouse SOCS1 siRNA DCs

The next series of experiments were performed to test whether DC stimulation of antigen-specific cytotoxic T lymphocytes (CTLs) is regulated by SOCS1. When immature SOSC1-siRNA-DCs or siRNA mutant DCs that had not been further stimulated to mature were pulsed with ovalbumin-I peptide (SIINFEKL; SEQ ID NO:11) and were cocultured with ovalbumin-specific TCR T cells (OT-I), OT-I cells proliferated more in the SOCS1-siRNA-DC coculture than in the siRNA-DC mutant coculture (FIG. 4A). Consistent with these data, higher levels of proinflammatory cytokines were secreted in the SOCS1-siRNA-DC coculture (FIG. 4B). In addition, CTL assays indicated of these cells indicated more active cytotoxicity against ovalbumin$^+$ syngeneic EG7 cells after coculture with SOCS1-siRNA-DCs, demonstrating that SOCS1 contributes to the regulation of DC stimulation of antigen-specific T cells.

Figure 5A:
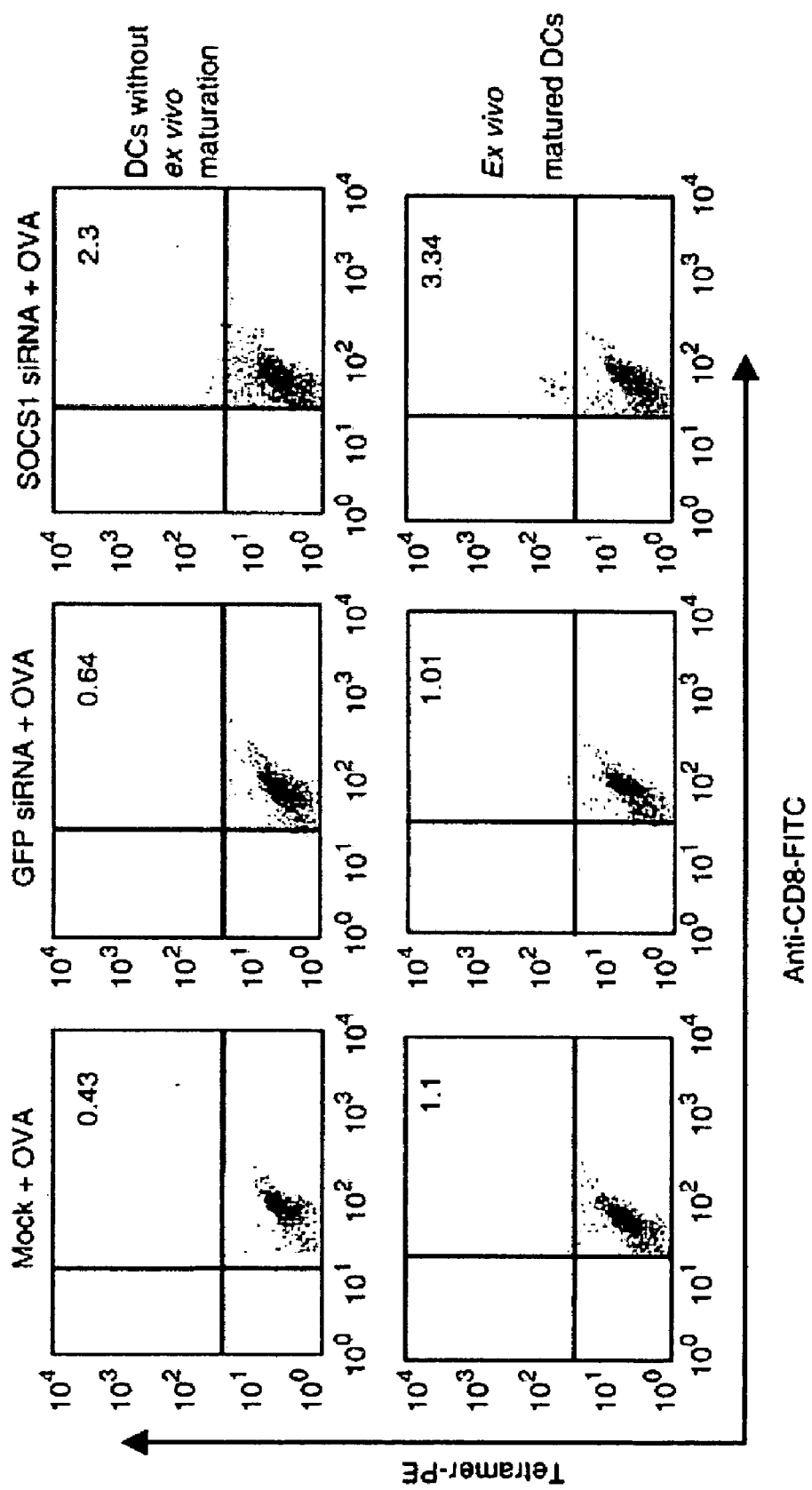
FIGS. 5A through 5C, is a series of charts demonstrating that SOCS1 negatively regulates the ability of DCs to prime the antigen-specific T-cell response in vivo.
Figure 5B:
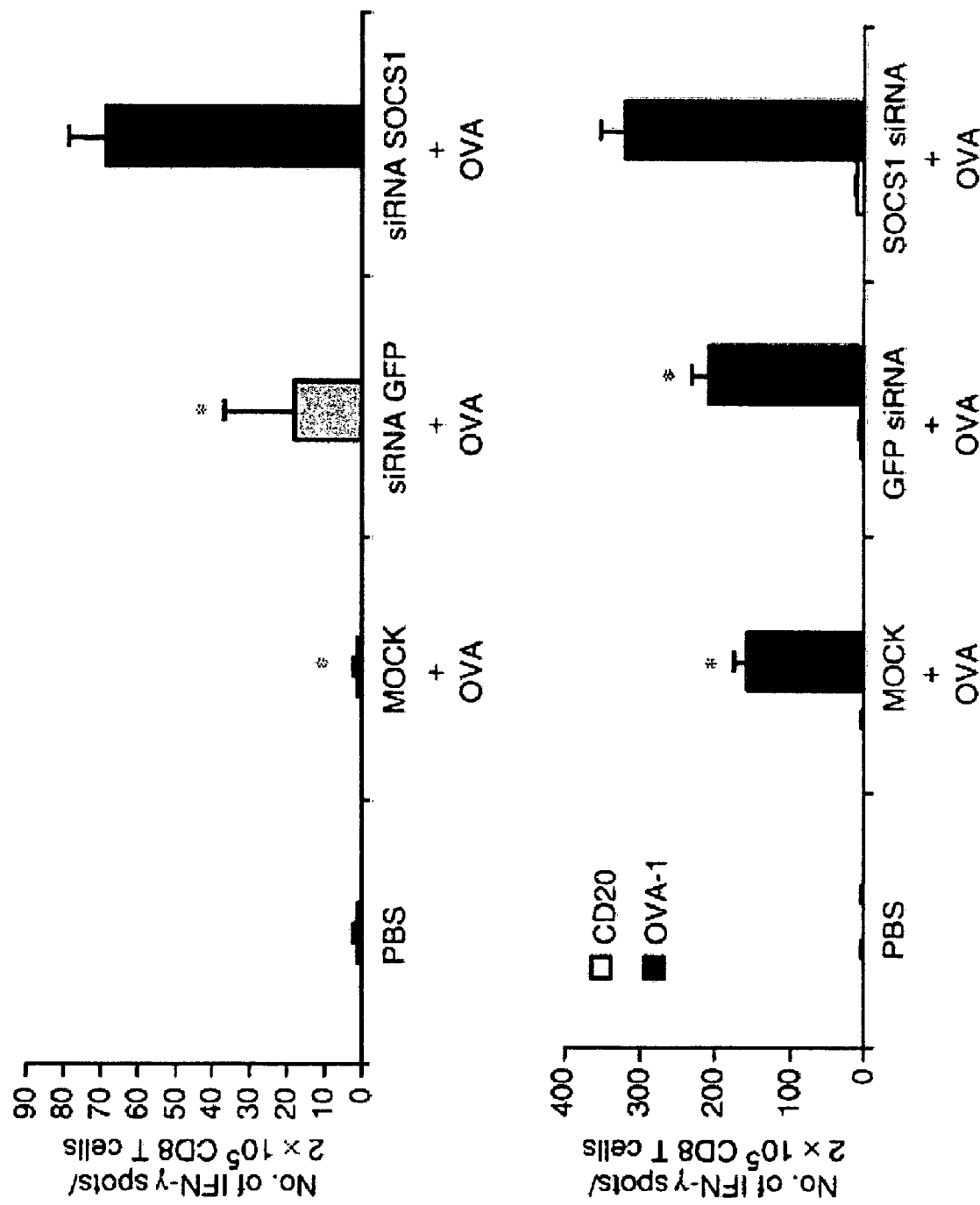
Figure 5C:
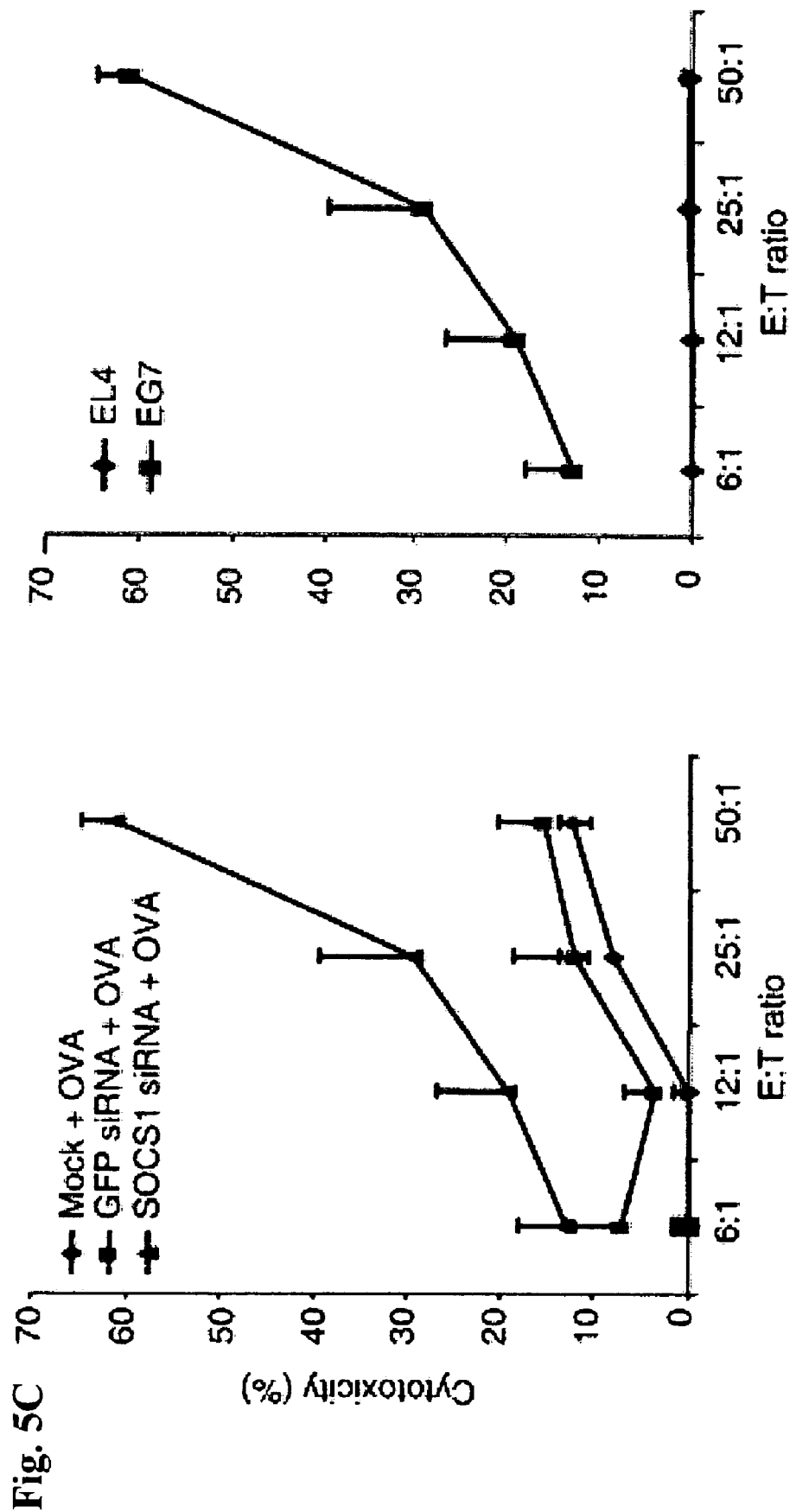

The ability of SOCS1-silenced DCs to prime an antigen-specific response in vivo was next tested by directly immunizing mice with ovalbumin-pulsed, transduced DCs in the absence of ex vivo maturation. Tetramer staining indicated that 2.3% of total CD8$^+$ T cells were positive for ovalbumin-tetramer in mice immunized with LV-SOCS1-siRNA-DCs, compared with only 0.64% and 0.43% in mice immunized with LV-GFP-siRNA-DCs or mock DCs, respectively (FIG. 5A). Because there were only minor differences in surface maturation markers between LV-SOCS1-siRNA-DCs or LV-GFP siRNA-DCs, these data suggest that increased DC maturation was not the sole factor contributing to the functional potency of LV-SOCS1-siRNA-DCs. The functional status of CD8$^+$ T cells in immunized mice was further evaluated using an interferon-$\gamma$ (IFN$\gamma$) ELISPOT assay. Mice immunized with immature LV-SOCS1-siRNA-DCs had 68 IFN$\gamma^+$ spots per $2\times10^5$ CD8$^+$ T cells, compared with 1 and 18 spots in those given immature mock DC or LV-GFP-siRNA-DCs, respectively (FIG. 5B). These results were consistent with CTL assays showing more potent cytotoxicity against ovalbumin$^+$ target cells of the splenocytes from mice given immature LV-SOCS1-siRNA-DCs (FIG. 5C). Immunization with immature LV-SOCS1-siRNA-DCs also induced an observable potent antigen-specific CD4$^+$ T-helper response. Thus, SOCS1 silencing allowed immature antigen-presenting DCs to attain an immunogenic state capable of priming antigen-specific CD8$^+$ CTL responses in vivo. Without wishing to be bound by any particular theory, it is believed that because SOCS1-silenced DCs prime adaptive immunity without prior maturation, SOCS1 plays a regulatory role in maintaining the tolerogenic state of DCs.

SOCS1-Mediated Regulation of Mature DCs In Vivo

The following experiment was conducted to investigate whether priming of the CTL response by SOCS1-silenced DCs, without prior maturation, resulted from the enhanced maturation of the DCs in response to endogenous environmental stimuli. Ovalbumin-pulsed LV-SOCS1-siRNA-DCs with LPS ex vivo for 24 hours were first matured, and then washed for three times before administering them into mice. LPS-matured LV-SOCS1-siRNA-DCs indicated a mature phenotype comparable to that of matured LV-GFP-siRNA-DCs, and both DCs primed CTLs more potently than DCs in the absense of ex vivo maturation. However, the matured LV-SOCS1-siRNA-DCs were still clearly superior to the matured LV-GFP-siRNA-DCs in inducing antigen-specific CTLs, as demonstrated by ovalbumin tetramer staining (FIG. 5A). IFN-$\gamma$ ELISPOT assays also indicated an enhanced ovalbumin-specific CD8$^+$ T-cell response in LV-SOCS1-siRNA-DCs mice (FIG. 5B), suggesting that SOCS1 silencing permits greater responsiveness of matured DCs to endogenous environmental stimuli, leading to an enhanced CTL response.

Figure 6A:
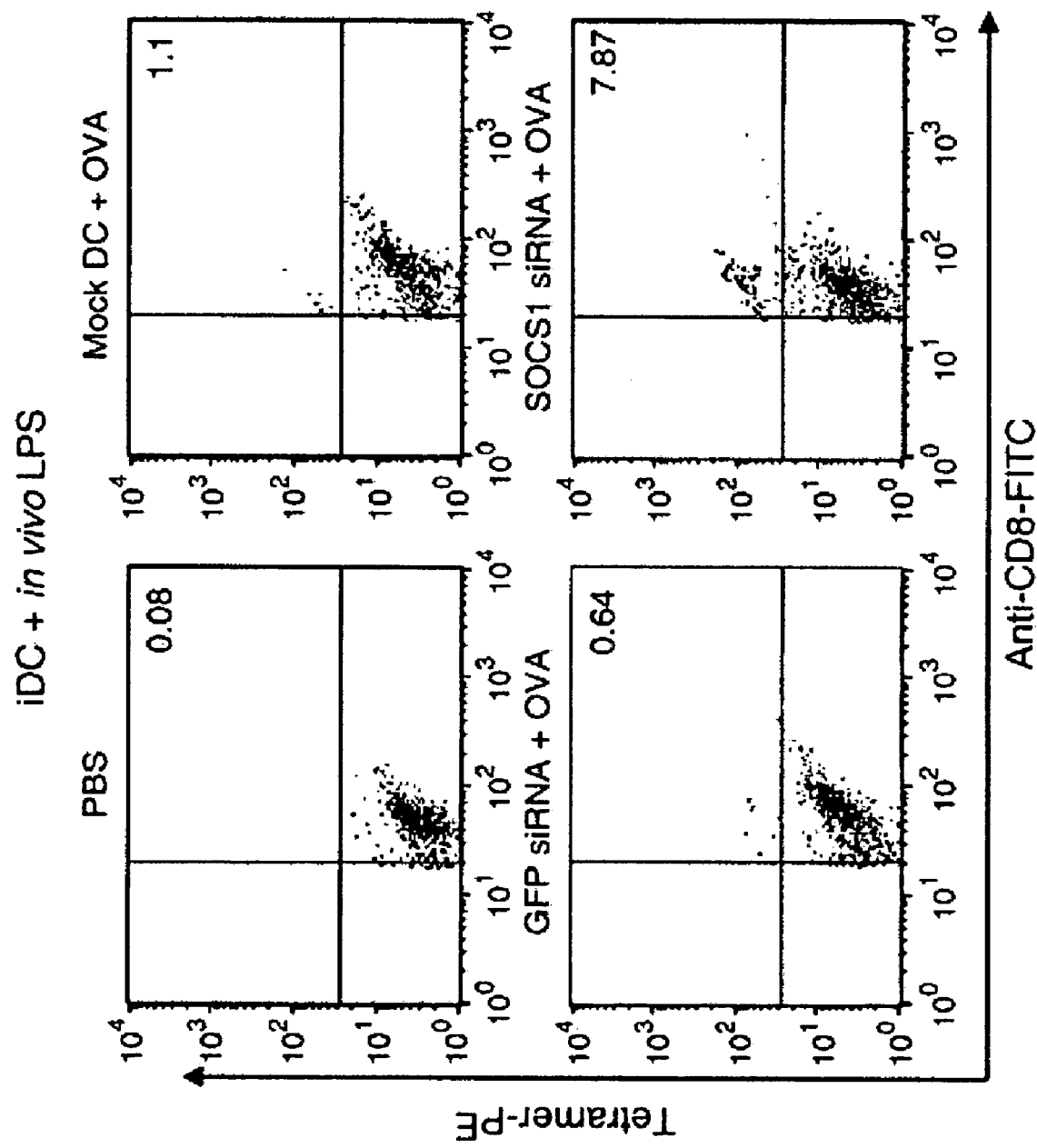
FIGS. 6A through 6E, is a series of charts demonstrating that in vivo LPS stimulation strongly enhanced CTL responses induced by SOCS1-silenced DCs.
Figure 6B:
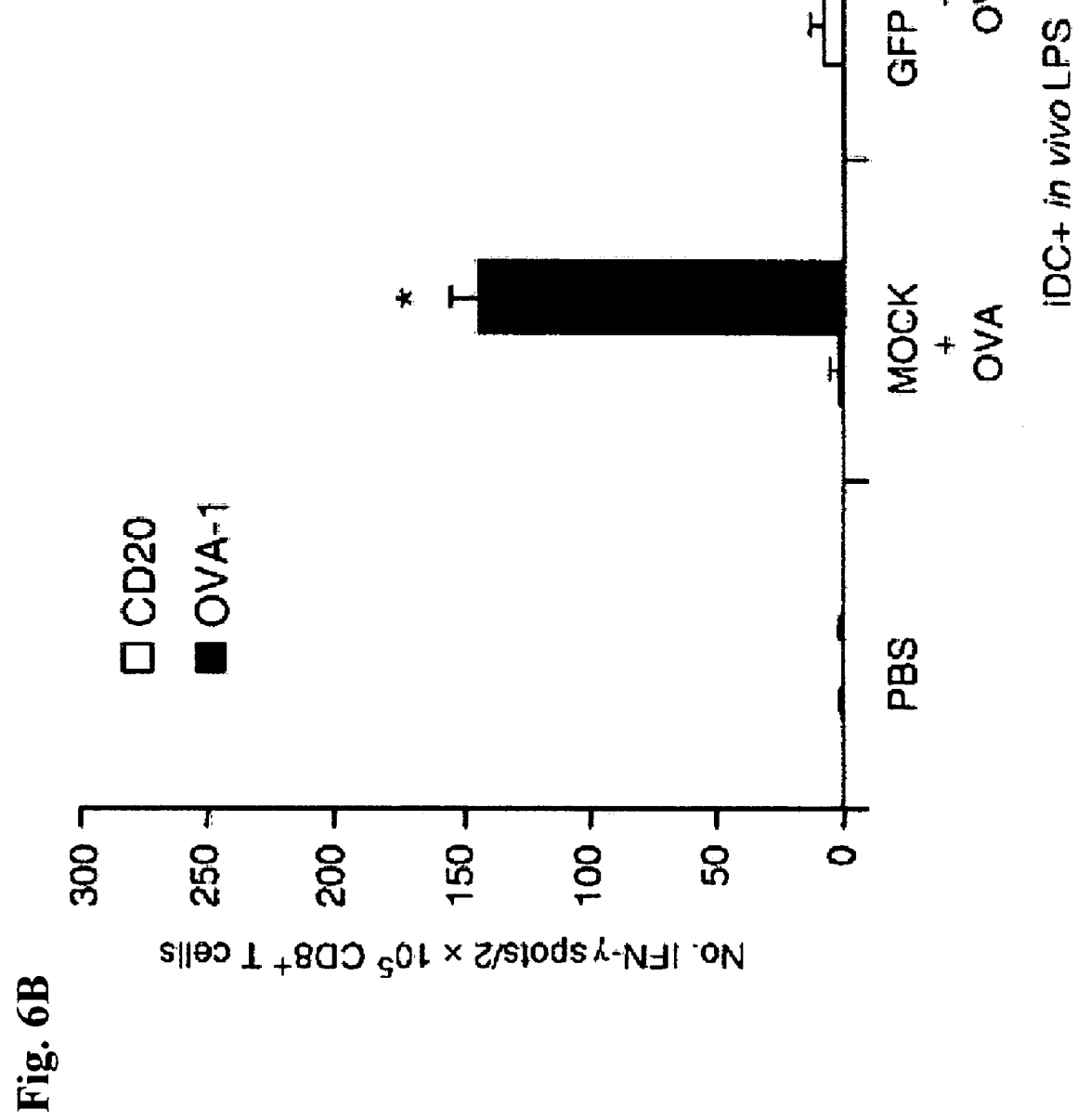

In further in vivo tests, mice that had been immunized with immature LV-SOCS1-siRNA-DCs one day earlier were injected with LPS once. This stimulation significantly (P<0.01) boosted CTL responses in immature LV-SOCS1-siRNA-DCs mice (7.87% ovalbumin-tetramer$^+$ in CD8$^+$ T cells), but less effectively in immature DC-GFP-siRNA mice (0.64% ovalbumin-tetramer$^+$ in CD8$^+$ T cells) (FIG. 6A). The enhanced ovalbumin-specific CTL response in immature LV-SOCS1-siRNA-DCs mice after in vivo LPS stimulation was confirmed by IFN-$\gamma$ ELISPOT assays (FIG. 6B).

Figure 6C:
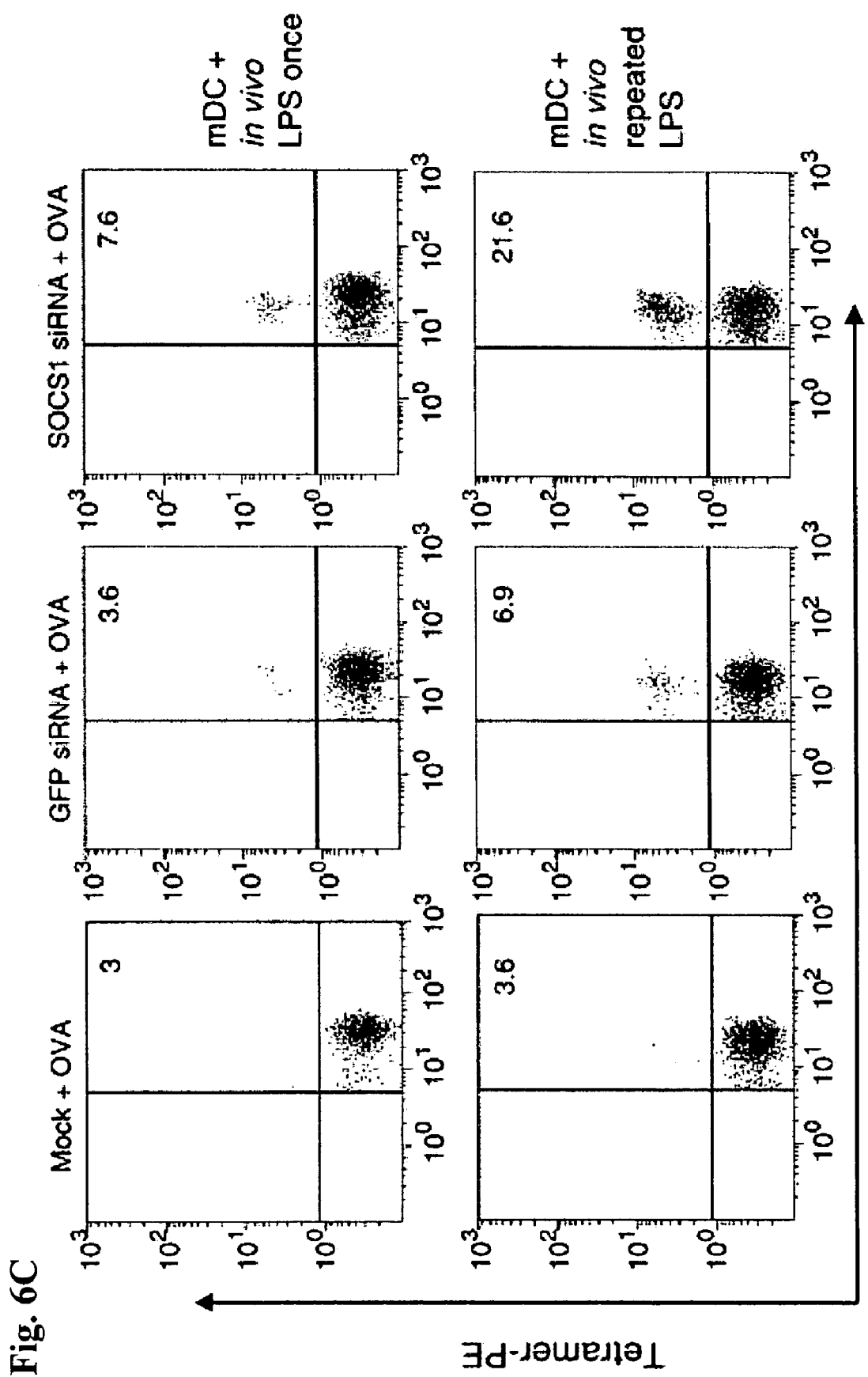
Figure 6D:
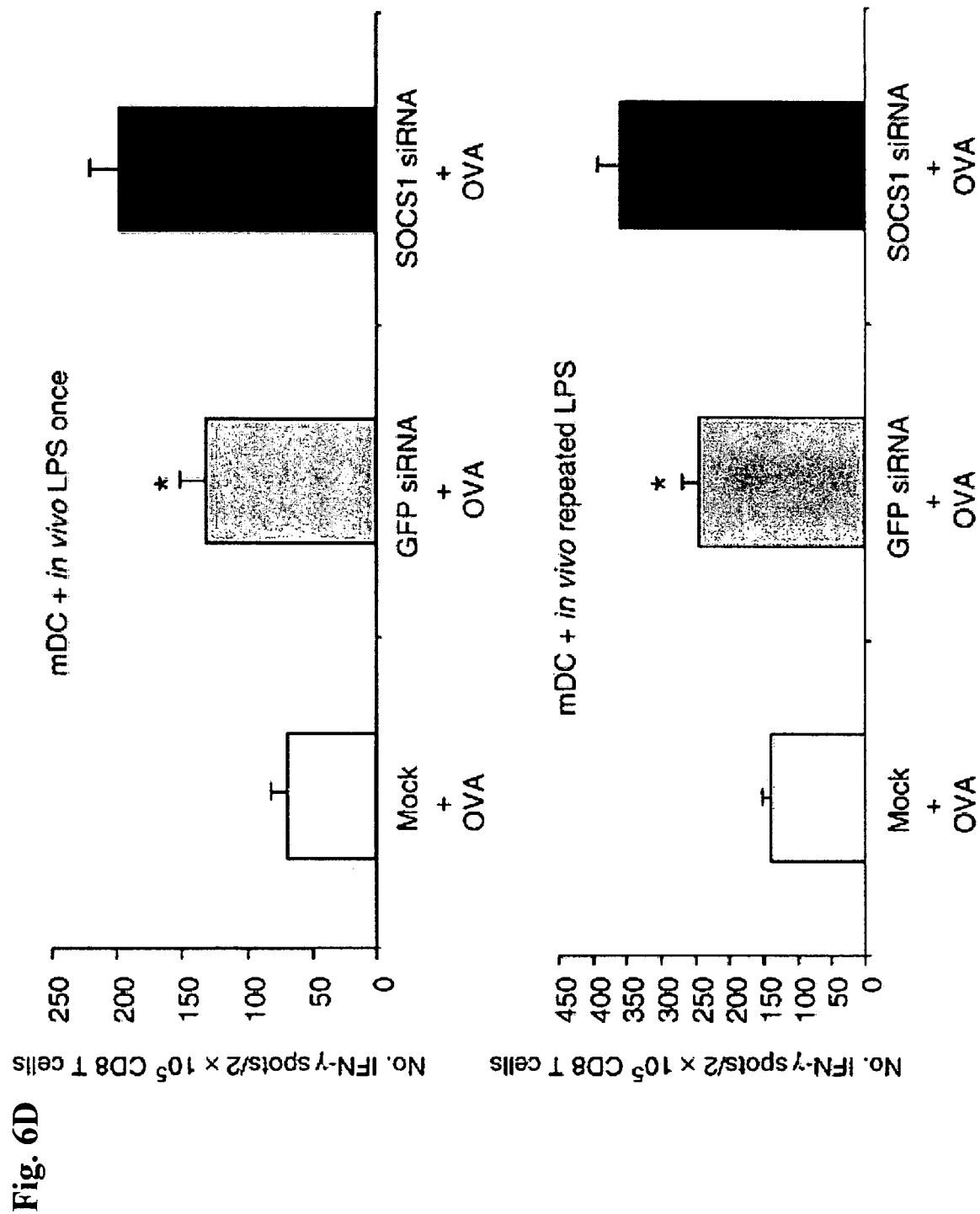

To test whether signaling of matured DCs in response to environmental stimuli plays a role in T-cell priming, mice that had been immunized with ex vivo matured LV-SOCS1-siRNA-DCs one day earlier were injected with LPS once or repeatedly. LPS injections significantly (P<0.01) boosted CTL responses in matured LV-SOCS1-siRNA-DCs mice, indicating the importance of signaling of matured DCs for priming T-cell responses (FIGS. 6C and 6D). Furthermore, LPS injections were more effective in boosting the ovalbumin-specific CTL responses in mice immunized with matured LV-SOCS1-siRNA-DCs.

To directly examine the responsiveness of DC-SOCS1-siRNA to repeated LPS stimulation, the ability of SOCS1-siRNA-DCs and GFP-siRNA-DCs to develop endotoxin tolerance in vitro were assessed. SOCS1-siRNA-DCs, but not GFP-siRNA-DCs, still responded strongly to repeated LPS stimulation by producing high levels of proinflammatory cytokines, suggesting SOCS1-silenced DCs continuously respond to stimuli. In addition, the threshold of DC responsiveness to endogenous stimuli such as heat shock proteins (HSP) that function as natural danger molecules was reduced by SOCS1 silencing.

Taken together, these data indicate that silencing of SOCS1 in DCs likely reduces the threshold of DC responsiveness and permits immature and matured antigen-presenting DCs to respond continuously to endogenous stimuli, resulting in enhanced antigen-specific CTL responses. This mechanism underscores the critical role of SOCS1 in the control of the extent of antigen presentation by matured DCs and hence the magnitude of adaptive immunity.

Enhancement of SOCS1-Silenced DC Immunization by In Vivo Stimulation

Figure 6E:
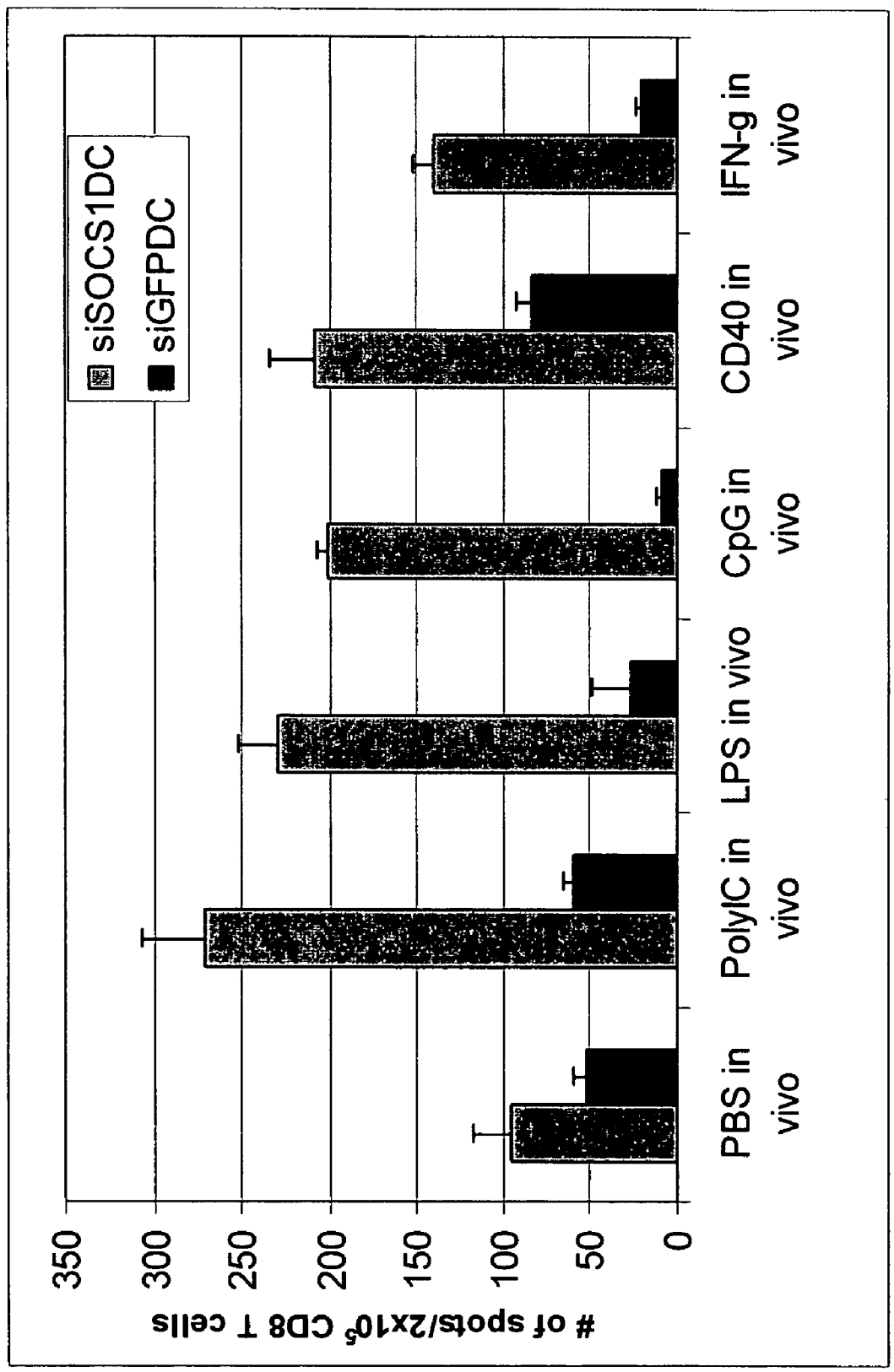

To investigate whether in vivo stimulation with a cytokine or a Toll-like receptor (TLR) agonist can further enhance the potency of SOCS1-silenced DCs, mice that had been immunized with OVA-pulsed DC-LV-SOCS1-siRNA were injected with LPS (30 µg/mouse), CpG (60 µg/mouse), Poly I:C (50 µg/mouse), anti-CD40 (100 µg/mouse), or IFN-g (1 µg/mouse) i.p. once a day for three consecutive days. It was observed that these stimuli preferentially boosted the CTL responses induced by DC-LV-SOCS1-siRNA mice (FIG. 6E). These results indicate that many stimuli, in addition to LPS, can further enhance the potency of SOCS1-silenced DC immunization.

Enhancement of Anti-Tumor Immunity by SOCS1 Silencing in DCs

Figure 7A:
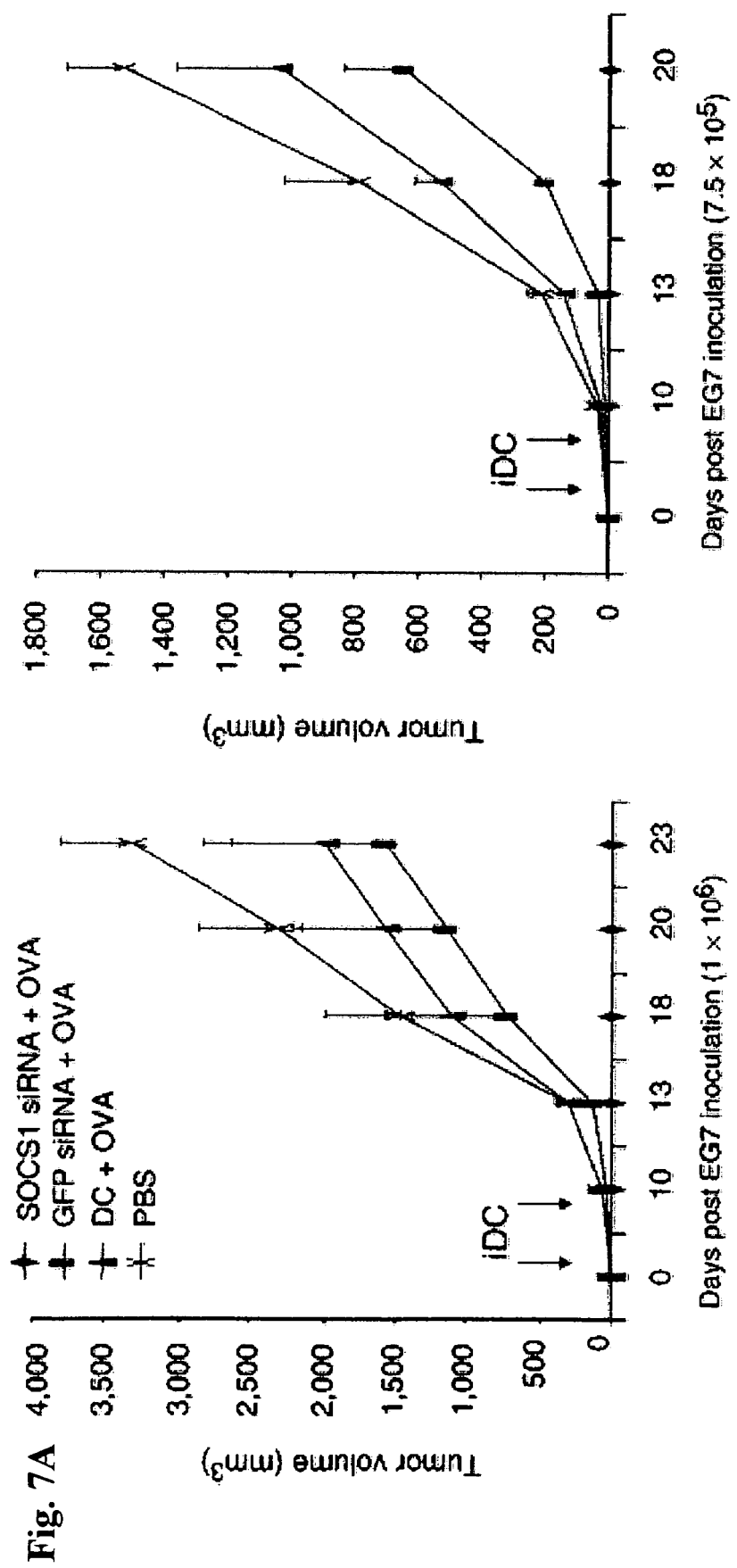
FIGS. 7A through 7E, is a series of charts demonstrating enhanced anti-tumor immunity induced by SOCS1-silenced DCs.
Figure 7B:
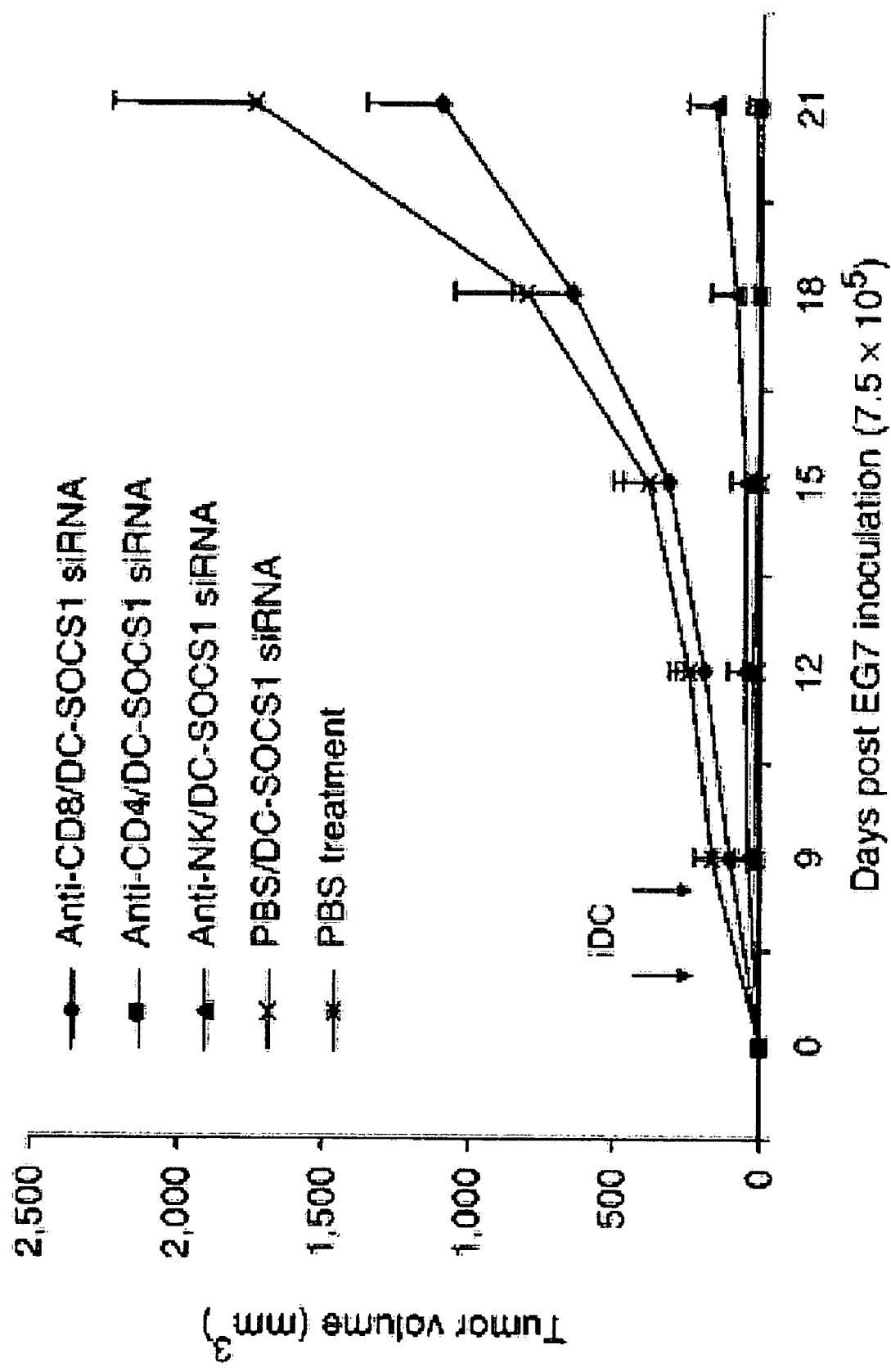

The observed regulatory role of SOCS1 in DC antigen presentation prompted the investigation of whether SOCS1-silenced DCs might induce more potent antigen-specific anti-tumor immunity, leading to the control of pre-established tumor growth. Immunization with ovalbumin-pulsed LV-SOCS1-siRNA-DCs in the absense of ex vivo maturation completely blocked the growth of pre-established ovalbumin$^+$ EG7 tumors in all mice tested, in contrast to the modest reduction of tumor growth in mice given ovalbumin-pulsed LV-GFP-siRNA-DCs or mock DCs in the absense of ex vivo maturation (FIG. 7A). In vivo antibody-blocking experiments demonstrated that anti-CD8 antibody blocking, but not anti-CD4, abolished the anti-tumor activity induced by ovalbumin-pulsed LV-SOCS1-siRNA-DCs (FIG. 7B), indicating the critical role of CD8$^+$ CTLs in the anti-tumor response.

Figure 7C:
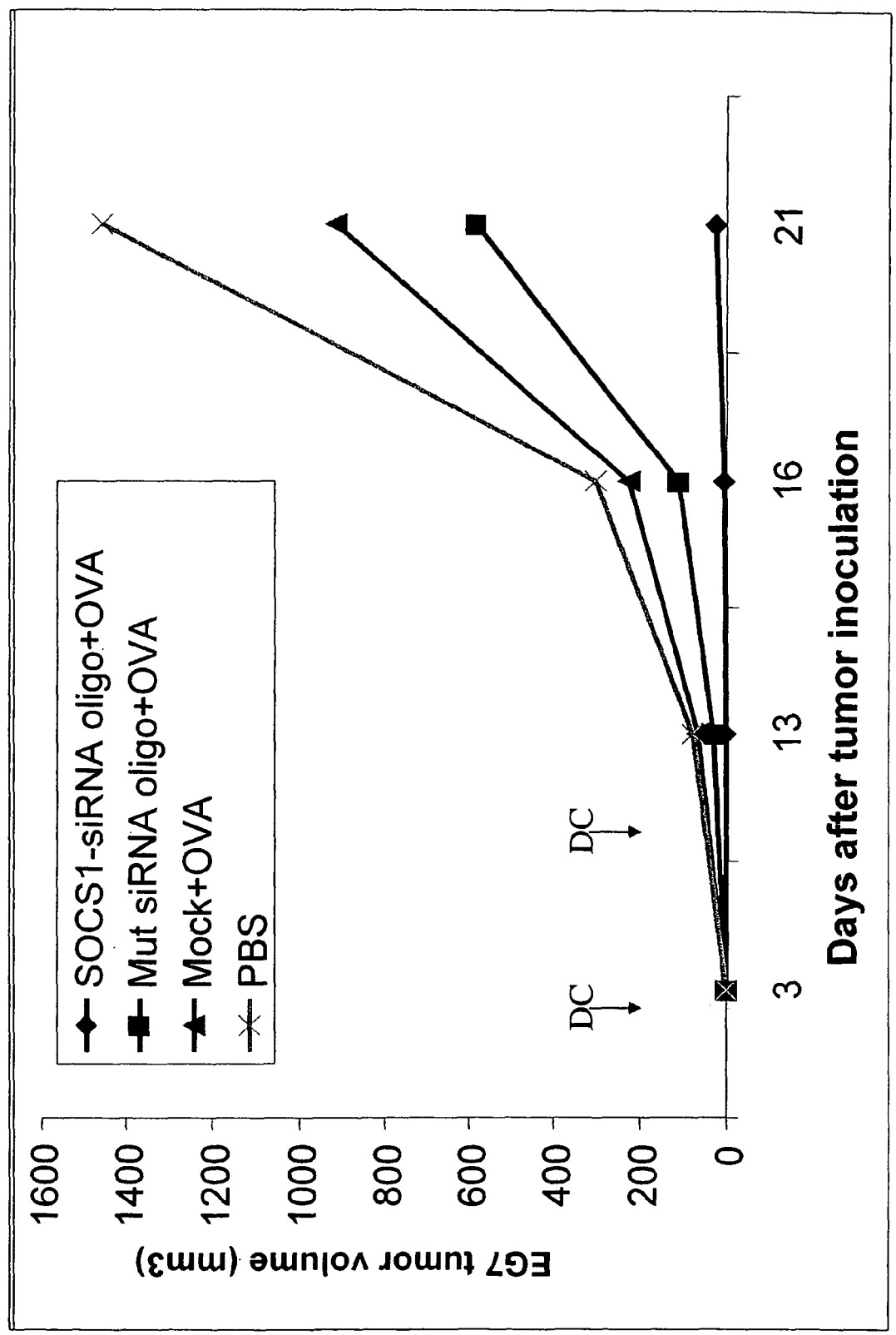
Figure 7D:
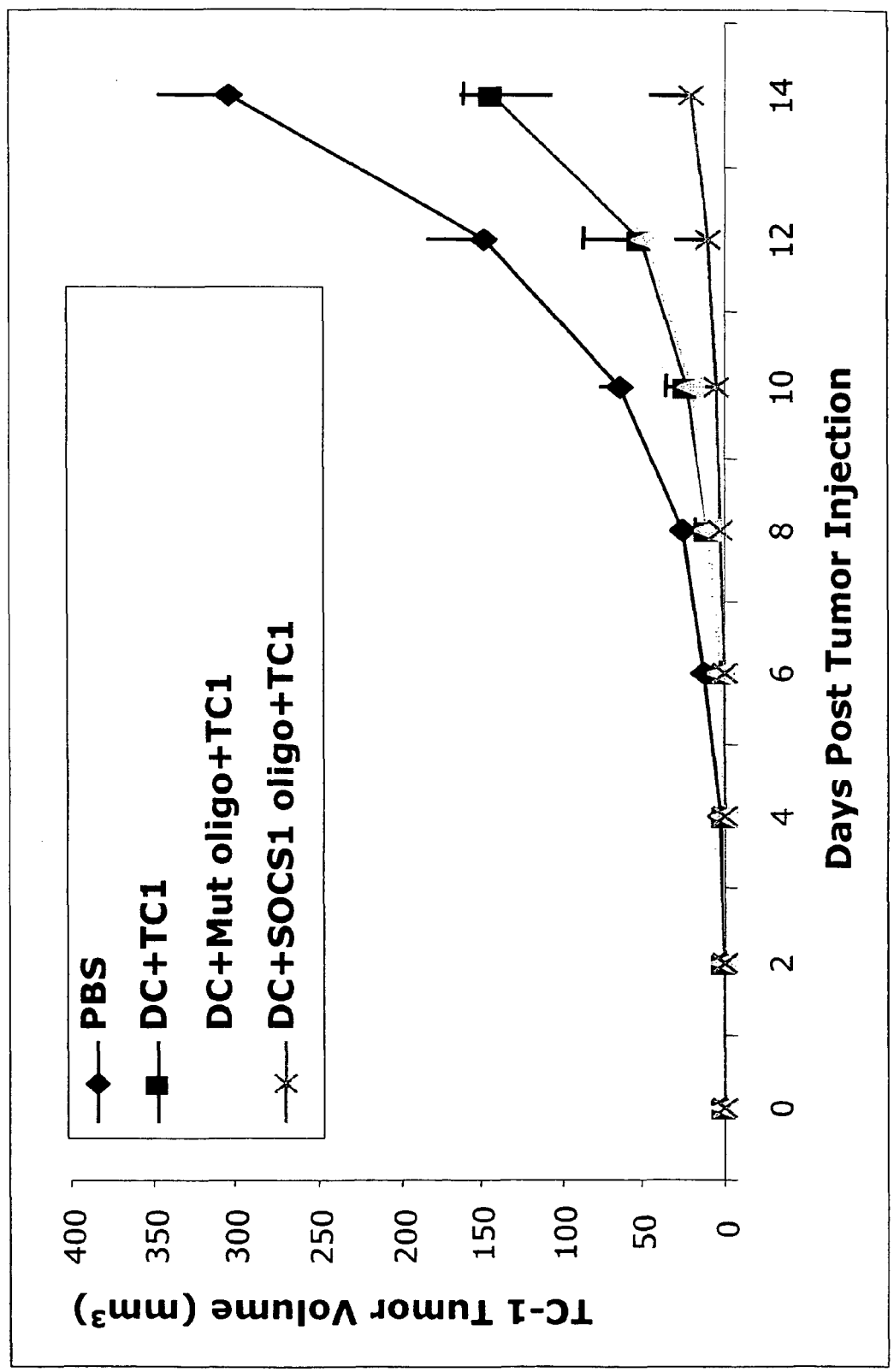
Figure 7E:
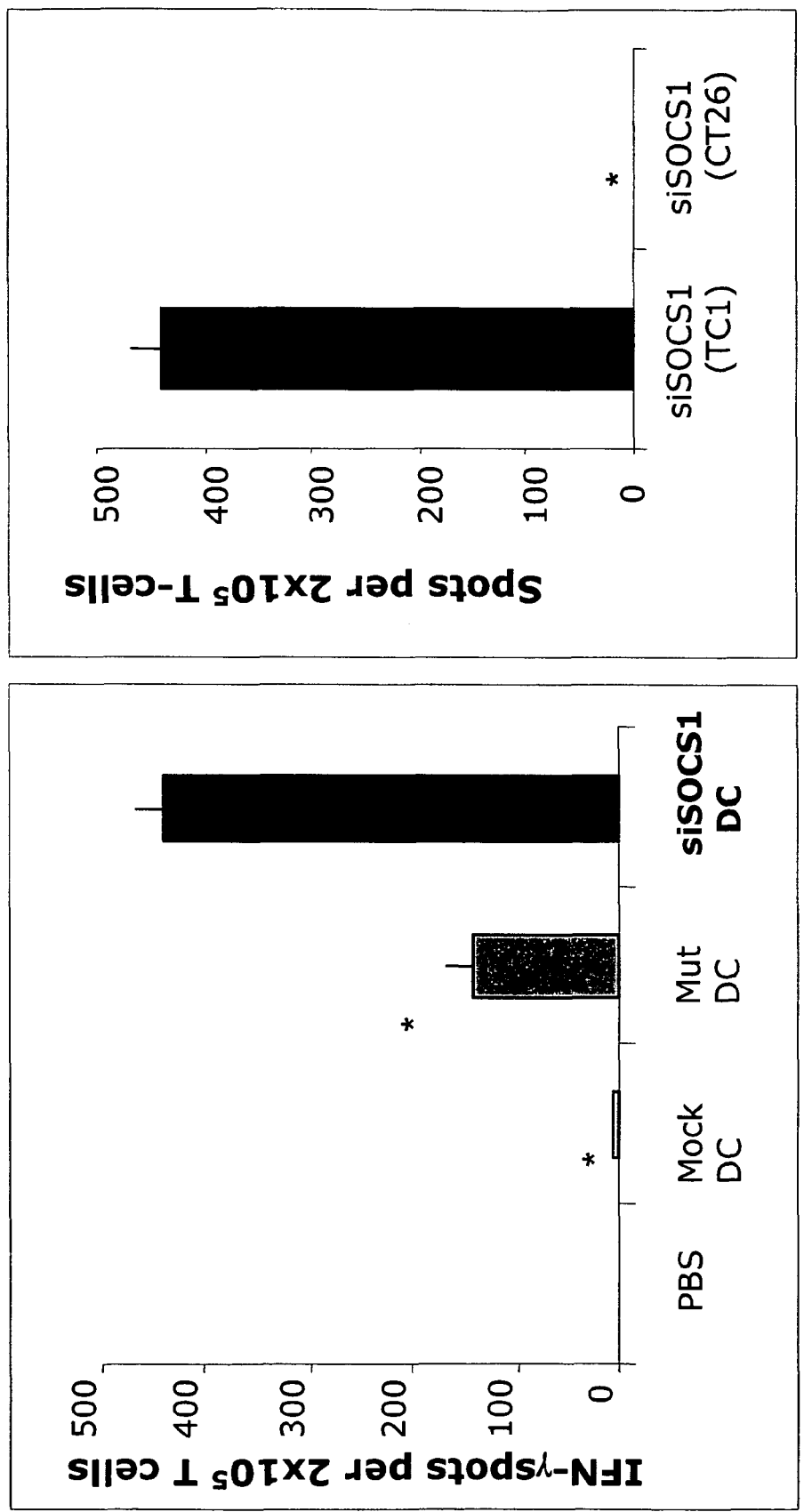

To test whether SOCS1 siRNA oligo duplex-transfected DCs have an enhanced antitumor activity, DCs were transfected with SOCS1 siRNA oligo duplex or control oligo duplex. Groups of mice were then immunized with the transfected DCs that have been pulsed with OVA or TC-1 tumor lysates. Following the immunization of the mice with the pulsed DCs, the mice were stimulated with LPS (30 µg/mouse) in vivo three times. Two weeks after DC immunization, the immunized mice were challenged with OVA+EG7 tumor or TC-1 tumor. Enhanced antitumor activities were observed in both EG7 and TC-1 tumor models (FIGS. 7C and 7D). Moreover, IFNγ ELISPOT assays showed enhanced tumor-specific CTL responses in the mice immunized with SOCS1 siRNA oligo-DCs pulsed with TC-1 tumor lysate (FIG. 7E).

Figure 8A:
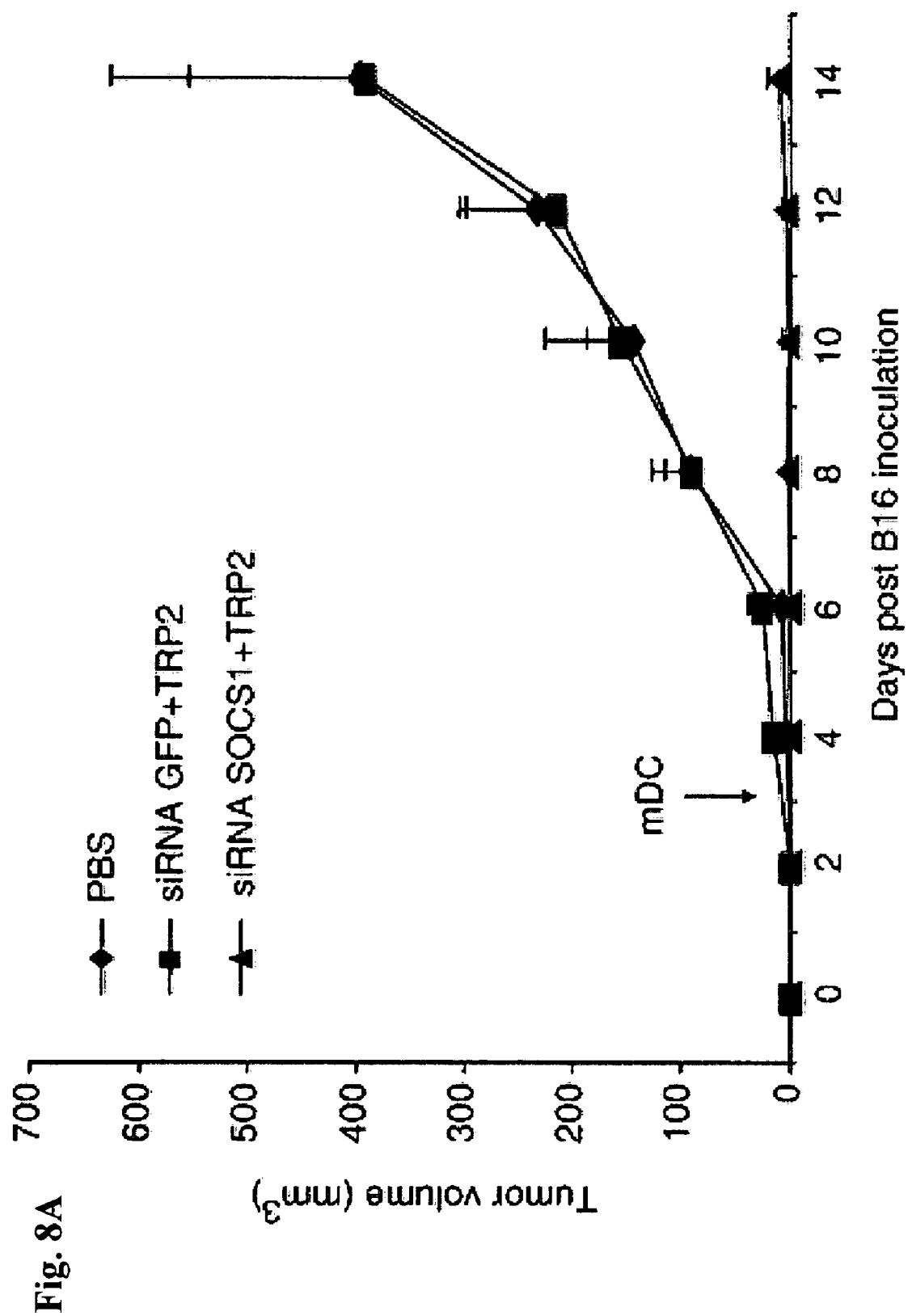
FIGS. 8A through 8C, is a series of charts demonstrating enhanced CTL response against a self tumor-associated antigen by SOCS1-silenced DCs.
Figure 8B:
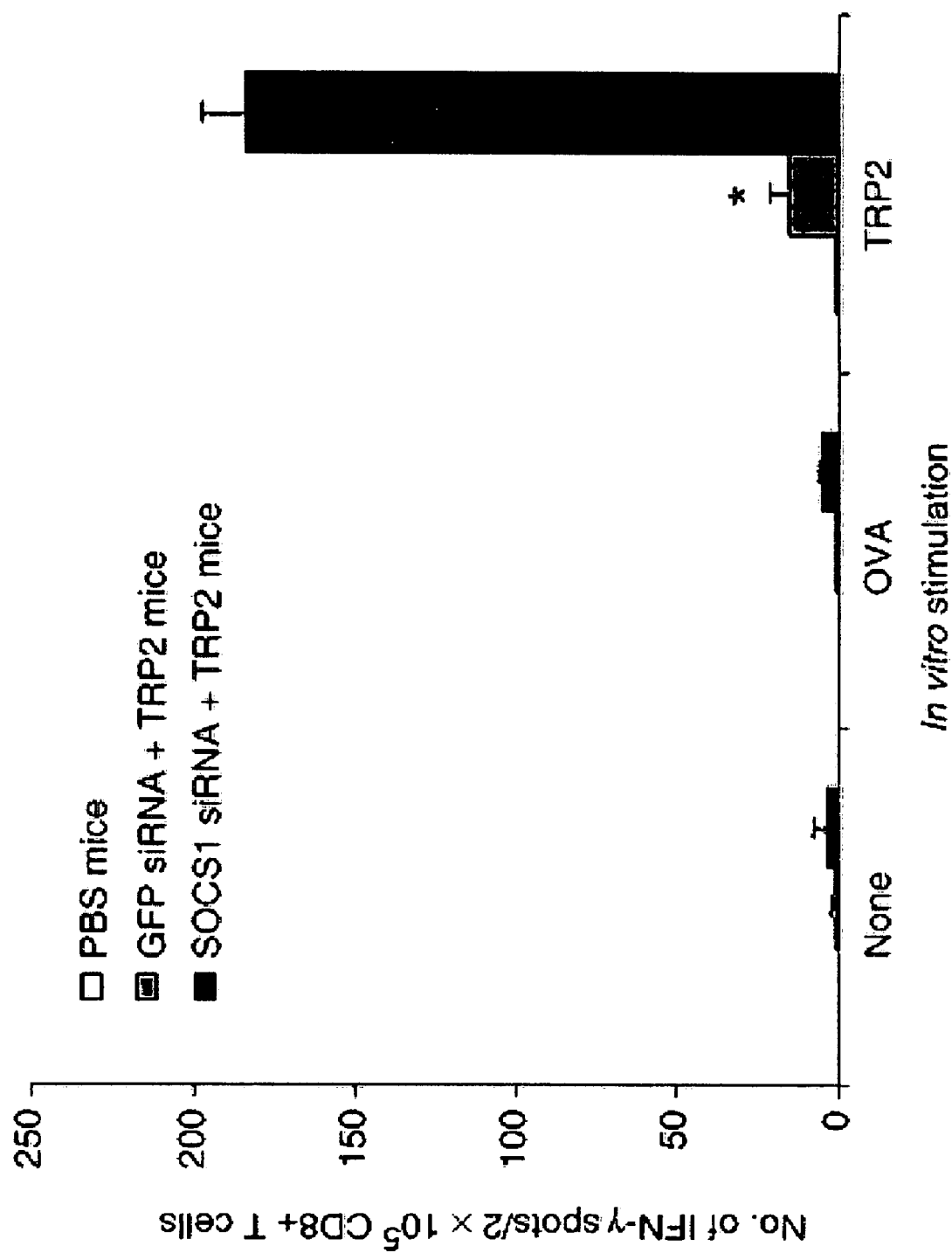
Figure 8C:
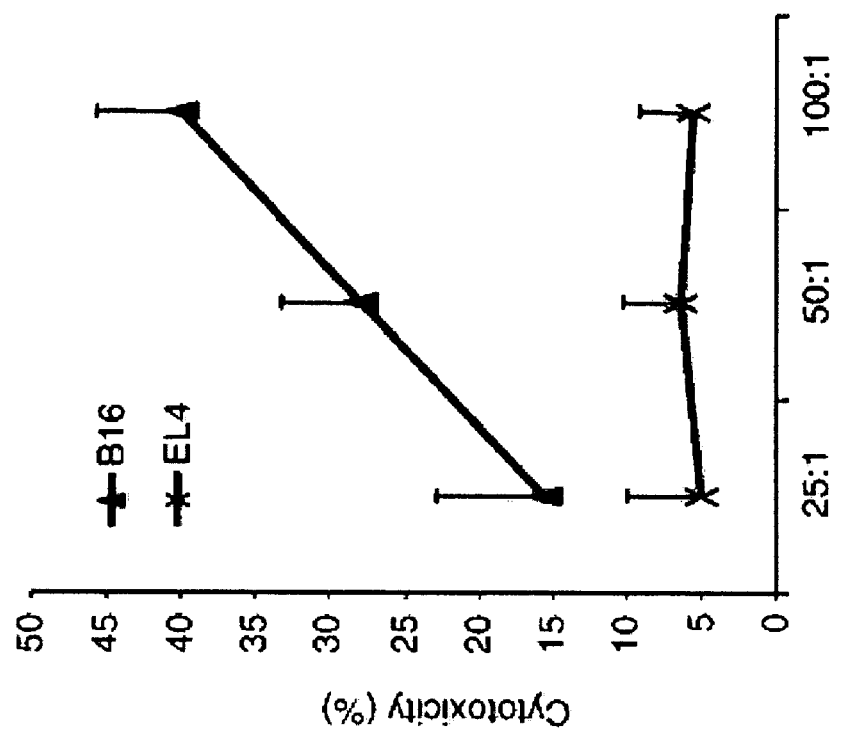
Figure 8C:
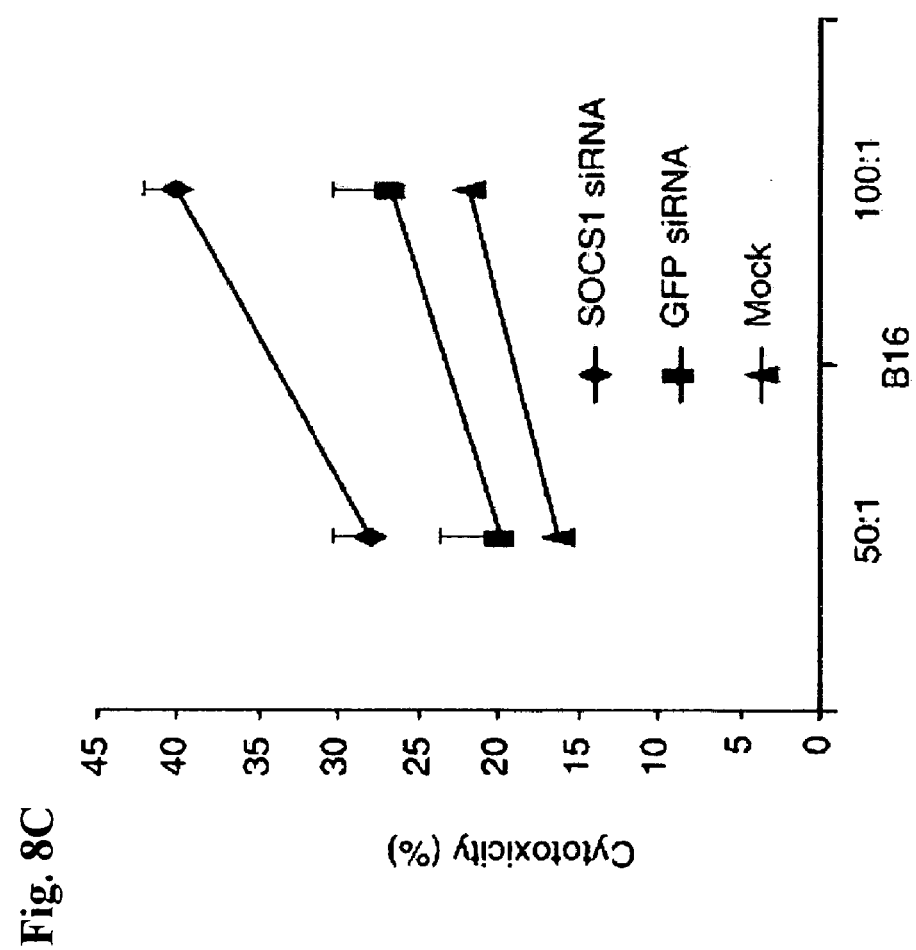

It was further tested whether SOCS1-silenced DCs can enhance immune response against self tumor-associated antigens. For these experiments, a murine melanocyte differentiation antigen tyrosinase-related protein (TRP) 2 that is naturally expressed in the weakly immunogenic B16 melanoma cells was used. C57BL/6 mice were inoculated with B16 tumor cells and three days later were treated once with TRP2 peptide-pulsed, mature LV-SOCS1-siRNA-DCs or LV-GFP-siRNA-DCs that were ex vivo stimulated with LPS. Mature LV-SOCS1-siRNA-DCs effectively blocked the growth of pre-established B16 tumors, whereas mature LV-GFP-siRNA-DCs did not have any inhibitory effect (FIG. 8A). The enhanced anti-tumor activity was correlated with the potent TRP2-specific CTL responses in LV-SOCS1-siRNA-DCs mice, as detected by IFN-γ ELISPOT and CTL assays (FIGS. 8B and 8C). Active NK activities were detected only in mice given mature LV-SOCS1-siRNA-DCs. In contrast to the results with ovalbumin$^+$ EG7 tumor, immunization with immature TRP2-pulsed LV-SOCS1-siRNA-DCs failed to produce significant (P>0.05) inhibitory effects on B16 tumors, suggesting that the full maturation of DCs and continuous signaling after maturation are required to generate effective anti-tumor immunity. The nonspecific stimulatory effect of GFP siRNA transduction on CTL responses against the foreign antigen (ovalbumin) was consistently observed. However, the nonspecific stimulatory effect was insufficient to enhance the CTL response against the self-antigen (TRP2).

Possible adverse autoimmune pathology induced by immunization with LV-SOCS1-siRNA-DCs was examined. Epigmentation (vitiligo) of mice immunized with SOCS1-silenced DCs that were pulsed with TRP2 was observed. However, no other apparent toxicity was observed in more than 200 mice immunized with LV-SOCS1-siRNA-DCs pulsed with ovalbumin or TRP2 up to three months after immunization. Histological analysis of all major organs and tissues of the immunized mice revealed no pathologic inflammation, and immunohistochemical staining did not show IgG or IgM deposits in the kidneys. Levels of IgG (IgG1, IgG2a) and anti-dsDNA were comparable in LV-SOCS1-siRNA-DCs and mock DC mice. These data suggest that LV-SOCS1-siRNA-DCs immunization does not cause pathological inflammation in mice. Without wishing to be bound by any particular theory, it is believed that SOCS1-silenced DCs have a strongly enhanced capacity to induce effective, antigen-specific, anti-tumor immunity capable of blocking the growth of pre-established, weakly immunogenic tumors.

Silencing of SOC1 Enhances Antigen Presentation by DCs and Antigen-Specific Anti-Tumor Immunity The results presented herein demonstrate that the stimulatory capacity of DCs and the magnitude of adaptive immunity are critically regulated by SOCS1 in DCs. Silencing SOCS1 in antigen-presenting DCs strongly enhances antigen-specific anti-tumor immunity. SOCS1 represents an inhibitory mechanism for qualitatively and quantitatively controlling antigen presentation by DCs and the magnitude of adaptive immunity.

The present disclosure demonstrates a critical role for SOCS1 in regulating the extent of antigen presentation by matured DCs, hence demonstrating a regulatory mechanism that allows DCs to control the magnitude and duration of adaptive immunity. The importance of SOCS1 in maintaining a DC tolerogenic state is exemplified herein in that, in contrast to wild-type DCs, SOCS1-silenced DCs are endowed with the stimulatory antigen-presenting capability to prime T-cell response in vivo in the absence of the need of ex vivo maturation. Without wishing to be bound by any particular theory, it is believed that the precise mechanisms by which SOCS1 in DCs controls the magnitude of adaptive immunity involve the regulation of the signaling and outputs of mature DCs in terms of antigenic peptide presentation, costimulation/coinhibition and cytokine production in response to stimulation with cytokines, microbial products and perhaps also cell-cell contact.

Mature DCs are generally believed to be short lived, based upon a limited number of studies. However, a recent study using a reliable genetic method demonstrates that the lifespan of mature antigen-presenting DCs is much greater than previously estimated, lasting for 2 weeks in vivo, supporting the necessity and importance of regulating the extent of antigen presentation by mature DCs.

The present invention relates to the novel principle of silencing SOCS1 in DCs as a generic means to enhance tumor vaccine potency by disabling a critical brake in DCs. Vaccination with SOCS1-silenced DCs strongly enhances antigen-specific anti-tumor immunity, because SOCS1 silencing permits antigen-presenting immunogenic DCs to persistently stimulate antigen-specific T cells in vivo. SOCS1-silenced DCs are capable of turning off regulatory T cells by enhancing DC maturation and the production of proinflammatory cytokines, such as IL-6, that inhibits regulatory T-cell suppression.

The blockade of CTLA-4 on T cells effectively breaks tolerance and enhances tumor vaccine potency, but causes severe nonspecific autoimmune inflammation in patients. By targeting SOCS1 in DCs at the antigen-presentation level, a more antigen-specific anti-tumor response can be achieved. First, immunization with SOCS1-silenced DCs that are abundantly loaded with tumor-associated antigens would induce antigen-specific immunity, in contrast to the targeting of CTLA-4 on effector CTLs, an approach that inevitably activates autoreactive T cells against vital normal tissues. Second, the use of partially SOCS1-silenced DCs with residual SOCS1 levels might not cause severe autoimmune inflammation, because heterozygous SOCS1$^{+/-}$ mice show no or only mild signs of autoimmune inflammation. In addition, the severe autoimmune inflammation seen in SOCS1$^{-/-}$ mice requires a complete deficiency of SOCS1 not only in DCs, but also in other lineages of immune cells, such as T and NKT cells. The results presented herein provide insight not only for understanding the quantitative and qualitative regulation of antigen presentation and adaptive immunity, but also for the development of effective vaccines against cancer and infectious diseases by enhancing the stimulatory potential of DCs.

Example 5

TRP2-Specific CTL and Antitumor Activity Induced by Mouse SOCS1 siRNA DCs

The present disclosure demonstrates that a lentiviral vector expressing SOCS1 siRNA-reduced SOCS1 expression in mature DCs can increase the magnitude of a self-antigen specific CTL response. A mouse melanocyte differentiation antigen, tyrosinase-related protein 2 (TRP2), was used as a model self-antigen for this study. TRP2 was used because it is naturally expressed in both normal melanocytes and weakly immunogenic B 16 melanoma cells, and multiple MHC class-I epitopes have been identified in TRP2 (van Elsas et al., 2001, J. Exp. Med. 194:481-9).

The Materials and Methods used in the experiments presented in this Example are now described.

Mice/Animal Model

Four to six week old female C57BL/6, CD4 KO, CD8 KO, or p35 (IL-12) KO mice were purchased from Jackson Laboratories (Ben Harbor, Me., USA) and maintained in a pathogen-free mouse facility at Baylor College of Medicine (Houston, Tex., USA) according to institutional guidelines.

Peptides

H2-K$^b$-restricted TRP2a (VYDFFVWL; SEQ ID NO:15) and TRP2b (SVYDFFVWL; SEQ ID NO:16) (van Elsas et al., 2001, J. Exp. Med. 194:481-9), and control H2-K$^b$-restricted OVA-I (SIINFEKL; SEQ ID NO:11) were synthesized and purified by HPLC to >95% purity by Genemed Synthesis Inc. (South San Francisco, Calif., USA). All peptides were dissolved in DMSO before final dilution in endotoxin-free PBS (Sigma, St. Louis, Mo.).

Transduction of BM-Derived DCs with Lentiviral Vectors

Recombinant lentiviral vectors (LV-SOCS1-siRNA and LV-GFP-siRNA) were produced, titrated and used to transducer DCs as described elsewhere herein.

Cytokine ELISA and Enzyme-Linked Immunospot (ELISPOT) Assay

Levels of various proinflammatory cytokines were quantitated using the supernatant of DC cultures for ELISA analysis (BD Biosciences, Lincoln Park, N.J.) according to the manufacturer's instructions at the indicated time points and with the indicated stimulus. ELISPOT assays of isolated CD4+ or CD8+ T cells were performed as described in Huang et al., 2003, Cancer Res. 63:7321-9. H2-K$^b$/TRP2 class I peptide was used for mouse CD8+ T-cell stimulation. Irrelevant peptide from OVA was also used as a negative control. CD8+ T cells were isolated from splenocytes by using MACS CD8 (Ly-2) MicroBeads (Miltenyi Biotec Inc., Auburn Calif.).

Flow Cytometric Analysis

Cells were stained with FITC or PE mAbs in PBS containing 0.1% NaN$_3$ and 2% FCS. Antibodies specific for mouse CD8 (53-6.7), CD11c (HL3), CD40 (3/23), CD80 (16-10A1), CD86 (GL1), OX40L (RM134L), or PDL1 (M1H5) and matched isotype controls were purchased from BD Pharmingen (Franklin Lakes, N.J.) or eBioscience (San Diego, Calif.). Stained cells were analyzed on a FACSCalibur (Becton Dickinson, Lincoln Park, N.J., Franklin Lakes, N.J.) flow cytometer.

Tetramer Staining

H2-K$^b$/TRP2-PE tetramer assays were used to detect TRP2-specific mouse CD8+ T cells. TRP2-tetramers were synthesized at the Baylor College of Medicine Tetramer Core Facility (Houston, Tex., USA). Splenocytes from immunized mice were co-stained with anti-CD8α-FITC/anti-CD3-PerCP and H2-K$^b$/TRP2-PE. Tetramer staining was done at 4° C., for 1 h with 1 μg of anti-CD8α-Fitc and a 1:100 dilution of TRP2-PE tetramers per 10$^6$ cells, according to the manufacturer's instruction.

DC Immunization and Tumor Mouse Study

BM-derived DCs (day 4-5 of BM culture) were transduced with SOCS1-siRNA or GFP-siRNA at an MOI of 5 as described elsewhere herein. Briefly, DCs were pulsed with peptides for 20 hours, washed with PBS three times, stimulated with LPS (100 ng/ml, Sigma, St. Louis, Mo.) or TNFα (500 ng/ml, R&D Systems, Minneapolis, Minn.) for 24 hr, washed with PBS three times, and then injected into C57BL/6, CD8 KO, CD4 KO, or p35 KO mice via a rear foot-pad. In the therapeutic model, B 16 tumor cells (2.5×10$^5$) were injected subcutaneously (s.c.) into the right flank of syngeneic mice to establish a tumor model. On three days post tumor inoculation, the mice were randomly divided into groups and injected with 30 μl of peptide-pulsed (50 μg/ml), transduced DCs (1.5×10$^6$), or PBS control. In some mice, LPS (30 μg/mouse) or recombinant murine IL-12 protein (1 μg/mouse, Peprotech, Rocky Hill, N.J.) was administered intraperitoneally (i.p.) at indicated days after DC vaccination. Tumor volumes were measured every two days with a caliper until the experiment was completed.

CTL Assays

CD8+ CTL responses were assessed with a standard chromium release assay, which measures the ability of in vitro-restimulated splenocytes to lyse target cells (Huang et al., 2003, Cancer Res. 63:7321-9). Splenocytes pooled from 2-3 immunized mice were restimulated in vitro in RPMI-1640 containing H2-K$^b$/TRP2 peptide for 4-6 days. TRP2+ target B 16 cells (H2-K$^b$), and control EG.7 cells (ATCC, Manassas, Va.) were labeled with sodium $^{51}$Cr chromate solution for 90 minutes at 37° C. with shaking. Different numbers of effector cells were incubated with a constant number of target cells (5×10$^4$/well) in 96-well U-bottomed plates (200 μl/well) for four hours at 37° C. The supernatants from triplicate cultures were collected and analyzed. Percent lysis was calculated as (experimental release−spontaneous release)/(maximum release−spontaneous release)×100.

Statistical Analysis

For statistical analysis, Student's t test was used, and a 95% confidence limit was taken to be significant, defined as p<0.05. Results are typically presented as means±standard errors (SE).

The results of the experiments presented in this Example are now described.

Figure 9A:
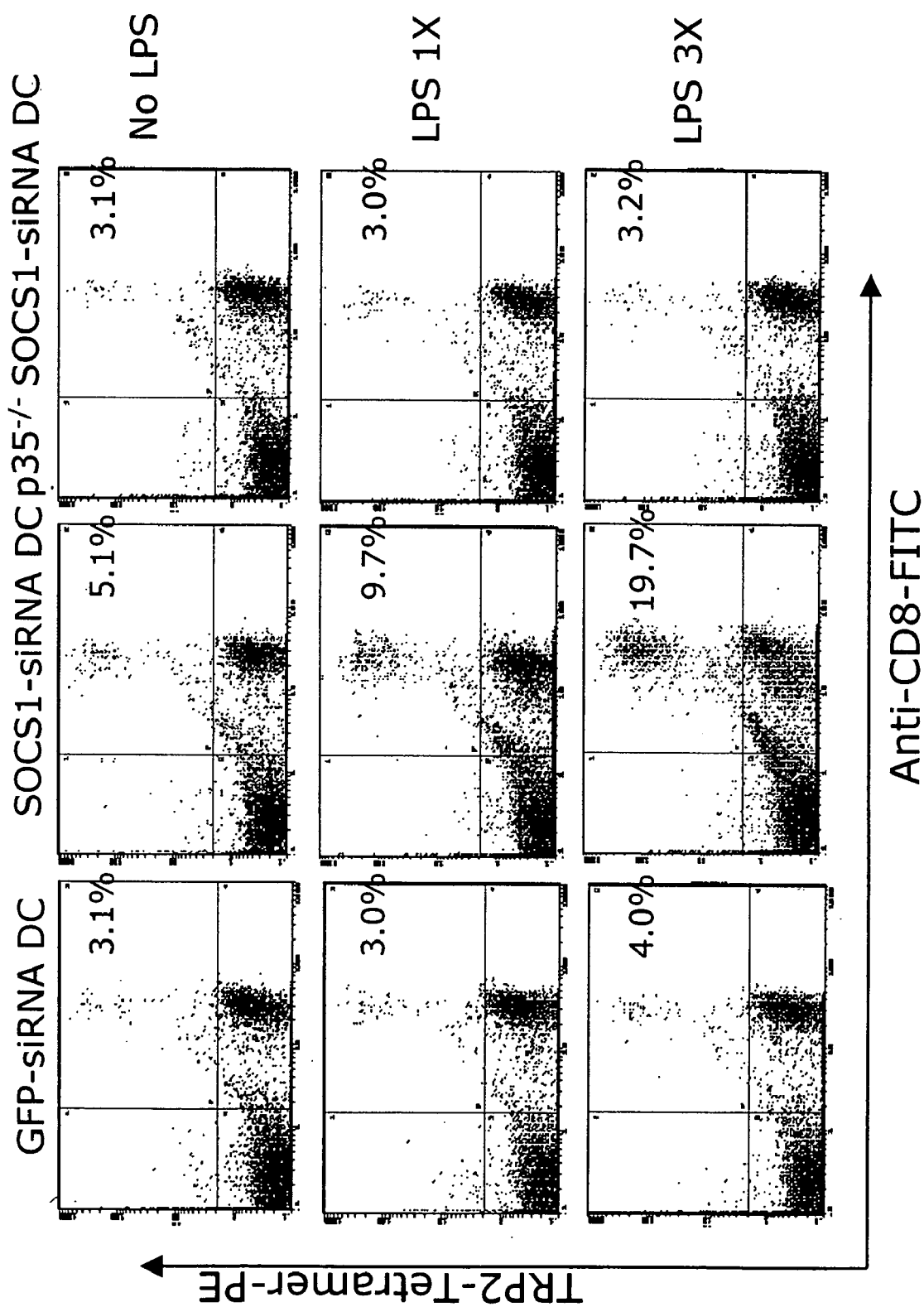
FIGS. 9A through 9C, is a series of images demonstrating that mature DC signaling restricted by SOCS1 controls the CTL response against a self-antigen and antitumor immunity.
Figure 9B:
Figure 9B:
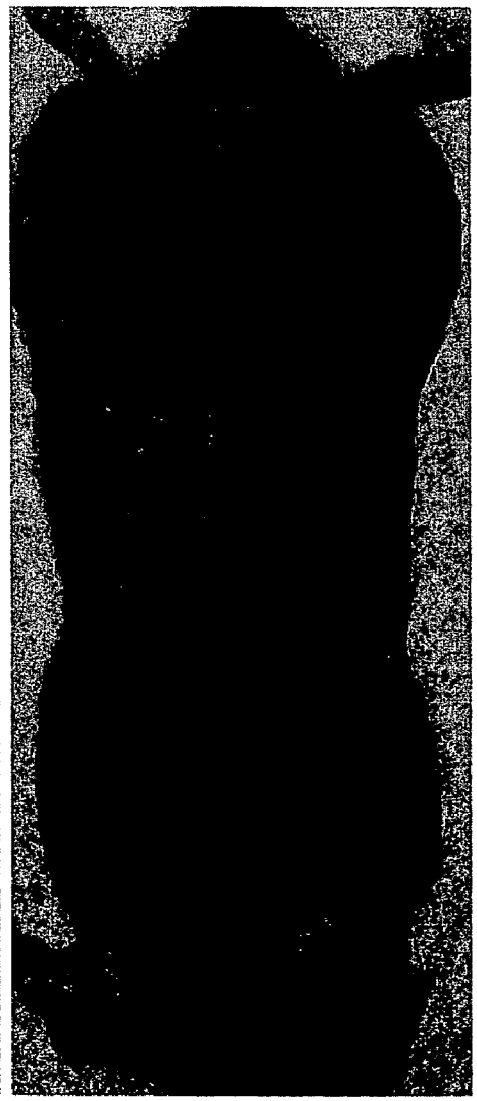
Figure 9C:
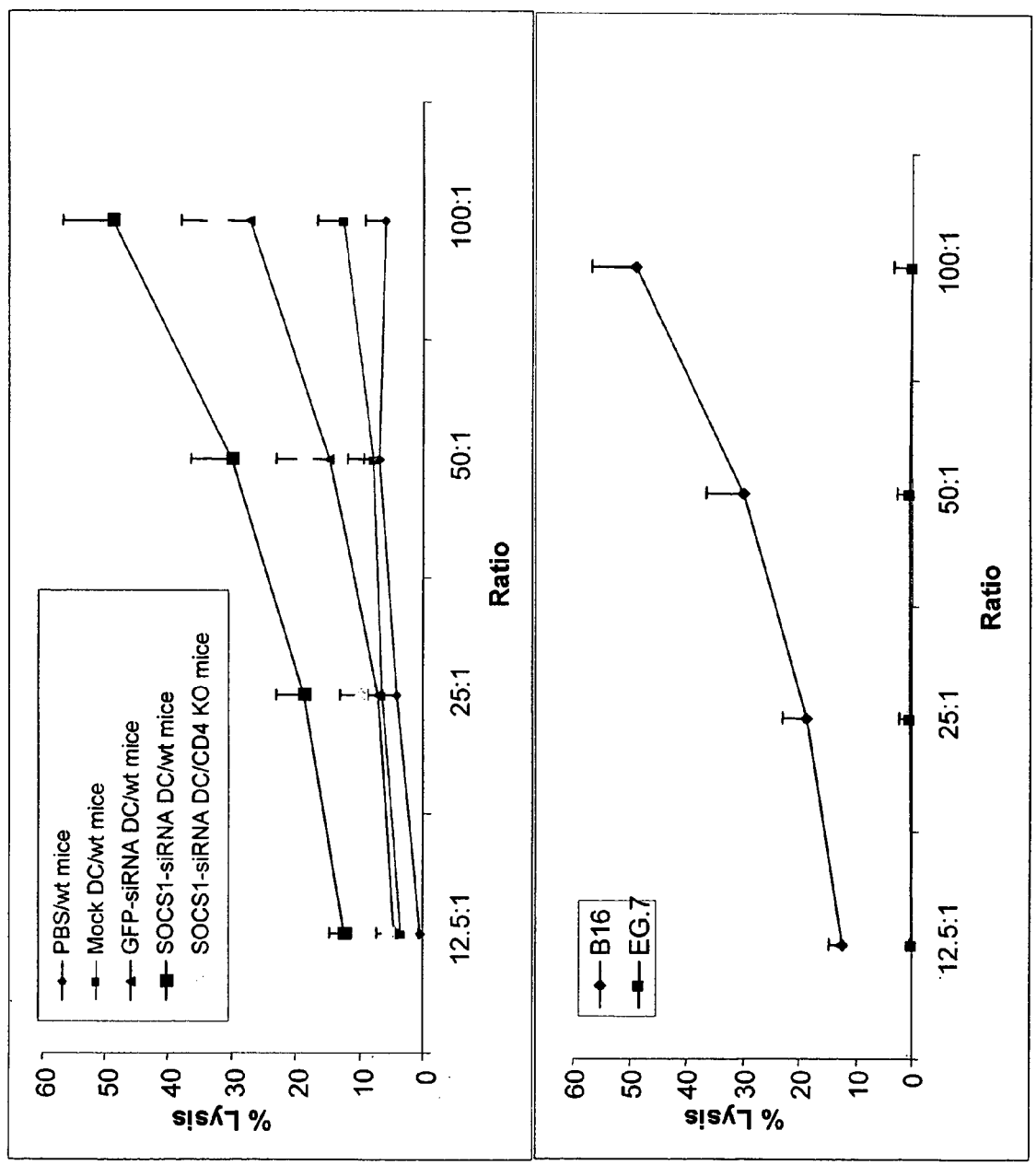

Signaling in Mature DCs, Restricted by SOCS1, Controls the Magnitude of Self-Antigen Specific CTL Responses and Tolerance C57BL/6 mice were immunized with TRP2 peptide-pulsed, transduced DCs that were matured ex vivo with LPS. The immunized mice were then stimulated in vivo in the presence or absence of LPS once or three times and TRP2-specific CTL responses were measured using tetramer analysis. LPS was chosen for in vivo stimulation due to the large number of pro-inflammatory cytokines it induces, many of which are regulated by SOCS1, as well as the documented role of SOCS1 in the direct regulation of NF-κB (p65) signaling (Ryo et al., 2003, Mol. Cell. 12:1413-26). In the absence of in vivo LPS stimulation, 5.1% of total CD8+ T cells were positive for TRP2-tetramer in mice immunized with SOCS1-siRNA DC, compared with only 3.1% in mice immunized with GFP-siRNA DC (FIG. 9A). With 1 or 3 times of in vivo LPS stimulation, the percentage of CD8+ T cells positive for TRP2-tetramer was substantially increased (9.7% and 19.4%, respectively) in mice immunized with SOCS1-siRNA DC, but largely unchanged in GFP-siRNA DC immunized mice (3.0% and 4.0%, respectively) (FIG. 9A). In agreement, CTL assay (FIG. 9C) and interferon-γ (IFNγ) ELISPOT indicated similar results. Furthermore, vitiligo (coat lightening, depigmentation and/or hair loss) was apparent in most of the TRP2 peptide-pulsed SOCS1-siRNA DC immunized mice co-injected with LPS at 3 months after immunization (FIG. 9B), indicating a break in self-tolerance to TRP2 normally expressed in host melanocytes. In contrast, no vitiligo was observed in any of the GFP-siRNA DC immunized mice, even with repeated in vivo LPS administrations, suggesting a critical role of SOCS1 in DCs for maintaining tolerance to self-antigens. These results demonstrate that signaling in mature antigen-presenting DCs controls the magnitude of CTL responses and self-tolerance, and that the signaling of mature DCs is strictly restricted by SOCS1.

Figure 10A:
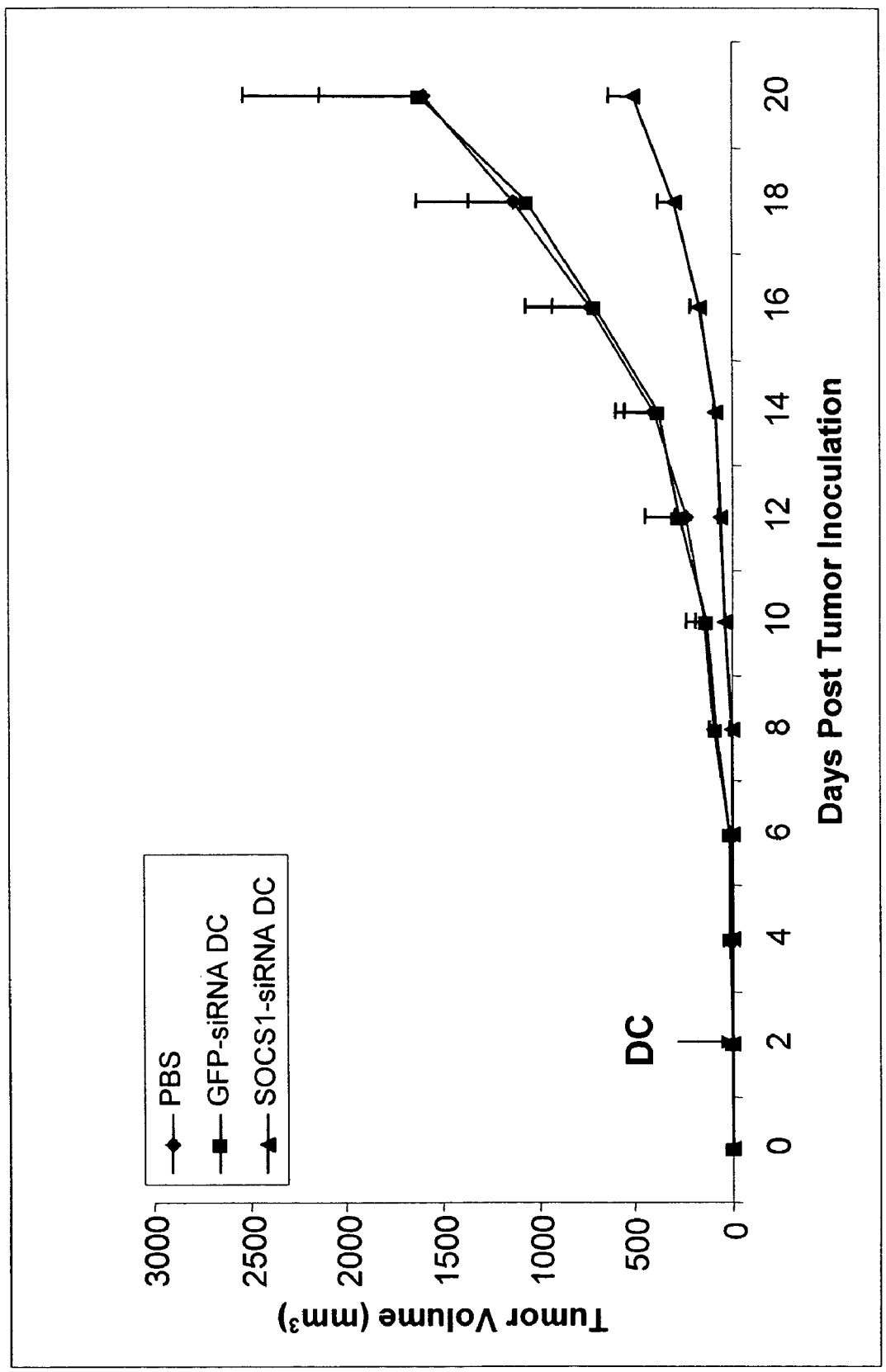
FIGS. 10A through 10D, is a series of charts demonstrating eradication of pre-established B16 tumors by SOCS1-siRNA DC immunization.
Figure 10B:
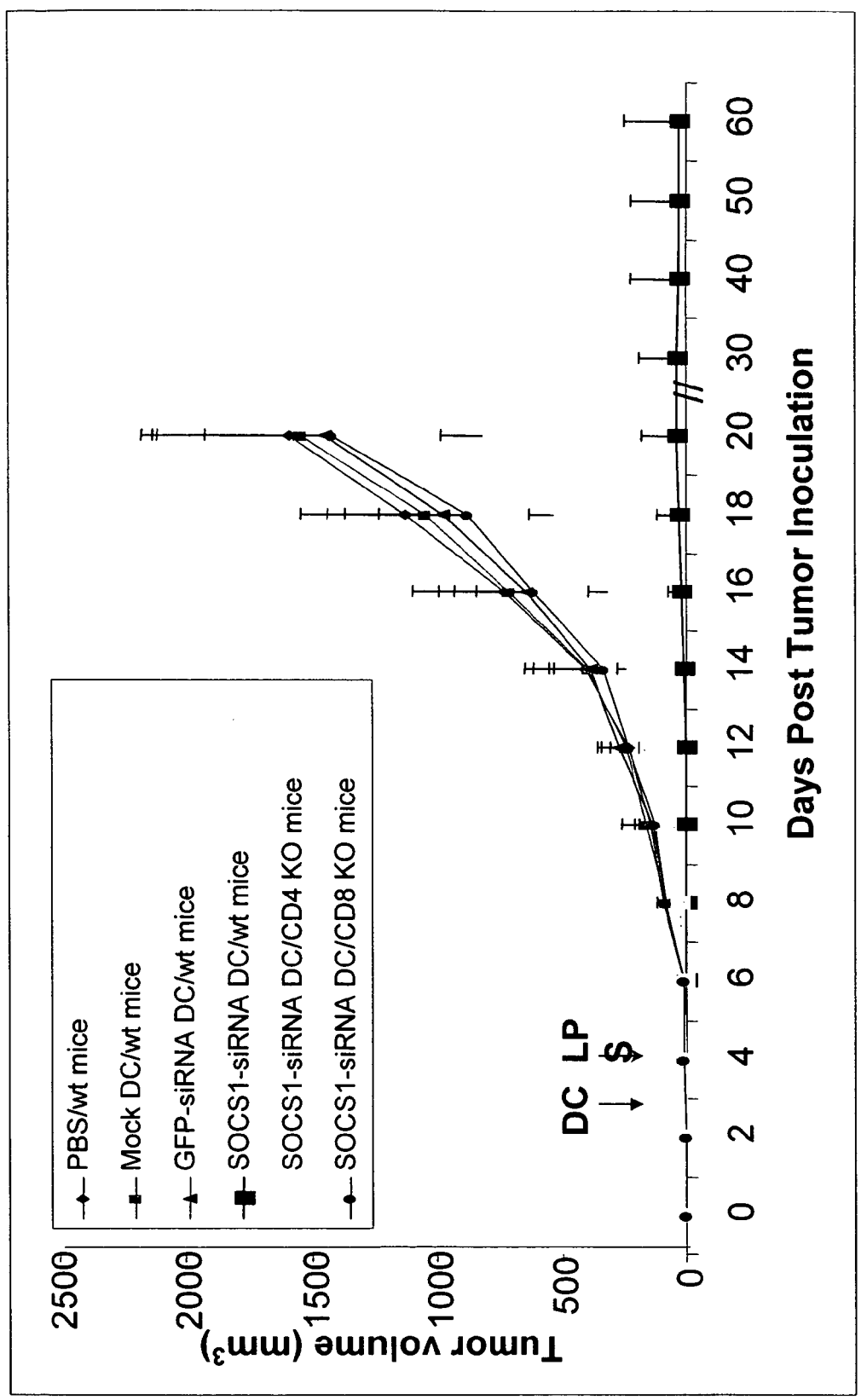
Figure 10C:
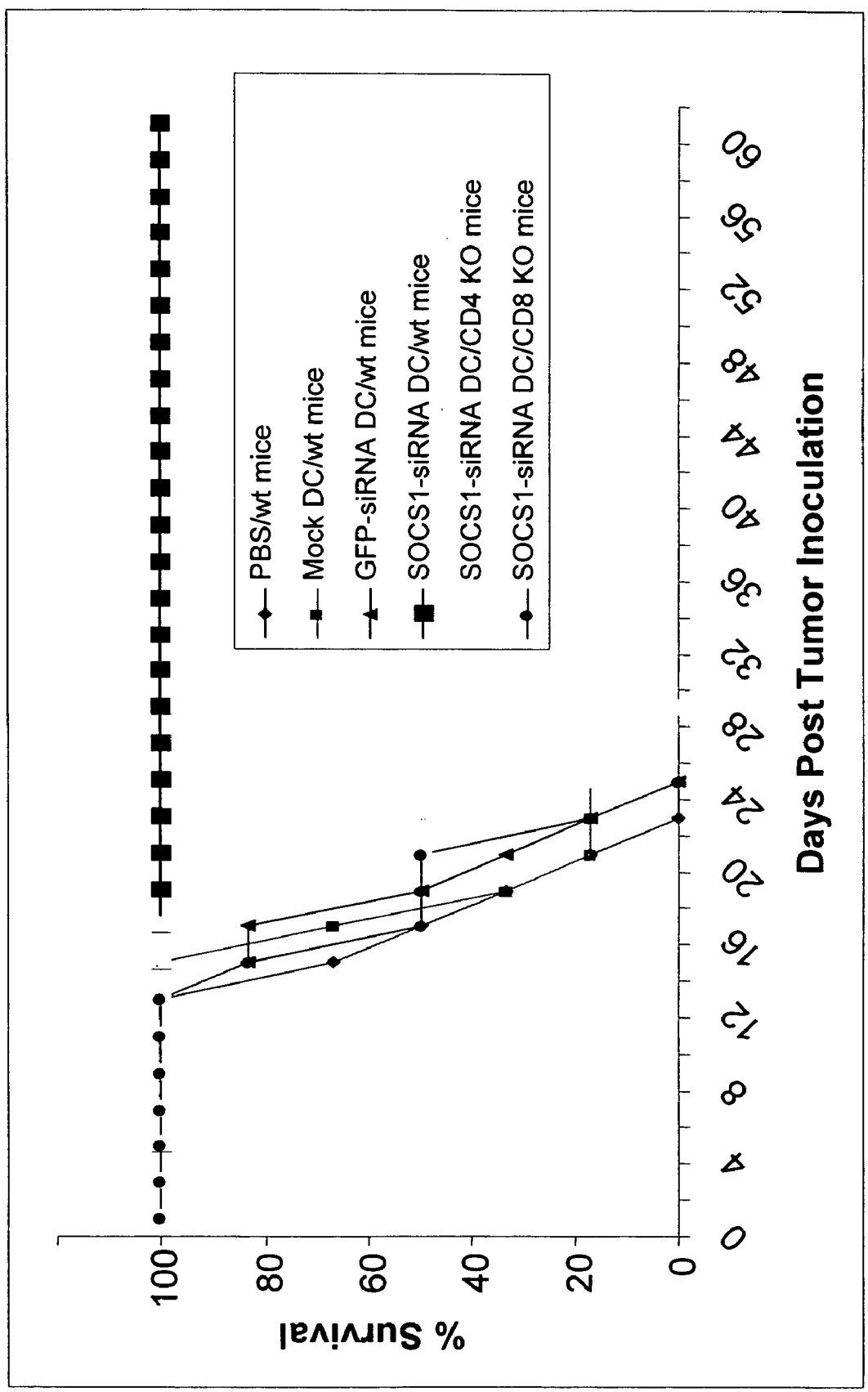
Figure 10D:
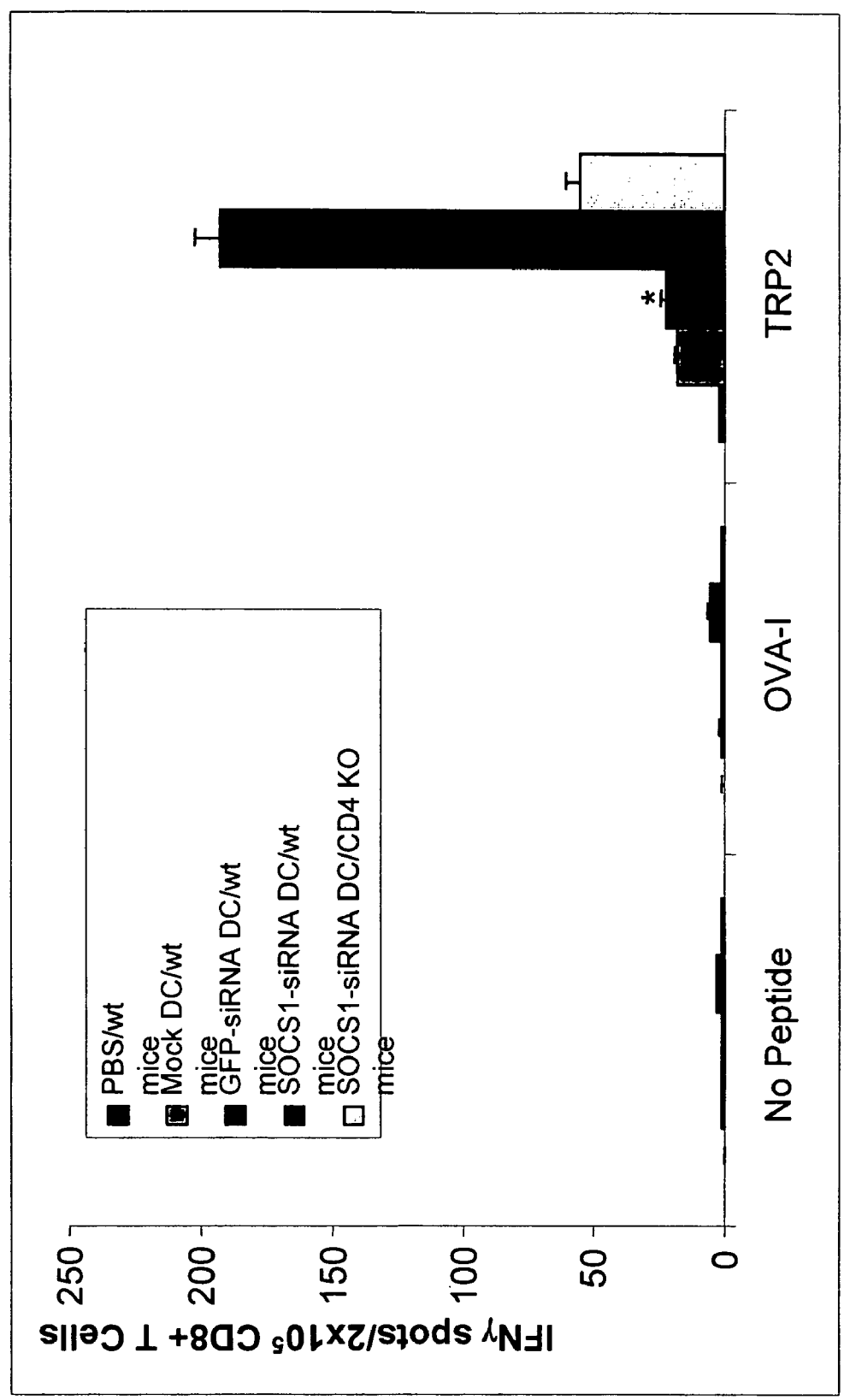

SOCS1-Restricted Signaling Controls the Ability of DCs to Break Self-Tolerance and Induce Effective Antitumor Immunity The primary goal of tumor vaccination is to break self-tolerance by inducing a strong adaptive immune response against self-antigens preferentially expressed on tumor cells. The observed role of SOCS1 in regulating the magnitude of self-antigen specific CTL responses and self-tolerance prompted the investigation of whether the ability of mature DCs to induce effective anti-tumor immunity is controlled by SOCS1 expression. To test this, C57BL/6 mice were inoculated subcutaneously with B16 tumor cells and three days later were immunized once with TRP2-pulsed, transduced DCs that were matured ex vivo with LPS. FIG. 10A shows that SOCS1-siRNA DC immunization alone was able to significantly inhibit the growth of B16 tumors compared with GFP-siRNA DC immunization (P<0.01). However, 50% of the SOCS1-siRNA DC immunized mice eventually succumbed to a tumor burden>1,500 mm$^3$ 30 days after tumor inoculation. To determine if mouse survival could be improved in SOCS1-siRNA DC immunized mice by enhancing pro-inflammatory signals, the mice were stimulated once in vivo with LPS one day after DC immunization. The addition of LPS stimulation to the immunization protocol substantially blocked the growth of B16 tumors in SOCS1-siRNA DC immunized mice (FIG. 10B). This was in contrast to GFP-siRNA DC and mock transduced DC controls which indicated no reduction in tumor burden compared to non-LPS stimulated mice (compare FIGS. 10A and 10B). Combination of SOCS1-siRNA DC immunization and LPS challenge also drastically increased mouse survival to 100% for >60 days (FIG. 10C). The enhanced anti-tumor activity was correlated with potent TRP2-specific CTL activities in SOCS1-siRNA DC immunized mice (FIG. 10D). By immunizing CD4 and CD8 knockout (KO) mice with SOCS1-siRNA DCs, it was further demonstrated that the anti-tumor activity required both CD8+ and CD4+ cells, although a weak anti-tumor activity was observed in immunized CD4 KO mice (FIG. 10B-10D). Collectively, these results indicate that SOCS1-restricted signaling in mature DCs controls their ability to break tolerance and induce effective anti-tumor immunity and that additional pro-inflammatory signals, normally regulated by SOCS1, can further increase the ability of the induced anti-tumor immune response to control a pre-established tumor burden.

Critical Role of SOCS1-Restricted Signal 3 in Control of Self-Tolerance and Anti-Tumor Immunity SOCS1 likely influences the signaling and outputs of mature DCs by regulating antigenic peptide/MHC presentation, co-stimulation and/or cytokine signaling and secretion. The following experiments were set out to investigate which of these three signal(s) is/are primarily regulated by SOCS1 for the control of self-antigen specific CTL responses and anti-tumor immunity.

Figures 1, 11A:
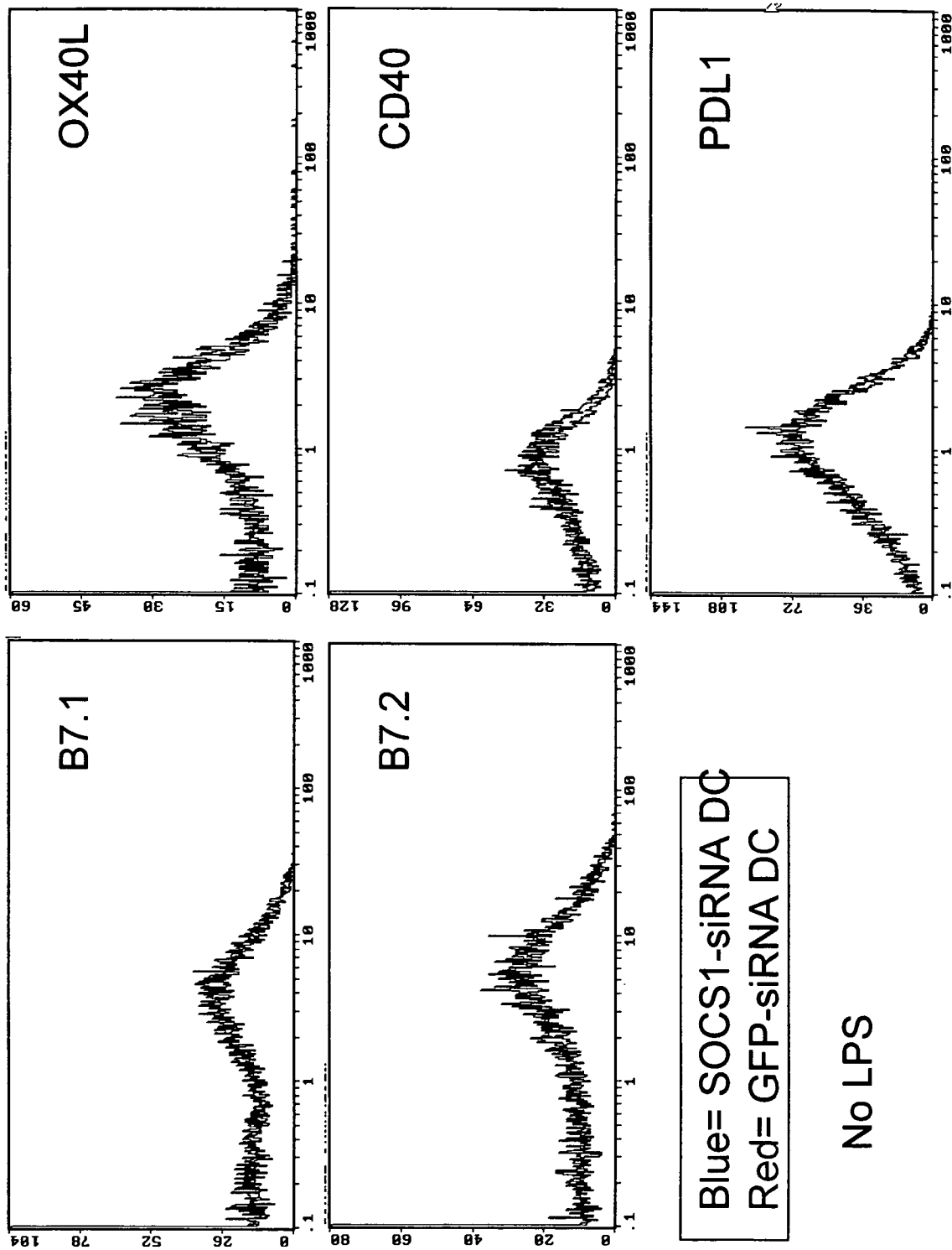
FIG. 1, comprising
FIGS. 11A through 11C, is a series of charts demonstrating potent CTL responses and antitumor activities induced by SOCS1-silenced DCs pulsed with either low or high affinity peptide.
Figures 2, 11A:
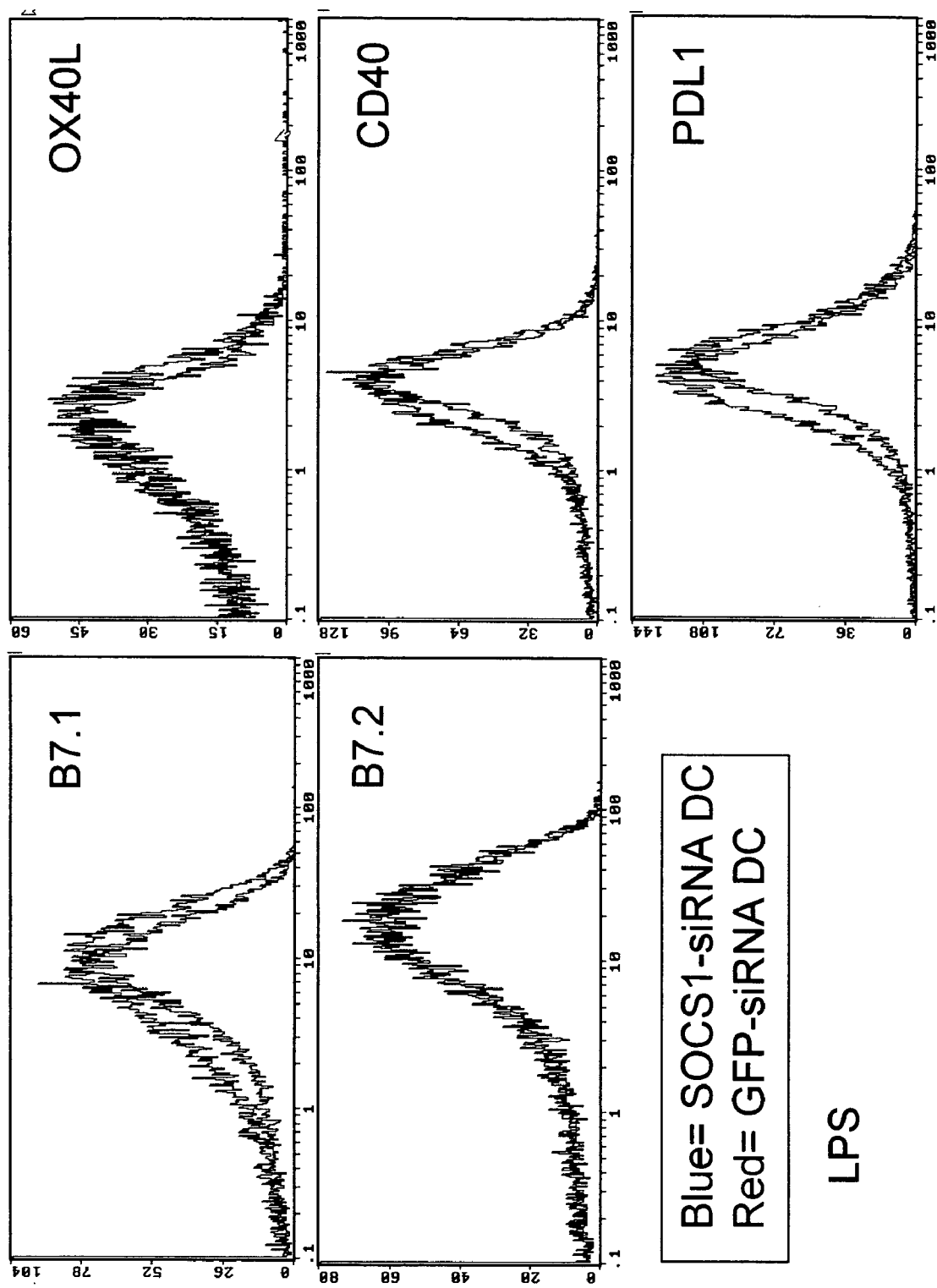

It was first tested whether SOCS1 silencing influences the expression of co-stimulatory molecules (signal 2). By flow cytometric assays, it was consistently observed that there were undetectable or only slightly enhanced surface levels of co-stimulatory/inhibitory molecules (B7.1, B7.2, OX40L, CD40 or PDL1) on SOCS1-siRNA DCs compared with those on GFP-siRNA DCs both before and after LPS-induced maturation (FIG. 11A). Comparable levels of MHC-I and II molecules were also detected on SOCS1-siRNA DCs and GFP-siRNA DCs.

Figure 11B:
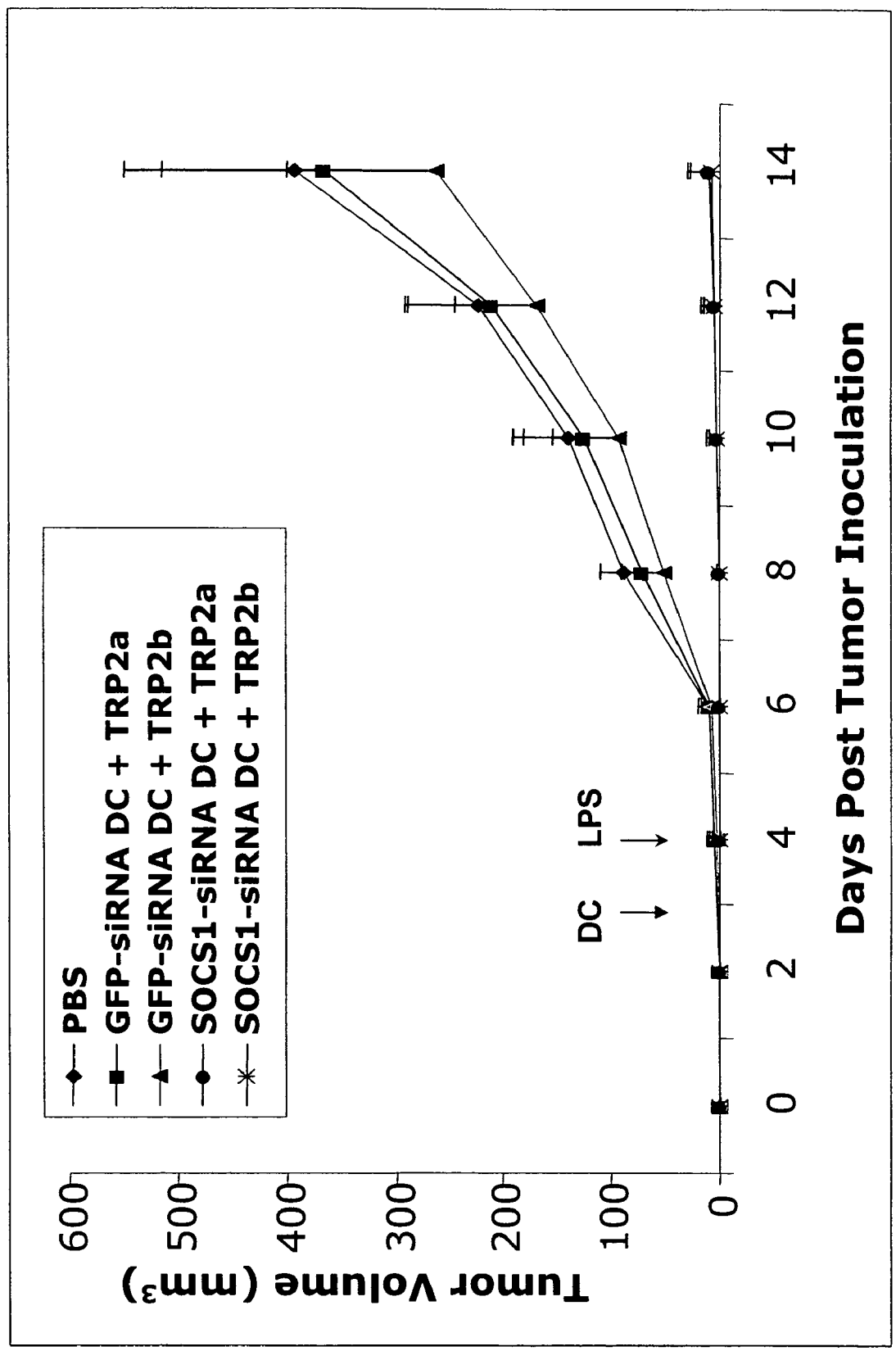
Figure 11C:
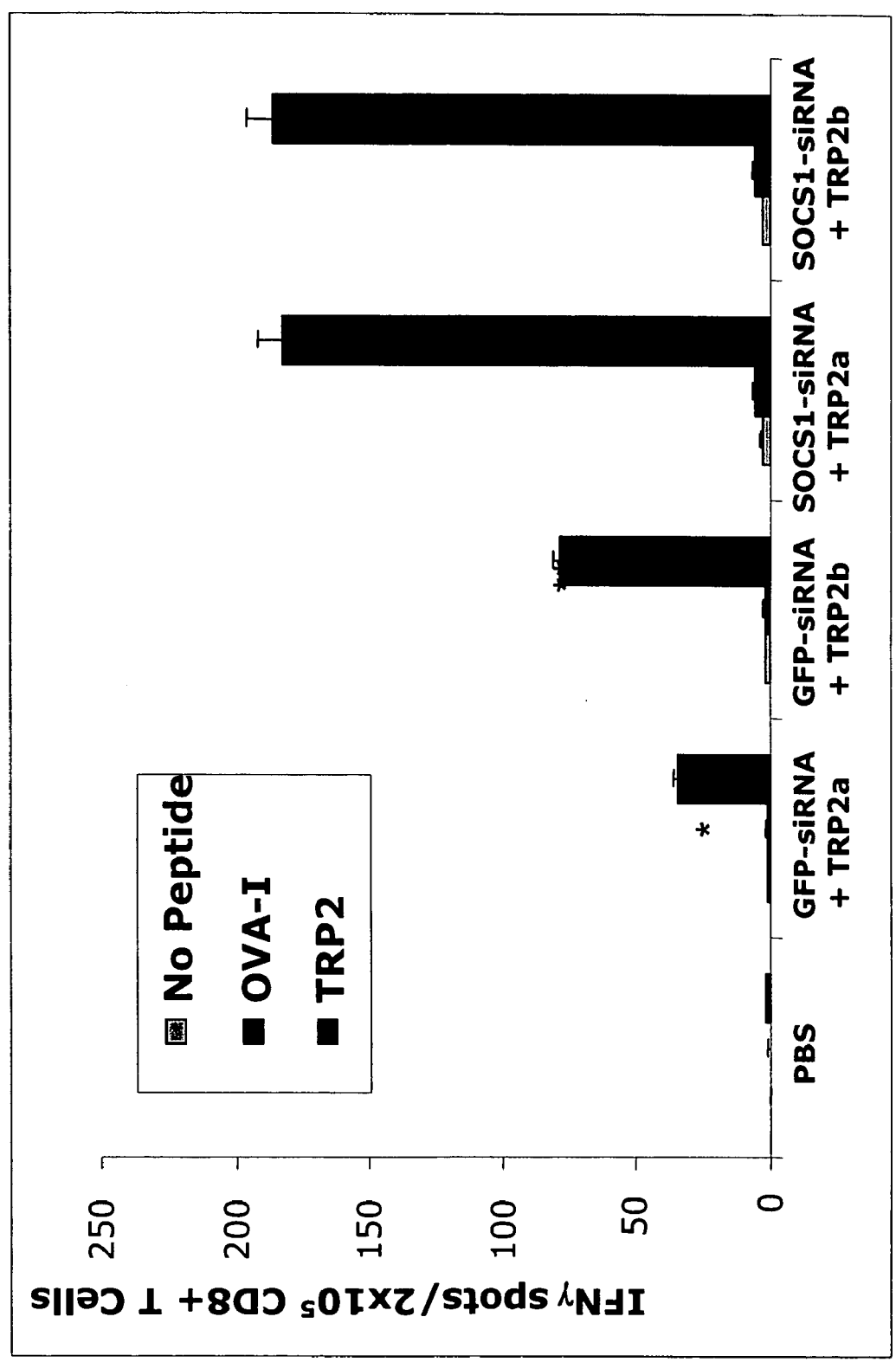

Given the importance of CD8+ T cells in inducing anti-tumor immunity it was further investigated whether MHC-I-restricted peptide immunogenicity (TCR affinity) plays an important role in SOCS1-restricted antigen presentation in vivo. Since a high affinity form (TRP2b) and a low affinity form (TRP2a) of the TRP2 CTL peptide were identified previously (van Elsas et al., 2001, J. Exp. Med. 194:481-9), both TRP2 peptides were used to test whether the strength of signal 1 can influence the ability of transduced DCs to induce an anti-tumor immune response. FIG. 11B shows that mature GFP-siRNA DCs loaded with either the low (TRP2a) or high affinity (TRP2b) peptide were unable to induce B16 tumor regression with in vivo LPS stimulation, although GFP-siRNA DCs loaded with the TRP2b peptide indicated a marginal anti-tumor activity (statistically insignificant). In contrast, both SOCS1-siRNA DC groups loaded with either the low or high affinity TRP2 peptide effectively blocked tumor growth. TRP2-specific CTL activities in immunized mice were also investigated using an IFNγ ELISPOT assay. FIG. 11C shows that GFP-siRNA DCs loaded with the high affinity peptide induced stronger IFNγ responses than did GFP-siRNA DCs loaded with the low affinity peptide. However, both SOCS1-siRNA DC groups loaded with either low or high affinity peptide induced much stronger IFNγ responses than GFP-siRNA DCs loaded with high affinity peptide (P<0.01), which is in agreement with the observed anti-tumor activity (FIG. 11B). In addition, SOCS1-siRNA DCs loaded with low or high affinity peptide induced similar IFNγ responses (FIG. 11C).

The results of these experiments demonstrate that SOCS1 silencing does not have a significant impact on the expression of co-stimulatory/inhibitory molecules (signal 2) and MHC-I and II molecules on DCs in the presence or absence of maturation; and mature DCs loaded with either high or low affinity TRP2 peptide (signal 1) are ineffective in inducing potent IFNγ responses and anti-tumor immunity unless SOCS1 is silenced.

Example 6

In Vivo IL-12 Enhancement of CTL and Antitumor Acitivity Induced by Mouse SOCS1 siRNA DCs Although the initiation of cytotoxic T cell (CTL) responses by dendritic cells (DCs) has been well studied, the mechanisms for regulating the maintenance or breaking of self-tolerance remain poorly defined. In this example, it is demonstrated that mature DCs in which suppressor of cytokine signaling (SOCS) 1 has been silenced, not mature wild-type DCs, are effective in breaking self-tolerance, especially when in vivo stimulated with a microbial product or IL-12. The experiments disclosed herein demonstrate that SOCS1-restricted signal 3 (IL-12), not the antigen affinity (signal 1) and levels of co-stimulatory molecules (signal 2), provided by antigen-presenting DCs critically controls self-tolerance. Further, the present disclosure demonstrates that SOCS1-silenced DCs induce potent immune responses against a self-antigen, blocking the growth of a pre-established B16 tumor. Moreover, human SOCS1-silenced DCs have a superior ability to fully activate self-antigen-specific human CTLs with lytic effector function, implying the translational potential of this SOCS1 silencing approach.

Figure 12A:
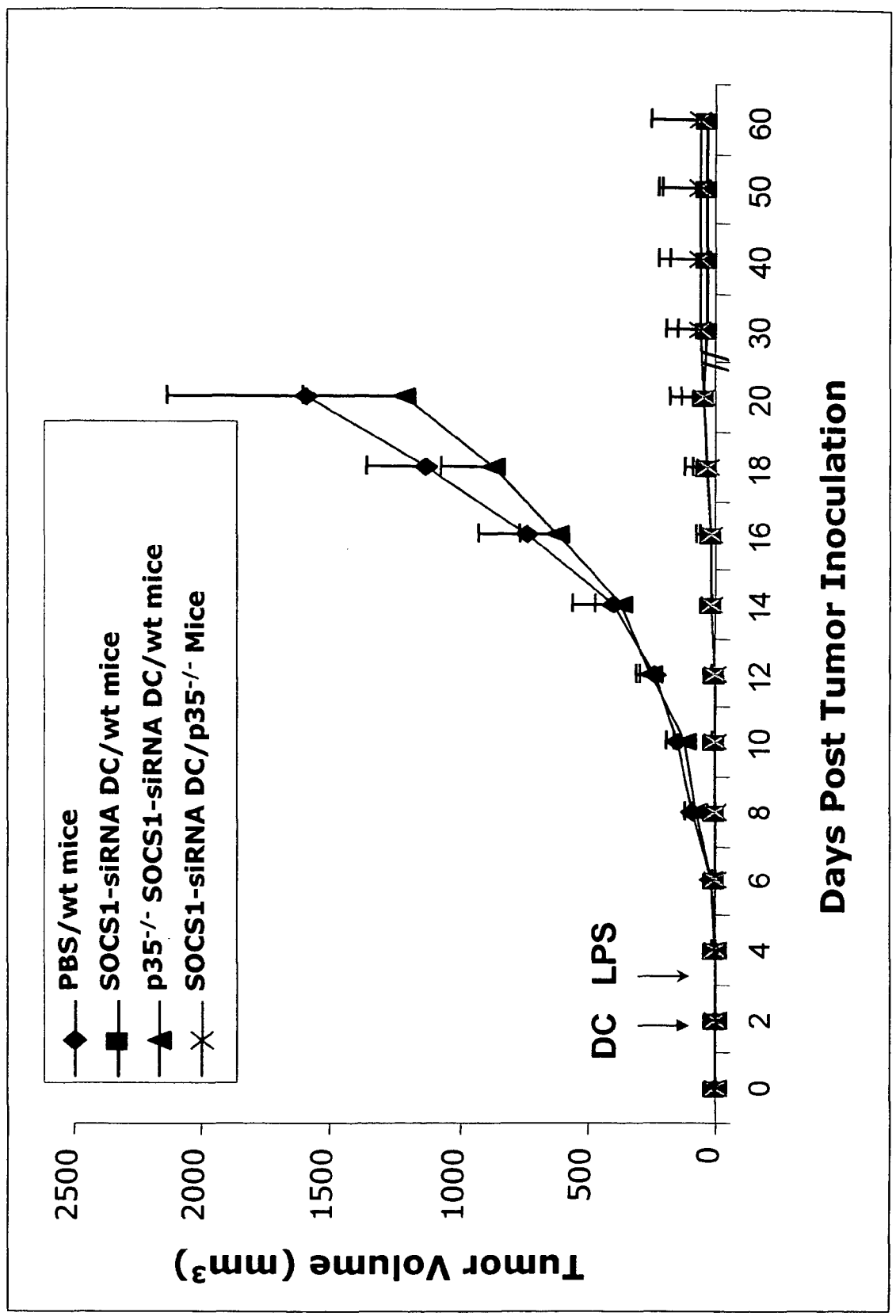
FIGS. 12A through 12D, is a series of charts demonstrating the lack of induction of effective anti-tumor responses by IL-12 KO SOCS1 siRNA-DCs.
Figure 12B:
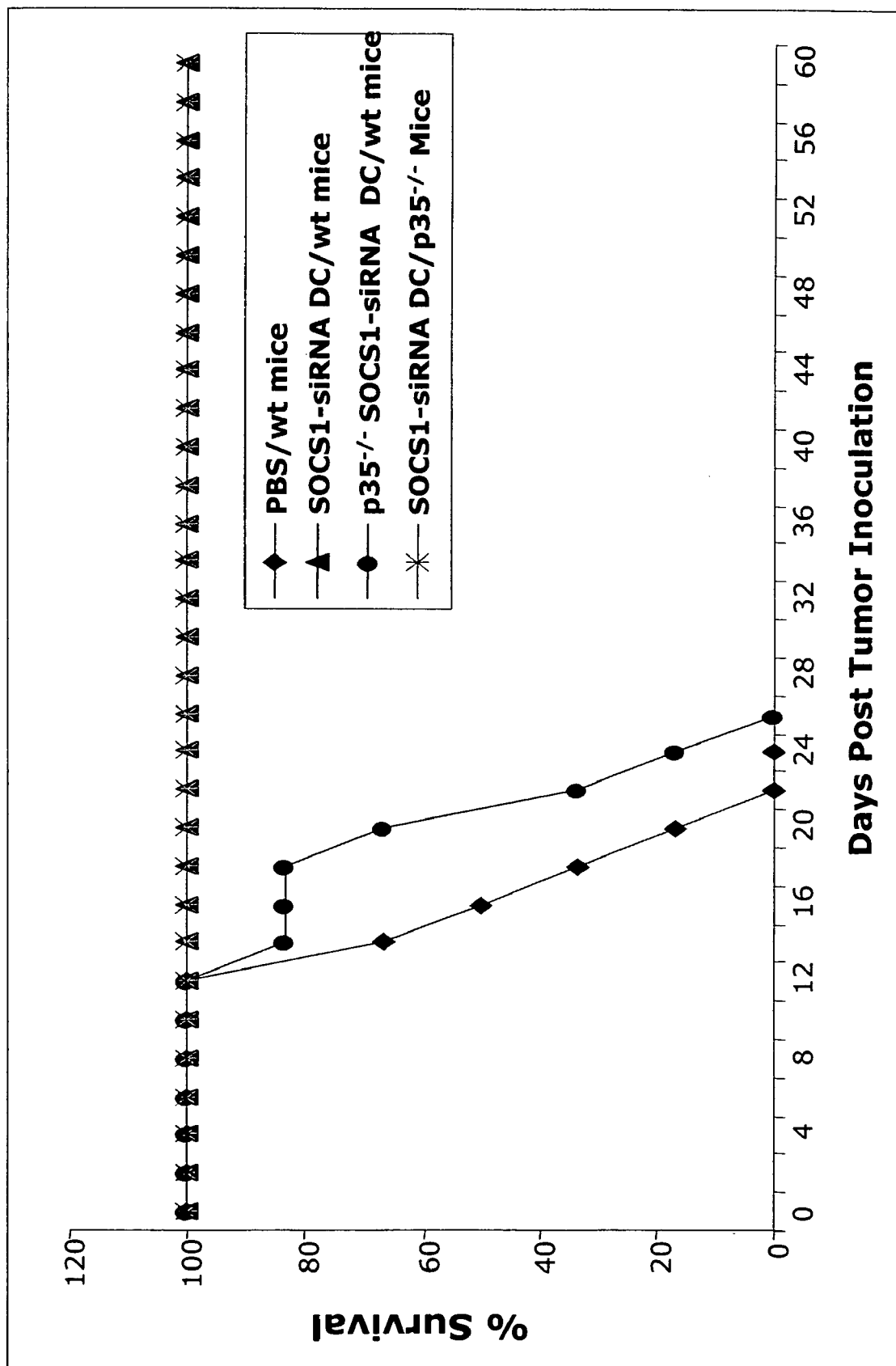
Figure 12C:
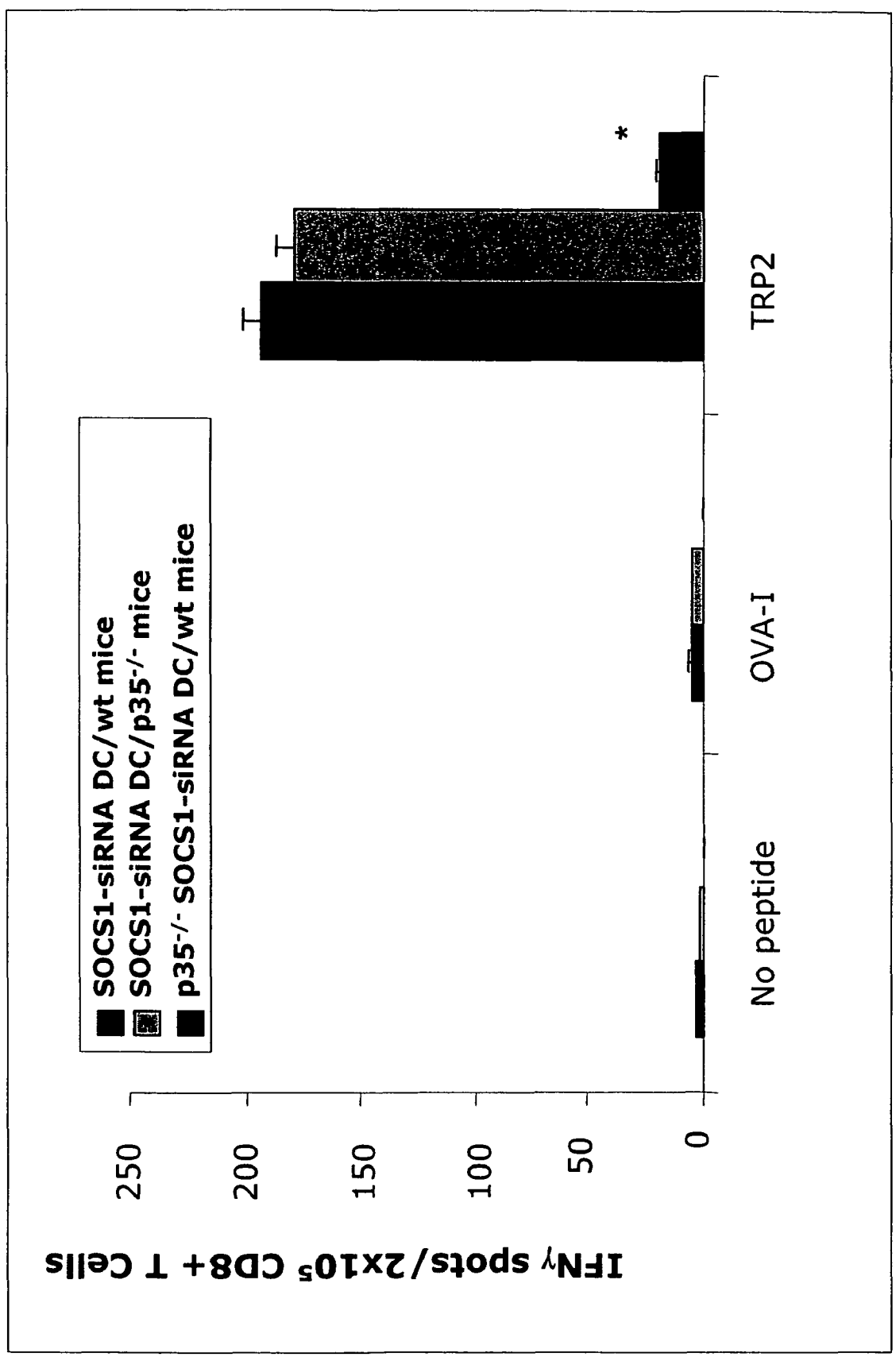
Figure 12D:
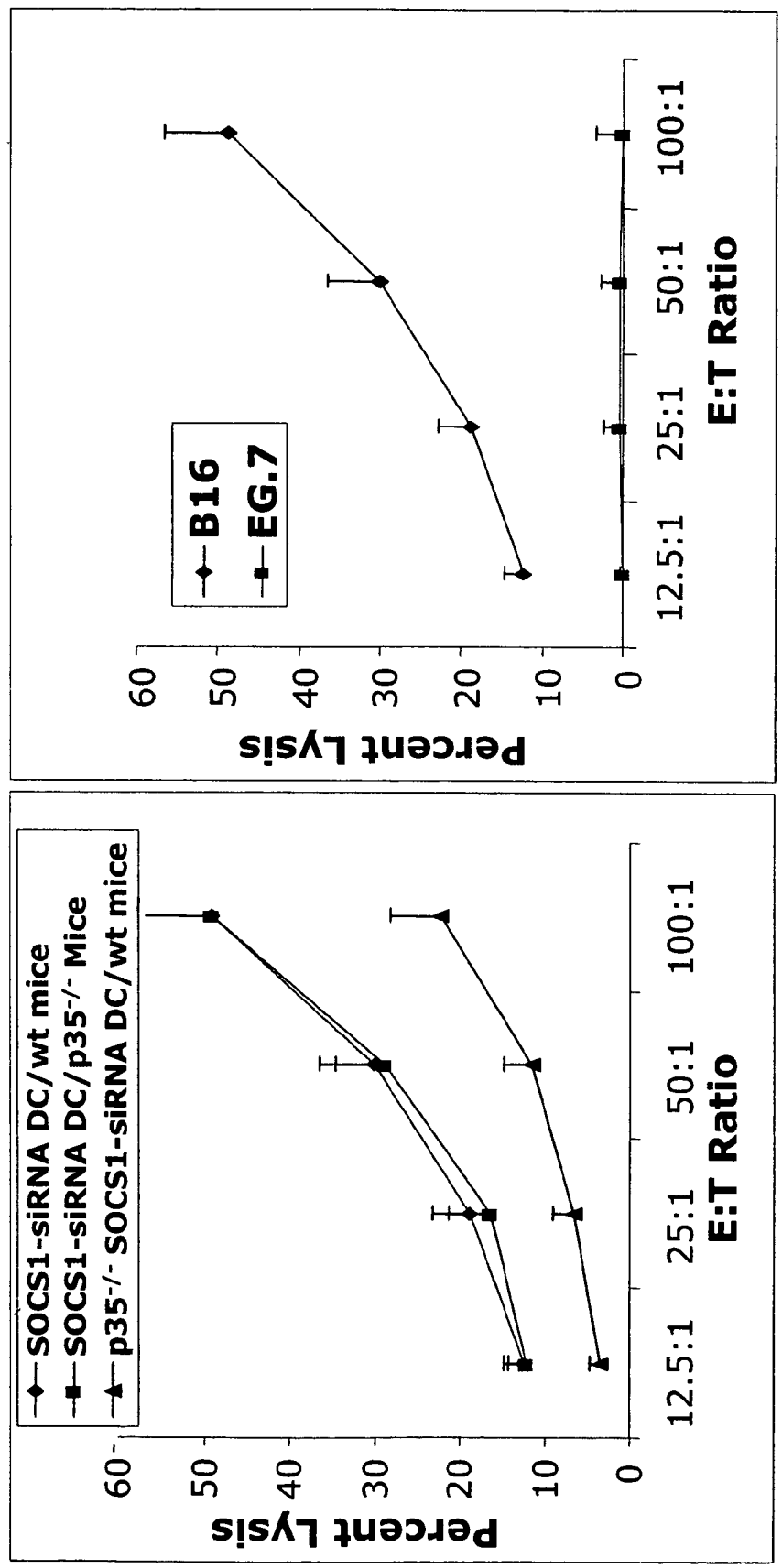

The likely importance of SOCS1-restricted signal 3 in the control of self-antigen specific CTL activation and tolerance prompted the identification of key cytokine(s) regulated by SOCS1 in mature DCs. The importance of several candidate pro-inflammatory cytokines known to influence CTL activation was initially tested by using DCs derived from different genetically homozygous KO mice for DC vaccination in combination with SOCS1 silencing. When DCs from IL-12 (p35$^{-/-}$) KO mice were used for immunization, p35$^{-/-}$ SOCS1-siRNA DCs loaded with the TRP2 peptide were observed to no longer inhibit the growth of B16 tumors (FIGS. 12A-12B), suggesting a critical role for SOCS1-restricted and DC produced IL-12 for tumor regression. To determine further the role of IL-12 in SOCS1-restricted DC function, CTL responses induced by p35$^{-/-}$ SOCS1-siRNA DCs was assessed. Using IFNγ ELISPOT and CTL assays, it was observed that p35$^{-/-}$ SOCS1-siRNA DCs had a significantly reduced ability to induce TRP2-specific CTL responses compared with wildtype SOCS1-siRNA DCs (FIGS. 12C and 12D). In addition, in vivo stimulation with LPS failed to boost CTL responses induced by p35$^{-/-}$ SOCS1-siRNA DCs as measured by TRP2-tetramer analysis (FIG. 9A). Interestingly, in contrast to the essential role of IL-12 produced by antigen-presenting DCs, IL-12 (p35$^{-/-}$) KO mice immunized with wildtype SOCS1-siRNA DCs were observed to also induced active anti-tumor immunity and CTL responses, indicating that IL-12 produced by resident host cells is not required for the induction of self-antigen specific CTL responses (FIGS. 12A-12D). Taken together, these results indicate that SOCS1-restricted IL-12 produced by antigen-presenting DCs is important for inducing a potent TRP2-specific CTL response and B16 tumor eradication.

Persistent and Enhanced Production of IL-12 and IL-12-Induced Cytokines by SOCS1-Silenced DCs Versus Transient and Low Production by wt DCs DCs produce significant amounts of IL-12 in response to microbial products such as LPS and CD40 ligation (Schulz et al., 2000, Immunity 13:453-62). IL-12 production by DCs is tightly restricted to a short time period (8-16 hours) following the induction of maturation (Langenkamp et al., 2000, Nat. Immunol. 1:311-6) and is regulated by SOCS1 (Eyles et al., 2002, J. Biol. Chem. 277:43735-40). Given the identified important role of SOCS1-restricted IL-12 in the regulation of adaptive immunity, the effect of SOCS1 silencing on the strength and duration of IL-12 production by DCs, which may be closely related to the ability of SOCS1-siRNA DCs to break immune tolerance and induce an effective anti-tumor immune response to TRP2, was examined.

Figure 13A:
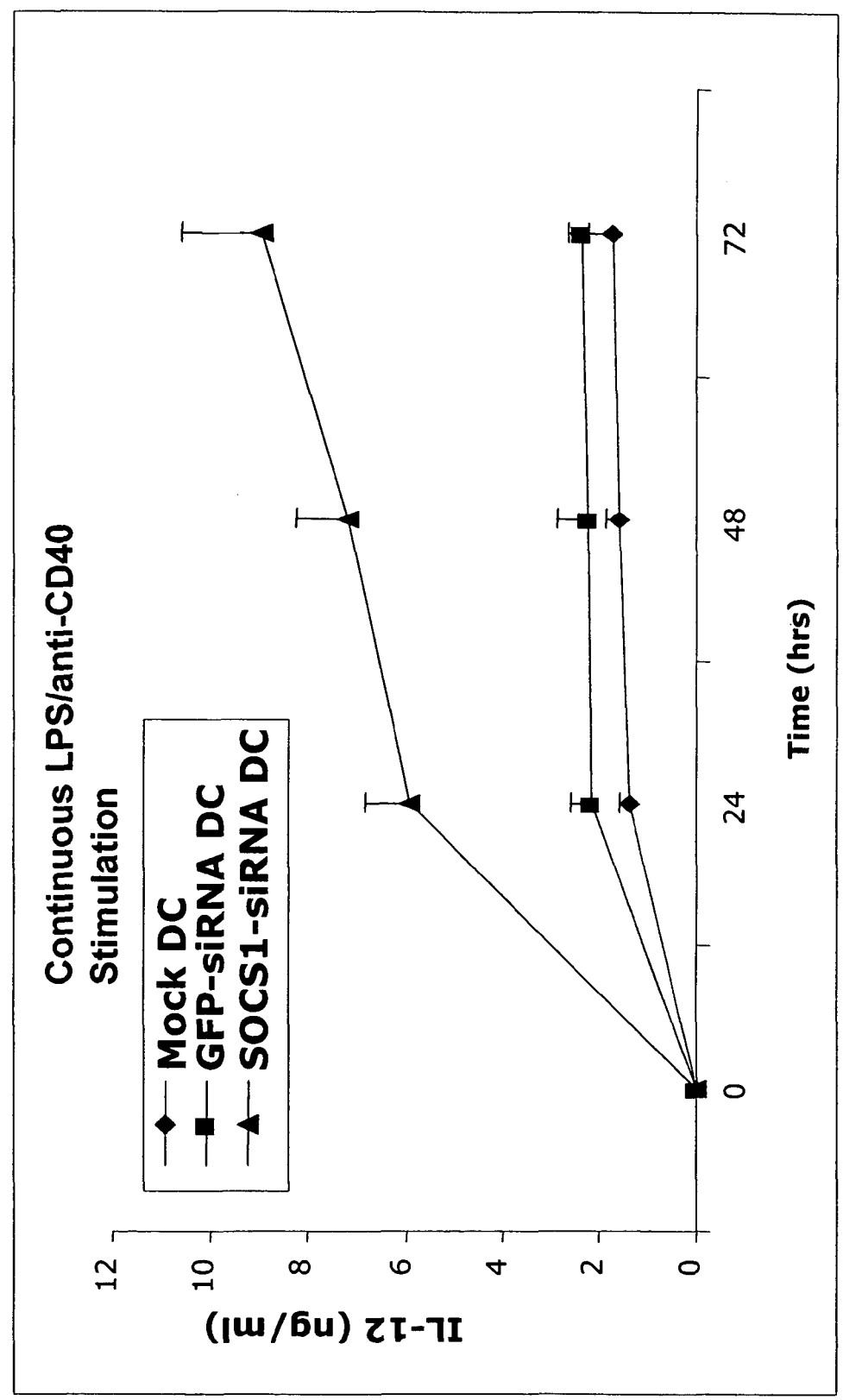
FIGS. 13A through 13D, is a series of charts demonstrating that SOCS1 controls IL-12 and IL-12-induced cytokine production by DCs.
Figure 13B:
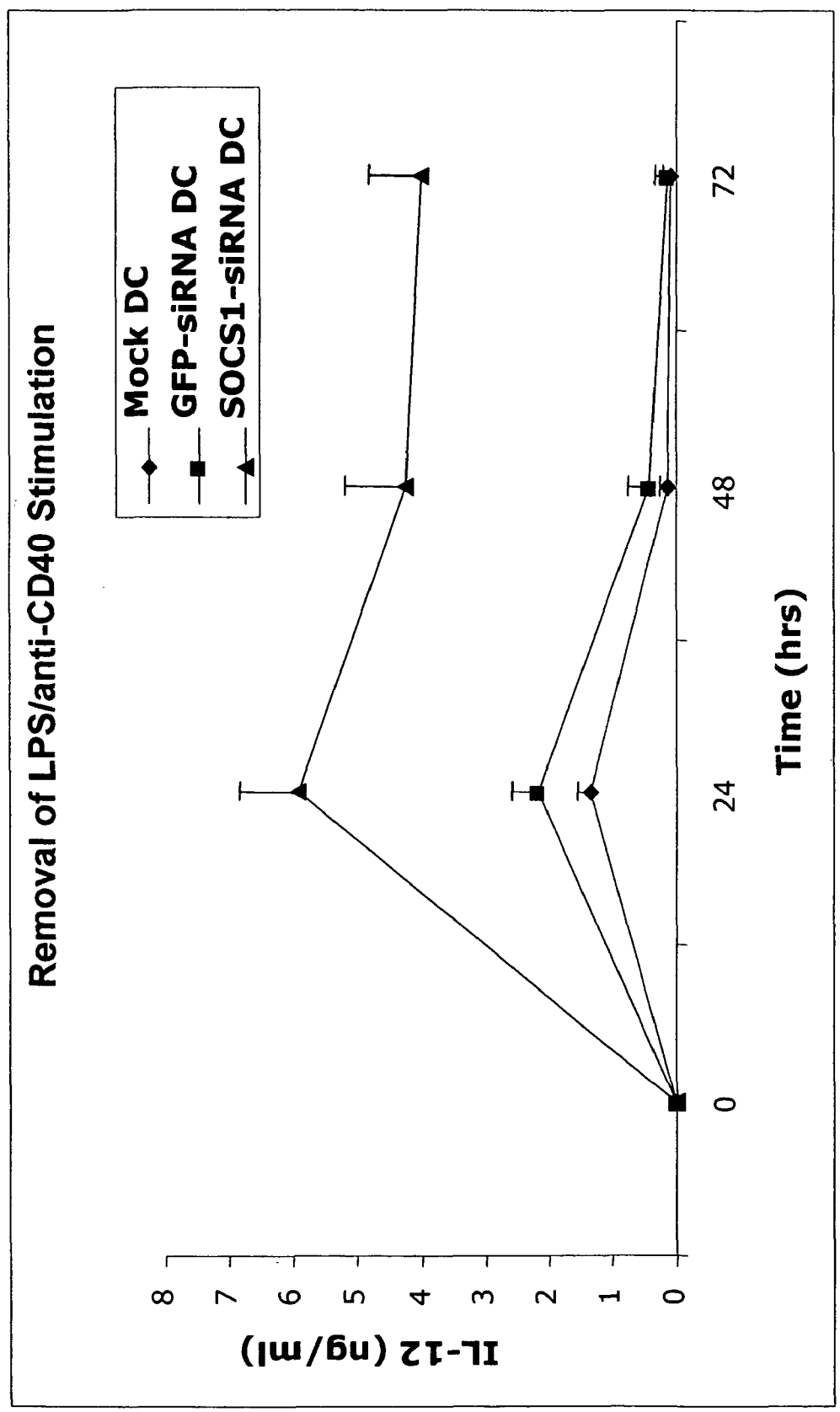

FIG. 13A shows that significantly increased levels of IL-12 (p70) were produced by SOCS1-siRNA DCs in response to continuous stimulation, with LPS and anti-CD40 mAb, over a 72 hour period compared with GFP-siRNA DCs and mock transduced DCs. The ability of SOCS1-siRNA DCs to maintain IL-12 levels, despite removal of the original stimuli was then examined, by stimulating them with LPS/anti-CD40 for 24 hours and then transferring the DCs in fresh medium that did not contain LPS into new culture plates. FIG. 13B shows that GFP-siRNA DCs and mock transduced DCs only transiently produced IL-12 upon stimulation, while SOCS1-siRNA DCs persistently produced significantly higher levels of IL-12 despite the removal of the stimuli. Without wishing to be bound by any particular theory, the prolonged and enhanced production of IL-12 by SOCS1-siRNA DCs after the removal of LPS/anti-CD40 may be due to the prolonged activation of signaling pathways induced by the original stimuli and/or possibly autocrine/paracrine stimulation by IL-12 or other DC-secreted pro-inflammatory cytokines. These results indicate that SOCS1 silencing allows DCs to produce sustained and increased levels of IL-12 in response to stimulation, which may be responsible for the ability of SOCS1-silenced DCs to break tolerance and eradicate pre-established tumors.

Since SOCS1 is a critical regulator of the Jak/Stat pathway which mediates the signaling of IL-12 and other cytokines (Kubo et al., 2003, Nat. Immunol. 4:1169-76; Alexander et al., 2004, Annu. Rev. Immunol. 22:503-29), the next set of experiments were set out to test whether SOCS1 silencing in DCs increases cytokine production through the development of a cytokine feedback loop between themselves and possibly other nearby DCs. To address this, the production of tumor necrosis factor (TNF)α and IL-6 by SOCS1-siRNA DCs was measured. (TNF)α and IL-6 was tested because these cytokines are known to be induced by IL-12 stimulation (Trinchieri et al., 2003, Nat. Rev. Immunol. 3:133-46).

Figure 13C:
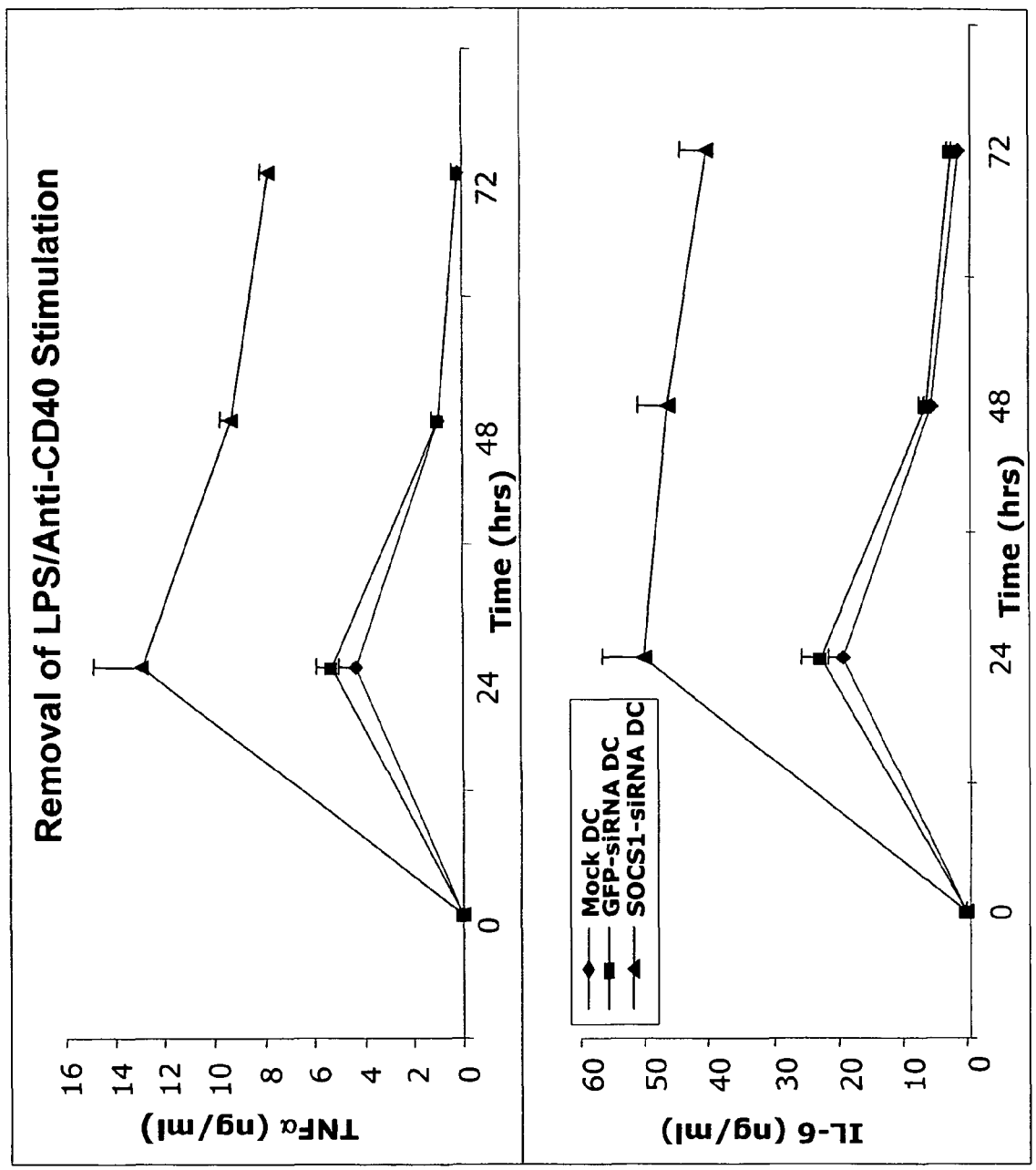
Figure 13D:
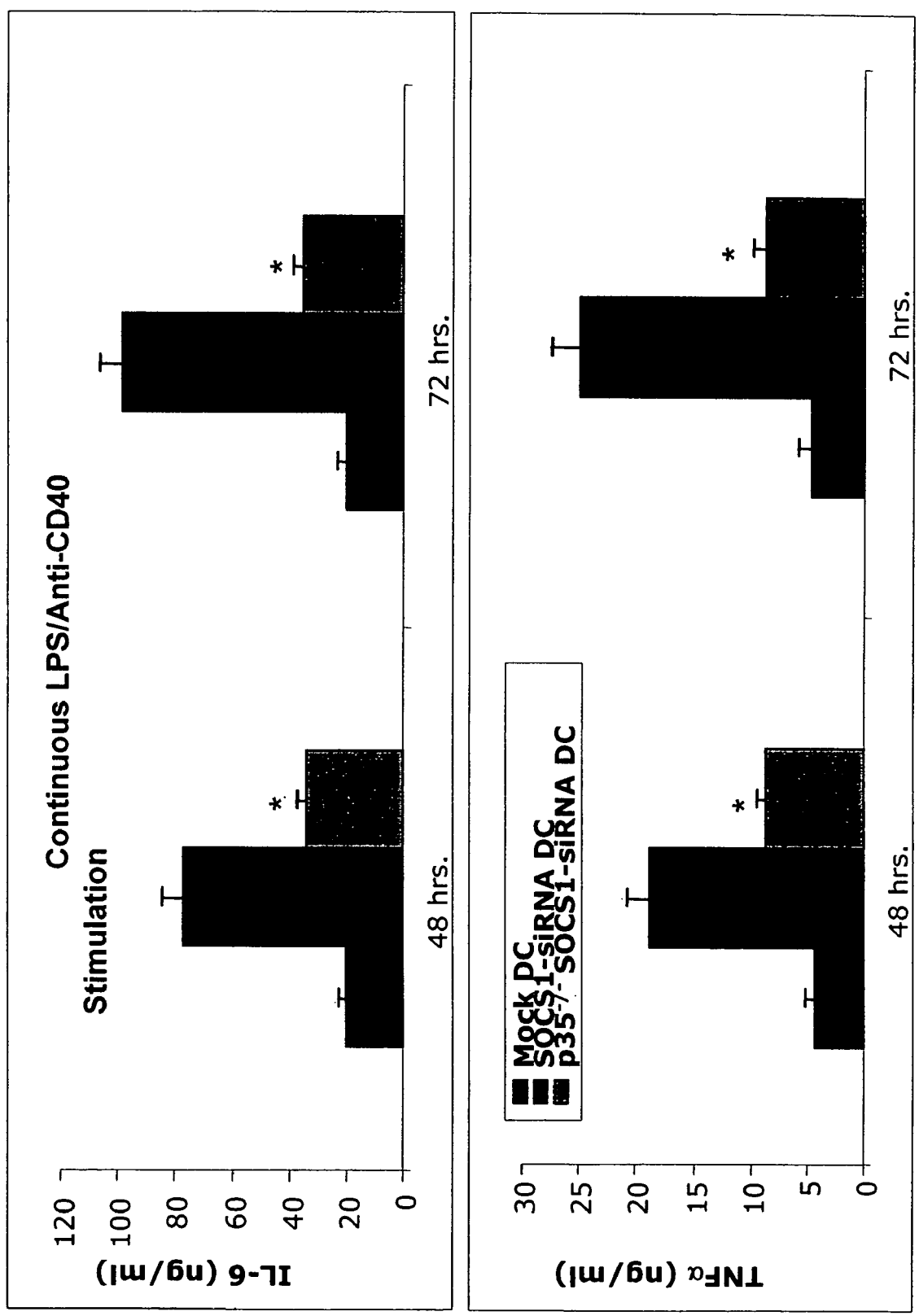

FIG. 13C shows that SOCS1-siRNA DCs persistently produced higher levels of TNFα and IL-6 following the removal of the original stimulus, as opposed to GFP-siRNA DCs and mock transduced DCs which only transiently produced low levels of TNFα and IL-6. To determine further the importance of IL-12 for the development of a feedback loop, TNFα and IL-6 production by p35$^{-/-}$ SOCS1-siRNA DCs and wt SOCS1-siRNA DCs was compared. FIG. 13D shows that p35$^{-/-}$ SOCS1-siRNA DCs were no longer able to produce increased and prolonged amounts of TNFα and IL-6, indicating that IL-12 feedback is a key inducer of TNFα and IL-6 production by SOCS1-siRNA DCs. These data indicate that SOCS1 silencing disables a critical signaling brake in DCs therefore allowing them to continuously respond to and produce not only IL-12, but also IL-12-induced pro-inflammatory cytokines via an enhanced feedback loop. The results disclosed herein provide a likely mechanism to explain the ability of TRP2-loaded SOCS1-siRNA DCs to induce both vitiligo and effective anti-tumor immunity to B16 tumor cells.

Importance of SOCS1-Restricted IL-12 Signaling for Controlling the Ability of DCs to Break Self-Tolerance The ability of SOCS1-siRNA DCs to induce potent CTL responses against self tumor-associated antigens suggests a therapeutic application of the SOCS1 silencing strategy. Since the clinical use of LPS as a stimulus in patients is too toxic, it was assessed whether IL-12, whose signaling is regulated by SOCS1, is also effective in enhancing the potency of SOCS1-siRNA DCs.

Figure 14A:
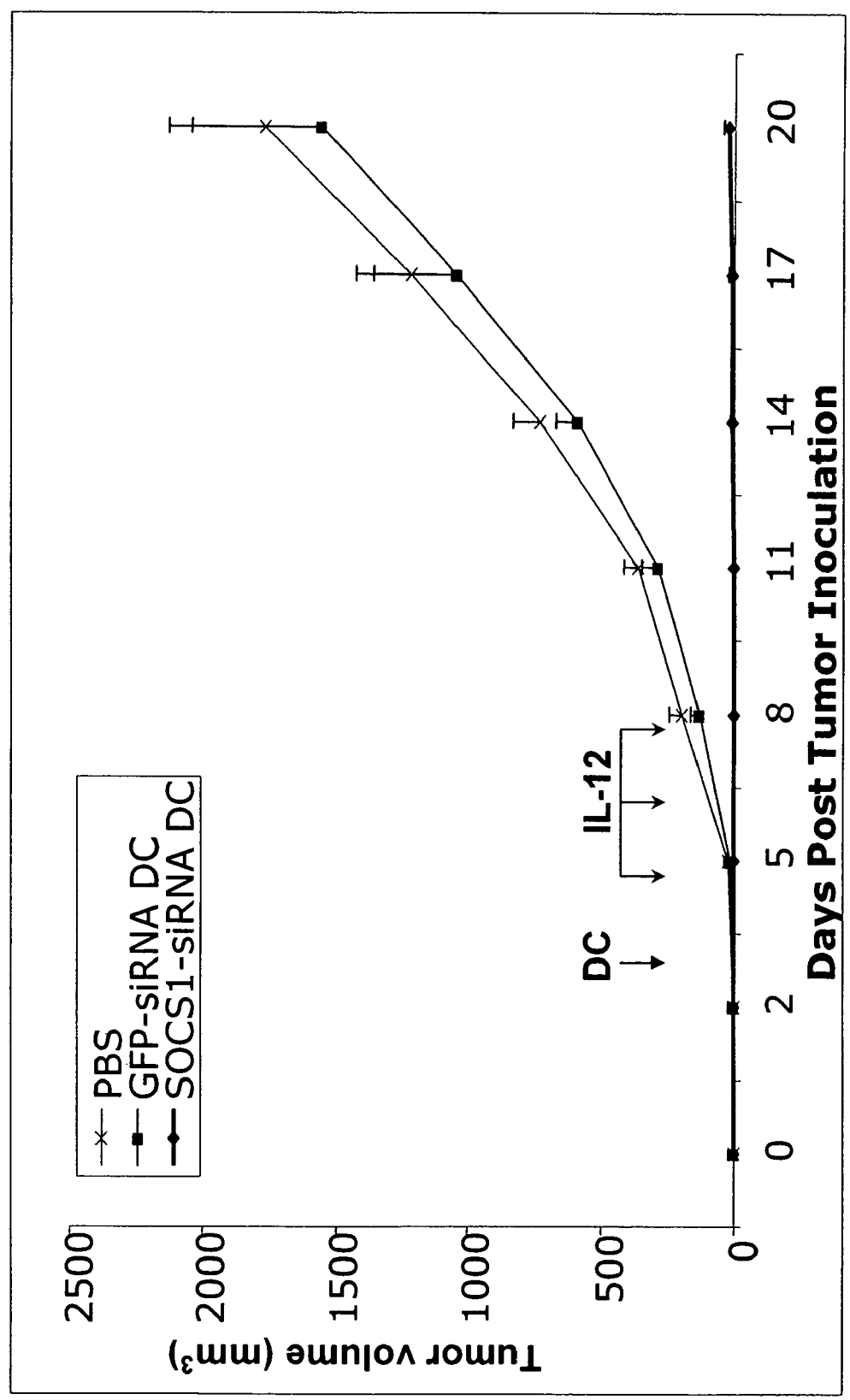
FIGS. 14A and 14B, is a series of charts demonstrating that in vivo IL-12 administration enhances SOCS1-silenced DC immunization.
Figure 14B:
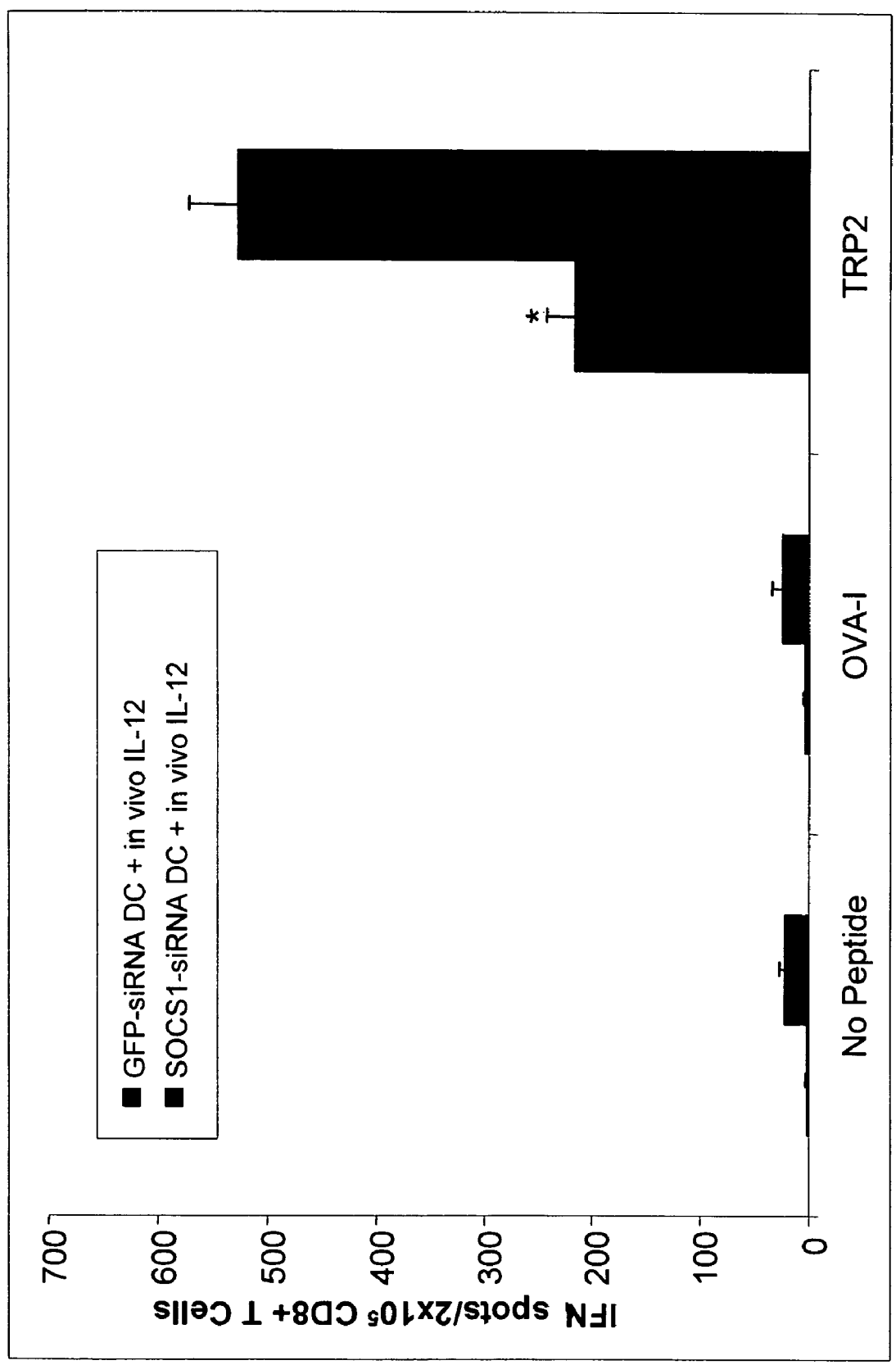

C57BL/6 mice were inoculated with B16 tumor cells and three days later, the mice were immunized once with TRP2-pulsed, transduced DCs that were matured ex vivo with recombinant mouse TNF$\alpha$. Following DC immunization, the recipient mice were in vivo stimulated three times with a low dose of recombinant mouse IL-12 (1 µg/mouse). FIG. 14A shows that the growth of B16 tumors in the SOCS1-siRNA DC immunized mice was efficiently blocked. In contrast, GFP-siRNA DC immunization, with in vivo administration with IL-12, had little effect on tumor growth compared to PBS controls. The anti-tumor activity was correlated with increased TRP2-specific CTL activities in SOCS1-siRNA DC immunized mice as shown by IFN$\gamma$ ELISPOT assay (FIG. 14B). Consistent with earlier observations (FIG. 10A), immunization with TRP2-pulsed, TNF$\alpha$-matured SOCS1-siRNA DCs in the absense of in vivo IL-12 stimulation also indicated increased anti-tumor activity compared to GFP-siRNA DC controls.

These results indicate that in vivo administration of IL-12 significantly enhances the immunostimulatory ability of SOCS1-silenced DCs, but not wildtype DCs, likely due to the enhanced signaling of IL-12 and IL-12-induced cytokines. These results further imply that SOCS1-restricted cytokine signaling in antigen-presenting DCs, not the systemic concentration of cytokines such as IL-12, is important for inducing effective antitumor immunity against self tumor-associated antigens.

No apparent toxicity, other than vitiligo, was observed in the TRP2-pulsed SOCS1-siRNA-DC mice co-injected with either LPS or IL-12 up to six months after immunization. Histological analysis of all major organs and tissues of the immunized mice revealed no pathologic inflammation. Levels of IgG and anti-dsDNA were comparable in SOCS1-siRNA-DC and mock DC mice. These data suggest that TRP2-pulsed SOCS1-siRNA-DC immunization does not cause pathological inflammation in mice.

Strength of SOCS1-Restricted Signal 3 Controls CTL Activiation, Tolerance, and Antitumor Immunity The results disclosed herein provide new insights into the regulation of CTL responses by mature DCs, which should have profound implications for the development of tumor vaccines. It is known that maturation is the control point for DC transition from the immature tolerogenic state to the mature immunogenic state (Banchereau et al., 1998, Nature 392:245-52; Steinman et al., 2003, Annu. Rev. Immunol. 21:685-711). The strength of the initial contact. (signals 1 and 2) between the antigen-presenting DC and T-cell is believed to determine the magnitude and fate of CTL responses, since mature DCs are thought to be short-lived based upon limited numbers of studies (Porgador et al., 1998, Journal of Experimental Medicine 188:1075-82; Ingulli et al., 1997, J. Exp. Med. 185:2133-41; Ruedl et al., 2000, J. Immunol. 165:4910-6). However, a more recent study using a reliable genetic method demonstrated that the lifespan of mature antigen-presenting DCs is much greater than previously estimated, lasting for two weeks in vivo (Garg et al., 2003, Nat. Immunol. 4:907-12), suggesting a possible regulatory role of mature DCs after the initial engagement with T cells.

The present results demonstrate that pro-inflammatory signaling in mature DCs, tightly restricted by SOCS1, critically controls the magnitude of the self-antigen specific CTL response. This indicates that CTL responses are controlled by DCs on at least two levels: DC maturation required for the initiation of CTL responses and the ongoing cytokine signaling of matured DCs with themselves and CTLs, the magnitude of which is regulated by SOCS1 expression. The present results further imply dynamic interactions between DCs and their surrounding environment of various immune cells and compositions/concentrations of cytokines and microbial products, which collectively determines the maintenance or breaking of self-tolerance and therefore the fate of the self-antigen specific CTL response.

The results disclosed herein reveal a novel mechanism for regulating the maintenance or breaking of self-tolerance. It was found that SOCS1-restricted signal 3 (IL-12), not the peptide affinity and co-stimulatory molecule levels, provided by DCs critically controls self-tolerance. The importance of cytokines for DC-mediated activation or overactivation of T cells has been implied in numerous studies of autoimmune diseases (Banchereau et al., 2004, Immunity 20:539-50) and other models (Curtsinger et al., 2003, J. Exp. Med. 197:1141-51; Valenzuela et al., 2002, J. Immunol. 169:6842-9).

Production of cytokines such as IL-12 by wt DCs is transient and inhibited by SOCS1 upon stimulation, as demonstrated herein and the studies of others (Langenkamp et al., 2000, Nat. Immunol. 1:311-6). It was observed that in contrast to wt DCs, SOCS1-silenced DCs can continually produce significantly enhanced IL-12 and IL-12-induced cytokines levels in response to an initial stimulus by forming an intricate autocrine (and possibly paracrine as well) signaling loop through the Jak/Stat signaling pathway in DCs after disabling the inducible feedback inhibitor of this pathway. In agreement, in vivo administration with a low dose of IL-12 was found to effectively enhance the ability of SOCS1-silenced DC, not wt DC, to break self-tolerance.

Collectively, these results indicate that the continuous and enhanced production and signaling of IL-12 and IL-12-induced cytokines produced by SOCS1-silenced DCs likely plays a key role in the breaking of self-tolerance and enhanced anti-tumor CTL responses. The present results further suggest that the intracellular inhibition of stimulatory signaling by SOCS1 in DCs contributes to the maintenance of self-tolerance. Although SOCS1 was found to directly block NF-$\kappa$B signaling by targeting p65 protein for ubiquitin-mediated proteolysis through its SOCS Box region (Ryo et al., 2003, Mol. Cell. 12:1413-26), Gingras et al. reported that SOCS1 indirectly regulates TLR signaling in macrophages for LPS-induced toxicity by inhibiting the signaling of type I IFN (Gingras et al., 2004, J. Biol. Chem. 279:54702-7). Different from LPS-induced toxicity through type I IFN signaling, the results herein demonstrate that the CTL responses induced by SOCS1-silenced DCs are mainly mediated by IL-12. The results herein also demonstrate the enhanced production of various cytokines such as TNF-$\alpha$, IL-6, and IL-12 by SOCS1-silenced DCs in response to LPS This study demonstrates the necessity of silencing SOCS1 in DCs for inducing effective antitumor immunity against self tumor-associated antigens. DC vaccines have been viewed as one of the most promising strategies for tumor vaccination, as evidenced in 98 published DC vaccine clinical trials involving over 1,000 patients in recent years (Rosenberg et al., 2004, Nat. Med. 10:909-15). These attempts, mainly aimed at promoting the antigen presentation and maturation of DCs by a wide variety of approaches, are largely disappointing with very low objective clinical response rates (Rosenberg et al., 2004, Nat. Med. 10:909-15). The data herein demonstrate that wt DCs loaded with a high-affinity peptide were still unable to break self-tolerance even after in vivo stimulation with LPS or IL-12. The results herein, therefore, may explain the general ineffectiveness of the currently described tumor vaccines (Rosenberg et al., 2004, Nat. Med. 10:909-15) and offer a new avenue to develop more effective tumor vaccines via silencing critical signaling inhibitors such as SOCS1 in combination with the current strategies promoting DC antigen presentation and maturation (Gilboa, 2004, Nat. Rev. Cancer 4:401-11; You et al., 2000, J. Immunol. 165:4581-4592; Soiffer et al., 2003, J. Clin. Oncol. 21:3343-50; Pardoll, 2002, Nat. Rev. Immunol. 2:227-38).

The present SOCS1 silencing approach, with the ability to specifically enhance an antigen-specific immune response induced by antigen-loaded DCs, would also be more attractive than the approach of systemically blocking CTLA4 on effector T cells, which non-discriminatorily overactivates self-reactive T cells including those against vital tissues and organs (Hodi et al., 2003, Proc. Natl. Acad. Sci. USA 100: 4712-7; Phan et al., 2003, Proc. Natl. Acad. Sci. USA 100: 8372-7). In summary, given that intensive efforts to enhance tumor vaccine have been focused on the improvement of antigen affinity/dose and costimulation, the new mechanism for regulating self-tolerance and the enhanced immunostimulatory capacity of SOCS1-silenced DCs found in this study should provide a generally applicable, novel vaccination strategy to break self-tolerance restriction against tumors.

Example 7

HIV-Specific Antibody and CTL Response Induced by Mouse SOCS1 siRNA DCs

The present example demonstrates an alternative strategy to induce anti-HIV immune responses by inhibiting the host's natural immune inhibitors. This study demonstrates that SOCS1, a negative regulator of the JAK/STAT pathway in DCs, controls not only HIV-specific cytotoxic T lymphocyte (CTL), but also antibody responses. SOCS1-silenced DCs are resistant to HIV envelope-mediated suppression and effectively induce a balanced, memory HIV envelope-specific antibody and CTL response in mice. This present disclosure represents the first attempt to elicit HIV-specific antibody and CTL responses by inhibiting the host's immune inhibitors.

The Materials and Methods used in the experiments presented in this Example are now described.

Transduction of BM-Derived DCs with Lentiviral Vectors

Recombinant lentiviral vectors, LV-SOCS1-siRNA and LV-GFP-siRNA, were produced, titrated and used to transducer DCs as described elsewhere herein.

Cytokine and Antibody ELISA Assays

Cytokine levels in cell culture supernatant were quantified by ELISA analysis (BD Biosciences, Lincoln Park, N.J.), according to the manufacturer's instructions. To determine gp120-specific antibody and subclass titers, gp120 proteins (5 µg/ml in carbonate buffer [pH9.6]) were coated overnight at 4° C., adding 12-fold serial dilutions of sera in PBS-5% FBS to the wells for 1 hour at room temperature. After eight washes, biotinylated antimouse antibodies (antimouse IgM, IgG, IgG1, IgG2a, IgG2b, or IgG3) were added to the wells for 1 hour at room temperature. Streptavidin-HRP was used as a peroxidase substrate. The reaction was stopped by addition of 50 µl of 2 M $H_2SO_4$. Optical densities were read at 450 nm on a Bio Assay Reader. The results are expressed as reciprocal endpoint titers, determined from a scatter plot with optical density (OD) values on the y axis and dilution-1 on the x axis, for which the x-axis scale was logarithmic. After the data were plotted, a logarithmic curve fit was applied to each individual dilution series, and the point where the curve fit intersects the positive-negative cutoff value was determined. The cut-off value was calculated for each antibody isotype as the mean (+3 SD) of all dilutions from control mouse sera. All samples tested in each experiment were assayed at the same time.

T-Cell Enzyme-Linked Immunospot (ELISPOT) Assay

ELISPOT assays of isolated CD4+ or CD8+ T-cells were performed as described elsewhere herein.

B Cell Isolation and gp120 Antibody-Producing B-Cell ELISPOT Assay

Single-cell suspensions prepared from spleens in complete RPMI 1640 medium were plated on plastic dishes for 1 hr at 37° C. in 5% $CO_2$ to remove adherent macrophages. Nonadherent cells were treated with anti-Thy1.2 and rabbit complement for 45 minutes at 37° C. to lyse T cells. The purity of the remaining B cell usually exceeded 90%. The B cell ELISPOT assay was performed by a modified method described before (Le Bon et al., 2001, Immunity 14:461-7023). Briefly, 96-well nitrocellulose-base plates (Millipore Multiscreen PI) were coated overnight with gp120 in PBS. The plates were washed six times with PBS and blocked with RPMI 1640 containing 10% FBS at 37° C. for 2 hours. The isolated B cells were seeded into wells ($5\times10^5$ cells/well) and incubated for 20 hours at 37° C. in 5% $CO_2$. The cells were then removed by six washes with PBS 0.5% Tween 20 (Sigma, St. Louis, Mo.). Biotinylated antimouse IgG (BD Pharmgen), diluted in PBS containing 0.5% FBS to 1 µg/ml, was added, and the mixture incubated at 37° C. for 2 hours. The avidin:biotinylated enzyme complex (ABC, Vector Laboratories, Inc. Burlingame, Calif.) was added for an additional hour. Anti-gp120 IgG was detected after a 4-minute reaction with AEC (3-amino-9-ethylcarbazole; Sigma, St. Louis, Mo.). The results were evaluated by ZellNet Consulting Inc. (New York, N.Y.) with an automated ELISPOT reader system (Carl Zeiss, Inc. Thornwood N.Y.), using KS ELISPOT 4.3 software.

Quantitative RT-PCR Analysis of BAFF and APRIL

The relative expression of SOCS1 in transfected mouse BM-DCs was evaluated by quantitative real-time PCR. Total RNA was extracted from DC, using Trizol reagent (Invitrogen, Carlsbad, Calif.), and 1.0 µg of total RNA for each sample was reverse transcribed with random hexamer primers and SuperScript First-Strand Synthesis Kit (Invitrogen, Carlsbad, Calif.). Real-time 5'-nuclease fluorogenic PCR analysis was performed on an ABI 7900HT Sequence Detection System (Applied Biosystems, Inc., Foster City, Calif.) in 20-µl quadruplicate reactions with the equivalent of 5 ng starting RNA material per reaction as template. The following primers were used for BAFF and APRIL: BAFF, sense 5'-TGCTATGGGTCATGTCATCCA-3' (SEQ ID NO:17) and antisense 5'-GGCAGTGTTTTGGGCATATTC-3' (SEQ ID NO:18); APRIL, sense 5'-TCACAATGGGTCAGGTGG-TATC-3' (SEQ ID NO:19) and antisense 5'-TGTAAAT-GAAAGACACCTGCACTGT-3' (SEQ ID NO:20). TaqMan probe, forward and reverse primer for 18S were obtained from Taqman Rodent 18S control reagents (Applied Biosystems, Inc., Foster City, Calif.). The PCR parameters were those recommended for the TaqMan Universal PCR Master Mix kit (Applied Biosystems, Inc., Foster City, Calif.), with BAFF, APRIL and 18S reactions performed in separate tubes. BAFF and APRIL levels were normalized to 18S rRNA, while BAFF or APRIL expression (relative to the control value of mock-transfected, stimulated DCs) was calculated by the Comparative Ct method (Livak et al., 2001, Methods 25:402-8).

CTL Assays

CD8+ CTL responses were assessed with a standard chromium release assay as described elsewhere herein, that measures the ability of in vitro-restimulated splenocytes to lyse target cells. Splenocytes pooled from immunized mice were restimulated in vitro in RPMI-1640 containing gp120 proteins (20 µg/ml) for 4-6 days. Target cells pulsed with 20 µg/ml of gp120 protein overnight were labeled with sodium $^{51}$Cr chromate solution for 90 minutes. Different numbers of effector cells were incubated with a constant number of target cells ($1 \times 10^4$/well) in 96-well V-bottomed plates (200 µl/well) for 3 hours at 37° C. The supernatants (100 µl) from triplicate cultures were collected. Percent cell lysis was calculated as (experimental release–spontaneous release)/(maximum release–spontaneous release)×100.

T and B Cell Proliferation Assay

CD4+ or CD8+ T cells ($1 \times 10^6$ per well) and B cells ($1 \times 10^5$ per well) isolated as described elsewhere herein were cultured in complete medium in triplicate wells of 96-well plates in the presence or absence of various stimuli. On the fourth day of culture, wells were pulsed with 1 µCi [$^3$H]-thymidine for 16 hours. Plates were then harvested and incorporated [$^3$H]-thymidine measured using a MicroBeta scintillation counter (TopCount NXT, Packard).

DC Immunization

Bone marrow-derived DCs (day 5 of BM culture) were transduced with LV-SOCS1-siRNA or LV-GFP-siRNA at an MOI of 5 as described elsewhere herein.

The results of the experiments presented in this Example are now described.

Silencing of SOCS1 in DCs Enhances the HIV Env-Specific Antibody Response

Figure 15A:
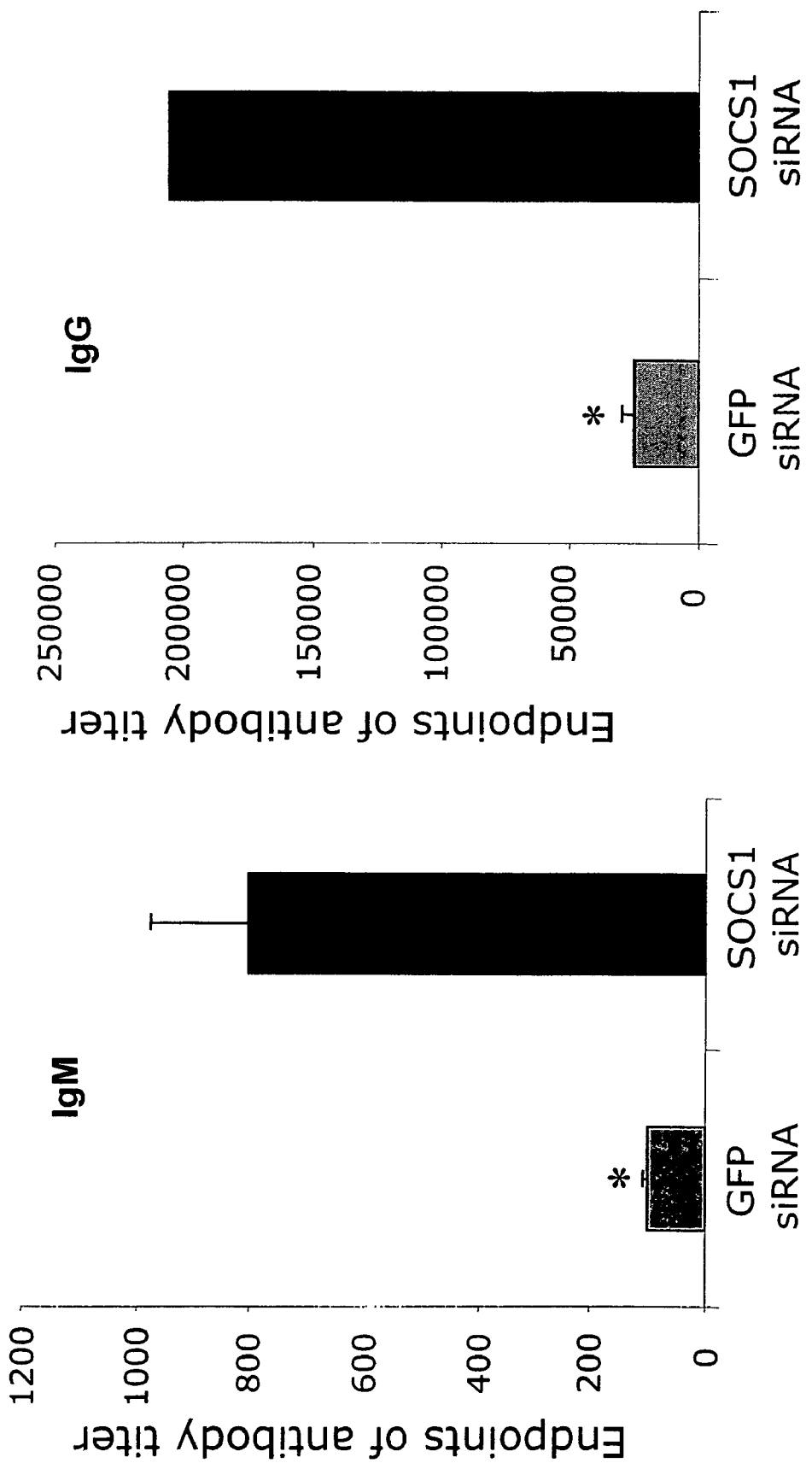
FIGS. 15A through 15D, is a series of charts demonstrating that gp120-specific antibody and CTL responses are enhanced by silencing of SOCS1 in DCs.

The effect of SOCS1 silencing on the ability of DCs to induce anti-HIV antibody responses was first investigated. HIV Env was used for this study since it can induce both cellular and neutralizing antibodies responses. A recombinant lentiviral vector (LV-SOCS1-siRNA) that expresses SOCS1 siRNA with the ability to downregulate about 90% of SOCS1 mRNA in transfected cells and a control vector (LV-GFP-siRNA) were generated, as described elsewhere herein. Mouse bone marrow (BM)-derived DCs were transduced with LV-SOCS1-siRNA or LV-GFP-siRNA, loaded with recombinant HIV gp120 proteins, and matured with LPS ex vivo. Groups of mice were then immunized with the transduced DCs twice at a weekly interval, followed by LPS stimulation in vivo after each DC immunization. In vivo stimulation was used based upon the observation that it can further enhance CTL responses against tumor-associate antigens induced by SOCS1-silenced DCs as disclosed elsewhere herein. FIG. 15A shows that LV-SOCS1-siRNA-DCs elicited significantly more robust gp120-specific IgM and IgG responses than did the control LV-GFP-siRNA-DCs.

Figure 15B:
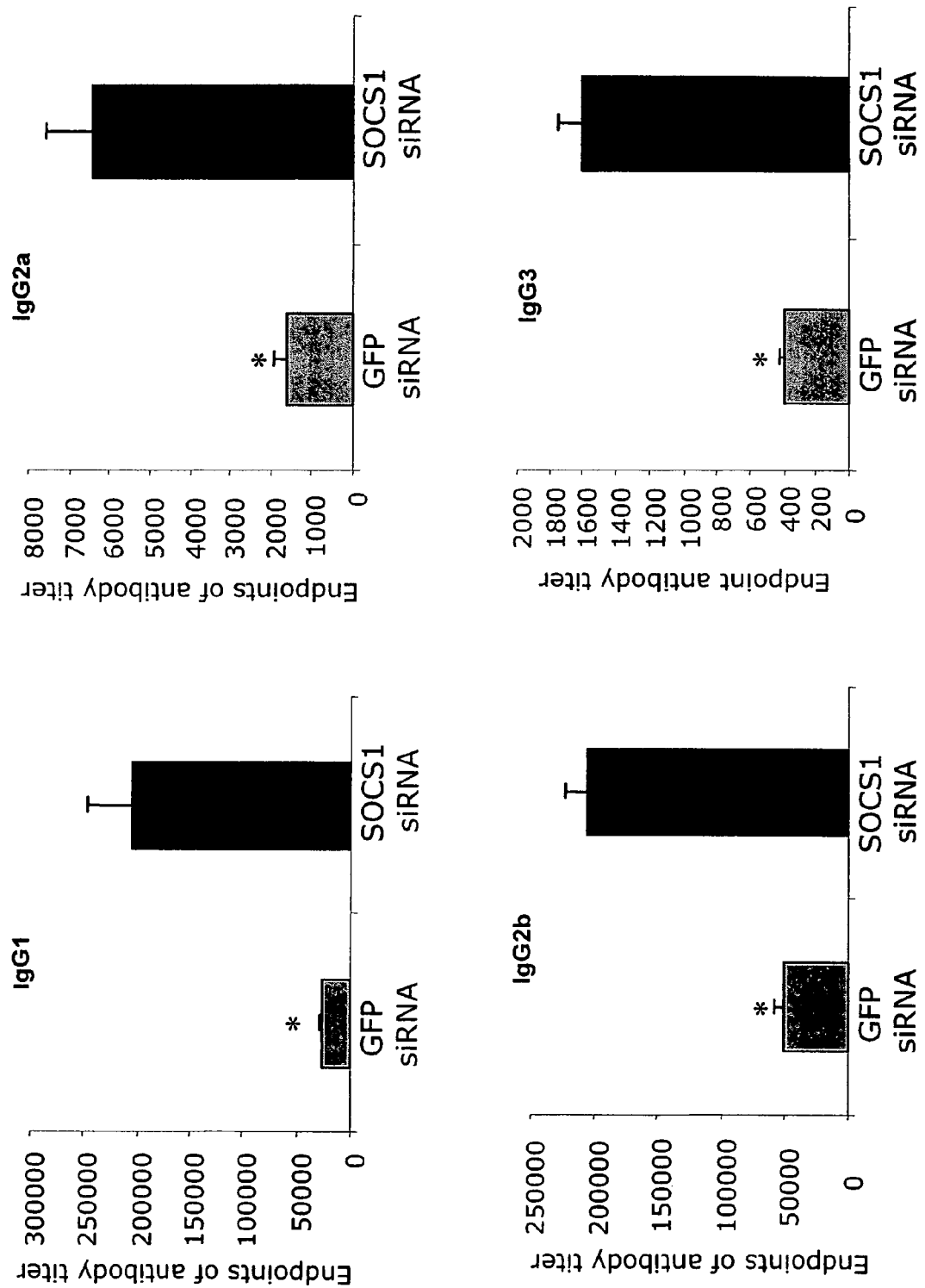

The production of different antibody subclasses whose profile represents distinct immunological states is dependent on CD4+ T-helper (Th)1- and Th2-polarizing cytokines and Th cell functions (Allen et al., 1997, Immunol. Today 18:387-92). FIG. 15B shows drastic increases in HIV Env-specific antibody titers in all IgG subclasses in mice immunized with LV-SOCS1-siRNA-DCs, compared with the corresponding subclasses in LV-GFP siRNA-DC mice. The Env-specific antibody subclass profile indicated a mixed response of IgG1, the product of a Th2 response, and IgG2a, a subclass associated with a Th1 response, indicating that both Th1- and Th2-dependent immune responses were induced by LV-SOCS1-siRNA-DCs. Similar results were obtained in repeated experiments. Neutralizing assays were not performed since mice are not an appropriate species for reliable testing of HIV neutralizing activities (Burton et al., 2004, Nat. Immunol. 5:233-6). It was further observed that SOCS1 silencing enhanced antibody responses to other strains of HIV Env proteins and antigens such as ovalbumin (OVA). These results demonstrate that HIV Env-specific antibody responses encompassing all IgG subclasses are drastically enhanced by the silencing of SOCS1 in DCs, implying a critical role for SOCS1 in DCs in controlling antigen-specific antibody responses.

Silencing of SOCS1 in DCs Enhances HIV gp120-Specific CTL Responses

Figure 15C:
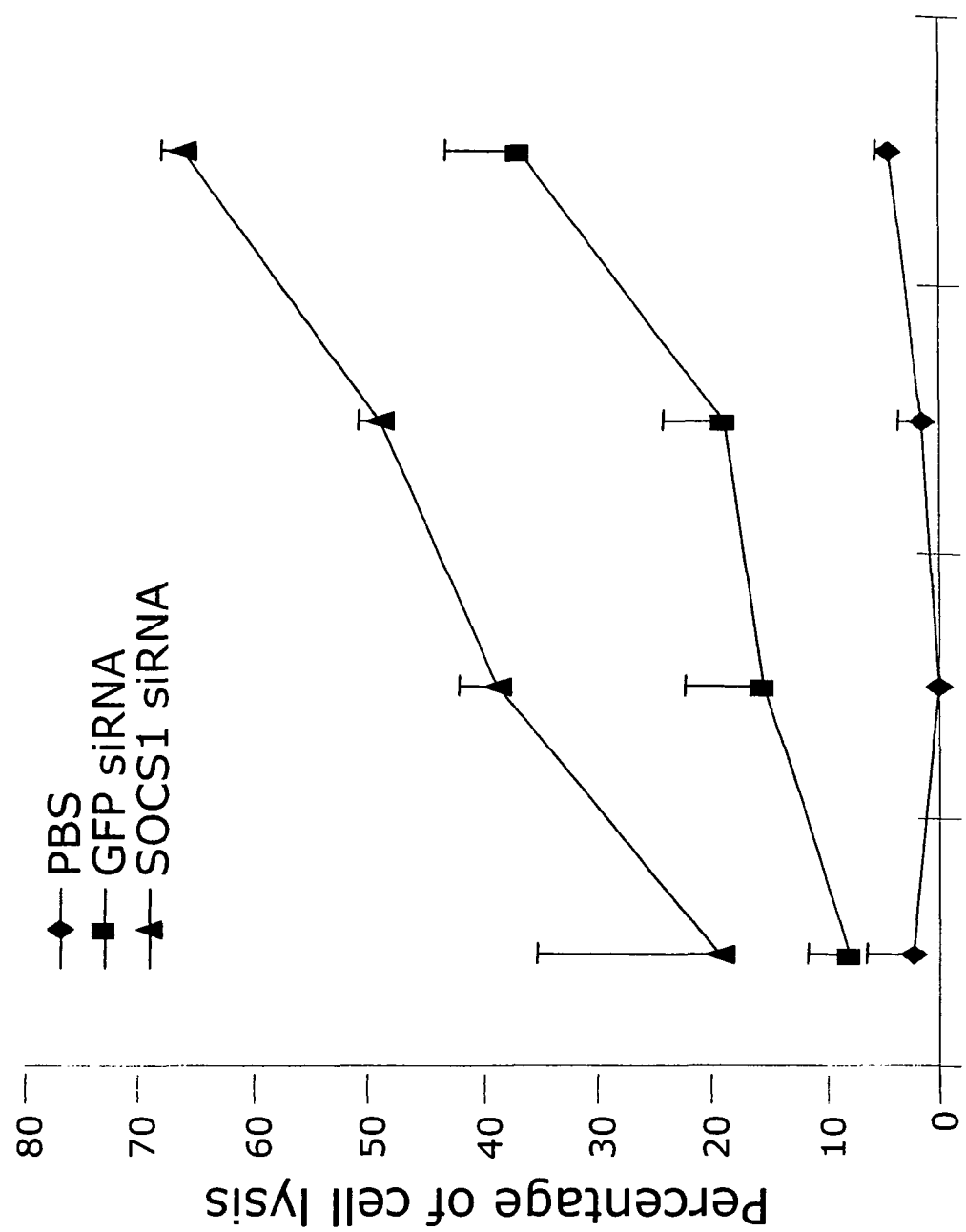
Figure 15D:
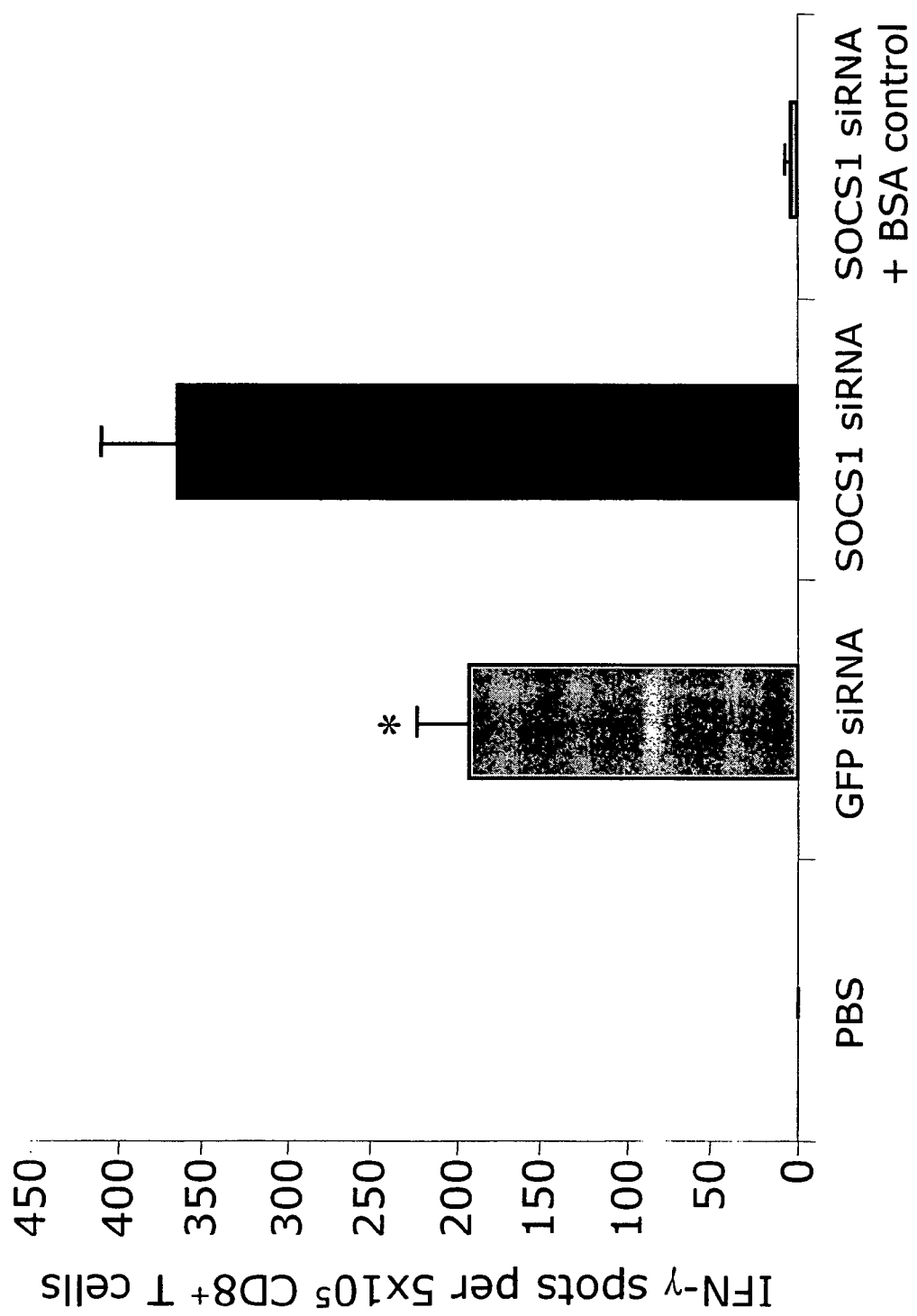

The following experiments were performed to assess whether SOCS1 silencing could enhance HIV Env-specific CTL responses. IFNγ ELISPOT, intracellular cytokine staining, and CTL assays were used to test the functional status of CD8+ T cells in the immunized mice. CTL activities against gp120-pulsed target cells in the LV-SOCS1-siRNA-DC mice were significantly more potent than those in the LV-GFP-siRNA-DC mice (P<0.01) (FIG. 15C). The CTL activity detected in these assays was gp120-specific, since splenocytes from LV-SOCS1-siRNA-DC mice lacked any apparent CTL activity against non-gp120-pulsed target cells. In agreement, in LV-SOCS1-siRNA-DC-immunized mice, 363 IFNγ+ spots per $5 \times 10^5$ CD8+ T-cells were detected, compared with 191 spots in LV-GFP-siRNA-DC mice, respectively (FIG. 15D). Intracellular staining of splenocytes with IFN-γ also indicated higher percentages of IFN-γ+ T cells in LV-SOCS-siRNA-DC mice. Taken together, these results demonstrate a balanced and enhanced antibody and CTL response against HIV Env in mice immunized with SOCS1-silenced DCs, suggesting that SOCS1 in DCs critically regulates both humoral and cellular immunity.

Mixed, Enhanced Th1 and Th2 Response Induced by SOCS1-Silenced DCs.

Figures 1, 16A:
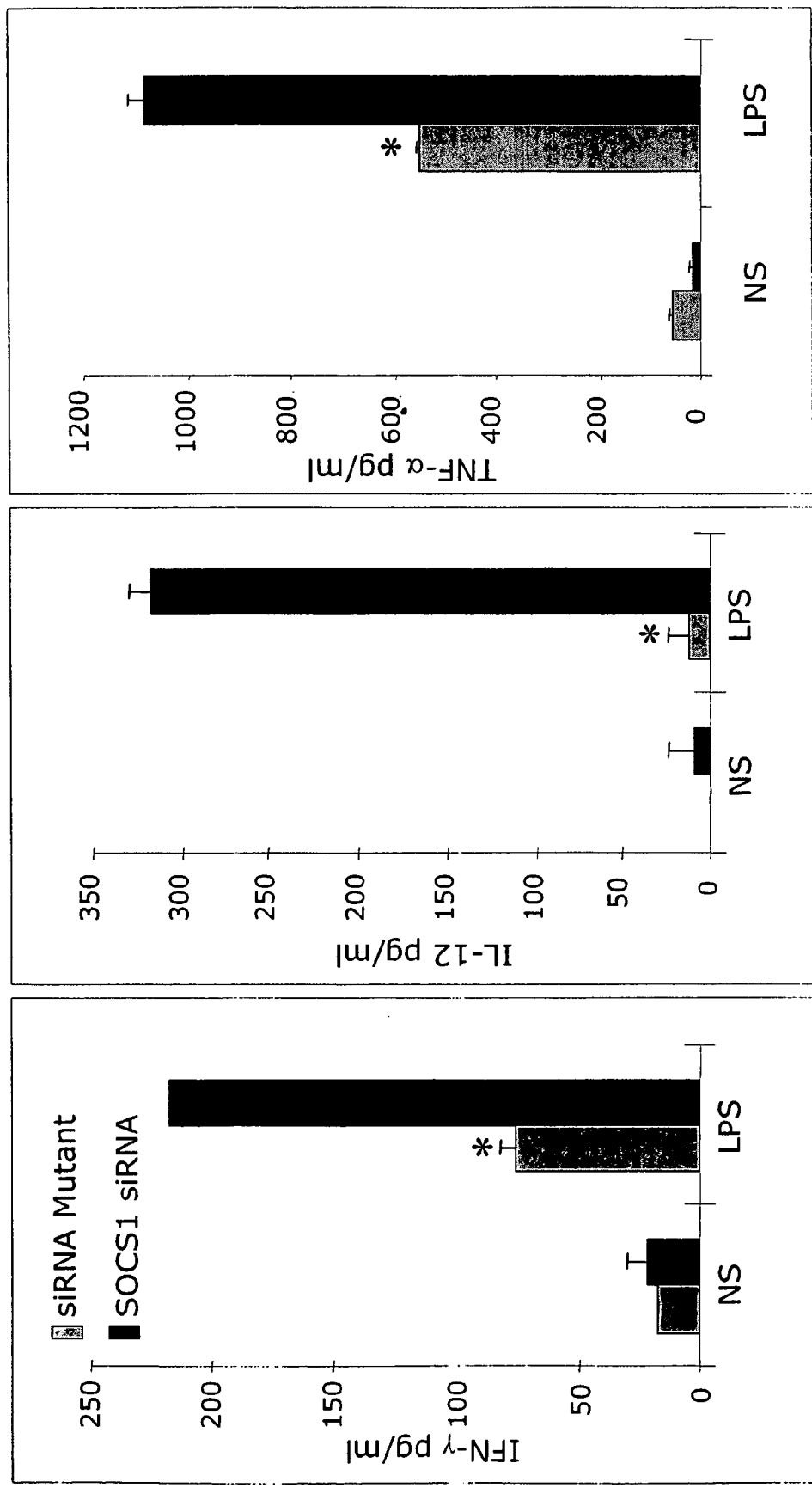
FIGS. 16A through 16D, is a series of charts demonstrating enhanced production of both Th1- and Th2-polarizing cytokines by SOCS1-silenced DCs.
Figures 2, 16A:
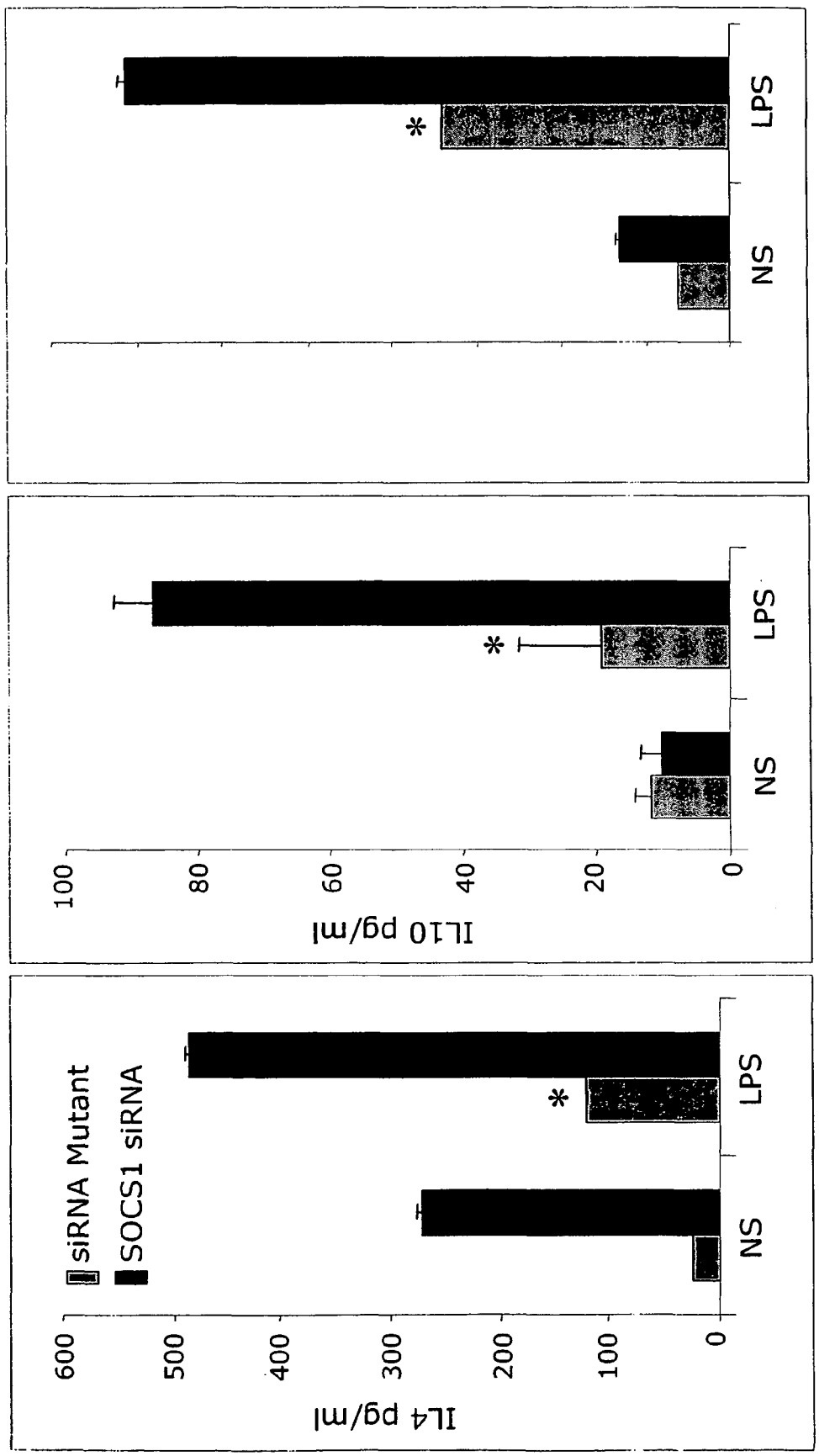

Without wishing to be bound by any particular theory, given the role of cytokines in programming Th1 vs. Th2 responses (MacDonald et al., 2002, J. Immunol. 168:3127-30; Gor et al., 2003, Nat. Immunol. 4:503-5), it is believed that SOCS1 silencing might affect CTL and antibody responses by regulating the production of cytokines by DCs. FIG. 16A demonstrates a significant increase in the levels of IL-12, IFN-γ, and TNFα, which promote Th1-polarized responses, produced by LV-SOCS1-siRNA-DCs, compared with GFP-siRNA-DCs after stimulation with LPS. Interestingly, significant increases of IL-4, IL-6, and IL-10, which promote Th2-polarized responses, were also seen in the SOCS1 silenced DCs (P<0.01). The higher levels of both Th1- and Th2-promoting cytokines produced by SOCS1-silenced DCs may account for the enhanced ability of SOCS1-silenced DCs to induce both HIV Env-specific CTL and antibody responses.

Figure 16B:
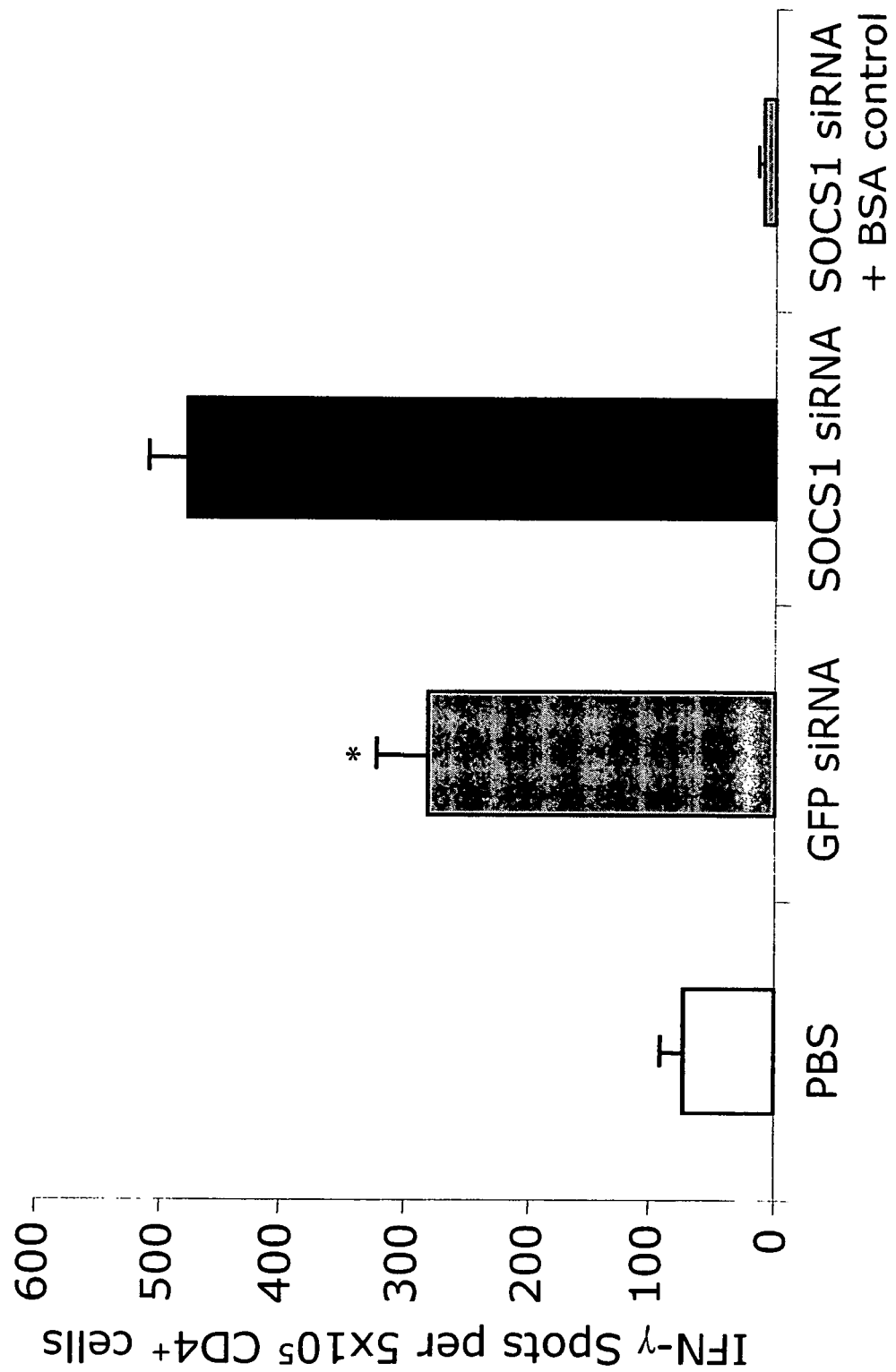
Figure 16C:
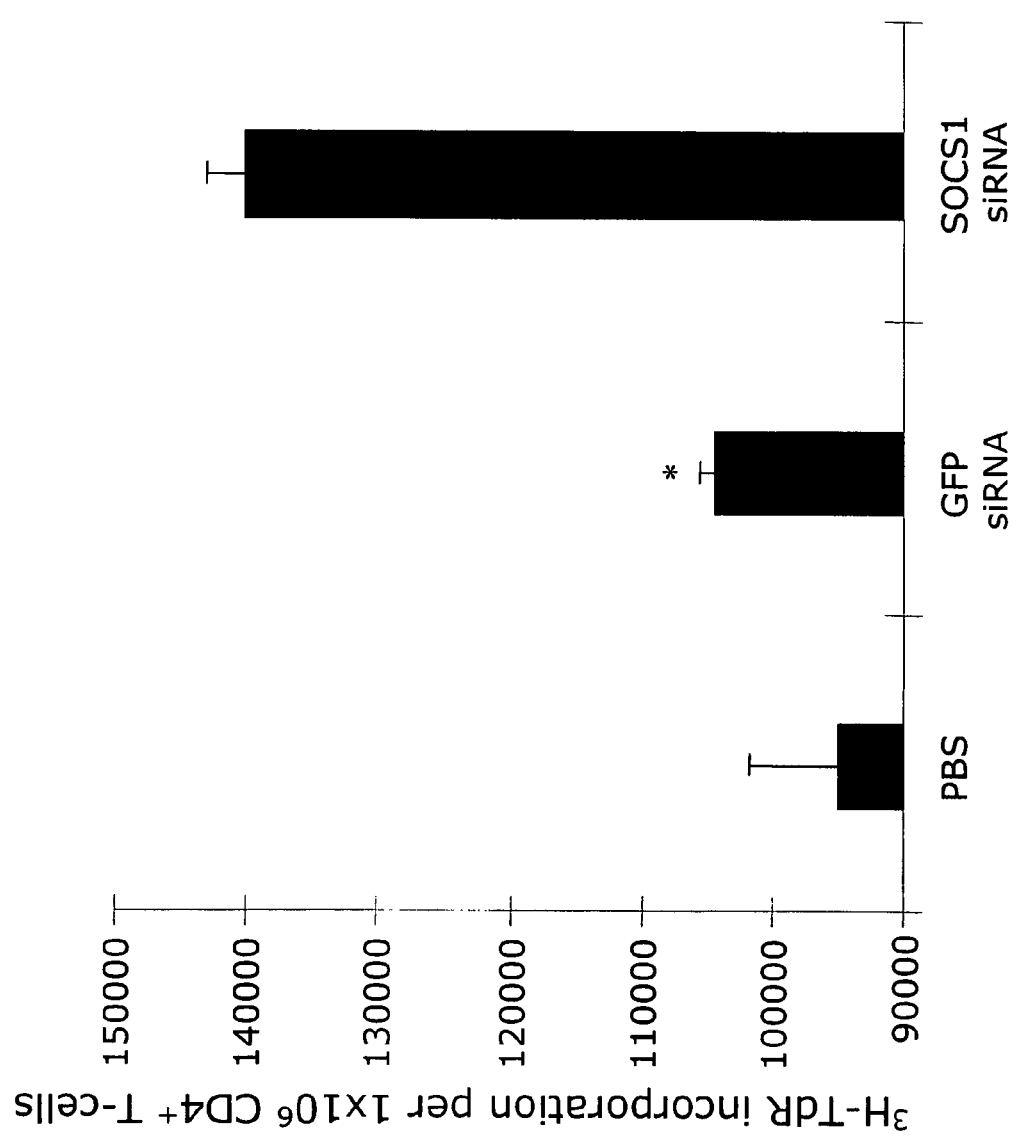
Figure 16D:
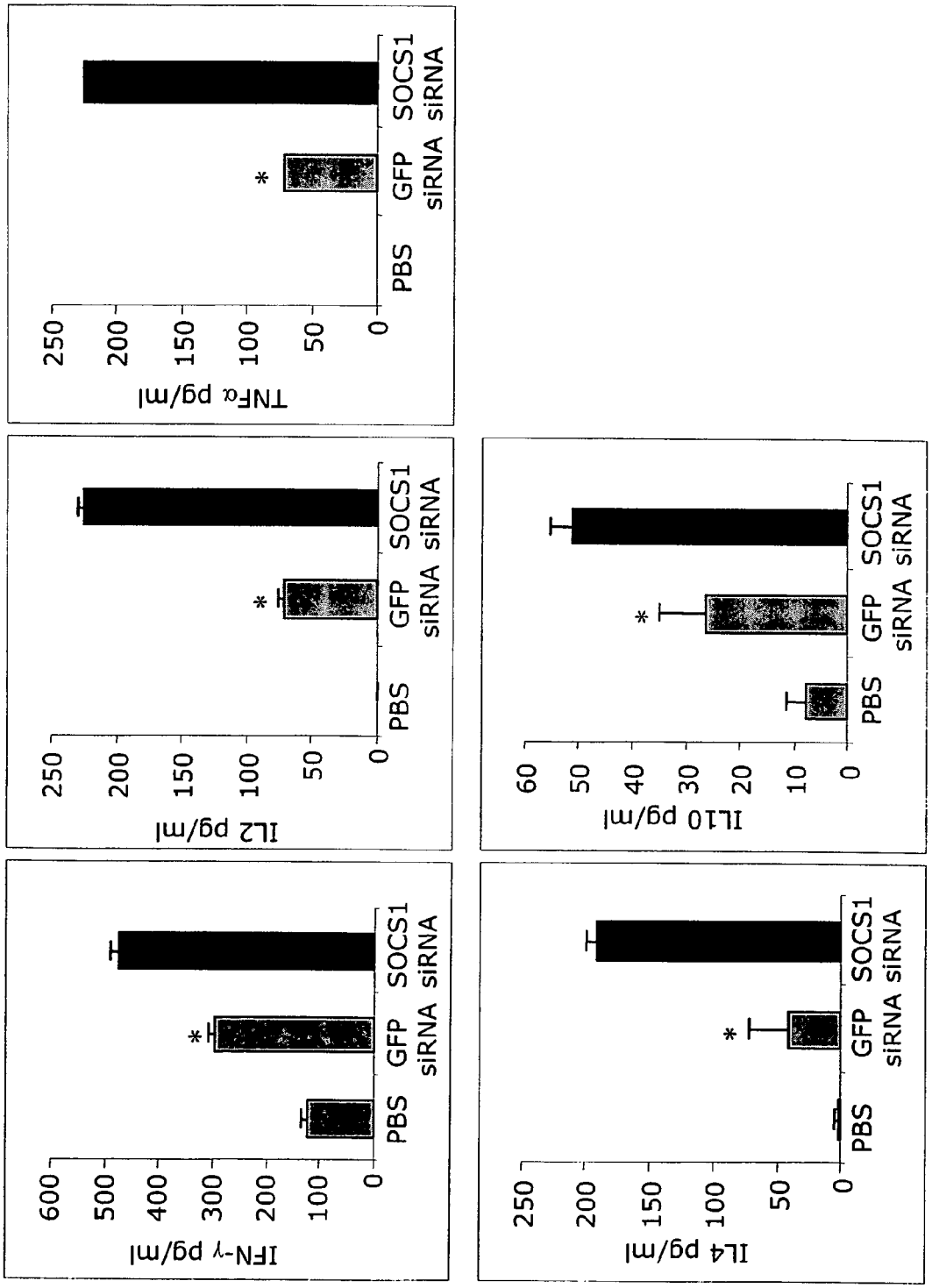

Based on the present results, SOCS1 silencing in DCs clearly promoted antibody and CTL responses. The following experiments address whether HIV Env-specific CD4+ Th responses, which are intimately involved in the induction of antibody and CTL responses, are also enhanced by SOCS1 silencing. CD4+ T cells were isolated from immunized mice using CD4+ microbeads and analyzed using various assays. As depicted in FIG. 16B, the frequencies of gp120-specific CD4+ T cells were significantly higher in LV-SOCS1-siRNA-DC mice than in LV-GFP-siRNA-DC mice. $^3$H-thymidine incorporation assays indicated that the CD4+ T cells from LV-SOCS1-siRNA-DC mice proliferated more actively than those from LV-GFP-siRNA-DC mice in response to stimulation with gp120-pulsed DCs (FIG. 16C). Analysis of the cytokine profiles produced by CD4+ T cells isolated from LV-SOCS1-siRNA-DCs mice after stimulation with gp120-pulsed DCs revealed increased levels of both Th1-polarizing (IFN-γ, IL-2, and TNFα) and Th2-polarizing (IL-4 and IL-10) cytokines (FIG. 16D). These results indicate that SOCS1-silenced DCs induce an enhanced, mixed Th1 and Th2 response against HIV Env, which is consistent with the mixed gp120-specific IgG subclass profile in FIG. 15B.

Enhanced gp120-Specific B Cell Activation by SOCS1-Silenced DCs

Figure 17A:
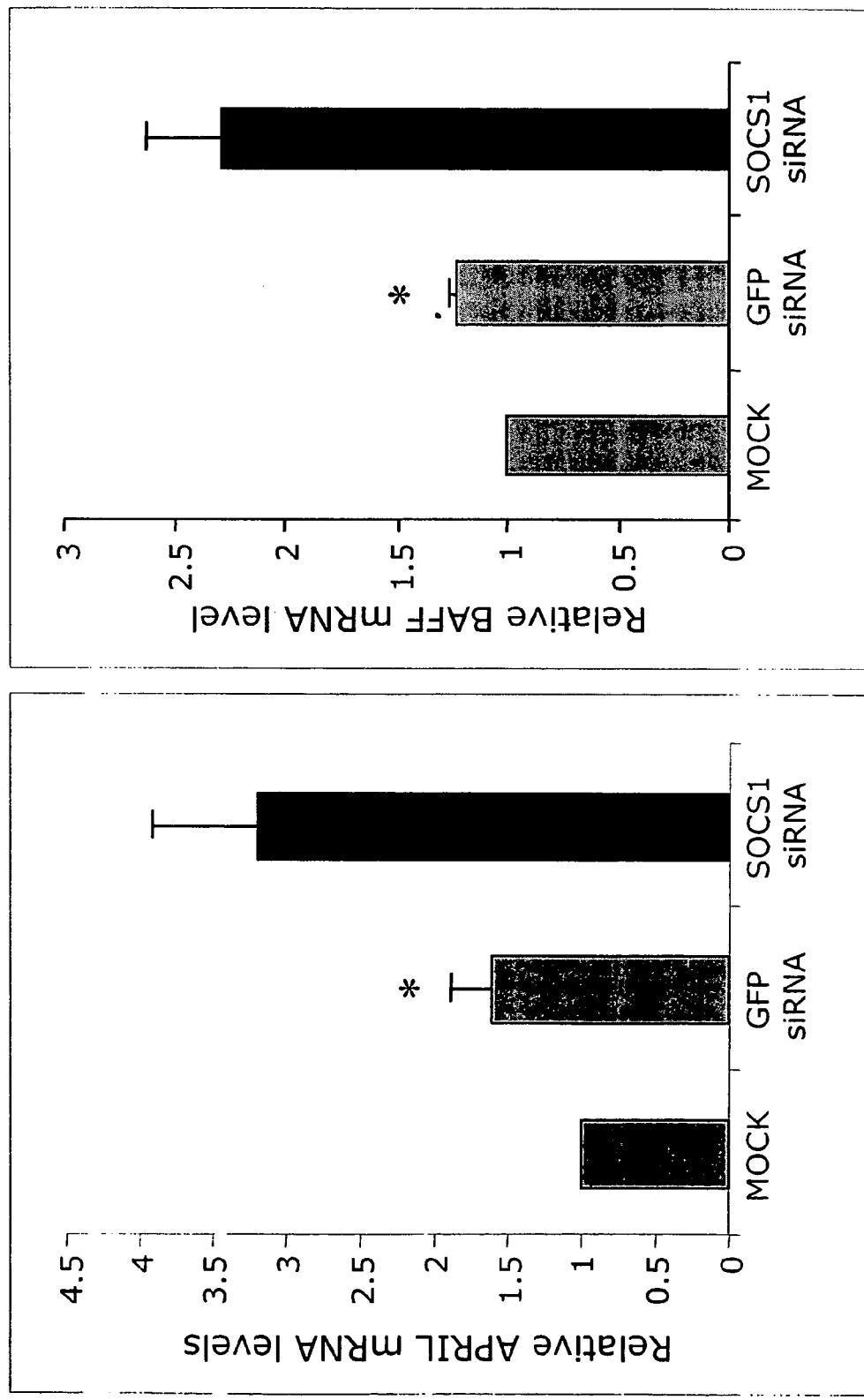
FIGS. 17A through 17D, is a series of charts demonstrating enhanced gp120-specific B cell activation by SOCS1-silenced DCs.

DCs have been shown to directly trigger B cell proliferation, maturation, and class-switch recombination by producing APRIL (a proliferation-inducing ligand) and BAFF (B-lymphocyte stimulator, also known as BLyS), members of the TNF superfamily (Balazs et al., 2002, Immunity 17:341-52; Litinskiy et al., 2002, Nat. Immunol. 3:822-9; MacLennan et al., 2002, Immunity 17:235-8). The effect of SOCS1 silencing on the production of APRIL and BAFF by DCs using real-time RT-PCR was therefore assessed. LV-SOCS1-siRNA-DCs expressed higher levels of APRIL and BAFF mRNA upon LPS stimulation than did LV-GFP-siRNA-DCs (FIG. 17A), in agreement with the increased expression of BAFF and APRIL in SOCS1$^{-/-}$ DCs (Hanada et al., 2003, Immunity 19:437-50).

Figure 17B:
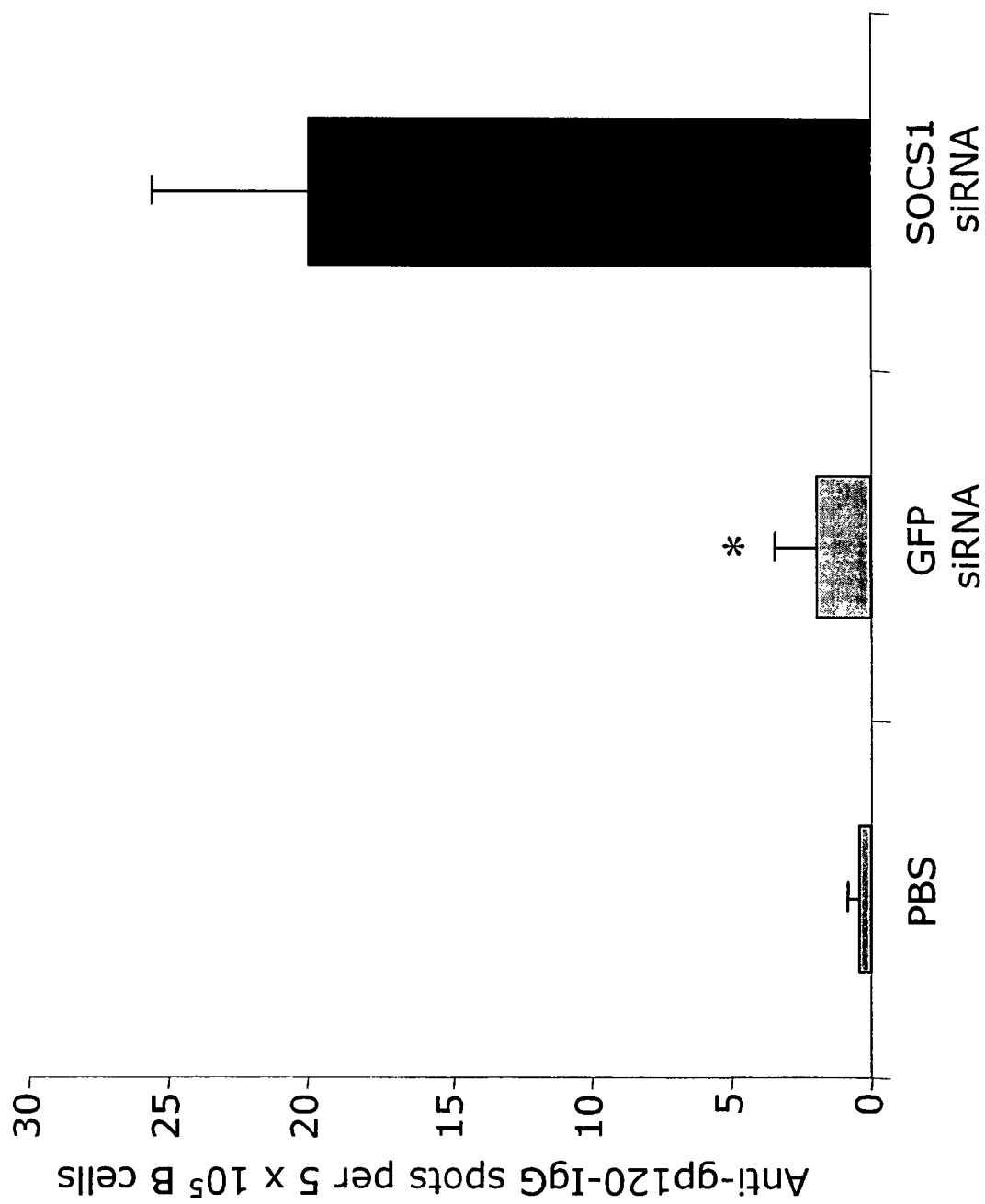
Figure 17C:
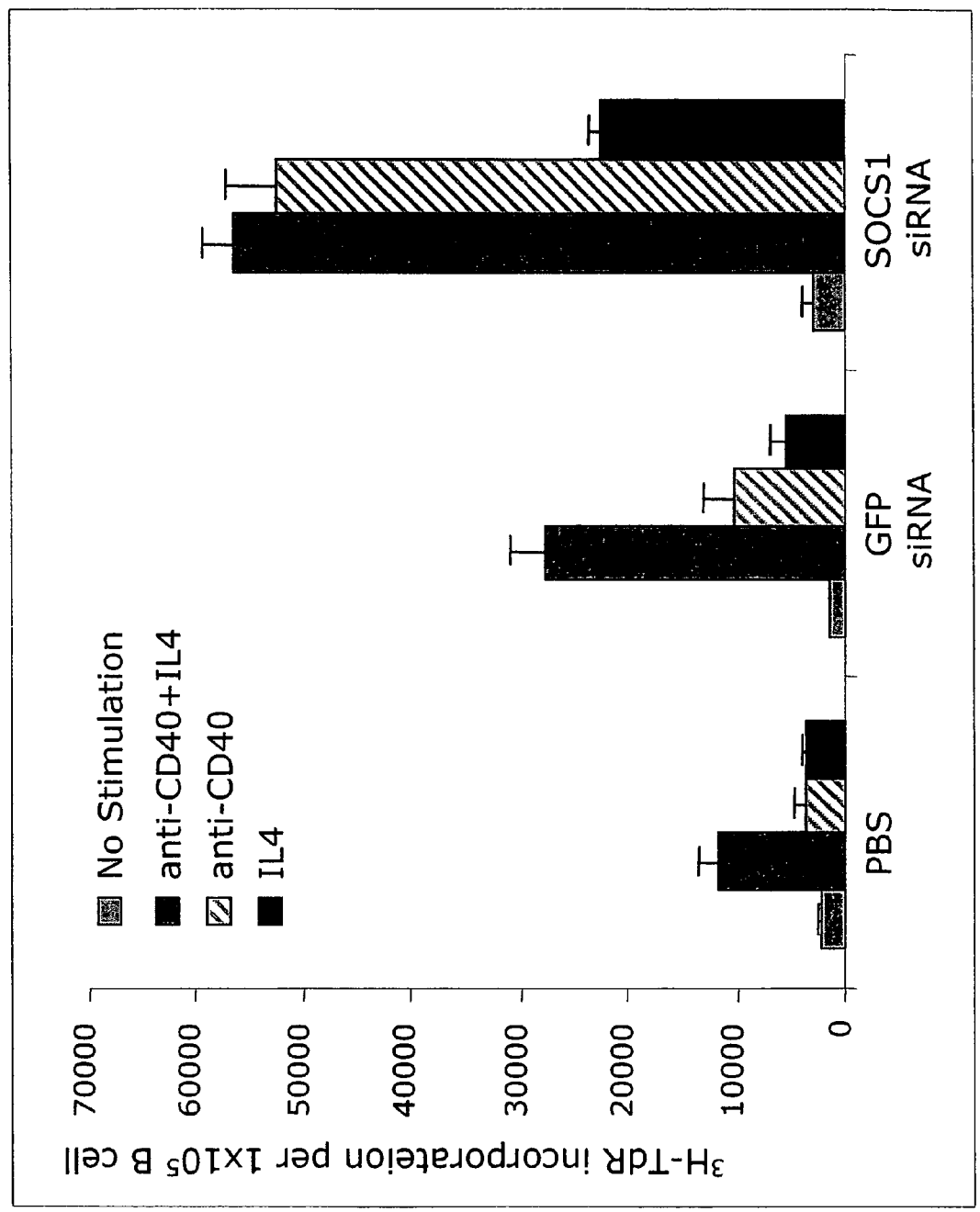
Figure 17D:
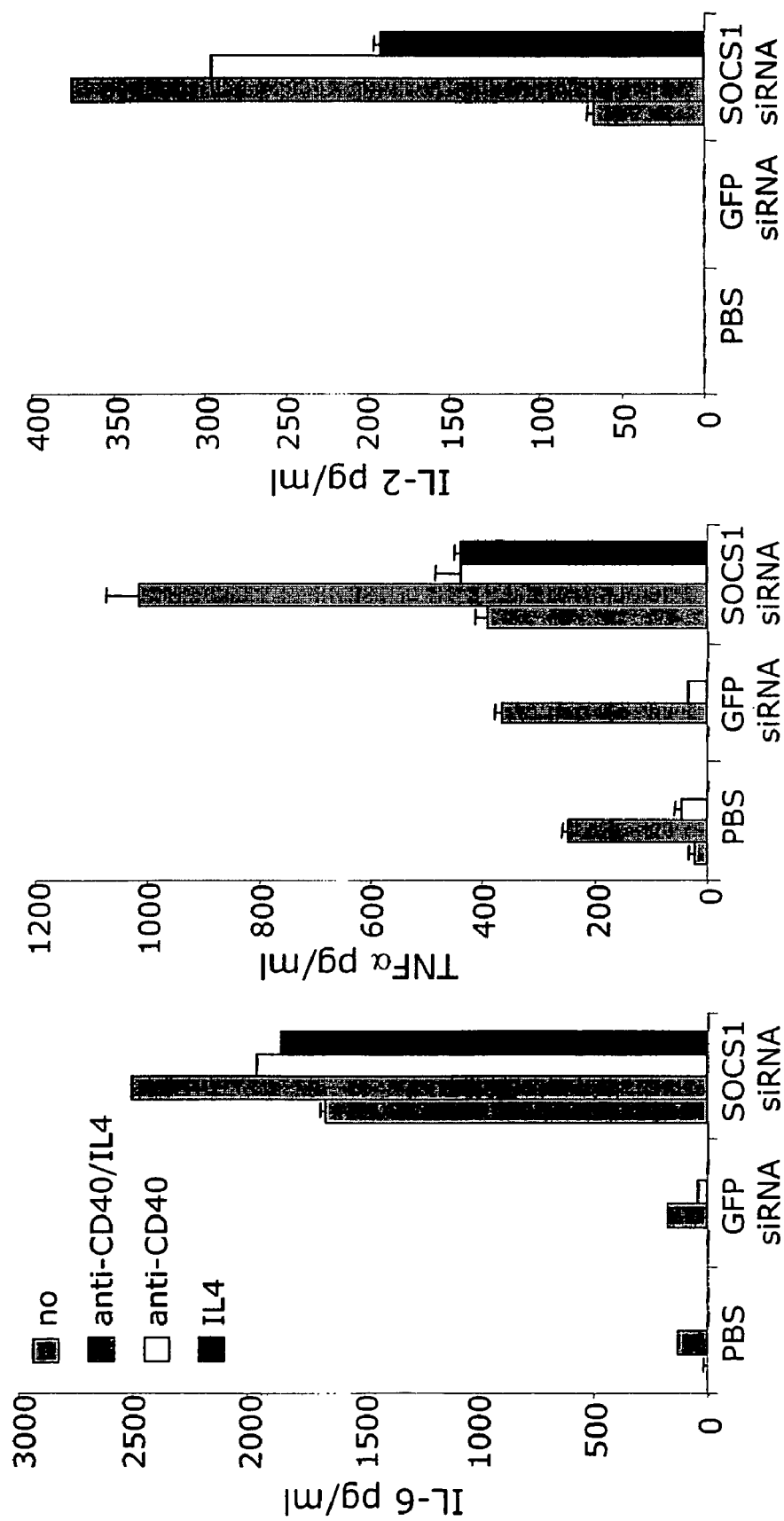

To test the ability of SOCS1-silenced DCs to enhance activation of gp120-specific B cells, an anti-gp120 IgG-specific B cell Elispot assay was used to directly examine the frequencies of anti-gp120 IgG-producing B cells in the immunized mice. Frequencies of anti-gp120 IgG-producing B cells were significantly higher in LV-SOCS1-siRNA-DC mice than in LV-GFP-siRNA-DCs mice (P<0.01) (FIG. 17B). Higher percentages of B cells exhibited an activated phenotype characterized by high levels of CD69, CD40, and CD86 in LV-SOCS1-siRNA-DCs mice, compared with B cells from LV-GFP-siRNA-DC mice. In addition, B cells from the spleens of immunized mice were purified and stimulated with various stimuli. FIG. 17C shows that B cells from LV-SOCS1-siRNA-DC mice proliferated more vigorously when co-stimulated with anti-CD40 and IL-4 than did B cells from LV-GFP-siRNA-DC mice. Interestingly, B cells from LV-SOCS1-siRNA-DC mice, but not those from LV-GFP-siRNA-DC mice, responded strongly to IL-4 or anti-CD40 only, suggesting that increased numbers of B cells were already activated in vivo by immunization with LV-SOCS1-siRNA-DCs. It was also observed that B cells from LV-SOCS1-siRNA-DCs mice produced higher levels of various cytokines, including IL-6, IL-2, and TNF-α, in response to various stimuli (FIG. 17D). Collectively, these results suggest that SOCS1-silenced DCs produce enhanced levels of B-lymphocyte stimulators (BAFF and APRIL) and Th2-polarizing cytokines, leading to more effective activation of HIV Env-specific B cells and Th cells.

Long-Term HIV Env-Specific CTL and Antibody Responses Induced by SOCS1-Silenced DCs Having shown that SOCS1 silencing in DCs enhances the primary HIV Env-specific CTL and antibody responses, it was further assessed whether SOCS1-silenced DCs would induce memory HIV-specific CTL and antibody responses.

Figure 18A:
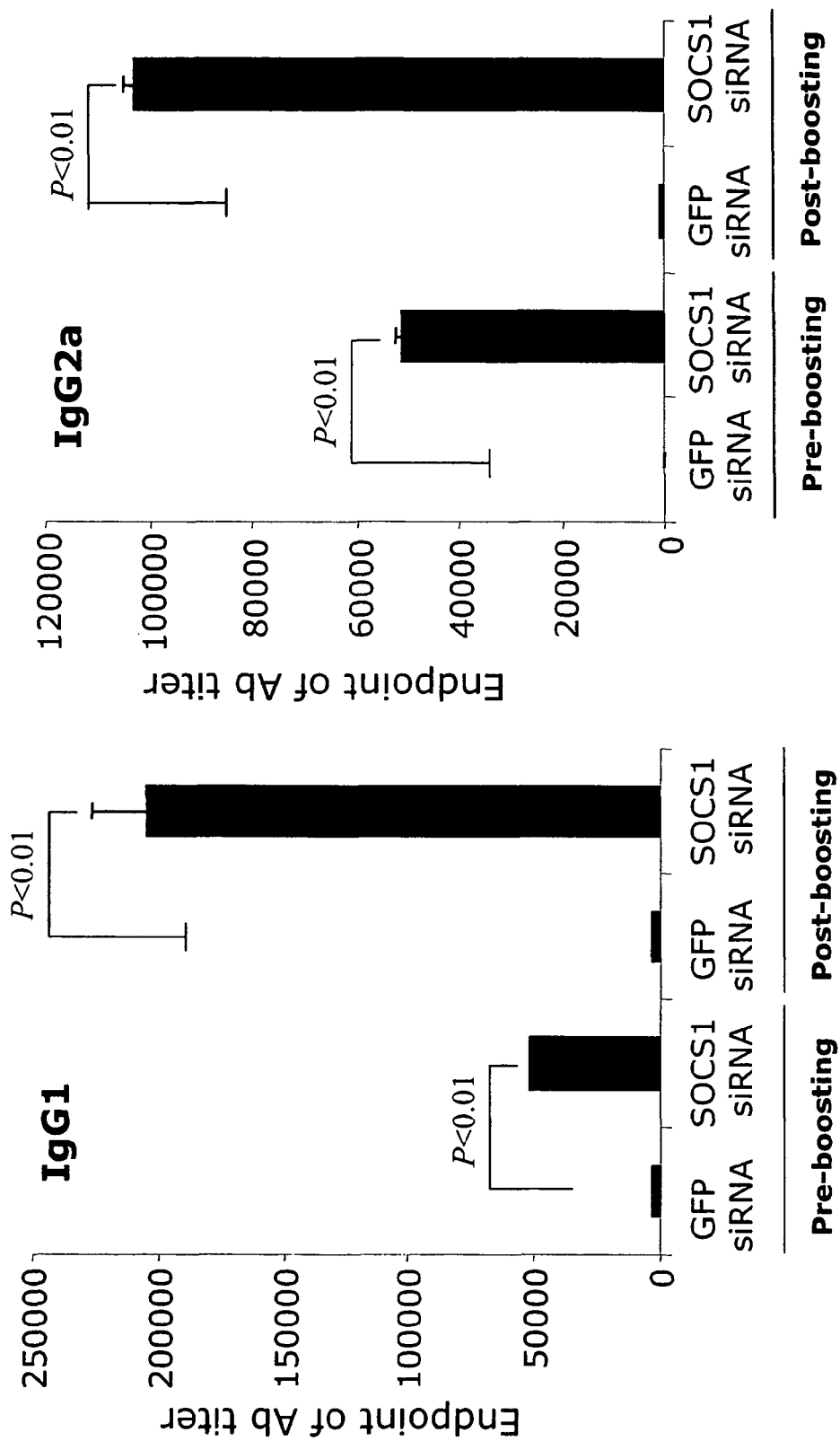
FIGS. 18A through 18B, is a series of charts demonstrating tong-term gp120-specific antibody and CTL responses induced by SOCS1-silenced DCs.

FIG. 18A shows that mice immunized with LV-GFP-siRNA-DCs had very low levels of gp120-specific antibodies at six months after immunization, while LV-SOCS1-siRNA-DC mice still retained significant titers of gp120-specific IgG1 and IgG2 antibodies in their sera. At one week after booster immunization, the LV-SOCS1-siRNA-DC mice indicated strong recall antibody responses, with a mean titer of anti-gp120 IgG1 at $2\times10^5$ and anti-gp120 IgG2 at $1\times10^5$, while the LV-GFP-siRNA-DC mice indicated poor recall antibody responses, with a mean titer of IgG1 at $3\times10^3$ and IgG2 at $4\times10^2$. These data show that SOCS1-silenced DCs exhibit about 64 and 255 fold increases in the titers of IgG1 and IgG2a antibodies, respectively, compared to GFP-siRNA-DCs.

Figure 18B:
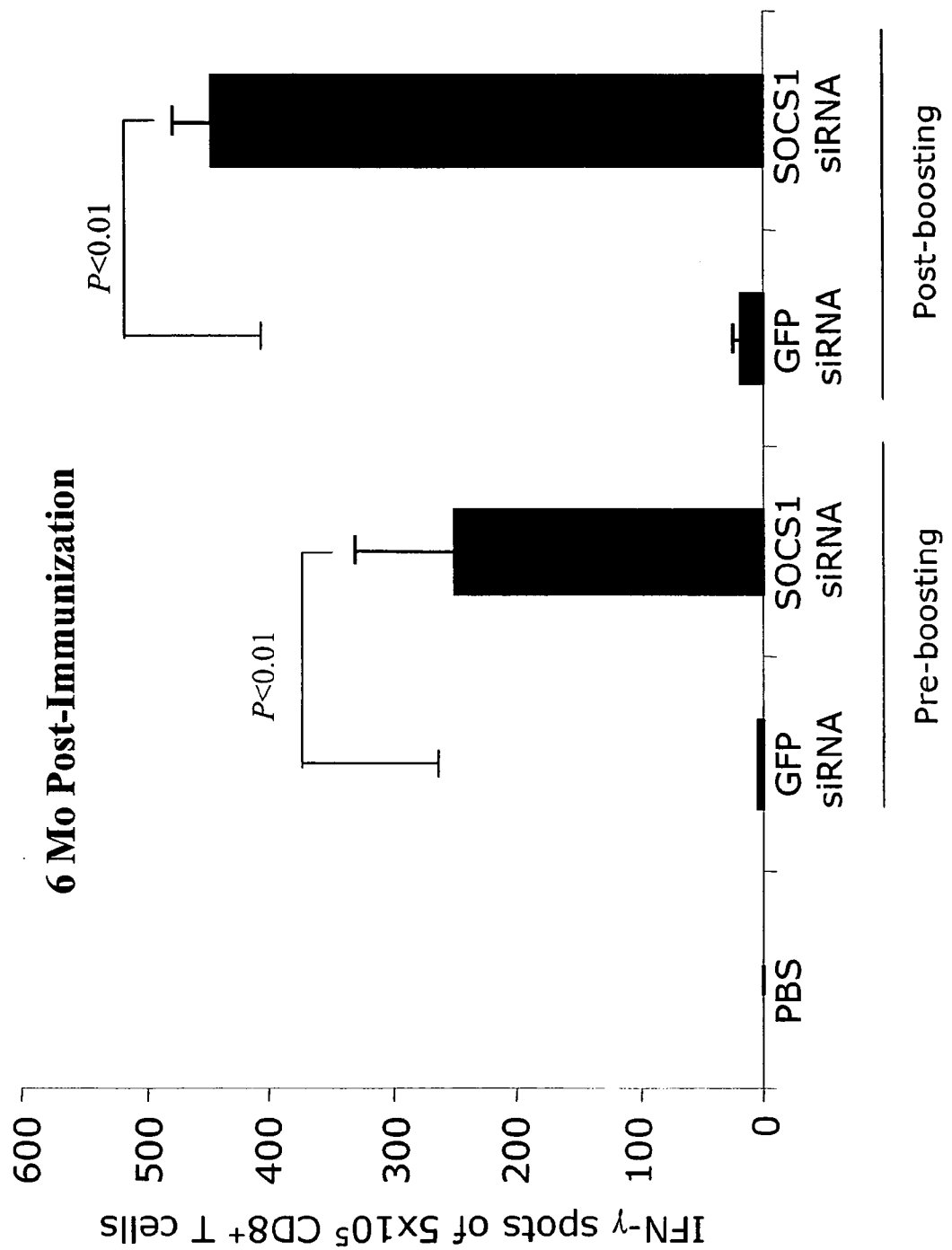
Figure 18C:
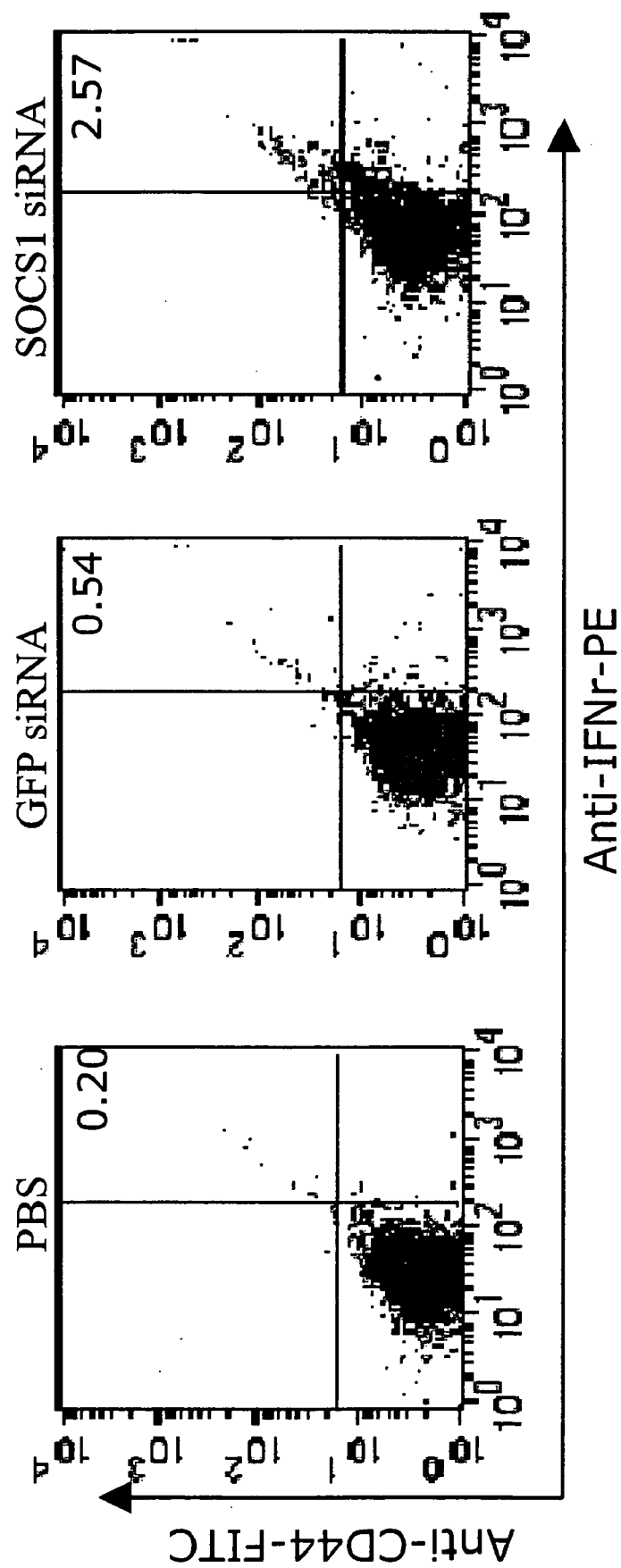
FIG. 18C illustrates percentages of CD44hi and IFNγ+ CD8+ T cells in LV-SOCS1-siRNA-DC mice, compared with LV-GFP siRNA-DC mice at six months post-immunization.
Figure 18D:
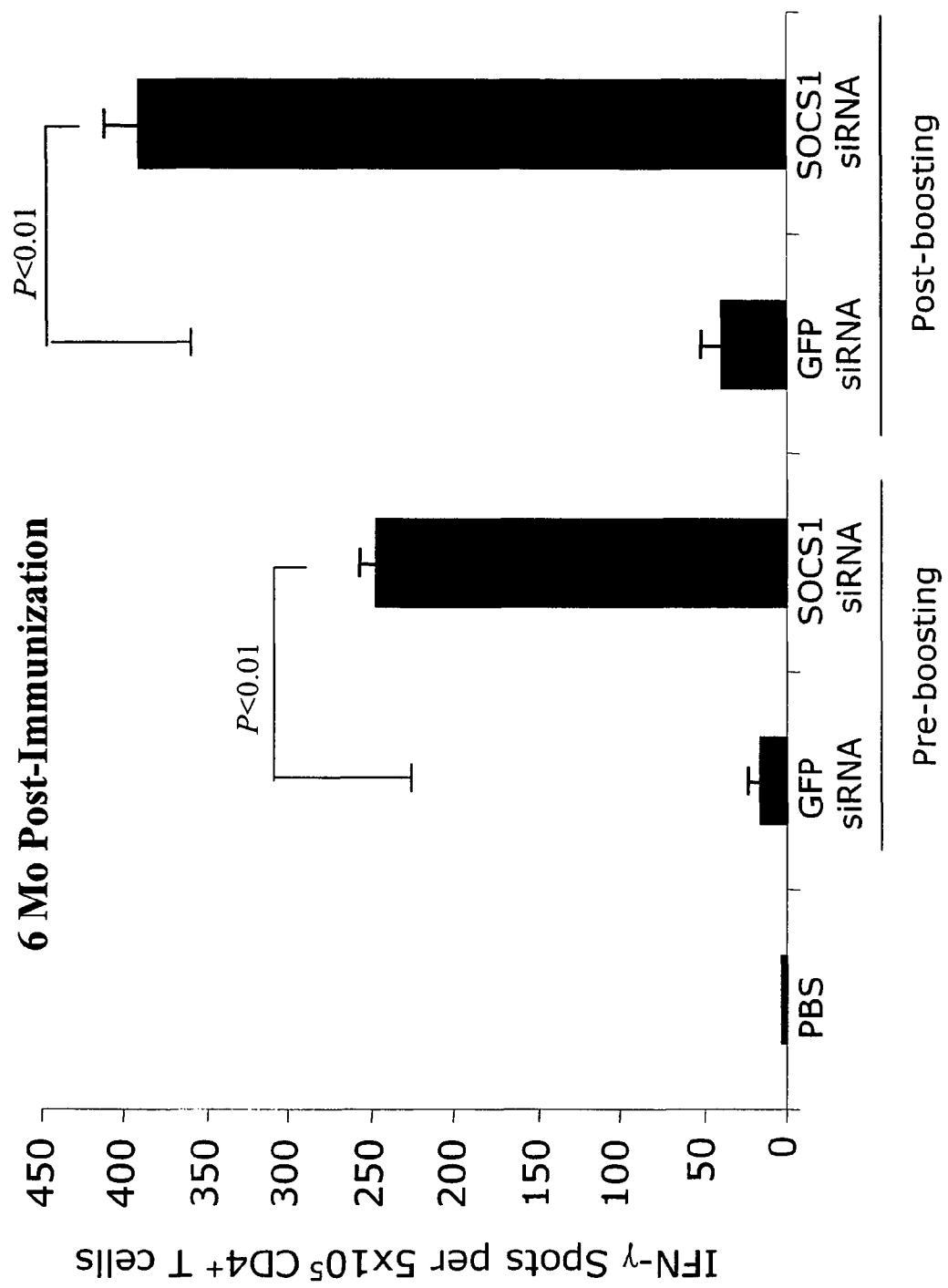
FIG. 18D illustrates that gp120-specific CD4+ Th responses were maintained and rapidly induced in LV-SOCS1-siRNA-DCs mice at six months after immunization.

The maintenance of memory HIV-specific CTLs and Th was assessed by examining gp120-specific CD8$^+$ and CD4+ T cell responses with IFN-γ ELISPOT assays. FIG. 18B shows that strong gp120-specific CTL responses were detected in LV-SOCS1-siRNA-DC mice, but not in LV-GFP-siRNA-DC mice, at six months after immunization (249 IFNγ spots per $5\times10^5$ CD8+ T-cells in LV-SOCS1-siRNA-DC mice vs. 3 IFNγ spots in LV-GFP-siRNA-DC mice). Vigorous gp120-specific CTL responses in LV-SOCS1-siRNA-DC mice were rapidly induced by booster immunization, but not in LV-GFP-siRNA-DC mice (446 IFNγ spots per $5\times10^5$ CD8+ T cells in LV-SOCS1-siRNA-DC mice vs. 16 IFNγ spots in LV-GFP-siRNA-DC mice on day 7 post-boosting) (FIG. 18B). Costaining of intracellular IFN-γ and the surface CD44 memory marker of CD8+ T cells also indicated a higher percentage of CD44hi and IFNγ+ CD8+ T cells in LV-SOCS1-siRNA-DC mice, compared with LV-GFP siRNA-DC mice at six months post-immunization (FIG. 18C). Similarly, gp120-specific CD4+ Th responses were maintained and rapidly induced in LV-SOCS1-siRNA-DCs mice at six months after immunization (391 IFNγ spots per $5\times10^5$ CD4+ T cells in LV-SOCS1-siRNA-DC mice vs. 37 IFNγ spots in LV-GFP-siRNA-DC mice on day 7 post-boosting) (FIG. 18D). Thus, immunization with SOCS1-silenced DCs effectively induces long-term HIV Env-specific CTL, Th, and antibody responses.

No apparent toxicity was observed in the mice immunized with LV-SOCS1-siRNA-DCs pulsed with gp120 up to seven months after immunization. Histological analysis of all major organs and tissues of the immunized mice revealed no pathologic inflammation. Levels of IgG and anti-dsDNA were comparable in DC-LV-SOCS1-siRNA and mock DC mice. These data suggest that gp120-pulsed LV-SOCS1-siRNA-DC Immunization does not cause pathological inflammation in mice.

Resistance of SOCS1-Silenced DCs to HIV Env-Mediated Immune Suppression

HIV viruses including gp120 proteins can suppress the ability of DCs to produce pro-inflammatory cytokines and to stimulate T cells (Fantuzzi et al., 2004, J. Virol. 78:9763-72; Granelli-Pipemo et al., 2004, Proc. Natl. Acad. Sci. USA. 101:7669-74; Barron et al., 2003, J. Infect. Dis. 187:26-37; Pacanowski et al., 2001, Blood 98:3016-21). The following experiments were set out to assess whether the enhanced activation of DCs by SOCS1 silencing might overcome the inhibitory effects of gp120 proteins on the cytokine production and immunostimulatory capacity of DCs. IL-12 was selected as a representative cytokine for these experiments, because DC-derived IL-12 was found to play a dual role: driving Th1 development as well as directly signaling B cells for developing humoral response (Dubois et al., 1998, J.

Immunol. 161:2223-31; Dubois et al., 1997, J. Exp. Med. 185:941-51; Skok et al., 1999, J. Immunol. 163:4284-91).

Figure 19A:
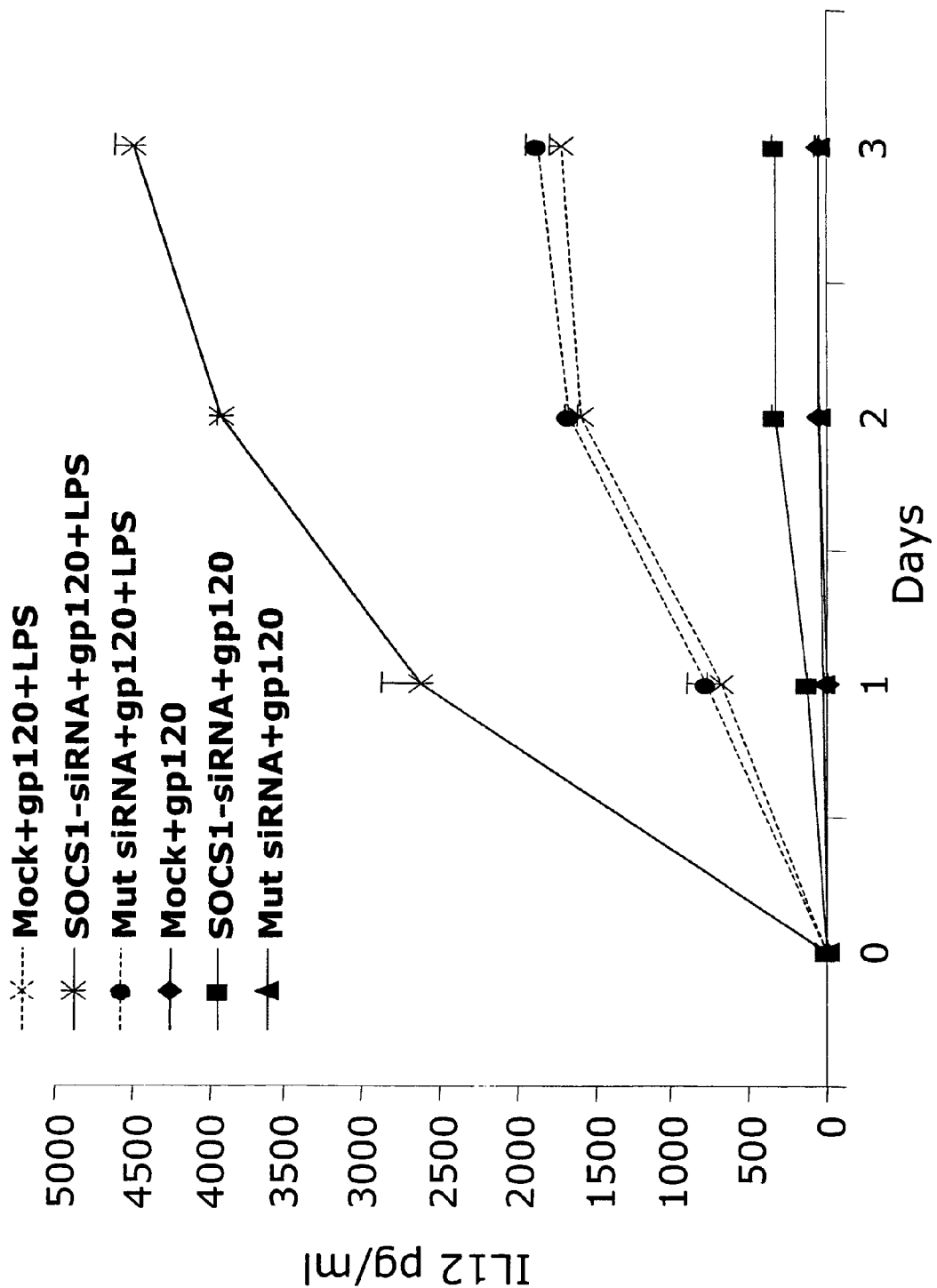
FIGS. 19A through 19E, is a series of charts demonstrating resistance of SOCS1-silenced DCs to HIV Env-mediated immune suppression.
Figure 19B:
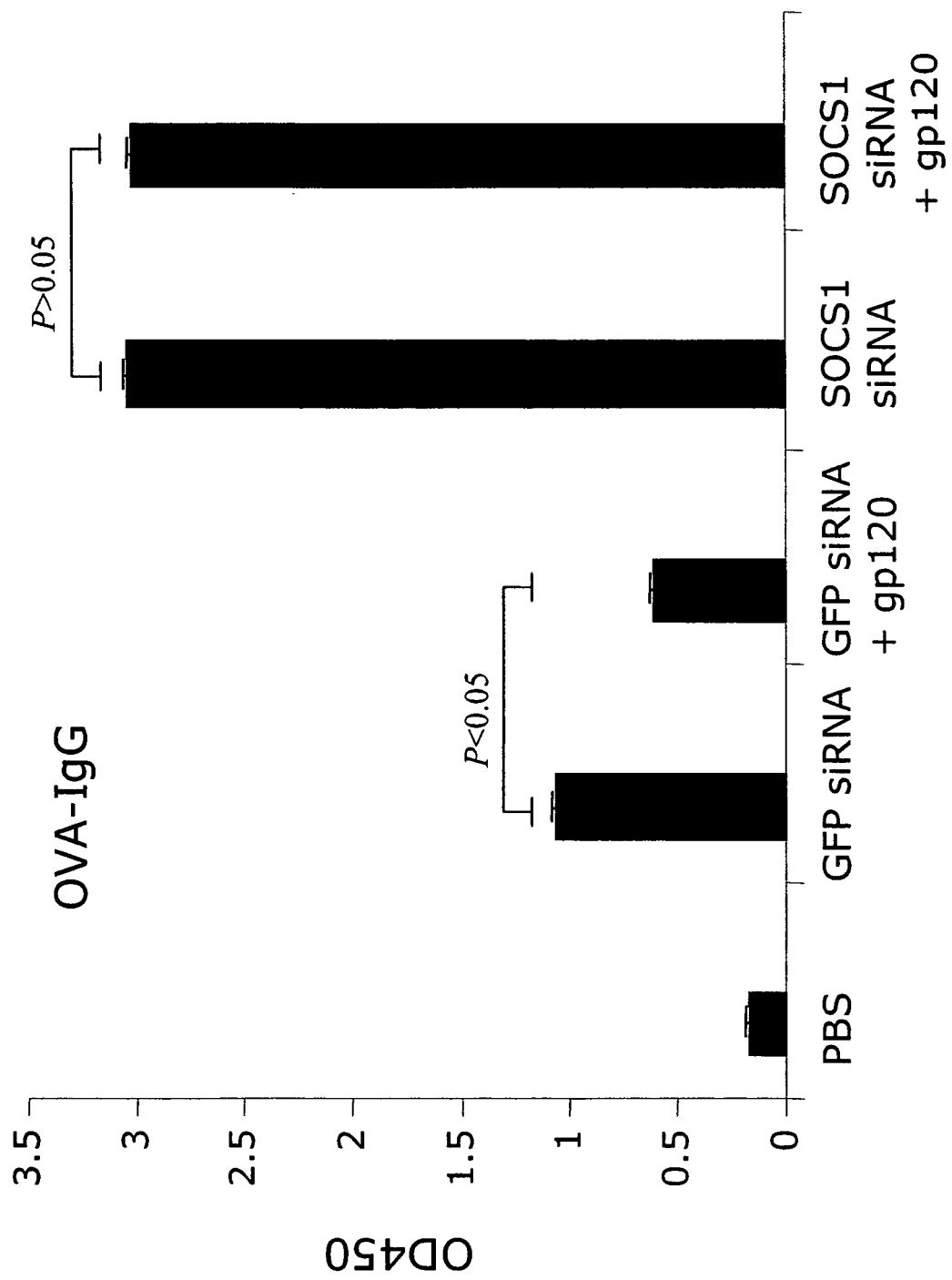
Figure 19C:
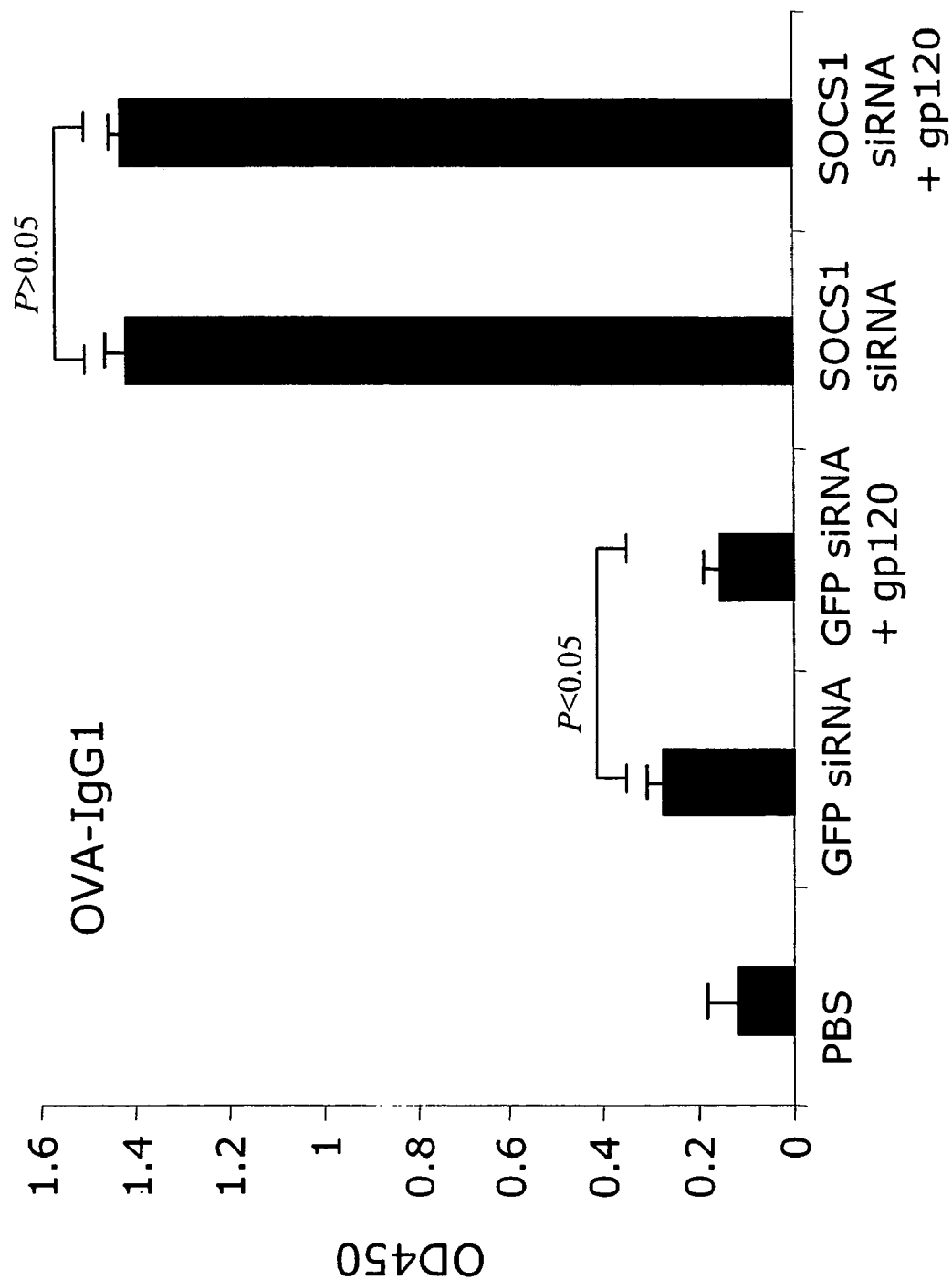
Figure 19D:
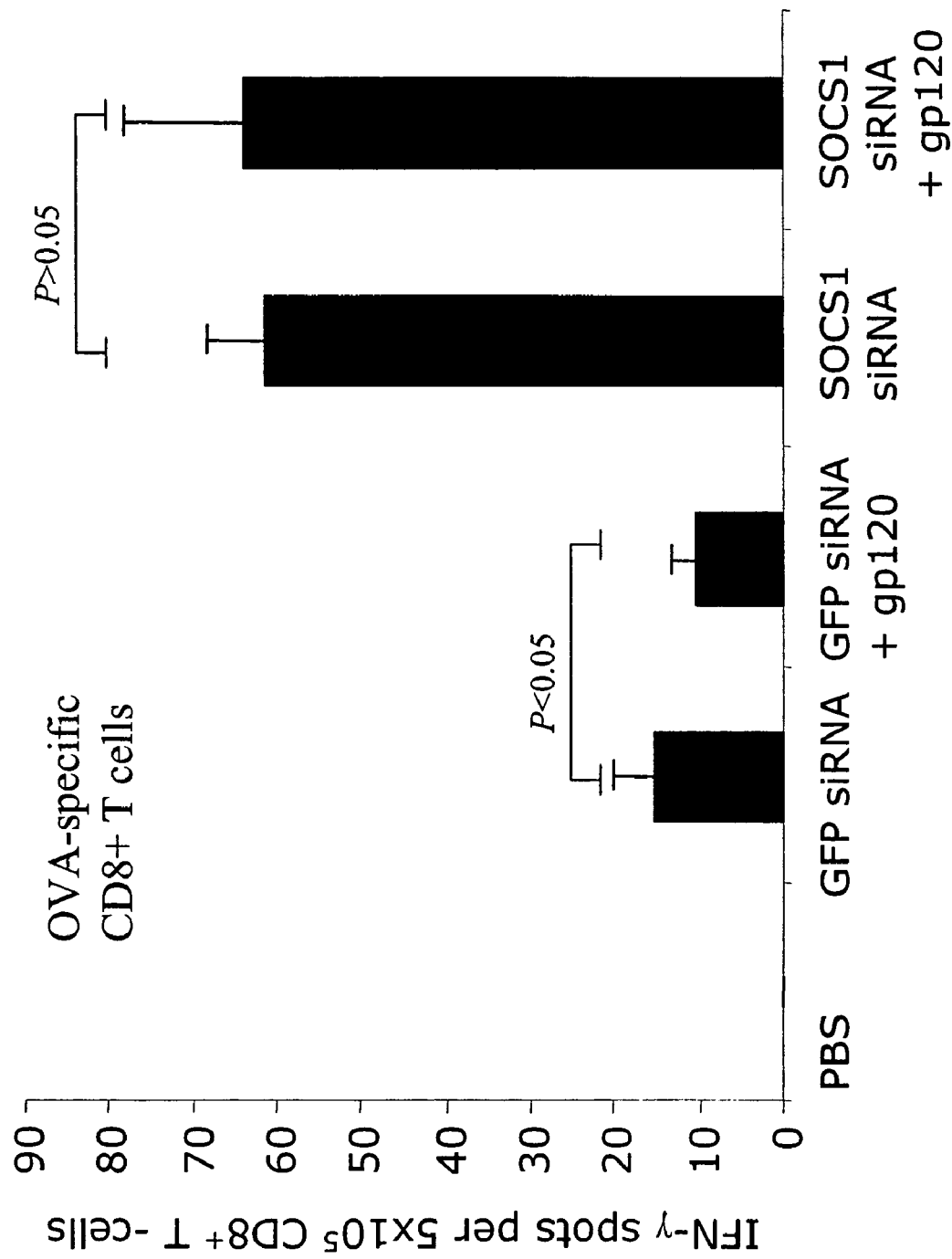
Figure 19E:
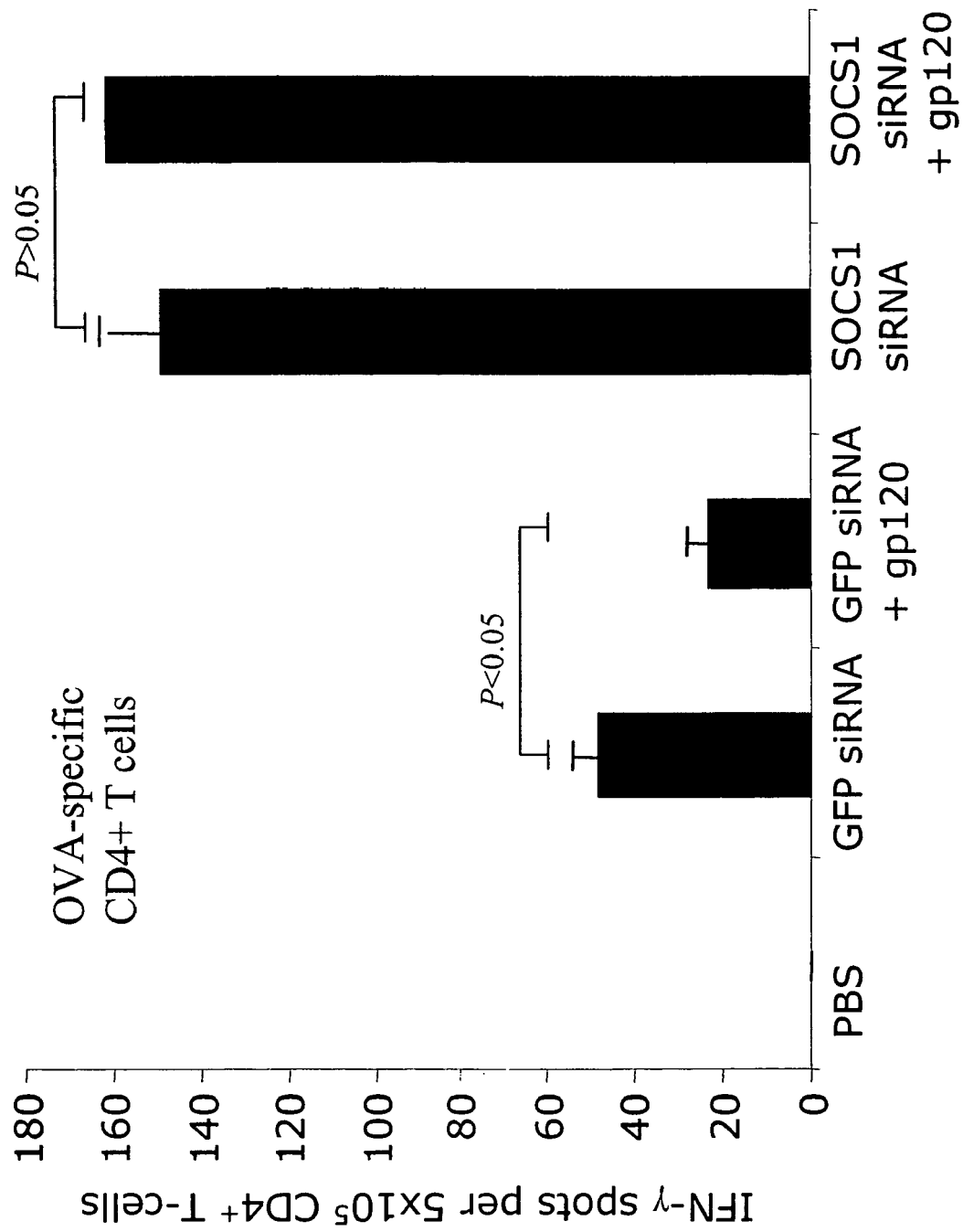

As shown in FIG. 19A, LV-SOCS1 siRNA-DCs in the presence of gp120 proteins retained the ability to respond to LPS. In contrast, the response of LV-GFP-siRNA-DCs to LPS stimulation was severely compromised by the presence of gp120 proteins. The susceptibility of SOCS1-silenced DCs to gp120-mediated suppression was further investigated in vivo. Mice were immunized with OVA-pulsed transduced DCs with or without pre-treatment of gp120 proteins ex vivo. Pre-exposure to gp120 proteins did not have apparent effects on the ability of LV-SOCS1-siRNA-DCs to induce OVA-specific antibody responses (FIGS. 19B and 19C), nor did it compromise OVA-specific CD8+ CTL and CD4+ Th responses induced by LV-SOCS1-siRNA-DCs (P>0.05) (FIGS. 19D and 19E). However, such pre-treatment significantly reduced the ability of LV-GFP-siRNA-DCs to induce OVA-specific antibody and CTL responses (P<0.05) (FIGS. 19B through 19E). These results indicate that SOCS1 silencing renders DCs resistant to HIV gp120-mediated suppression, likely due to the enhanced cytokine production and hyperactivated state of SOCS1-silenced DCs (Hanada et al., 2003, Immunity 19:437-50).

Example 8

In Vivo DNA Vaccination to Enhance the HIV-Specific Antibody and CTL Responses

The present example demonstrates the potency of HIV DNA vaccination is significantly enhanced by co-immunization with SOCS1 siRNA expressor DNA. This study represents the first attempt to elicit HIV-specific antibody and CTL responses by inhibiting the host's immune inhibitors, which presents a new avenue to develop more effective HIV vaccines.

The Materials and Methods used in the experiments presented in this Example are now described.

DNA Vaccination

The pSuper-SOCS1-siRNA expression vector was generated, as described previously elsewhere herein. To generate an HIV Env retrogen expression vector, a gp140CF plasmid was first constructed by deleting the gp120/gp41 cleavage site and fusion domain of gp41 of HIV gp160 (codon usage optimized-JRFL) to facilitate the secretion of HIV Env. The resultant pCMV/R-gp140CF-Fc retrogen vector contains the gp 140CF gene fused to the IgG Fc fragment under control of the CMV promoter. Recombinant gp120 (JFRL) proteins were produced from CHO cells and provided by the NIH AIDS Research and Reference Program. Endotoxin-free DNA was prepared with a Qiagen Kit, resuspended in endotoxin-free PBS (Sigma, St. Louis, Mo.-Aldrich Corp., St. Louis, Mo.) at a final concentration of 1 µg/µl, and stored at −20° C. until used for injection. Scheduled day of vaccination, 50 µg of gp140CF-Fc DNA or 200 µg of the mixture of gp140CF-Fc DNA (50 µg) and pSuper-SOCS1-siRNA expressor DNA (150 µg) was injected i.m. into the quadriceps of each mouse (Hauser et al., 2004, Gene Ther. 11:924-32; You et al., 2001, Cancer Research 61:3704-11). The immunized mice were then treated with LPS (30 µg/mouse) (IP) three times on days 1, 3 and 5 after each DNA immunization.

The results of the experiments presented in this Example are now described.

Potency of HIV DNA Vaccine Enhanced by Coimmunization with SOC1 siRNA DNA

The ability of SOCS1-silenced DCs to enhance both HIV Env-specific CTL and antibody responses suggested that the present SOCS1 silencing approach might be useful in improving the potency of HIV DNA vaccination. A "retrogen" immunization strategy using receptor-mediated endocytosis to enhance DC targeting and MHC presentation of antigens was used according to Hauser et al., 2004, Gene Ther. 11:924-32 and You et al., 2001, Cancer Research 61:3704-11. Briefly, a gp140CF retrogen was generated by in-frame fusing the IgG Fc fragment to the gp 140CF gene, in which the gp120/gp41 cleavage site and fusion domain of gp41 were deleted. The resultant gp140CF-Fc fusion proteins were expressed and secreted from cells transfected with the gp140CF-Fc vector.

Figure 20A:
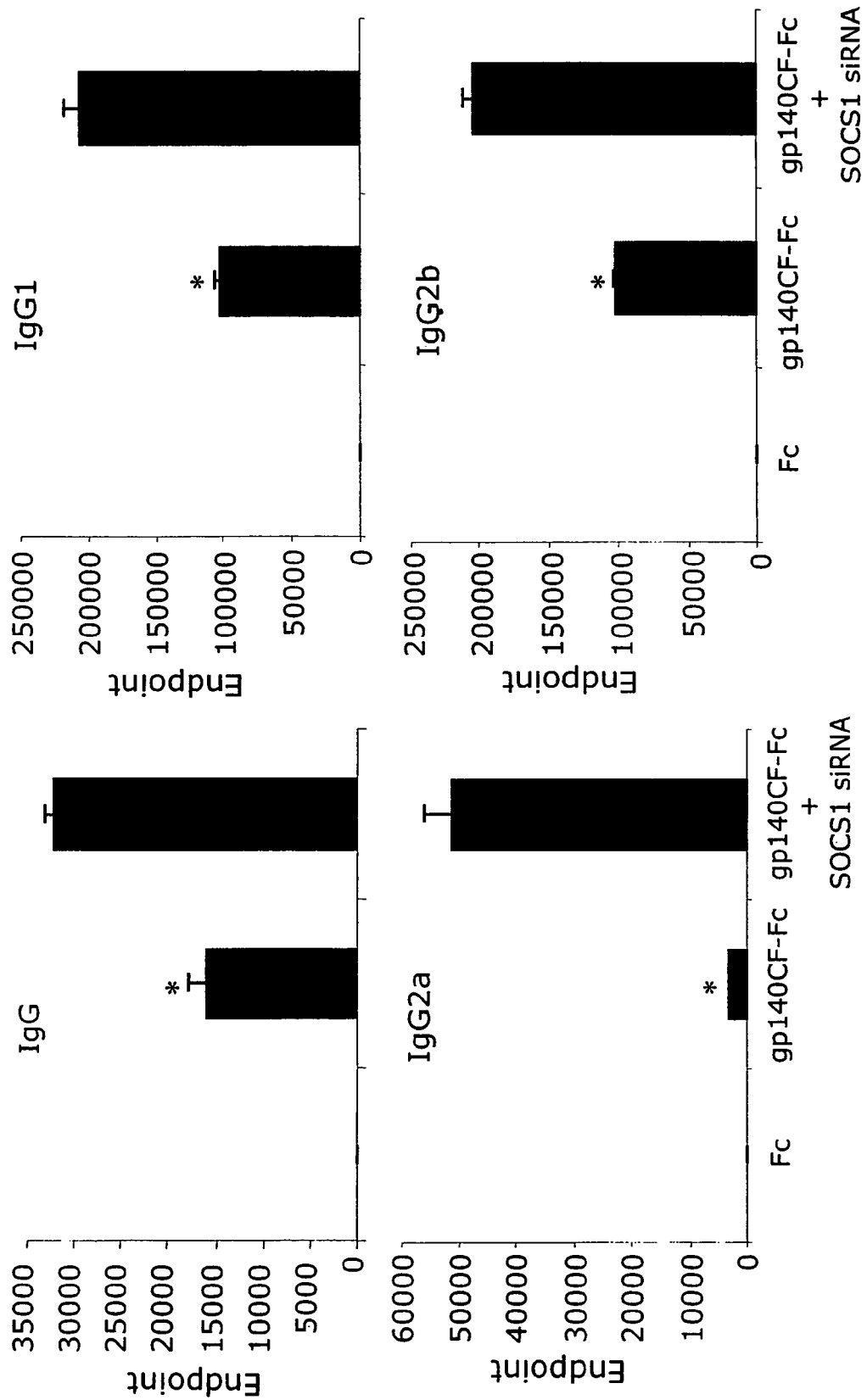
FIGS. 20A through 20D, is a series of charts demonstrating enhancement of HIV DNA vaccine by SOCS1 siRNA.
Figure 20B:
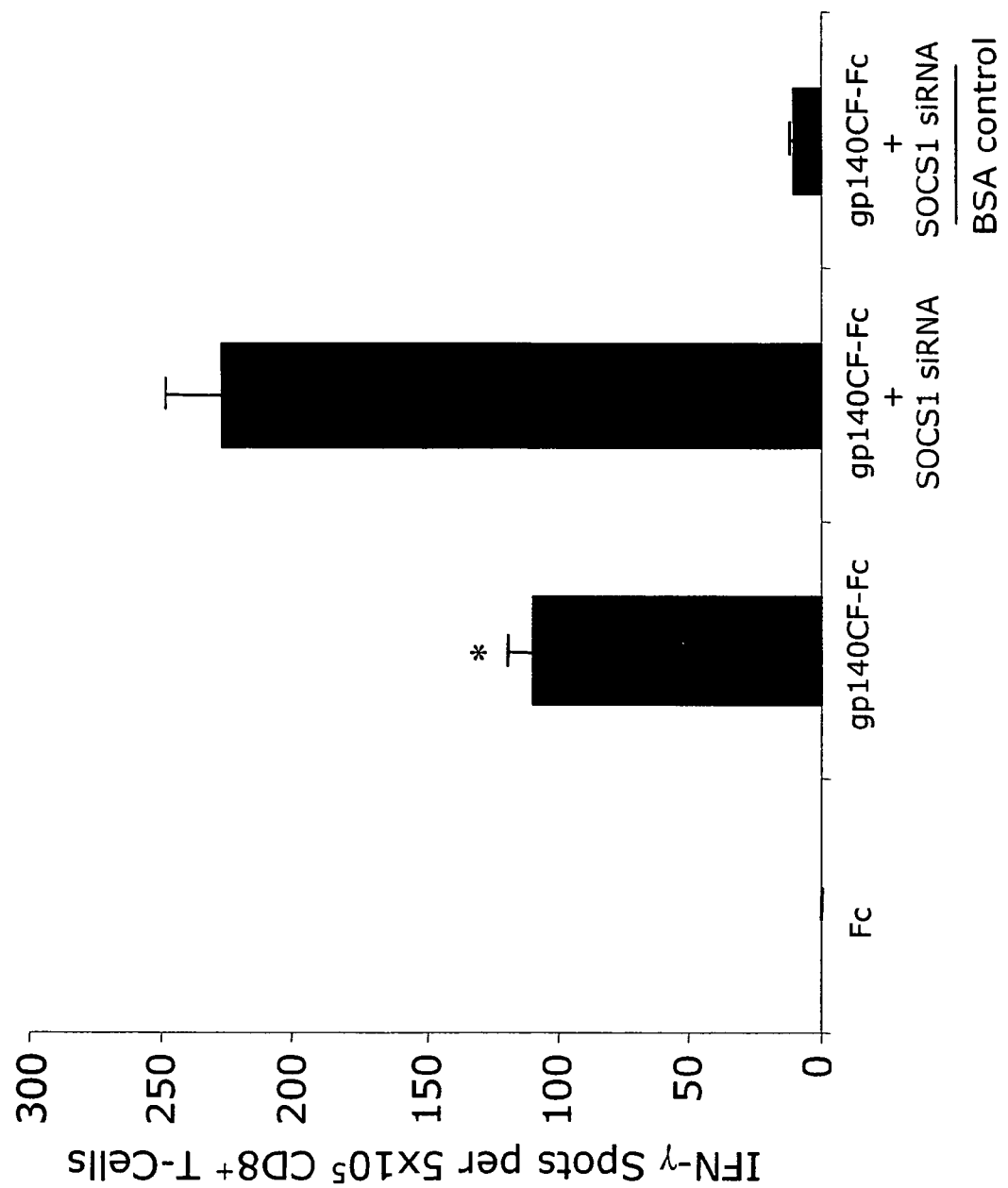
Figure 20C:
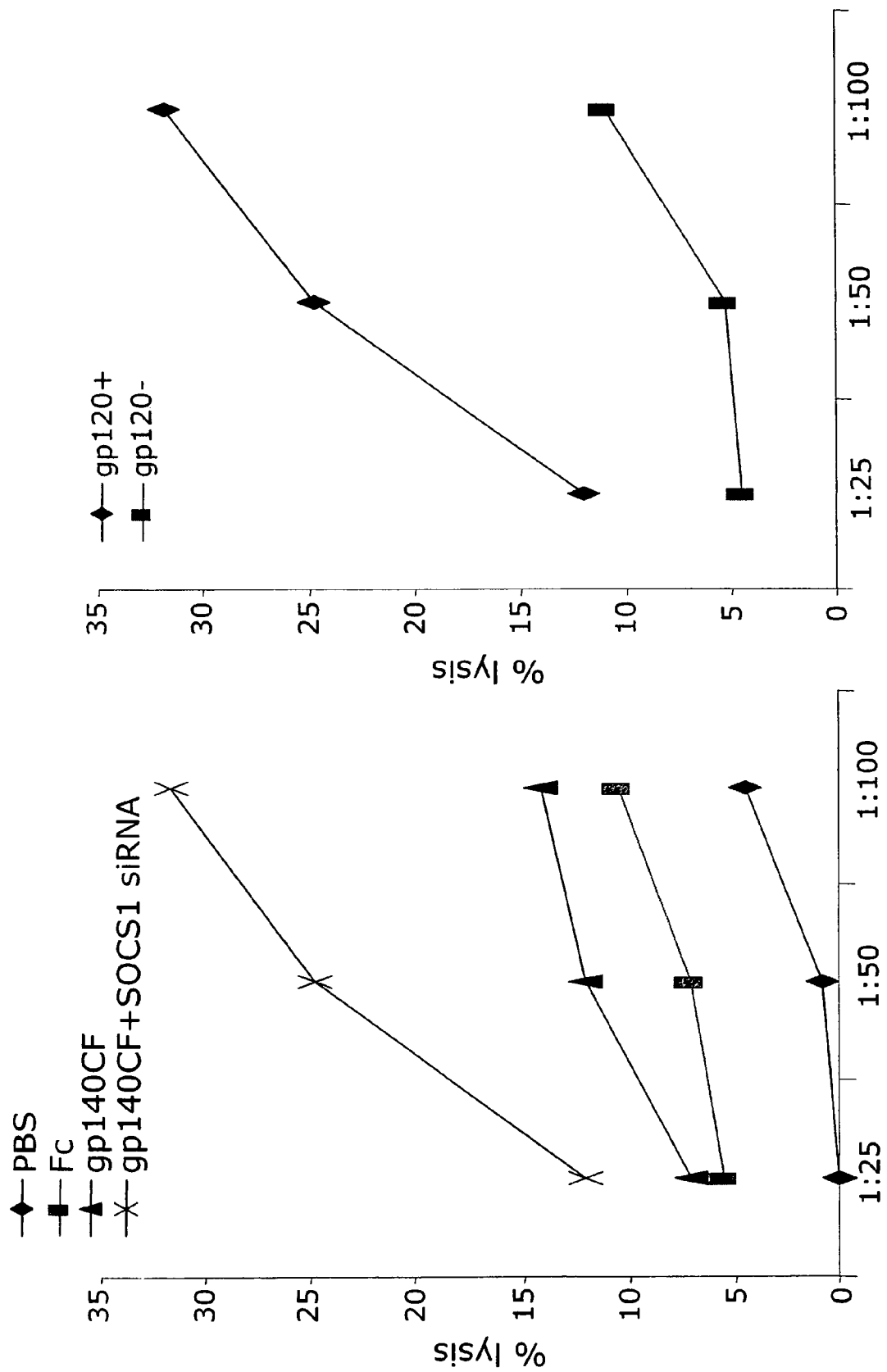
Figure 20D:
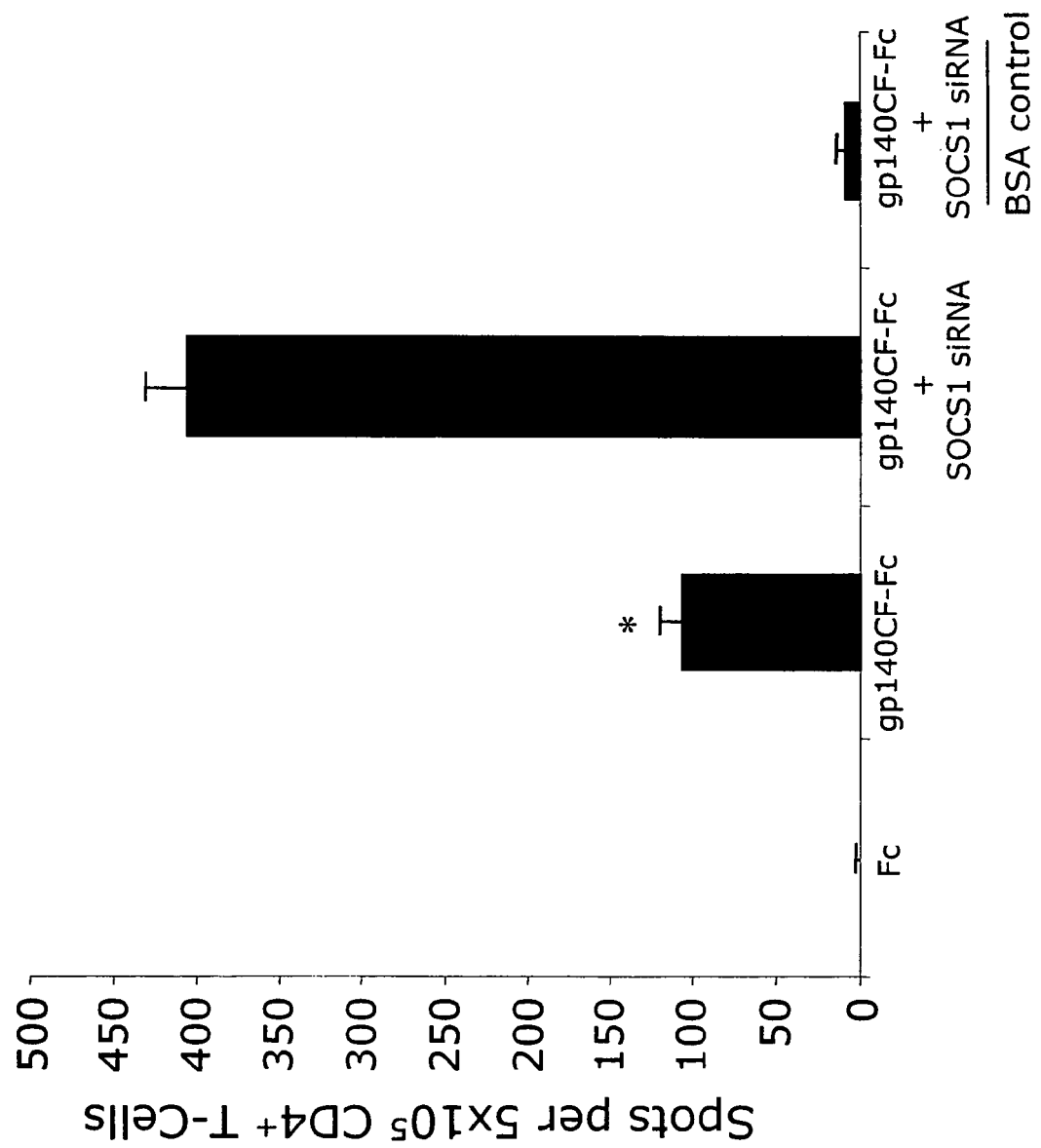

To test the effect of SOCS1 siRNA on DNA vaccination, mice were injected with gp140CF-Fc DNA only or with a mixture of gp140CF-Fc DNA and pSuper-SOCS1-siRNA expressor DNA weekly for three weeks, and then monitored the mice for HIV Env-specific immune responses one week later. Enhanced HIV Env-specific antibody titers were evident in mice coimmunized with pSuper-SOCS1-siRNA DNA (FIG. 20A). HIV Env-specific CTL responses were significantly enhanced by co-injection of pSuper-SOCS1-siRNA DNA, as demonstrated by CTL and ELISPOT assays (FIGS. 20B and 20C). Moreover, HIV Env-specific CD4+ Th responses were enhanced by co-injection of SOCS1-siRNA DNA (FIG. 20D). Intracellular staining with cytokines also indicated enhanced gp120-specific CD4+ T cell responses in mice coimmunized with pSuper-SOCS1 siRNA DNA. These results indicate that pSuper-SOCS1 siRNA DNA co-immunization enhances the potency of HIV DNA vaccination, due to the enhanced immunostimulatory capacity of the co-transfected antigen-presenting cells in the immunized mice. Thus, the SOCS1 silencing strategy presented herein is applicable to ex vivo DC-based and in vivo vaccination settings.

An Alternative and Effective HIV Vaccination Approach Based on Inhibition of Natural Immune Inhibitors in DCs The present disclosure demonstrates that silencing of the negative signaling regulator SOCS1 in DCs results in drastic enhancement of both HIV Env-specific antibody and CTL responses in mice. It was observed that both HIV Env-specific antibody and CTL responses induced by SOCS1-silenced DCs are long-lasting. In addition, the results demonstrated that co-immunization with SOCS1 siRNA DNA significantly enhances the potency of HIV DNA vaccination. Thus, a balanced, memory humoral and cellular response against HIV can be induced with SOCS1-silenced DCs and this SOCS1 silencing strategy is applicable to both therapeutic and prophylactic HIV vaccination settings.

The role of DCs in the induction of humoral responses has been traditionally viewed as a consequence of CD4+ Th priming for cognate interaction between T cells and B cells. However, the direct role of DCs in stimulation of the humoral response has been documented in vitro and in vivo (Dubois et al., 1997, J. Exp. Med. 185:941-5138; Inaba et al., 1983, Proc. Natl. Acad. Sci. USA 80:6041-5). Notably, DCs were found to strongly enhance both proliferation and antibody production of CD40-activated B cells (Dubois et al., 1997, J. Exp. Med. 185:941-51). Immunization with DCs loaded with antigens can induce a protective humoral response (Flamand et al., 1994, Eur. J. Immunol. 24:605-10). The results herein demonstrate that SOCS1-silenced DCs enhance the production of Th2-polarizing cyokines as well as B-lymphocytes stimulatory cytokines (BAFF and APRIL), which is likely responsible for the enhanced Th and B cell activation seen in SOCS1-silenced DC immunized mice. The present findings are supported by a previous report that SOCS1-/- DCs induce aberrant expansion of B cells and autoreactive antibody production (Hanada et al., 2003, Immunity 19:437-50). Hence, this study demonstrates the critical role of SOCS1 in DCs in controlling HIV-specific antibody responses and implies that the silencing of SOCS1 can be generically used to boost antibody responses against antigens other than HIV Env.

An important finding of this study is that SOCS1-silenced DCs induce a balanced, memory HIV-Env-specific antibody and CTL response, which may be desirable for preventing or controlling HIV infection (Burton et al., 2004, Nat. Immunol. 5:233-6; McMichael et al., 2003, Nat. Med. 9:874-80; Nabel, 2001, Nature 410:1002-7; Letvin et al., 2002, Annu. Rev. Immunol. 20:73-99; Zolla-Pazner, 2004, Nat Rev. Immunol. 4:199-210; Imami et al., 2002, J. Virol. 76:9011-23; Letvin et al., 2003, Nat. Med. 9:861-6). Without wishing to be bound by any particular theory, the mechanism(s) by which SOCS1 silencing induces a balanced, memory humoral and cellular response may involve the production of a mixed pattern of Th1- and Th2-polarizing cytokines by SOCS1-silenced DCs and gp120-specific CD4+ T cells. These results are consistent with mixed antibody and CTL responses naturally generated against many pathogens such as viruses (Allen et al., 1997, Immunol. Today 18:387-92), indicating that Th1 and Th2 polarization is not mutually exclusive (Gor et al., 2003, Nat. Immunol. 4:503-5; Colonna, 2001, Nat. Immunol. 2:899-900).

SOCS1 functions as a feedback inhibitor of the JAK/STAT signaling pathway used by a variety of cytokines and is involved in regulating the TLR-signaling pathway directly or indirectly (Baetz et al., 2004, J. Biol. Chem. 279:54708-15; Gingras et al., 2004, J. Biol. Chem. 279:54702-7). The results herein consistently indicated the enhanced production of various cytokines such as TNF-α, IL-6, and IL-12 by SOCS1-silenced DCs in response to LPS. LPS-TLR signaling activates a wide array of NF-κB-responsive genes including many inflammatory cytokines, which can function in autocrine and paracrine fashions (Baetz et al., 2004, J. Biol. Chem. 279:54708-15; Grohmann et al., 1998, Immunity 9:315-23; Pan et al., 2004, Immunol. Lett. 94:141-51). In view of the fact that SOCS1 is involved in attenuating TLR signaling indirectly, disabling of the critical brake of the JAK/STAT pathway should permit cytokines to establish autocrine or/and paracrine stimulation loops, leading to the enhancement, not reduction, of cytokine production. The results disclosed herein involving the use of cytokine and cytokine receptor knockout mice, suggest that the autocrine cytokine stimulation loops contribute to the overproduction of cytokines by SOCS1-silenced DCs.

Functional defects and depletion of DCs are common in HIV-infected individuals, likely contributing to the progressive immunodeficiency. HIV gp120 proteins can suppress the ability of DCs to produce pro-inflammatory cytokines and to stimulate T-cells (Fantuzzi et al., 2004, J. Virol. 78:9763-72; Carbonneil et al., 2004, J. Immunol. 172:7832-40). It was demonstrated that SOCS1 silenced DCs resist HIV gp120-mediated suppression, because of the enhanced production of proinflammatory cytokines and the hyperactivated state of SOCS1-silenced DCs (Hanada et al., 2003, Immunity 19:437-50). This finding is especially relevant to the development of therapeutic HIV vaccines, which would be used in immunosuppressed HIV-infected individuals (Lu et al., 2004, Nat. Med. 10: 1359-1365).

The vaccination strategy described here, represents the first effort to enhance anti-HIV immune responses by inhibiting the host's immune inhibitors in DCs. Since natural immunity is ineffective in controlling HIV-1 infection, disabling the host's immune inhibitors may be critical to generate effective anti-HIV immune responses. However, mere enhancement of HIV-specific immune responses may not lead to the induction of protective HIV antibodies and CTL responses. In this regard, the present strategy offers the opportunity for combinational immunization with currently available vaccines, as demonstrated by the co-immunization of DNA vaccine and SOCS1 siRNA DNA. When used with improved HIV immunogens and delivery systems (Burton et al., 2004, Nat. Immunol. 5:233-6; Yang et al., 2002, J. Virol. 76:4634-42), this vaccination approach may provide a new avenue to enhance weak protective immune responses or generate broader and stronger responses not only against dominant epitopes, but also against weakly immunogenic or cryptic, yet protective epitopes. In summary, the present disclosure demonstrates the principle of inhibiting a host's signaling inhibitor in DCs to enhance both HIV-specific antibody and CTL responses, imploring further investigation to determine if protective anti-HIV responses can be induced by this strategy in monkeys and ultimately in humans. In addition, this SOCS1 silencing strategy could be used to enhance immune responses against other pathogens.

Example 9

Identification and Analysis of Human SOCS1 siRNA

A computer program was used to select siRNA sequences targeting human SOCS1: hSOCS1-siRNA1 (CACGCACU-UCCGCACAUUC.dT.dT; SEQ ID NO:21), hSOCS1-siRNA2 (UUCCGUUCGCACGCCGAUU.dT.dT; SEQ ID NO:22) and hSOCS1-siRNA3 (GAGCUUCGACUGCCU-CUUC.dT.dT; SEQ ID NO:23). All target sequences were subjected to NCBI Blast query to confirm the lack of homology to other known genes. The designation of ".dT.dT" refers to poly dT sequence immediately downstream of the siRNA target sequence.

Example 10

Transfection of Human Monocyte-DCs with GenePorter

To investigate the role of human SOCS1 in the regulation of human DCs, a small interfering RNA (siRNA) with the ability to specifically downregulate human SOCS1 was first identified. A computer program was used to select siRNA sequences targeting human SOCS1 and 293T cells. Each synthetic human SOCS-1-siRNA oligonucleotide duplex was then co-transfected with a flag-tagged human SOCS1 expression at a 10:1 ratio using GenePorter transfection reagent into 293T cells. 48 hours after transfection, the cells were harvested, and analyzed by Western blotting as described elsewhere herein.

Figure 21A:
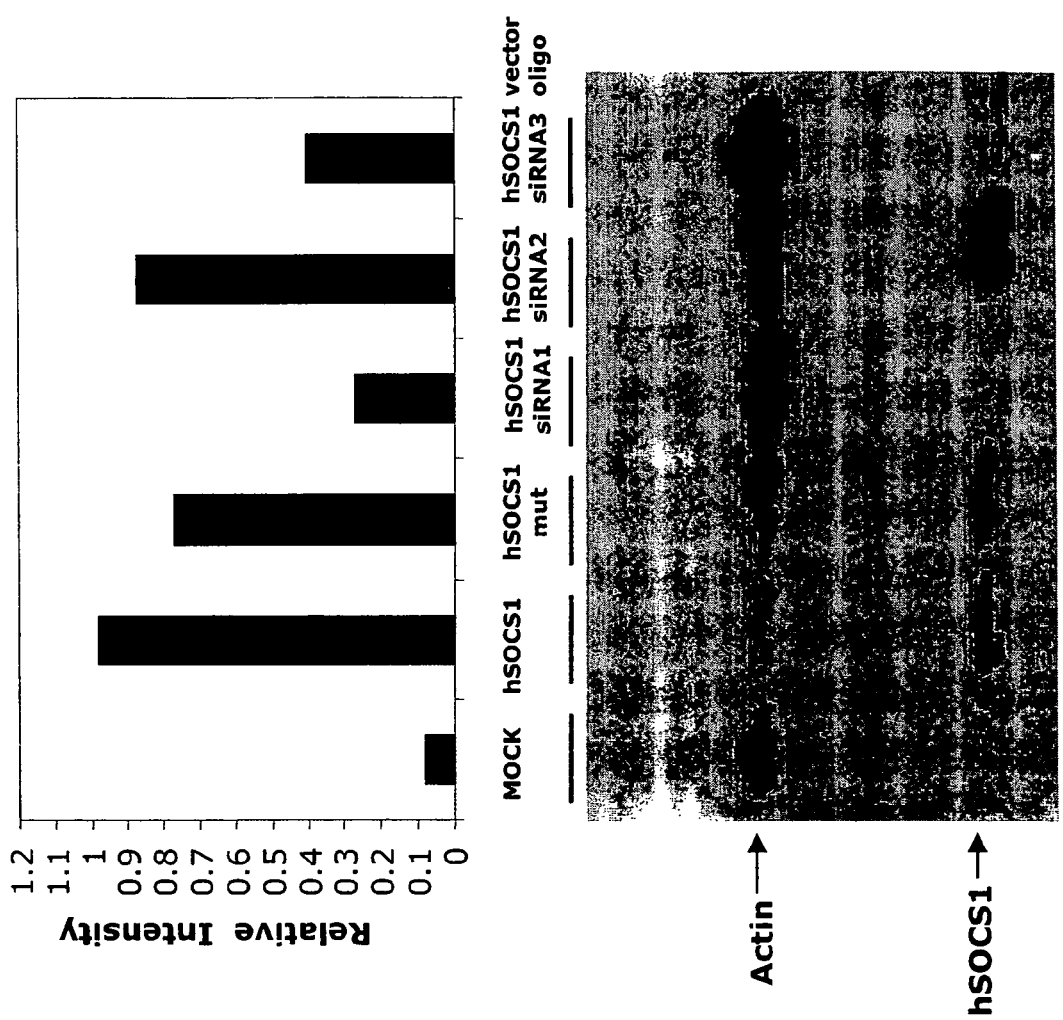
FIGS. 21A through 21C, is a series of charts demonstrating silencing of human SOCS1 in human monocyte-derived DCs.
Figure 21B:
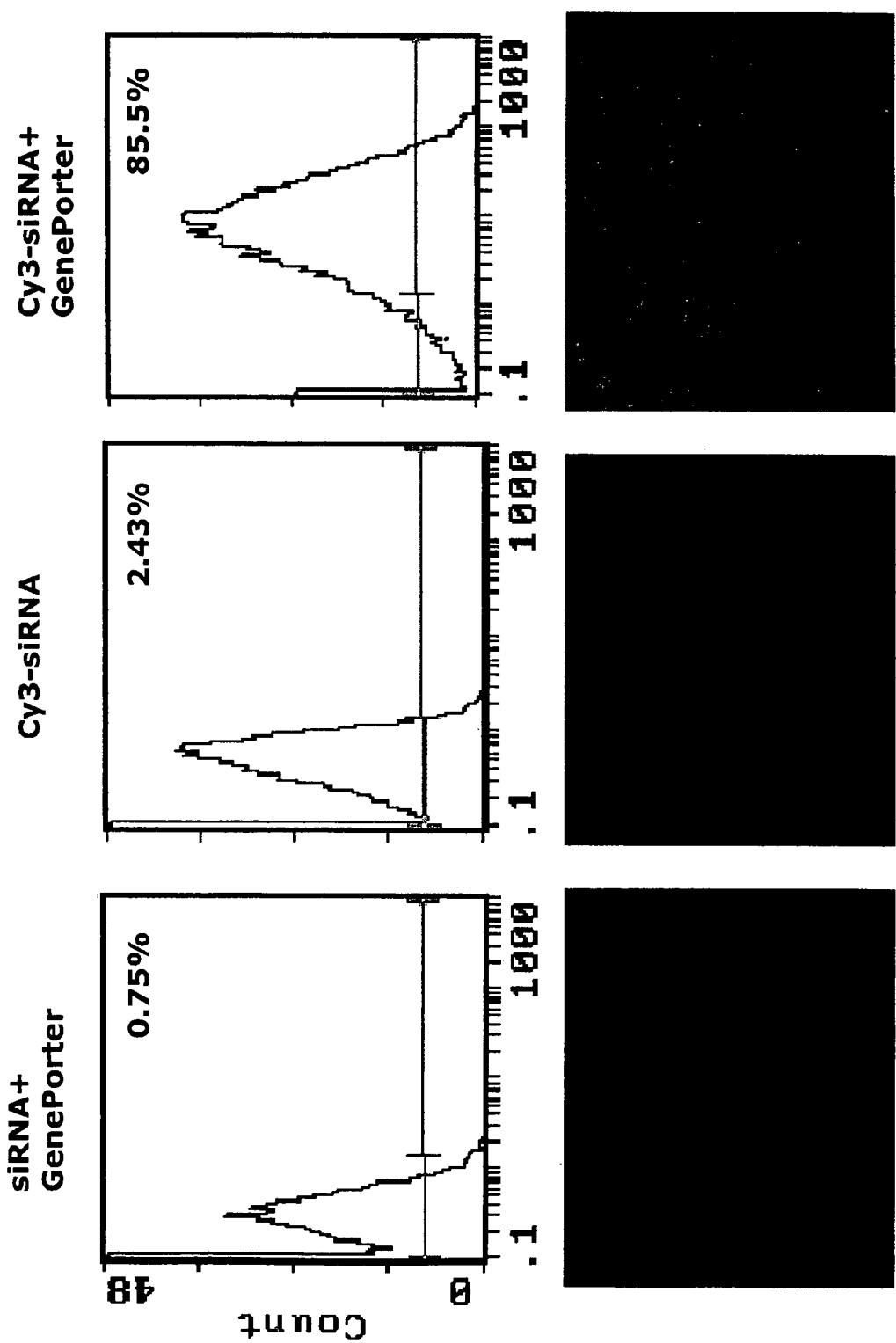
Figure 21C:
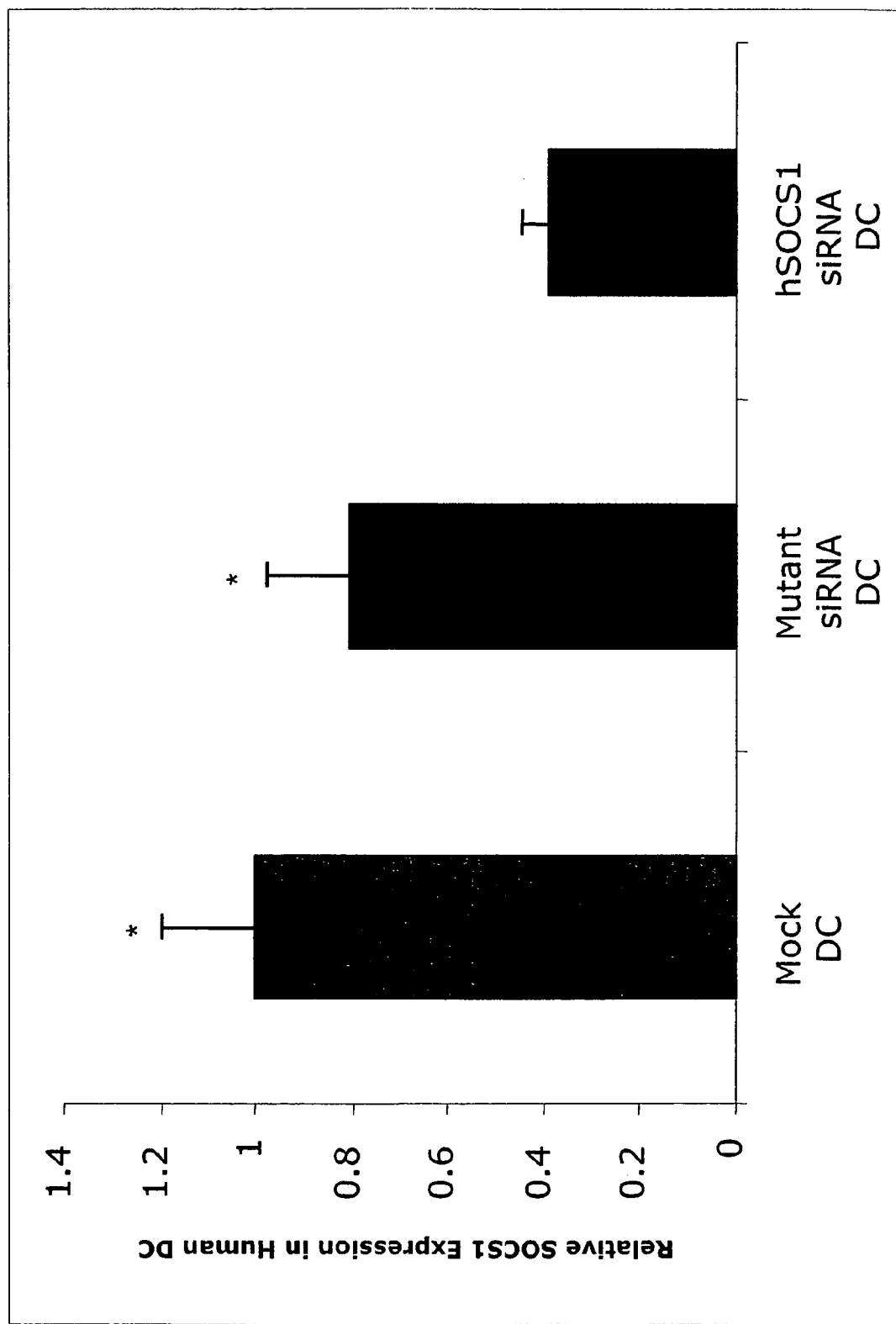

FIG. 21A shows that human SOCS1 siRNA1 efficiently down-regulated human SOCS1 expression. The specificity of human SOCS1 mRNA down-regulation by siRNA was confirmed by the inability of a scrambled siRNA1 oligonuleotide duplex to down-regulate SOCS1 mRNA. Human SOCS1 siRNA1 was therefore selected for further study. Synthetic siRNA duplexes were transfected by GenePorter into DCs derived from human monocytes with a transfection efficiency of 85.5% (FIG. 21B). As verified by quantitative RT-PCR assays, the level of hSOCS1 mRNA in the total DC population transfected with the hSOCS1 siRNA1 duplexes was specifically decreased by approximately 60%, compared with levels in mock-transfected DCs (FIG. 21C, p<0.01). The siRNA efficiency and SOCS1 RNA reduction are similar to those observed in experiments using synthetic siRNA duplexes targeting mouse SOCS1 in the total mouse bone marrow-derived DC population.

The relative expression of human SOCS1 in human DCs was evaluated by quantitative real-time RT-PCR as described elsewhere herein. Pre-developed primer/probe sets for human SOCS1 (primers, 5'-TTTTTCGCCCTTAGCGGGAA-3'; SEQ ID NO:24 and 5'-CTGCCATCCAGGTGAAAGC-3'; SEQ ID NO:25, and the probe, 6FAM-ATGGCCTCGG-GACCCACGAG-TAMRA; SEQ ID NO:26) from Applied Biosystems, Inc., Foster City, Calif. were used.

Characterization of Human SOCS-1 Silenced DCs

Figure 22A:
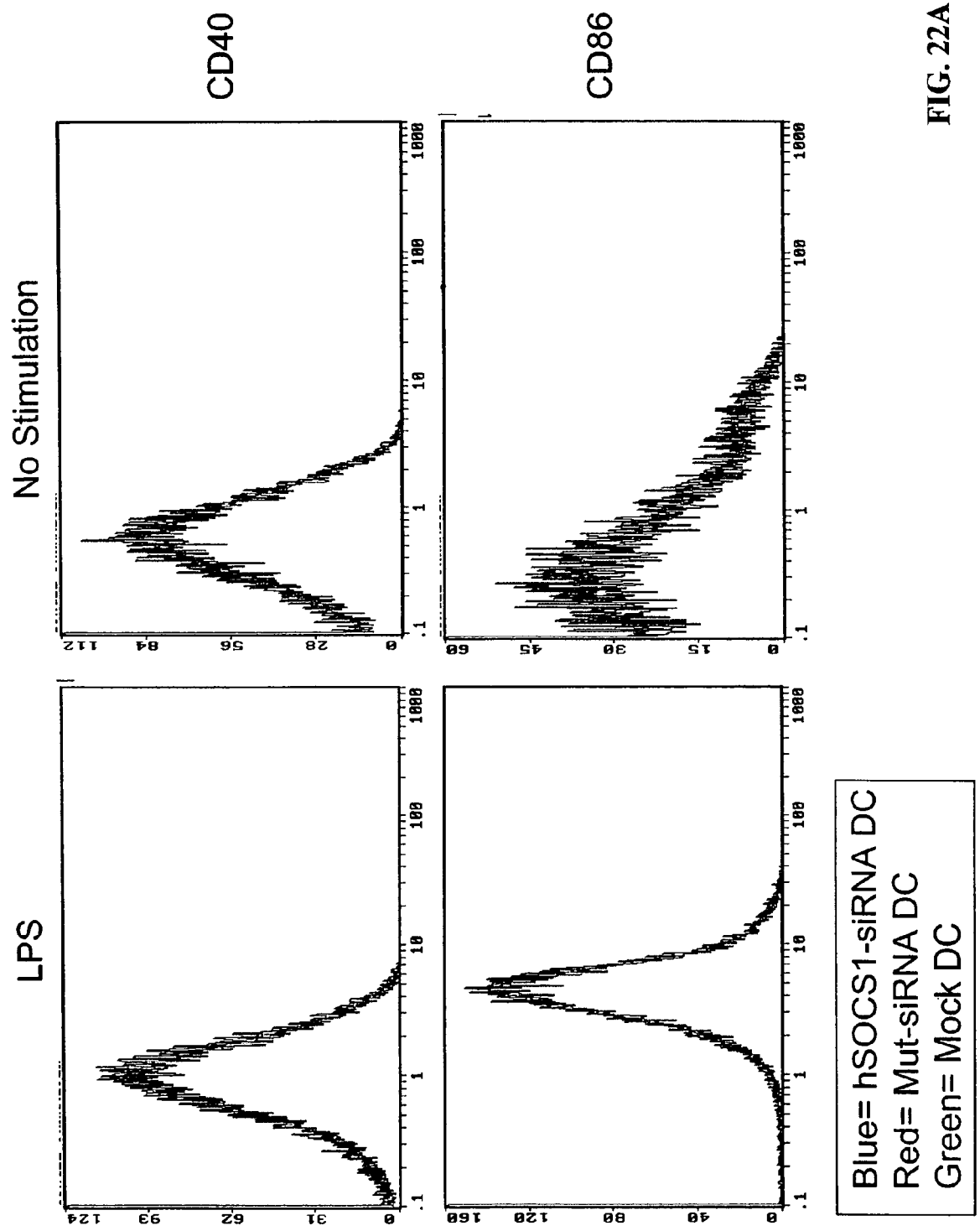
FIGS. 22A through 22C, is a series of charts characterizing human SOCS-1 silenced DCs.
Figure 22B:
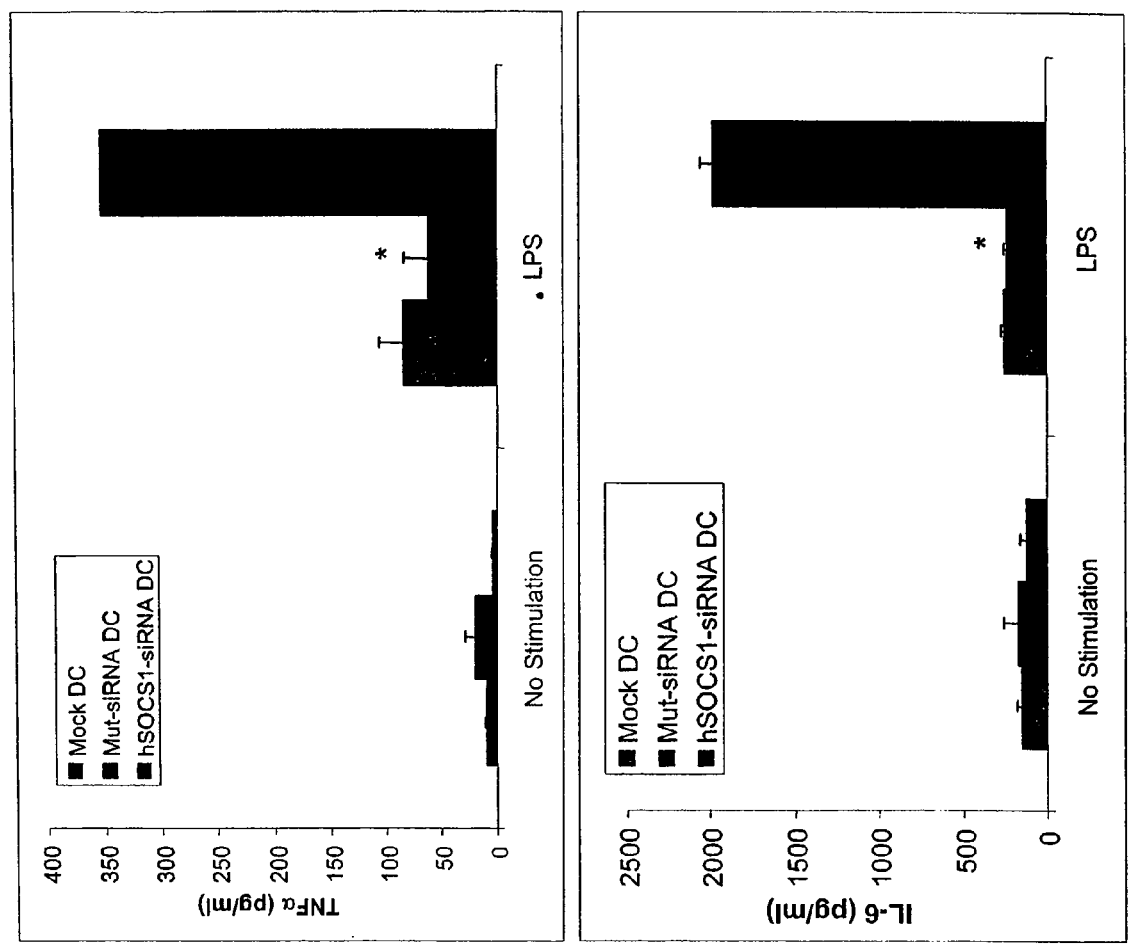
Figure 22C:
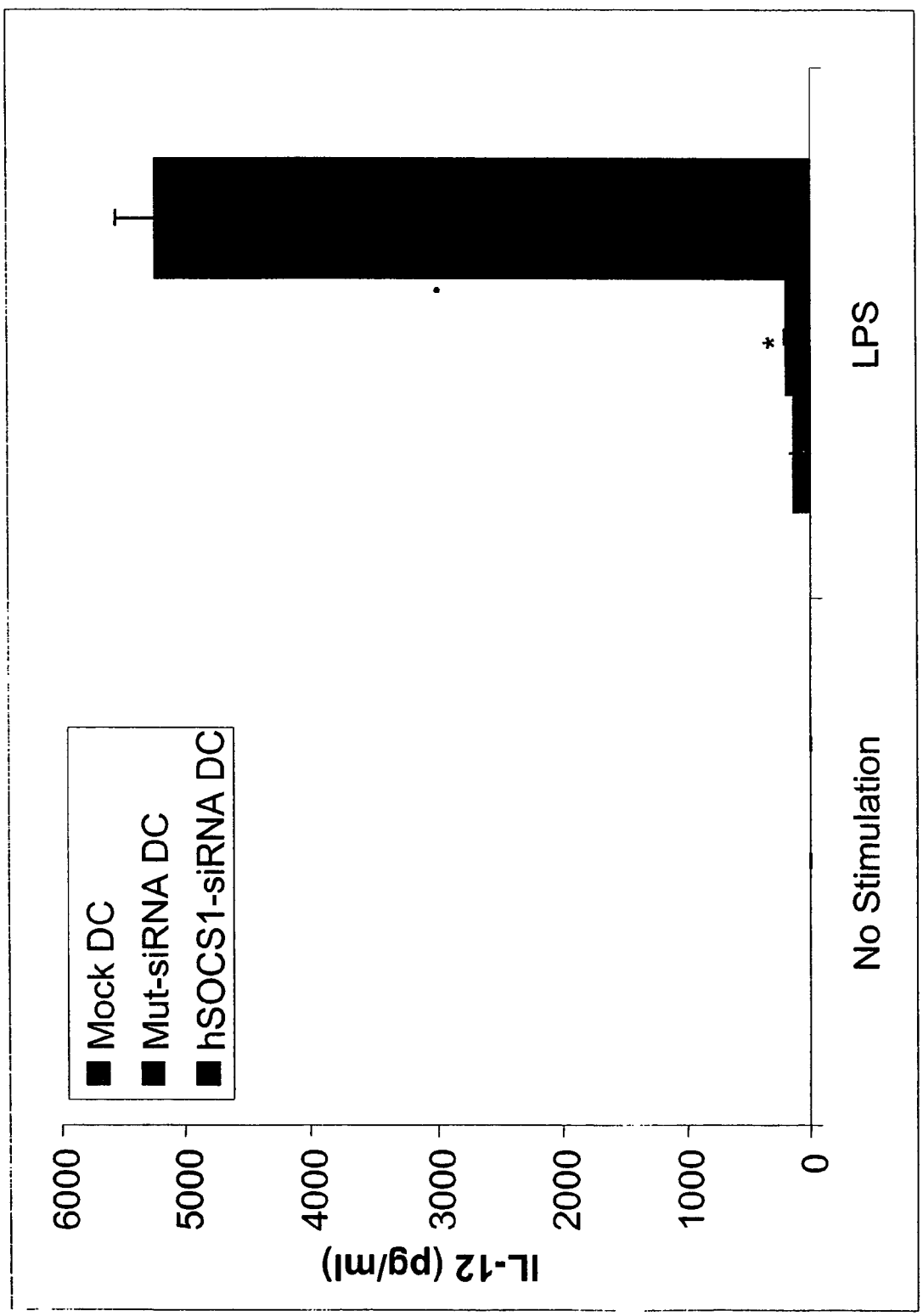

The next set of experiments were performed to assess whether human SOCS1 regulates the expression of costimulatory molecules on DCs by flow cytometric analysis. Flow cytomic analysis for human SOCS1 was followed according to those used in assessing murine SOCS1 as discussed elsewhere herein. It was observed that hSOCS1-siRNA-transfected DCs and control hSOCS1-siRNA mutant-transfected DCs indicated only a slight difference in their expression of representative costimulatory molecules before and after LPS-induced maturation (FIG. 22A), consistent with observations in murine DCs. Comparable levels of MHC-I and II molecules were also detected on hSOCS1-siRNA DCs and mutant-siRNA DCs. In contrast, it was observed that hSOCS1 siRNA transfected DCs were more responsive to stimulation with LPS than were human DCs transfected with siRNA mutant, as indicated by drastically enhanced secretion of proinflammatory cytokines, such as IL-12, IL-6 and TNF-α (FIGS. 22B and 22C).

Generation of a Recombinant Adenoviral Vector Expressing a Human SOCS1 siRNA

Figure 28:
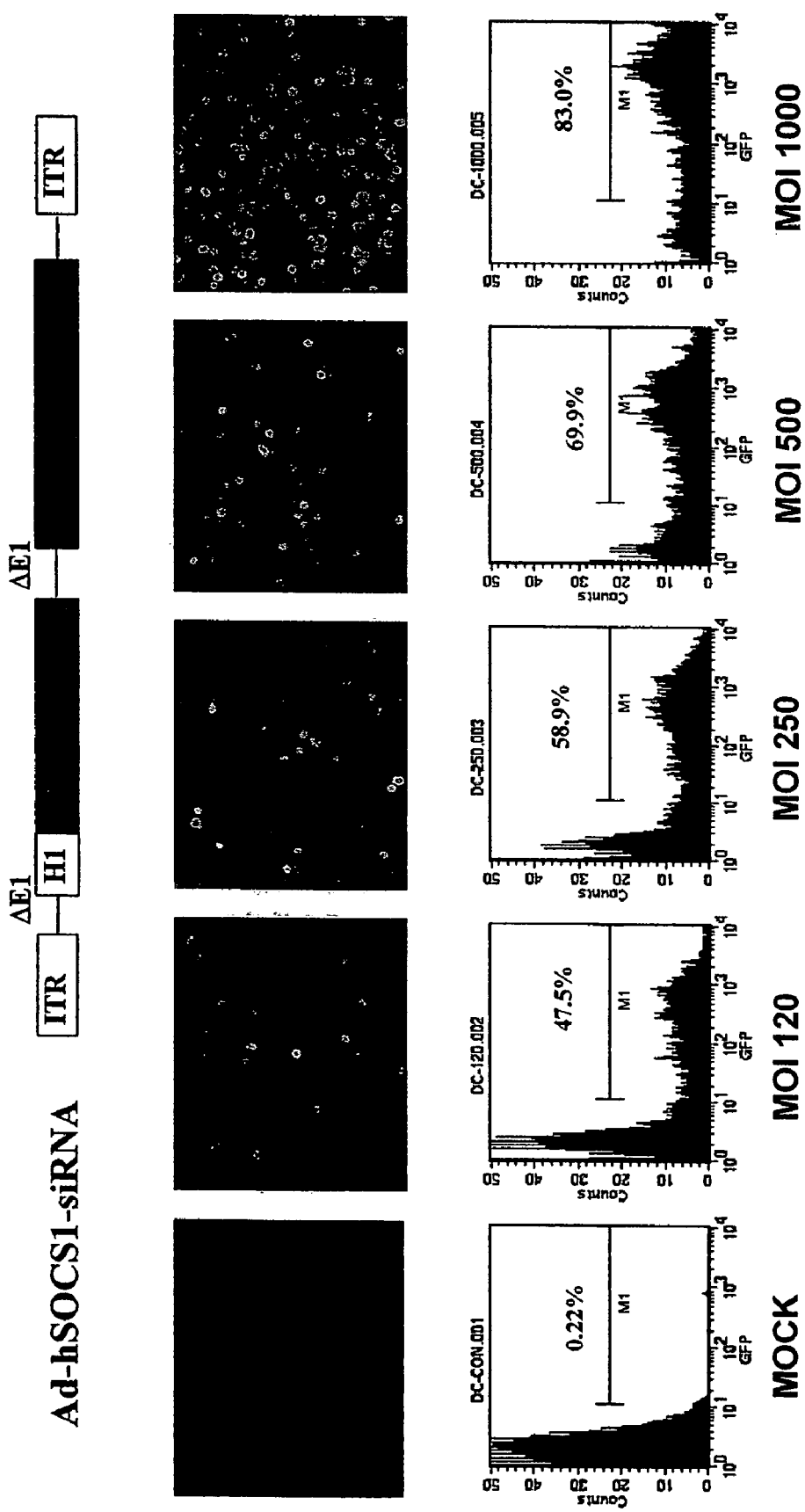
FIG. 28 is a chart depicting a schematic of a replication-defective adenoviral vector expressing human SOCS1 siRNA.

An AdEasy system (E1 and E3 deleted Ad(5); Quantum Biotechnologies Inc., Palo Alto, Calif.) was used to construct and generate replication-defective adenoviruses. The shuttle vector Ad-hSOCS1-siRNA was constructed by inserting H1-human SOCS1-siRNA DNA fragment into the AdEasy vector (FIG. 28). The insertion of human SOCS1-siRNA was confirmed by DNA sequencing. The recombinant adenovirus Ad-hSOCS1-siRNA was subsequently generated according to the manufacturer's instructions (Quantum Biotechnologies Inc., Palo Alto, Calif.). Recombinant adenoviruses were produced and titrated in 293 cells according to the manufacturer's instructions (Quantum Biotechnologies Inc., Palo Alto, Calif.). It was observed that the recombinant Ad(5) virus was able to transfect human monocyte-derived DCs.

Example 11

MAGE3-Specific CTL Responses Primed by Human SOCS1 siRNA DCs

The following experiments were set out to investigate the role of human SOCS1 in regulating the immunostimulatory capacity of human DCs. The results presented in this example demonstrates that human SOCS1-silenced DCs are hyperactive to stimulation with microbial products and have an enhanced stimulatory ability to prime self antigen-specific human cytotoxic T lymphocytes (CTLs). Importantly, human SOCS1-silenced DCs, but not wild-type DCs, are capable of fully activating CTLs that have an active lytic activity to natural antigen-expressing human tumor cells. Also, it is believed that the capacity of human SOCS1-silenced DCs to prime CTLs is likely controlled by SOCS1 restriction of IL-12 production and signaling. These results indicate a critical role of human SOCS1 in negatively regulating human DCs and implicate a translational potential of the present SOCS1 silencing approach to develop more effective tumor vaccines for human patients.

The materials and methods employed in the experiments disclosed herein are now described.

Peptides

An HLA-A2-restricted MAGE3 CTL peptide (FLWG-PRALV; SEQ ID NO:27) (van der Bruggen et al., 1994, European Journal of Immunology 24:3038-43) and control H-2K$^b$-restricted OVA-I (SIINFEKL; SEQ ID NO:11) were synthesized and purified by HPLC to >95% purity by Genemed Synthesis Inc. (South San Francisco, Calif., USA). Peptides were dissolved in DMSO before final dilution in endotoxin-free PBS (Sigma, St. Louis, Mo.).

Western Blot Analysis of Human SOCS1 Expression 293T cells were co-transfected with a synthetic human SOCS-1-siRNA oligonucleotide duplex (21 bp) or an irrelevant oligo duplex and a flag-tagged human SOCS1 expression vector (pCMV-hSOCS1) at a 10:1 ratio using GenePorter reagent as discussed elsewhere herein. 48 hours after transfection, the cells were harvested, and subjected to SDS-PAGE. After transfer to Hybond-P membrane (Amersham, Arlington Heights, Ill.), the samples were analyzed by Western blotting with anti-Flag (Sigma, St. Louis, Mo.) or actin (Santa Cruz Biotechnology, Inc. Santa Cruz, Calif.) antibodies, followed by detection with ECL-Plus reagent (Amersham, Arlington Heights, Ill.). Films were scanned with a Densitometer SI and SOCS-1/actin bands were quantified with ImageQuant software (Molecular Dynamics, Piscataway, N.J.). The intensity of SOCS1 bands was normalized to the intensity of beta-actin bands.

Quantitative RT-PCR Analysis of Human SOCS1 Expression

The relative expression of human SOCS1 in human DCs was evaluated by quantitative real-time RT-PCR as discussed elsewhere herein.

Transfection of Human Monocyte-Derived DCs and In Vitro Priming of Human T Cells Human DCs derived from PBMCs were generated and cultured as described in Schroers et al., 2003, Clinical Can. Res. 9:4743-4755; and Schroers et al., 2004, Methods Mol. Biol. 246:451-9. Heparinized blood was collected from HLA-A2+ healthy volunteers. HLA-typing was performed by PCR-SSP-DNA-based procedures (The Methodist Hospital, Houston, Tex.). PBMCs were resuspended in serum-free DC medium (CellGenix, Antioch, Il) and incubated at 37° C. in humidified 5% $CO_2$ The cell fraction adherent to plastic was cultured in serum-free DC medium with 1000 IU/ml recombinant human GM-CSF (rhGM-CSF; R&D Systems Inc., Minneapolis, Minn.) and 1000 IU/ml rhIL-4 (R&D Systems Inc., Minneapolis, Minn.). On day 5 or 6, monocyte-derived DCs were transfected with 120 nM siRNA oligonucleotides using GenePorter according to the manufacturer's instructions. The transfected DCs were then pulsed with MAGE3 peptide (20 µg/ml) overnight. A total of $1 \times 10^6$ human T-cells per well of a 24-well plate were co-cultured with $5 \times 10^4$ MAGE3-pulsed, transfected DC (20:1) in 0.5 ml of RPMI-1640 supplemented with 5% AB human serum, rhIL-2 (50 U/ml), and TNFα (10 ng/ml, R&D Systems Inc., Minneapolis, Minn.). The co-cultured T-cells were re-stimulated once with autologous MAGE3-pulsed, transfected DCs on day 7 of co-cultures. For some experiments, anti-human IL-12 (p70) antibodies (20 μg/ml, R&D Systems Inc., Minneapolis, Minn.) were added into the co-culture of DCs and T cells every three days. After two weeks of co-cultures, the T cells were used for immune assays.

Cytokine ELISA and Enzyme-Linked Immunospot (ELISPOT) Assays

Levels of various proinflammatory cytokines were quantitated using the supernatant of DC cultures for ELISA analysis (BD Biosciences, Lincoln Park, N.J.) according to the manufacturer's instructions at the indicated time points and with the indicated stimulus. ELISPOT assays of human peripheral lymphocytes were performed as described elsewhere herein.

Flow Cytometric Analysis

Cells were stained with FITC or PE mAbs in PBS containing 0.1% $NaN_3$ and 2% FCS. Antibodies specific for human CD40, CD80, and CD86 and matched isotype controls were purchased from BD Biosciences, San Jose, Calif. Stained cells were analyzed on a FACSCalibur (Becton Dickinson, Lincoln Park, N.J.) flow cytometer.

Tetramer Staining

Human MAGE3/HLA-A2 tetramers were synthesized at the Baylor College of Medicine Tetramer Core Facility (Houston, Tex., USA). Human peripheral blood lymphocytes or lymphocytes in the cocultures were co-stained with anti-hCD8α-FITC/anti-hCD3-PerCP and MAGE3-PE tetramers. Tetramer staining was done at 4° C., for 1 h with 1 μg of anti-CD8α and a 1:100 dilution of MAGE3-PE tetramers per $10^6$ cells, according to the manufacturer's instruction.

DC Immunization of HLA-A2 Transgenic Mice

Four to six week old female HLA-A2.1 transgenic mice were purchased from the Jackson Laboratory (Maine, USA) and maintained in a pathogen-free mouse facility at Baylor College of Medicine (Houston, Tex., USA) according to institutional guidelines. Mouse BM-derived DCs were prepared from HLA-A2.1 transgenic mice and transduced with the recombinant lentiviral vectors LV-SOCS1-siRNA or LV-GFP-siRNA at an MOI of 5, as described elsewhere herein. DCs were then pulsed with MAGE3 peptides for 20 hr, washed with PBS three times, and stimulated with TNFα (500 ng/ml, R&D Systems Inc., Minneapolis, Minn.) for 24 hr. The DCs were then injected into HLA-A2 transgenic mice via a rear foot-pad. In some mice, LPS (30 μg/mouse) or recombinant murine IL-12 (1 μg/mouse, PeproTech, Inc., Rocky Hill, N.J.) was administered intraperitoneally (i.p.) on indicated days after DC vaccination.

CTL Assays

CD8+ CTL responses were assessed with a standard chromium release assay, which measures the ability of in vitro-restimulated splenocytes to lyse target cells as disclosed elsewhere herein (Huang et al., 2003, Cancer Res. 63:7321-9). Splenocytes pooled from 2-3 immunized mice were restimulated in vitro in RPMI-1640 containing MAGE3 peptide for 4-6 days. Human MAGE3+, HLA-A2+ melanoma cells (SK-Mel-37) and control human MAGE3+, HLA-A2- melanoma cells (NA-6-Mel) were labeled with sodium $^{51}Cr$ chromate solution for 90 min at 37° C. Different numbers of effector cells were incubated with a constant number of target cells ($5 \times 10^4$/well) in 96-well U-bottomed plates (200 μl/well) for 4 h at 37° C. The supernatants from triplicate cultures were collected and analyzed. Percent lysis was calculated as (experimental release−spontaneous release)/(maximum release−spontaneous release)×100.

The results of the experiments presented in this Example are now described.

Figure 23A:
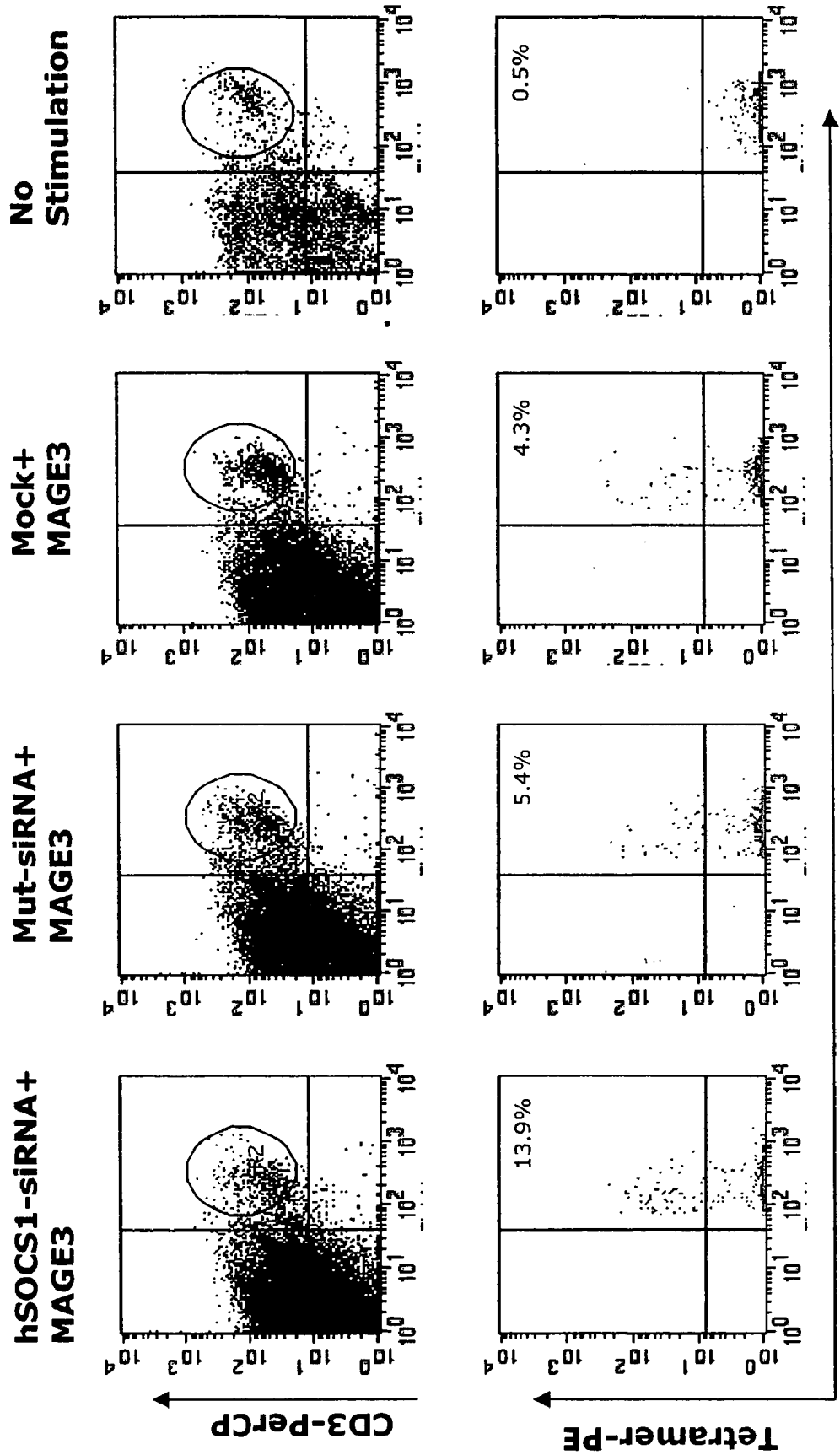

Enhanced Immunostimulatory Potency of Human SOCS1-Silenced DCs to Prime Antigen-Specific CTL Responses The next set of experiments were set out to assess whether silenced human SOCS1 could enhance the stimulatory potency of human DCs in priming self-antigen specific CTLs. An HLA-A2-restricted peptide derived from human MAGE3, an embryonic tumor antigen known to be expressed in adult human testis and melanoma cells (van der Bruggen et al., 1994, European Journal of Immunology 24:3038-43), was used as a model human self-antigen. Human monocyte-derived DCs from HLA-A2+ healthy volunteers were transfected with hSOCS1 siRNA oligonucleotides and then pulsed with MAGE3 peptide (20 μg/ml) overnight. A total of $1 \times 10^6$ autologous human T cells per well were cocultured with $5 \times 10^4$ MAGE3-pulsed, transfected DC (20:1) in the presence of TNFα (a maturation stimulus) (10 ng/ml, R&D Systems Inc., Minneapolis, Minn.). The co-cultured T cells were restimulated once with autologous MAGE3-pulsed, transfected DCs on day 7 of co-cultures. After two weeks of cocultures, the T cells were used for immune assays. In cocultures with hSOCS siRNA-transfected DCs pulsed with MAGE3 peptide, 13.9% of the CD8+ T cells were positive for the MAGE3-tetramer, compared with only 5.4% and 4.3% in cocultures with MAGE3-pulsed mut-siRNA DCs or mock DCs, respectively (FIG. 23A). Tetramer staining of naïve (unstimulated) primary human lymphocytes from the same donors indicated a low level of positive MAGE3 tetramer staining (0.5% of the CD8+ T cells). In agreement, intracellular IFNγ staining (FIG. 23B) indicated that hSOCS1-siRNA DCs substantially improved MAGE3-specific CTL responses (11.18% of IFNγ+ CD8+ T cells) compared to MAGE3 peptide-pulsed, mut-siRNA DC (6.9% of IFNγ+ CD8+ T cells) or mock DCs (5.7% IFNγ+ CD8+ T cells). Furthermore, IFNγ ELISPOT assays (FIG. 23C) indicated that an increased number of MAGE3-specific CTLs were activated by hSOCS1-siRNA DCs. Repeated experiments from HLA-A2+ donors indicated similar results. Most of the primary human T cells were dead after a two-week coculture with DCs not pulsed with antigens. Collectively, these results indicate that human SOCS1-silenced DCs have an enhanced immunostimulatory ability to prime self antigen-specific CTLs.

Critical Role of SOCS1-Restricted IL-12 in CTL Priming

Figure 23B:
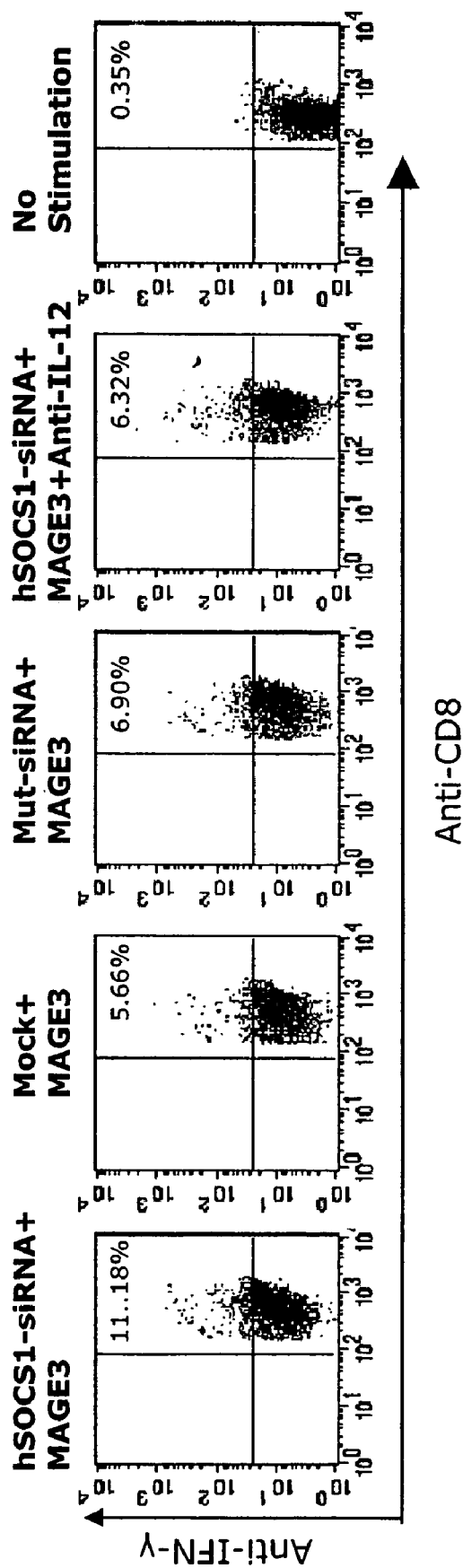

Since SOCS1-silenced DCs produce enhanced amounts of IL-12, a key cytokine in the activation of CTL responses (Trinchieri, 2003, Nat. Rev. Immunol. 3:133-46), in response to stimulation with microbial products and since IL-12 signaling is restricted by SOCS1 (Eyles et al., 2002, J. Biol. Chem. 277:43735-40), the role of IL-12 in priming CTLs by human SOCS1-silenced DCs was examined. Accordingly, anti-human IL-12 antibodies were added to the cocultures of T cells and MAGE3-pulsed, transfected DCs every 3 days. FIGS. 23A through 23C show that the inhibition of IL-12 using anti-IL 12 (p70) antibodies abrogated the enhanced ability of hSOCS1-siRNA DCs to stimulate MAGE3-specific CTLs, as demonstrated by tetramer staining, intracellular IFN-γ staining, and ELISPOT assays.

Figure 24:
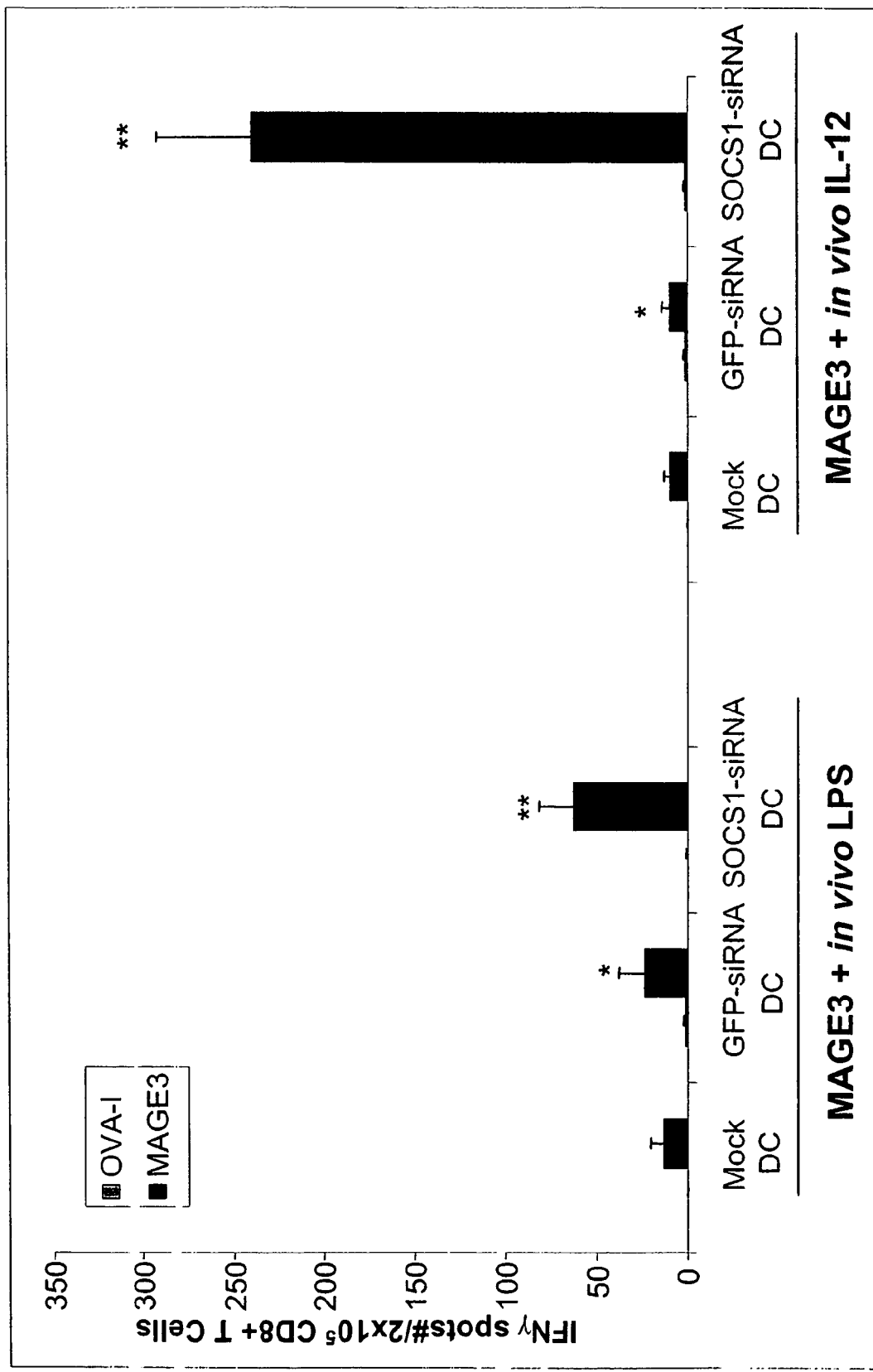
FIG. 24 is a chart depicting enhanced human MAGE3-specific CTL responses in humanized HLA-A2.1 transgenic mice.

Humanized HLA-A2.1 transgenic mice were used to further test the role of IL-12 in the enhanced CTL response induced by SOCS1-silenced DCs. HLA-A2.1 transgenic mouse BM-derived DCs were transduced with a recombinant lentiviral vector expressing murine SOCS1 siRNA (LV-mSOCS1 siRNA) or a control vector LV-GFP siRNA and pulsed with A2-restricted MAGE3 peptide. After maturation with TNFα, transduced DCs were administered into HLA-A2.1 transgenic mice via a foot-pad twice at a weekly interval. After each DC immunization, the mice were stimulated in vivo three times with either LPS or a low dose of recombinant IL-12 cytokines. LPS was used because of the large number of pro-inflammatory cytokines it induces, many of which are regulated by SOCS1 and because of the possible direct role of SOCS1 in the regulation of NF-κB (p65) signaling (Ryo et al., 2003, Mol. Cell 12:1413-26). With in vivo IL-12 stimulations, 239 IFNγ+ spots per $2\times10^5$ T cells were detected in mice immunized with MAGE3-pulsed SOCS1-siRNA DCs, compared with only 10 IFNγ+ spots per $2\times10^5$ T cells in mice immunized with MAGE3-pulsed GFP-siRNA DCs (FIG. 24). In vivo LPS stimulations also preferentially enhanced the CTL responses induced by SOCS1-siRNA DCs (63 IFNγ+ spots per $2\times10^5$ T cells in SOCS1-siRNA-DC mice vs. 24 IFNγ+ spots per $2\times10^5$ T cells in GFP-siRNA-DC mice) (FIG. 24). However, IL-12 stimulation was more effective than LPS stimulation to boost MAGE3-specific CTL responses in SOCS1-siRNA-DC immunized mice (P<0.01). This superior stimulatory ability of IL-12 is likely due to the ability of SOCS1 to directly regulate IL-12 stimulation through the Jak/Stat pathway, as well as the direct effect of IL-12 on CTLs (Trinchieri, 2003, Nat. Rev. Immunol. 3:133-46) that have been activated in SOCS1-siRNA DC-immunized mice. Taken together, these results provide further evidence that SOCS1 restricts the signaling of IL-12 in antigen-presenting cells. These results also underscore the importance of cytokine signaling in determining the efficacy of cytokine-based tumor therapy.

Figure 25B:
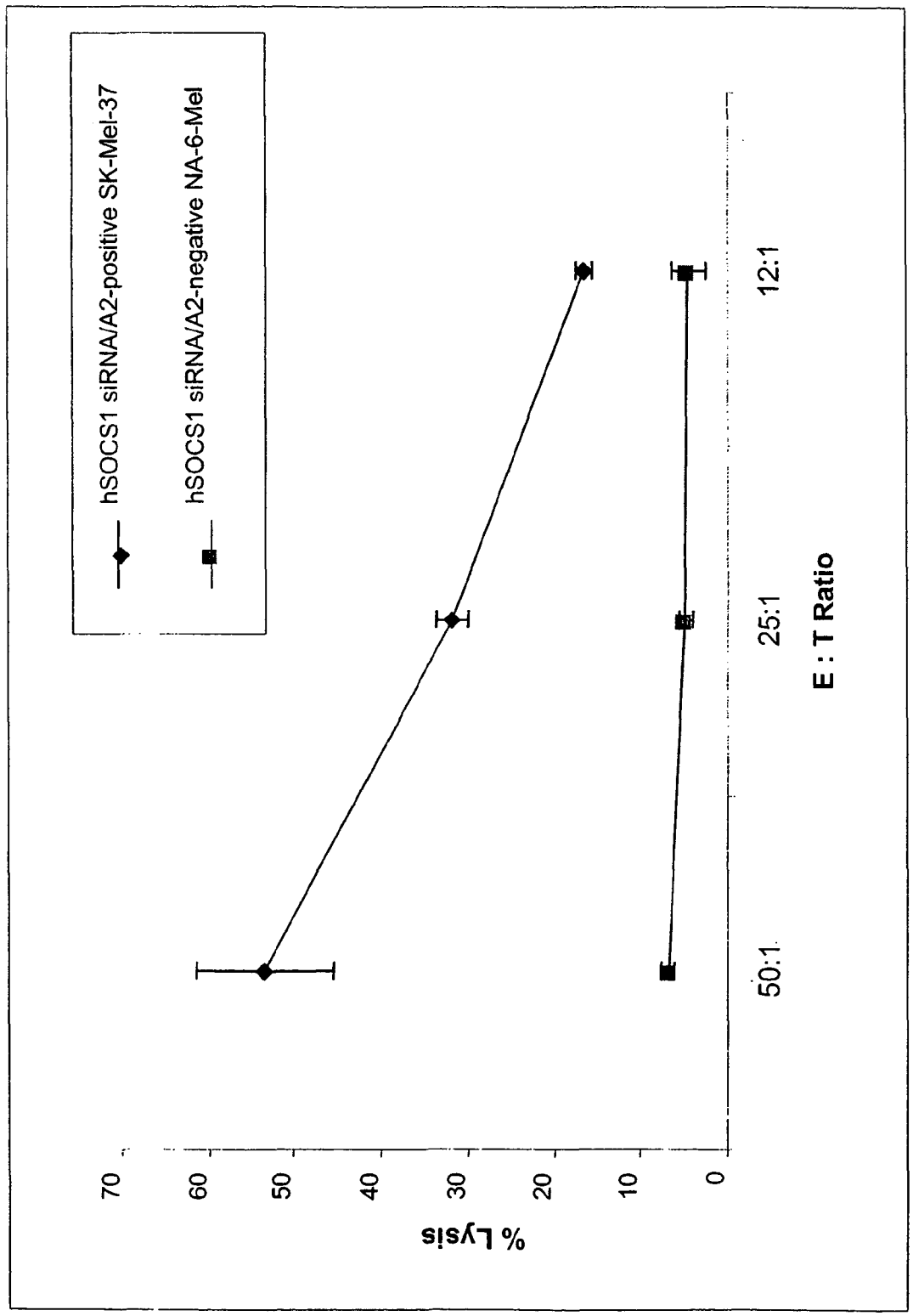

Human CTLs Activated by Human SOCS1-Silenced DCs, but not by Wild-Type DCs have Tumor Lytic Effector Function To determine whether activated T cells specific for the self tumor-associated antigen MAGE3 possess tumor lytic effector function, natural MAGE3+ human tumor cells was used as target cells for CTL assays. Human T cells activated by MAGE3-pulsed SOCS1-siRNA DCs or mut-siRNA DC readily killed MAGE3 peptide-pulsed, MAGE3+ HLA-A2+ melanoma cells (SK-Mel-37). However, human T cells activated by MAGE3-pulsed mut-siRNA DCs indicated only a weak cytolytic activity to natural SK-Mel-37 cells not pulsed with MAGE3 (FIG. 25). In contrast, those T cells activated by MAGE3-pulsed SOCS1-siRNA DCs still had a strong cytolytic activity against natural SK-Mel-37 cells not pulsed with MAGE3 (FIG. 25). The tumor lytic activity of T cells in the coculture with hSOCS1-siRNA DCs was significantly compromised by anti-hIL-12 antibody treatment. The tumor cytolytic activity was specifically mediated by CTLs, since the human T cells activated by MAGE3-pulsed SOCS1-siRNA DCs only had a background cytolytic activity against the HLA-A2-negative, MAGE3+ melanoma cells (NA-6-Mel). Repeated experiments from different donors indicated similar results.

Figure 26A:
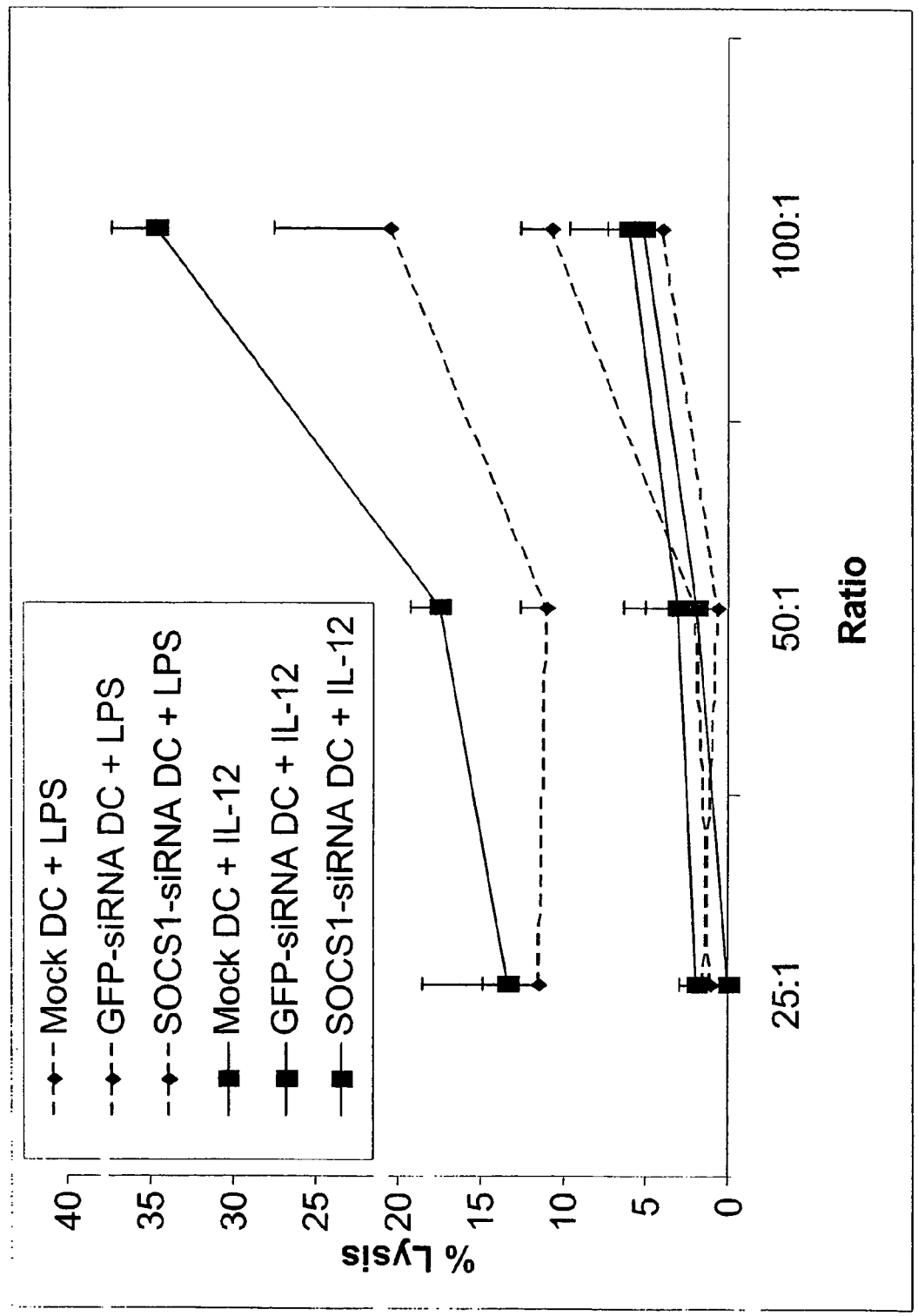
FIGS. 26A and 26B, is a series of charts demonstrating tumor lytic activities of activated CTLs of immunized HLA-A2.1 transgenic mice. Cytotoxicities against human SK-Mel-37 cells (FIG. 26A) and control human HLA-A2$^-$ NA-6-Mel cells (FIG. 26B) were determined after in vitro restimulation with MAGE3 peptide for 5 days and are presented from one of three experiments.
Figure 26B:
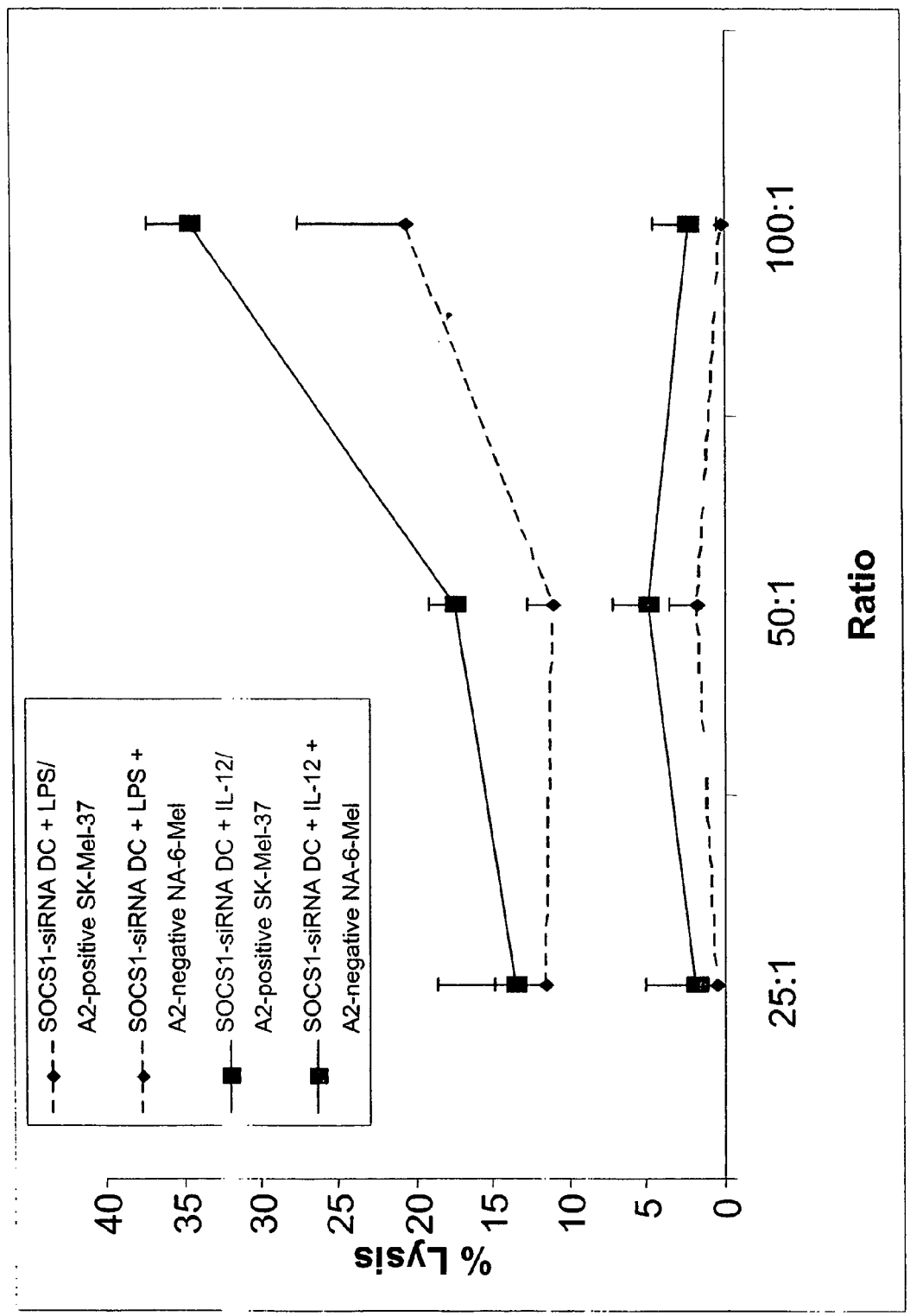

To confirm the above observations, the tumor lytic activity of T cells from the HLA-A2.1 transgenic mice that were immunized with MAGE3-pulsed SOCS1-siRNA DCs or GFP-siRNA DCs was tested. FIG. 26 shows that T cells from the transgenic mice immunized with MAGE3-pulsed, mSOCS1 siRNA DCs had an active cytolytic activity against the natural MAGE3+ HLA-A2-positive melanoma cells SK-Mel-37. In contrast, T cells from the transgenic mice immunized with MAGE3-pulsed, GFP-siRNA DCs only had a weak cytolytic activity against the natural melanoma cells, in agreement with the results shown in FIG. 25. Furthermore, it was observed that in vivo stimulation with a low dose of recombinant IL-12 significantly enhanced the CTL responses induced by SOCS1 siRNA DCs, but not GFP-siRNA DCs (FIG. 26). Taken together, the results herein indicate that human SOCS1-silenced DCs possess a unique ability to fully activate CTLs that have an active lytic effector function against natural tumor cells, likely due to the enhanced production and signaling of IL-12 by antigen presenting cells.

Full Activation of Self Antigen-Specific Human CTLs by Human SOCS-Silenced DCs

The present disclosure demonstrates a regulatory role of human SOCS1 in human DCs and provides an alternative strategy to enhance the immunostimulatory potency of human DCs by silencing the inhibitor of the JAK/STAT signaling pathway. The results disclosed herein demonstrate a critical role of human SOCS1 in negatively regulating the immunostimulatory ability of human DCs to prime antigen-specific CTLs. Human SOCS1-silenced DCs have a unique ability to fully activate human CTLs that possess a robust lytic function against natural, antigen-expressing tumor cells. The capacity of human SOCS1-silenced DCs to prime CTLs is likely controlled by SOCS1 restriction of IL-12 production and signaling. Thus, the present disclosure demonstrates a translational potential of this generally applicable, SOCS1 silencing approach to develop more effective tumor vaccines.

The SOCS1 silencing approach of the present invention has the ability to enhance an antigen-specific immune response induced by DCs loaded with tumor-associated antigens. During the last decade, a major advance in tumor immunology has been the identification and validation of a large number of human tumor-specific or associated antigens (Van den Eynde et al., 1997, Current Opinion in Immunology 9:684-93). Thus, vaccination with SOCS1-silenced DCs loaded with tumor-associated antigens would be more attractive than blocking of CTLA4 on CTLs to induce antigen-specific antitumor responses. The use of SOCS1-silenced DC immunization provides an additional therapeutic benefit in that the SOCS1-silenced DC may not cause severe autoimmune inflammation, since heterozygous SOCS1$^{+/-}$ mice show no or only mild signs of autoimmune inflammation. Moreover, the severe autoimmune inflammation seen in SOCS1$^{-/-}$ mice requires a complete deficiency of SOCS1 not only in DCs, but also in other lineages of immune cells, such as T and NKT cells (Kubo et al., 2003, Nat. Immunol. 4:1169-76; Alexander et al., 2004, Annu. Rev. Immunol. 22:503-29; Metcalf et al., 2003, Proc. Natl. Acad. Sci. USA 100:8436-41; Chong et al., 2003, Immunity 18:475-87; Hanada et al., 2003, Immunity 19:437-50; Kinjyo et al., 2002, Immunity 17:583-91).

Extensive efforts to enhance the efficacy of tumor vaccines have focused on the improvement of the affinity/dose (signal 1) of tumor-associated antigens and the levels of costimulatory molecule-mediated signal 2 (Gilboa, 2004, Nat. Rev. Cancer 4:401-11; Rosenberg et al., 2004, Nat. Med. 10:909-15). The present disclosure shows that the superior ability of human SOCS1-silenced DCs to prime antigen-specific CTLs is likely due to the enhanced production and signaling of IL-12 (signal 3). This conclusion is based upon the following observations: 1) human SOCS1-silenced DCs produce enhanced levels of IL-12 in response to stimulation with microbial products; 2) antibody blocking of IL-12 compromises the immunostimulatory capability of human SOCS1-silenced DCs; and 3) in vivo administration of a low dose of IL-12 drastically enhances antigen-specific CTL responses induced by SOCS1-silenced DCs, but not by wild-type DCs. These results are supported by the finding of murine SOCS1 regulation of IL-12 signaling by Eyles, J. L. et al. (Eyles et al., 2002, J. Biol. Chem. 277:43735-40) and by the results disclosed elsewhere herein.

Cytokines have been proposed as a third signal provided by DCs to activate CTLs (Curtsinger et al., 2003, J. Exp. Med. 197:1141-51). Cytokine production and signaling are tightly regulated in order to activate immune responses against foreign antigens, while limiting excessive autoimmune activation (Darnell et al., 1994, Science 264:1415-21). Cytokines commonly activate JAKs, which then phosphorylate the cytoplasmic domain of the cytokine receptors, creating a docking site for members of the signal transducer and activator of transcription (STAT) (Alexander et al., 2004, Annu. Rev. Immunol. 22:503-29). Cytokines also upregulate the expression of SOCS1 as a feedback inhibitor, which then turns off the production and signaling of pro-inflammatory cytokines by DCs, thus attenuating the ongoing immune response and maintaining self-tolerance (Alexander et al., 2004, Annu. Rev. Immunol. 22:503-29). SOCS1 suppresses STAT by specifically binding to the JAK activation loop as a pseudosubstrate inhibitor via its SH2 domain and targeting JAK2 for ubiquitin-dependent protein degradation (Kubo et al., 2003, Nat. Immunol. 4:1169-76; Alexander et al., 2004, Annu. Rev. Immunol. 22:503-29). Taken together, the results disclosed herein indicate the critical importance of the production and signaling of IL-12 restricted by SOCS1 in antigen-presenting cells in determining the magnitude of CTL responses.

A significant finding of this study is that human SOCS1-silenced DCs possess a unique capacity to fully activate self-reactive T cells with an active lytic effector function. It has been frequently observed in the clinic and laboratory studies that self antigen-specific T cells can be activated by DC vaccination or in vitro sensitization, as determined by various immune assays such as tetramer staining and ELISPOT assays. However, although such activated T cells can effectively kill artificial antigen-pulsed tumor cells or tumor cells genetically modified to express the self-antigen, they usually show a weak cytolytic activity against natural tumor cells, which has been considered to be a main reason for the poor efficacy of current tumor vaccines (Zaks et al., 1998, Cancer Research 58:4902-8; Yu et al., 2002, J. Clin. Invest. 110:289-94). The results disclosed herein suggest that persistent and enhanced antigen presentation/stimulation provided by SOCS1-silenced DCs may be required to fully activate self-reactive, low affinity T cells and endow them with active lytic effector function against natural tumor cells.

Example 12

SOCS1 siRNA Oligo Duplex Enhances Protein Immunization

Figure 27A:
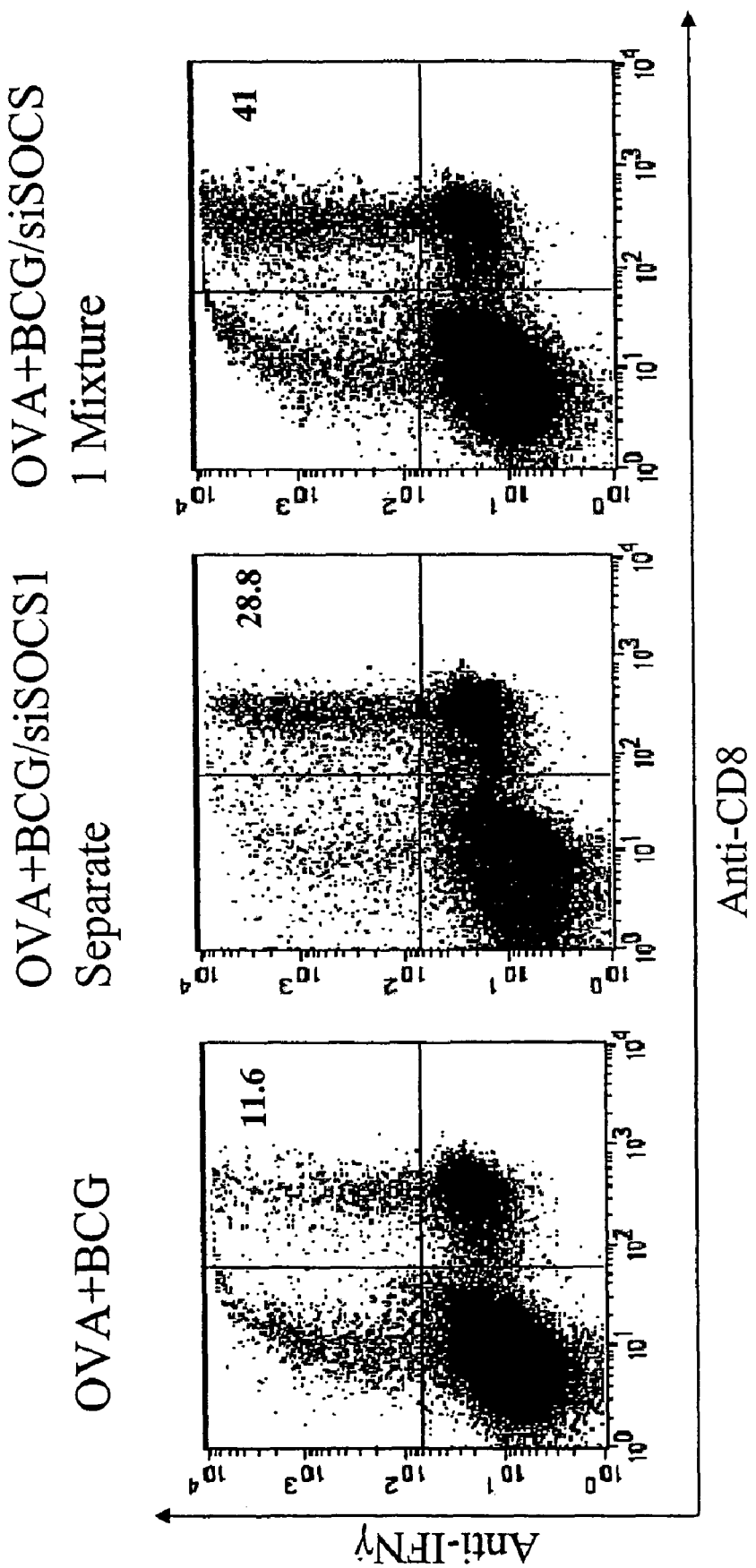
FIGS. 27A and 27B, is a series of charts demonstrating coimmunization with SOCS1 siRNA oligo duplex enhances in vivo protein immunization.
Figure 27B:
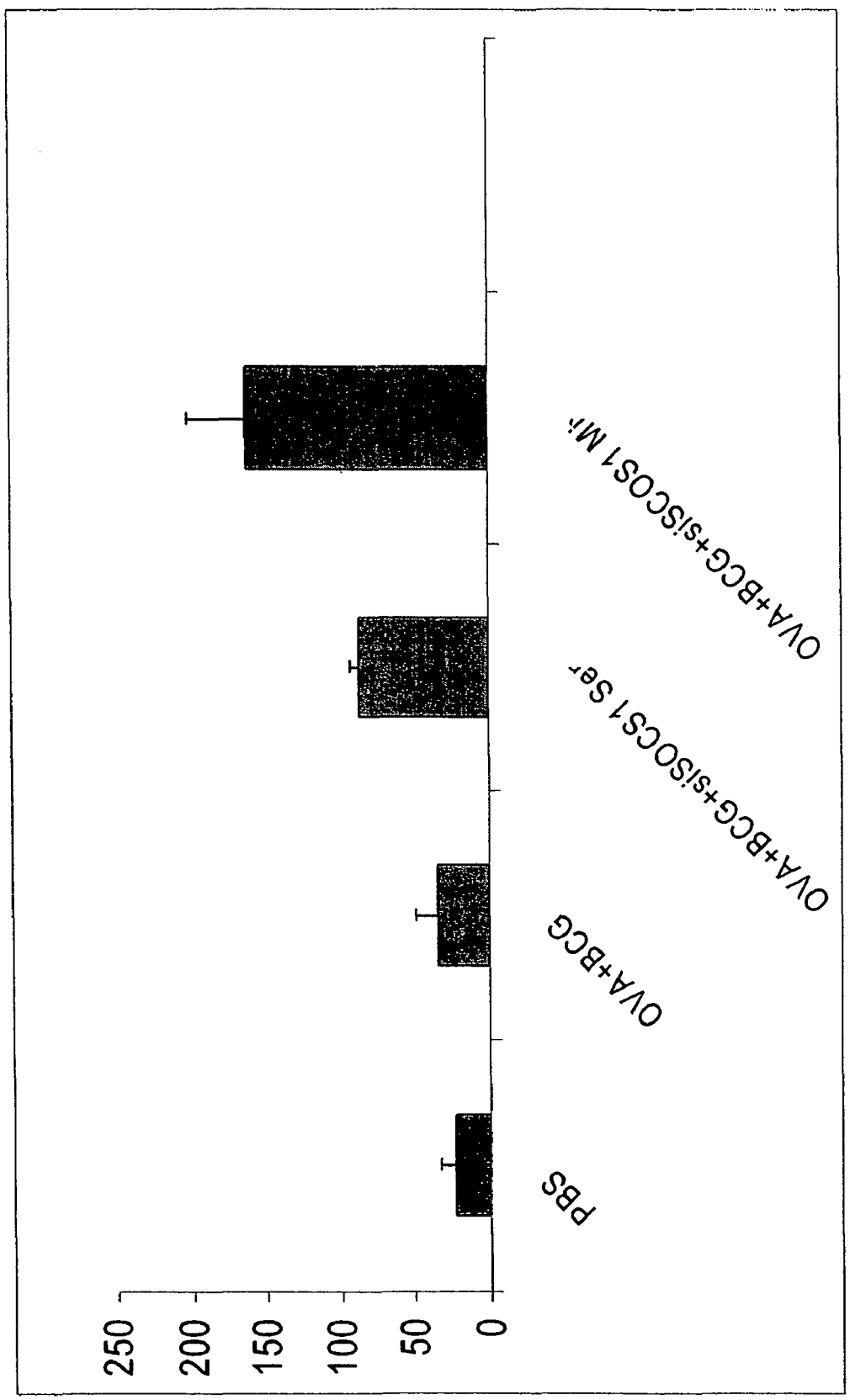

To test whether in vivo immunization with SOCS1 siRNA oligo duplex could enhance protein immunization, CTL responses induced by immunization with 1) OVA protein with BCG were compared with 2) coimmunization with SOCS1 siRNA oligo duplex-liposome and OVA protein with BCG. Groups of mice were immunized with the mixture of OVA protein and BCG, a mixture of SOCS1 siRNA oligo duplex-liposome and OVA protein and BCG, or co-injected with the mixture of OVA protein and BCG and SOCS1 siRNA oligo duplex-liposome via foot-pad twice at a one week interval. It was observed that two weeks after the second immunization, intracellular cytokine staining and ELISPOT assays (IFNγ) showed that more potent OVA-specific CTL responses were induced in the mice co-immunized with SOCS1 siRNA oligo duplex (FIGS. 27A and 27B).

Example 13

SOCS1-Silenced CTLs have an Enhanced Cytolytic Activity

Figure 29:
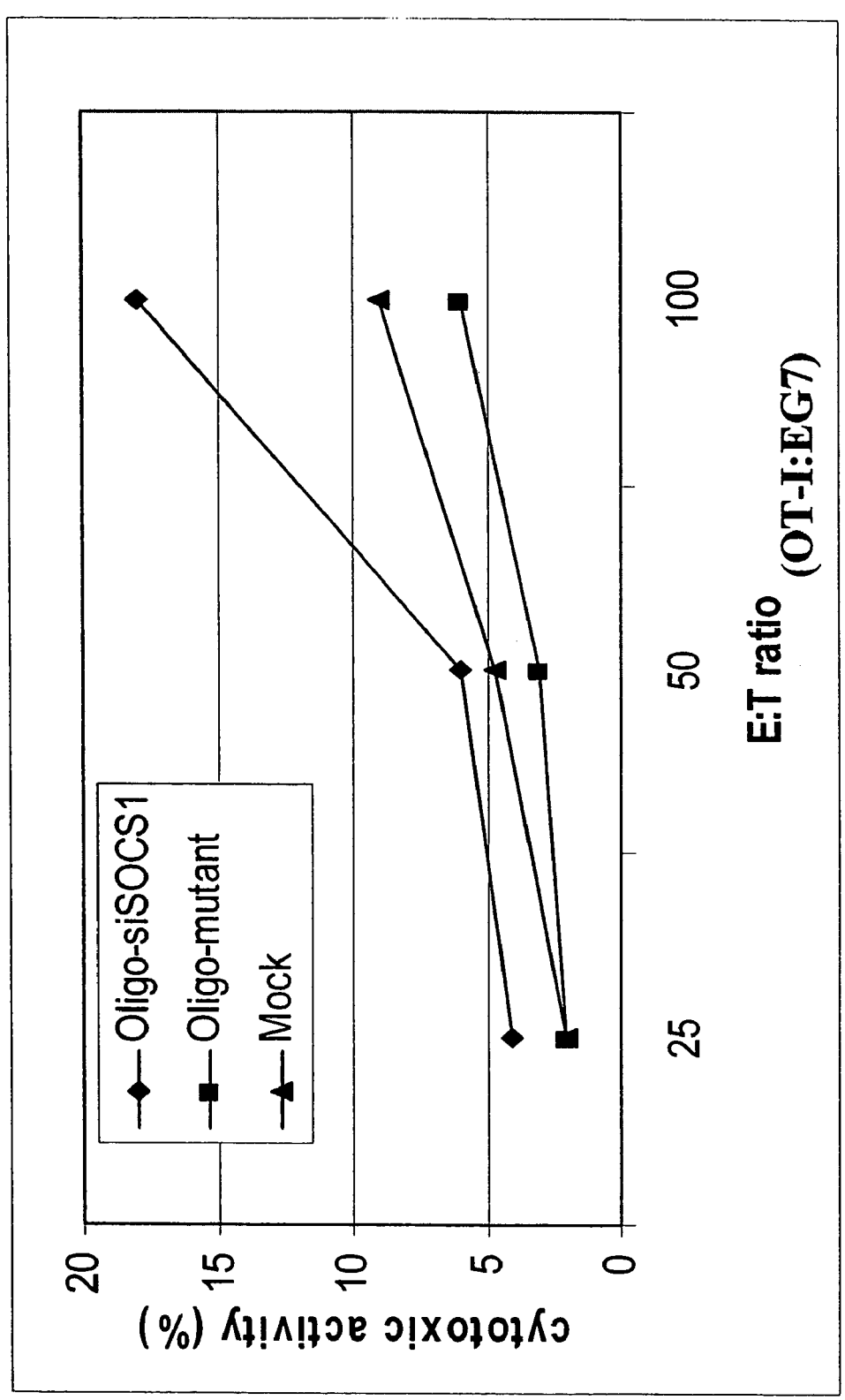
FIG. 29 is a chart depicting enhanced CTL activities by SOCS1 siRNA oligo duplex transfection of T cells.

To investigate whether SOCS1 in T cells plays a role in regulating CTL activities, CD8+ OT-I cells that have transgenic TCR specific for an OVA epitope isolated from OT-I transgenic mice (Jackson Laboratory, Bar Harbor, Me.) were transfeced with SOCS1 or mutant siRNA oligo using Gene-Porter. The transfected OT-I cells were used for CTL assays without further stimulation. It was observed that SOCS1-siRNA oligo-transfected OT-I had an enhanced cytolytic activity to syngeneic OVA-positive EG7 cells in comparison with mutant siRNA-oligo-transfected OT-I cells (FIG. 29). This result indicates that SOCS1 silencing in T cells enhance their cytolytic activities.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition for enhancing the immunopotency of an immune cell, said composition comprising
   (i) an inhibitor of the expression of any one or more of a suppressor of cytokine signaling (SOCS) selected from the group consisting of: SOCS1, SOCS2, SOCS3, SOCS4, SOCS5, SOCS6, SOCS7 and a cytokine-inducible SH2-domain-containing protein (CIS); and
   (ii) a cytokine or a Toll-like receptor (TLR) agonist, wherein the TLR agonist is selected from the group consisting of: Poly I:C, lipopolysaccharide (LPS), and a CpG oligonucleotide,
   wherein said inhibitor is a small interfering RNA (siRNA).

2. The composition of claim 1, wherein said siRNA is selected from the group consisting of a double stranded oligonucleotide, a single stranded oligonucleotide, and a polynucleotide.

3. The composition of claim 1, wherein said siRNA is chemically synthesized.

4. The composition of claim 1, further comprising a physiologically acceptable carrier.

5. The composition of claim 4, wherein said physiologically acceptable carrier is a liposome.

6. The composition of claim 1, wherein said inhibitor is encoded by an isolated polynucleotide cloned into an expression vector.

7. The composition of claim 6, wherein said expression vector is selected from the group consisting of a plasmid DNA, a viral vector, a bacterial vector and a mammalian vector.

8. The composition of claim 6, wherein said expression vector further comprises an integration signal sequence which facilitates integration of said isolated polynucleotide into the genome of a host cell.

9. The composition of claim 1 further comprising an antigen having at least one epitope, wherein said epitope is capable of eliciting an immune response in a mammal.

10. The composition of claim 9, wherein said antigen is expressed by an expression vector.

11. The composition of claim 9, wherein said antigen is an isolated polypeptide.

12. The composition of claim 9, wherein said at least one epitope induces a CD4+ T-cell response in a mammal.

13. The composition of claim 9, wherein said at least one epitope induces a CD8+ T-cell response in a mammal.

14. The composition of claim 9, wherein said at least one epitope induces a B cell response in a mammal.

15. The composition of claim 9, wherein said antigen is associated with a disease.

16. The composition of claim 15, wherein said disease is selected from the group consisting of an infectious disease, a cancer and an autoimmune disease.

17. The composition of claim 15, wherein said antigen is associated with an infectious disease.

18. The composition of claim 17, wherein said infectious disease is caused by a pathogenic microorganism selected from the group consisting of a virus, a bacterium, a fungus and a protozoan.

19. The composition of claim 9, wherein said antigen is encoded by a viral gene.

20. The composition of claim 19, wherein said viral gene is derived from a virus selected from the group consisting of a hepatitis B virus, a hepatitis C virus, a human immunodeficiency virus, a papillomavirus, and a herpesvirus.

21. The composition of claim 19, wherein said antigen is encoded by a viral gene selected from the group consisting of a hepatitis B virus e antigen gene, a hepatitis B virus surface antigen gene, and a hepatitis B virus core antigen gene.

22. The composition of claim 19, wherein said antigen is encoded by a viral gene selected from the group consisting of a human immunodeficiency virus Env gp160 gene, Gag gene, Pol gene, Rev gene, Tat gene, Vif gene, and Nef gene.

23. The composition of claim 19, wherein said antigen is encoded by a viral gene selected from the group consisting of a papillomavirus E7 gene and a papillomavirus E6.

24. The composition of claim 20, wherein said antigen is encoded by a viral gene derived from a herpesvirus selected from the group consisting of a herpes simplex virus type 1, a herpes simplex virus type 2, an Epstein-Barr virus, a cytomegalovirus, a human herpes virus 6, a human herpes virus 7 and a human herpes virus 8.

25. The composition of claim 16, wherein said cancer is selected from the group consisting of a breast cancer, a cervical cancer, a melanoma, a renal cancer and a prostate cancer.

26. The composition of claim 9, wherein said antigen is a tumor-associated antigen is selected from the group consisting of an overexpressed tumor-associated antigen, a testis-tumor antigen, a mutated tumor-associated antigen, a differentiation tumor-associated antigen tyrosinase, MART, tip, MAGE-1, MAGE-2, MAGE-3, gp100, HER-2, Ras and PSA.

27. The composition of claim 26, wherein said tumor-associated antigen is selected from the group consisting of BCR-ABL, CASP, CDK, Ras, p53, HER-2/neu, CEA, MUC, TW1, PAP, survivin, telomerase, EGFR, PSMA, PSA, PSCA, tyrosinase, MART, TRP, gp100, MART, MAGE, BAGE, GAGE, LAGE/NY-ESO, RAGE, SSX-2, CD19, and CD20.

28. The composition of claim 15, wherein said disease is selected from the group consisting of rheumatoid arthritis, systemic lupus erythematosus, multiple sclerosis, psoriasis and Crohn's disease.

29. The composition of claim 1, wherein said cytokine or TLR agonist is expressed by an expression vector.

30. The composition of claim 1, wherein said cytokine is an isolated polypeptide.

31. The composition of claim 1, wherein said cytokine is selected from group consisting of IL-12, TNFα, IFNα, IFNβ, IFNγ, IL-7, IL-2, IL-6, IL-15, IL-21, and IL-23.

32. A composition for enhancing immunopotency of a cell, said composition comprising a pharmaceutically acceptable carrier and a vector comprising a first polynucleotide encoding a siRNA inhibitor wherein said inhibitor inhibits the expression of any one or more of a suppressor of cytokine signaling (SOCS) selected from the group consisting of SOCS1, SOCS2, SOCS3, SOCS4, SOCS5, SOCS6, SOCS7 and a cytokine-inducible SH2-domain-containing protein (CIS) in said cell, and a second polynucleotide encoding an antigen having at least one epitope, wherein said at least one epitope induces an immune response in a mammal.

33. The composition of claim 32, wherein said vector is selected from the group consisting of a plasmid DNA, a viral vector, a bacterial vector and a mammalian vector.

34. A composition for enhancing immunopotency of a cell, said composition comprising a pharmaceutically acceptable carrier and a vector comprising a first polynucleotide encoding a siRNA inhibitor, wherein said inhibitor inhibits the expression of any one or more of a suppressor of cytokine signaling (SOCS) selected from the group consisting of SOCS1, SOCS2, SOCS3, SOCS4, SOCS5, SOCS6, SOCS7 and a cytokine-inducible SH2-domain-containing protein (CIS) in said cell, and a second polynucleotide encoding a cytokine or TLR agonist, wherein the TLR agonist is selected from the group consisting of: Poly I:C, lipopolysaccharide (LPS), and a CpG oligonucleotide.

35. The composition of claim 34, wherein said second polynucleotide encoding a cytokine is selected from group consisting of IL-12, TNFα, IFNα, IFNβ, IFNγ, IL-7, IL-2, IL-6, IL-15, IL-21, and IL-23.

36. An isolated cell comprising one or more of a suppressor of cytokine signaling (SOCS) selected from the group consisting of SOCS1, SOCS2, SOCS3, SOCS4, SOCS5, SOCS6, SOCS7 and a cytokine-inducible SH2-domain-containing protein (CIS) and a cytokine or a Toll-like receptor (TLR) agonist, wherein the TLR agonist is selected from the group consisting of: Poly I:C, lipopolysaccharide (LPS), and a CpG oligonucleotide.

37. The cell of claim 36, wherein the cell is an immune cell selected from the group consisting of an APC, a dendritic cell, a monocyte/macrophage, a T cell and a B cell.

38. The cell of claim 37, wherein the T cell is a cytotoxic T cell, a helper T cell, and a regulatory T cell.

39. The cell of claim 36 further comprising an antigen having at least one epitope, wherein said epitope is capable of eliciting an immune response in a mammal.

* * * * *

UNITED STATES PATENT AND TRADEMARK OFFICE
CERTIFICATE OF CORRECTION

PATENT NO.       : 7,868,158 B2                                                 Page 1 of 1
APPLICATION NO.  : 11/165091
DATED            : January 11, 2011
INVENTOR(S)      : Si-Yi Chen et al.

It is certified that error appears in the above-identified patent and that said Letters Patent is hereby corrected as shown below:

Please replace column 99, line 43 with the following corrected version:

--entiation, tumor-associated antigen tyrosinase, MART, trp [[tip]]--

Signed and Sealed this

Seventeenth Day of May, 2011

David J. Kappos
*Director of the United States Patent and Trademark Office*